(12) United States Patent
Molnar

(10) Patent No.: US 11,147,442 B2
(45) Date of Patent: Oct. 19, 2021

(54) MEDICAL DEVICES AND METHODS OF PLACEMENT

(71) Applicant: WM & DG, Inc., Deerfield, IL (US)

(72) Inventor: Robert Molnar, Long Grove, IL (US)

(73) Assignee: WM & DG, INC., Deerfield, IL (US)

( * ) Notice: Subject to any disclaimer, the term of this patent is extended or adjusted under 35 U.S.C. 154(b) by 1459 days.

(21) Appl. No.: 15/163,361

(22) Filed: May 24, 2016

(65) Prior Publication Data

US 2016/0262603 A1    Sep. 15, 2016

Related U.S. Application Data

(63) Continuation-in-part of application No. 14/798,751, filed on Jul. 14, 2015, now Pat. No. 10,722,110, (Continued)

(51) Int. Cl.
*A61B 1/267* (2006.01)
*A61B 1/00* (2006.01)
(Continued)

(52) U.S. Cl.
CPC ............ *A61B 1/267* (2013.01); *A61B 1/0014* (2013.01); *A61B 1/00016* (2013.01); *A61B 1/00135* (2013.01); *A61B 1/00137* (2013.01); *A61B 1/00142* (2013.01); *A61B 1/00154* (2013.01); *A61B 1/05* (2013.01); *A61B 1/07* (2013.01); *A61B 1/233* (2013.01); *A61B 1/24* (2013.01);
(Continued)

(58) Field of Classification Search
CPC . A61B 1/267; A61B 1/00052; A61B 1/00078; A61B 1/05; A61M 16/0488; A61M 2202/0208; A61M 16/0463; A61M 16/0409; A61M 16/0434
See application file for complete search history.

(56) References Cited

U.S. PATENT DOCUMENTS

| | | | |
|---|---|---|---|
| 4,231,365 A | 11/1980 | Scarberry | |
| 4,360,008 A | 11/1982 | Corazzelli, Jr. | |

(Continued)

FOREIGN PATENT DOCUMENTS

| | | |
|---|---|---|
| EP | 0665029 A2 | 8/1995 |
| KR | 20120095385 | 8/2012 |

(Continued)

OTHER PUBLICATIONS

ETView Medical, Ltd., Announces the Appointment of David Amar, MD to Its Scientific Advisory Board, 2012; http://finance.yahoo.com/news/etview-medical-ltd-announces-appointment-104300770.html, Jun. 4, 2012, 3 pages.
(Continued)

*Primary Examiner* — Baisakhi Roy
(74) *Attorney, Agent, or Firm* — Greer, Burns & Crain, Ltd.

(57) ABSTRACT

The present invention provides improved medical devices, including oral airway devices, equipped with a visualization device for intubation, extubation, ventilation, drug delivery, feeding and continuous remote monitoring of a patient. The present invention also provides methods for rapid and accurate placement of a medical device in a patient and continuous real time monitoring, including a remote monitoring, of the patient after the placement.

21 Claims, 83 Drawing Sheets

Related U.S. Application Data which is a continuation-in-part of application No. 14/455,470, filed on Aug. 8, 2014, now Pat. No. 9,918,618.

(51) Int. Cl.
| | | |
|---|---|---|
| *A61M 16/04* | (2006.01) | |
| *A61B 1/05* | (2006.01) | |
| *A61B 1/303* | (2006.01) | |
| *A61M 16/06* | (2006.01) | |
| *A61B 1/07* | (2006.01) | |
| *A61B 1/24* | (2006.01) | |
| *A61B 1/233* | (2006.01) | |
| *A61B 1/015* | (2006.01) | |
| *A61B 1/018* | (2006.01) | |

(52) U.S. Cl.
CPC ............ *A61B 1/2673* (2013.01); *A61B 1/303* (2013.01); *A61M 16/0409* (2014.02); *A61M 16/0434* (2013.01); *A61M 16/0456* (2014.02); *A61M 16/0463* (2013.01); *A61M 16/0465* (2013.01); *A61M 16/0488* (2013.01); *A61M 16/0666* (2013.01); *A61B 1/00078* (2013.01); *A61B 1/015* (2013.01); *A61B 1/018* (2013.01); *A61M 16/0497* (2013.01)

(56) References Cited

U.S. PATENT DOCUMENTS

| | | |
|---|---|---|
| 4,577,638 A | 3/1986 | Graham |
| 4,584,998 A | 4/1986 | McGrail |
| 4,607,643 A | 8/1986 | Bell et al. |
| 4,846,153 A | 7/1989 | Berci |
| 5,052,386 A | 1/1991 | Fischer, Jr. |
| 5,025,778 A | 6/1991 | Silverstein et al. |
| 5,174,283 A | 12/1992 | Parker |
| 5,193,692 A | 3/1993 | Farley et al. |
| 5,241,956 A | 9/1993 | Brain |
| 5,353,787 A | 10/1994 | Price |
| 5,372,131 A | 12/1994 | Heinen, Jr. |
| 5,400,771 A | 3/1995 | Pirak et al. |
| 5,499,625 A | 3/1996 | Frass et al. |
| 5,511,915 A | 4/1996 | Farley et al. |
| 5,511,916 A | 4/1996 | Farley et al. |
| 5,513,627 A | 5/1996 | Flam |
| 5,515,844 A | 5/1996 | Christopher |
| 5,551,947 A | 9/1996 | Kaali |
| 5,632,271 A | 5/1997 | Brain |
| 5,665,052 A | 9/1997 | Bullard |
| 5,682,880 A | 11/1997 | Brain |
| 5,733,242 A | 3/1998 | Rayburn et al. |
| 5,740,791 A | 4/1998 | Aves |
| 5,819,733 A | 10/1998 | Bertram |
| 5,879,306 A | 3/1999 | Fontenot et al. |
| 5,888,195 A | 3/1999 | Schneider |
| 6,038,629 A | 3/2000 | Ogilvie et al. |
| 6,115,523 A | 9/2000 | Choi et al. |
| 6,142,144 A | 11/2000 | Pacey |
| 6,189,533 B1 | 2/2001 | Simon et al. |
| 6,196,225 B1 | 3/2001 | Allgeyer |
| 6,349,720 B1 | 2/2002 | Clark |
| 6,386,199 B1 | 5/2002 | Alfery |
| 6,439,232 B1 | 8/2002 | Brain |
| 6,440,061 B1 | 8/2002 | Wenner et al. |
| 6,443,156 B1 | 9/2002 | Niklason et al. |
| 6,527,704 B1 | 3/2003 | Chang et al. |
| 6,543,447 B2 | 4/2003 | Pacey |
| 6,626,169 B2 | 9/2003 | Gaitini |
| 6,631,720 B1 | 10/2003 | Brain |
| 6,634,354 B2 | 10/2003 | Christopher |
| 6,655,377 B2 | 12/2003 | Pacey |
| 6,860,264 B2 | 3/2005 | Christopher |
| 6,860,270 B2 | 3/2005 | Sniadach |
| 6,918,391 B1 | 7/2005 | Moore |
| 6,929,600 B2 * | 8/2005 | Hill ............... A61B 1/00052 600/120 |
| 7,052,456 B2 | 5/2006 | Simon |
| 7,128,509 B2 | 10/2006 | Farley et al. |
| 7,156,091 B2 | 1/2007 | Koyama et al. |
| 7,237,993 B2 | 7/2007 | Farley et al. |
| 7,331,925 B2 | 2/2008 | McMorrow et al. |
| 7,421,877 B2 | 9/2008 | Frenken |
| 7,450,746 B2 | 11/2008 | Yang et al. |
| 7,520,857 B2 | 4/2009 | Chalana et al. |
| 7,527,601 B2 | 5/2009 | Dubey et al. |
| 7,611,466 B2 | 11/2009 | Chalana et al. |
| 7,654,970 B2 | 2/2010 | Dubey |
| 7,713,189 B2 | 5/2010 | Hanke |
| 7,713,216 B2 | 5/2010 | Dubey et al. |
| 7,727,150 B2 | 6/2010 | Chalana et al. |
| 7,744,534 B2 | 6/2010 | Chalana et al. |
| 7,749,165 B2 | 7/2010 | McMorrow et al. |
| 7,749,176 B2 | 7/2010 | Dubey |
| 7,811,239 B2 | 10/2010 | Dubey et al. |
| 7,819,806 B2 | 10/2010 | Yang et al. |
| 7,854,324 B2 | 12/2010 | Farley et al. |
| 7,896,007 B2 | 3/2011 | Brain |
| 7,921,847 B2 | 4/2011 | Totz |
| 7,942,813 B2 | 5/2011 | Mackin |
| 7,976,458 B2 | 7/2011 | Stefanchik et al. |
| 8,016,760 B2 | 9/2011 | Chalana et al. |
| 8,038,629 B2 | 10/2011 | Solanki et al. |
| 8,202,215 B2 | 6/2012 | Xiao et al. |
| 8,215,307 B2 | 7/2012 | Nasir |
| 8,297,275 B2 | 10/2012 | Ogilvie et al. |
| 8,308,644 B2 | 11/2012 | McMorrow et al. |
| 8,371,303 B2 | 2/2013 | Schaner et al. |
| 8,529,442 B2 | 9/2013 | Pacey et al. |
| 8,663,099 B2 * | 3/2014 | Tydlaska ............ A61B 1/00105 600/186 |
| 8,677,990 B2 | 3/2014 | Gabriel |
| 8,863,746 B2 | 10/2014 | Totz |
| 8,928,746 B1 | 1/2015 | Stevrin et al. |
| 9,211,060 B2 | 12/2015 | Waldron et al. |
| 9,415,179 B2 | 8/2016 | Molnar |
| 9,427,142 B2 | 8/2016 | Terliuc |
| 9,545,249 B2 * | 1/2017 | Cole .................. A61B 1/00078 |
| 9,579,012 B2 | 2/2017 | Vazales et al. |
| 9,833,587 B2 | 12/2017 | Cook |
| 10,286,231 B2 * | 5/2019 | Pederson .................. A61N 7/02 |
| 10,772,693 B2 * | 9/2020 | Kernbaum ............. A61B 34/30 |
| 2002/0108610 A1 | 8/2002 | Christopher |
| 2002/0195103 A1 | 12/2002 | O'Mara |
| 2003/0220542 A1 | 11/2003 | Belson et al. |
| 2005/0182297 A1 | 8/2005 | Gravenstein et al. |
| 2005/0228226 A1 | 10/2005 | Muckner |
| 2005/0244801 A1 | 11/2005 | DeSalvo |
| 2005/0268917 A1 | 12/2005 | Boedeker et al. |
| 2006/0004260 A1 | 1/2006 | Boedeker et al. |
| 2006/0032505 A1 | 2/2006 | Alfery et al. |
| 2006/0111633 A1 | 5/2006 | McMorrow et al. |
| 2006/0149129 A1 | 7/2006 | Watts et al. |
| 2006/0162730 A1 | 7/2006 | Glassenberg et al. |
| 2006/0180155 A1 | 8/2006 | Glassenberg et al. |
| 2006/0276694 A1 | 12/2006 | Acha Gandarias |
| 2007/0095351 A1 | 5/2007 | Globel |
| 2007/0137651 A1 | 6/2007 | Glassenberg et al. |
| 2007/0156068 A1 | 7/2007 | Dubey |
| 2007/0175482 A1 * | 8/2007 | Kimmel ................ A61B 1/018 128/207.14 |
| 2007/0180887 A1 | 8/2007 | Frenken |
| 2007/0203393 A1 | 8/2007 | Stefanchik |
| 2007/0239197 A1 | 10/2007 | Dubey |
| 2007/0255185 A1 | 11/2007 | Dubey |
| 2008/0029100 A1 | 2/2008 | Glassenberg et al. |
| 2008/0114268 A1 | 5/2008 | Dubey |
| 2008/0115783 A1 | 5/2008 | Brain |
| 2008/0146879 A1 | 6/2008 | Pacey |
| 2008/0188774 A1 | 8/2008 | Dubey |
| 2008/0276932 A1 | 11/2008 | Bassoul |
| 2009/0090356 A1 | 4/2009 | Cook |
| 2009/0194102 A1 | 8/2009 | Chen et al. |

(56) References Cited

U.S. PATENT DOCUMENTS

| | | |
|---|---|---|
| 2009/0194114 A1 | 8/2009 | Chen et al. |
| 2009/0227835 A1 | 9/2009 | Terliuc |
| 2009/0264708 A1 | 10/2009 | Pacey et al. |
| 2009/0287050 A1* | 11/2009 | Barthel ............ A61M 25/1002 600/115 |
| 2010/0051024 A1 | 3/2010 | Abrons |
| 2010/0113916 A1 | 5/2010 | Kumar |
| 2010/0147309 A1 | 6/2010 | Cuevas et al. |
| 2010/0180737 A1* | 7/2010 | Klepper ............ A61M 16/0486 83/39 |
| 2010/0204546 A1 | 8/2010 | Hassidov et al. |
| 2010/0249639 A1 | 9/2010 | Bhatt |
| 2010/0261967 A1 | 10/2010 | Pacey et al. |
| 2010/0312069 A1 | 12/2010 | Sutherland et al. |
| 2011/0030694 A1 | 2/2011 | Schaner et al. |
| 2011/0130632 A1 | 6/2011 | McGrail et al. |
| 2011/0137127 A1 | 6/2011 | Schwartz et al. |
| 2011/0178372 A1* | 7/2011 | Pacey ................ A61B 1/00142 600/188 |
| 2011/0201882 A1 | 8/2011 | Schwartz et al. |
| 2011/0315147 A1* | 12/2011 | Wood .................. A61M 16/042 128/207.15 |
| 2012/0059223 A1* | 3/2012 | McGrath ................ A61B 1/267 600/185 |
| 2012/0259173 A1* | 10/2012 | Waldron ............ A61M 16/0479 600/109 |
| 2012/0260921 A1 | 10/2012 | Sangwan |
| 2012/0302833 A1 | 11/2012 | Hayman et al. |
| 2013/0006051 A1 | 1/2013 | Stace et al. |
| 2013/0030249 A1 | 1/2013 | Vazales et al. |
| 2013/0085497 A1* | 4/2013 | Chang .................... A61B 17/32 606/45 |
| 2013/0096379 A1 | 4/2013 | Goldberg |
| 2013/0109918 A1 | 5/2013 | Pagan |
| 2013/0158351 A1 | 6/2013 | Daher et al. |
| 2013/0197303 A1 | 8/2013 | Chun |
| 2013/0253368 A1 | 9/2013 | Are et al. |
| 2013/0324798 A1 | 12/2013 | Molnar et al. |
| 2014/0018626 A1 | 1/2014 | Lee |
| 2014/0073853 A1 | 3/2014 | Swisher et al. |
| 2014/0076309 A1 | 3/2014 | Takeda et al. |
| 2014/0096766 A1 | 4/2014 | Avitsian et al. |
| 2014/0166020 A1 | 6/2014 | Chang |
| 2014/0194694 A1 | 6/2014 | Chen |
| 2014/0323806 A1 | 10/2014 | Brain |
| 2014/0357951 A1 | 12/2014 | Muller et al. |
| 2015/0122251 A1 | 5/2015 | Azhir et al. |
| 2015/0367094 A1* | 12/2015 | Hingley .................. B29C 65/64 600/112 |
| 2016/0038008 A1 | 2/2016 | Molnar |
| 2016/0038014 A1 | 2/2016 | Molnar |
| 2016/0114117 A1* | 4/2016 | Cook ...................... A61B 1/051 600/109 |
| 2016/0279365 A1* | 9/2016 | Esnouf .............. A61M 16/0488 |
| 2017/0072154 A1 | 3/2017 | Hoftman et al. |
| 2017/0196445 A1* | 7/2017 | Gardner ............ A61M 16/0434 |
| 2017/0209022 A1 | 7/2017 | Molnar |
| 2018/0104427 A1 | 4/2018 | Avitsian et al. |
| 2018/0169365 A1 | 6/2018 | Sawyer et al. |
| 2019/0059710 A1 | 2/2019 | Molnar |

FOREIGN PATENT DOCUMENTS

| | | |
|---|---|---|
| WO | WO9405200 | 3/1994 |
| WO | 03/084719 A2 | 10/2003 |
| WO | 2008123934 A1 | 10/2008 |
| WO | 2009025843 A1 | 2/2009 |
| WO | WO2010120950 | 10/2010 |
| WO | 2012/080293 A2 | 6/2012 |
| WO | 2013/017535 A2 | 2/2013 |
| WO | WO2015013172 A2 | 1/2015 |

OTHER PUBLICATIONS

Bledsoe, "The Disappearing Endotracheal Tube"., Clinical Professor of Emergency Medicine, University of Nevada School of Medicine.

"Incubation Threatened by New Devices and Lack of Paramedic Practice", Patient Care, Jems.com; http://www.jems.com/article/patient-care/incubation-threatened-new-devi.

"Incubation Threatened by New Devices and Lack of Paramedic Practice", Patient Care; http://www.jems.com/article/patient-care/intubation-threatened-new-devi.

"Continuous Airway Control"; Vivasight.

Genzwuerker, MD. et al. "Laryngeal tube: a review of current literature" AJA-Online.com 2011:vol. 12.

Kidali MD, "Capnography in emergency medicine—911" http://www.capnography.com/outside/922.htm.

VivaSight, Airway management for lung isolation, ETVIEW.

ETView Medical, Ltd., Announces Exclusive Patent License Agreement—Feb. 22, 2012. ETVIEW.

ETVIEW, http://www.etview.com/index_old.php.

VivaSight-SL, ETVIEW.

How to Use a Jem Endotracheal Tube Changer.

ETView Medical, Ltd., Announces Exclusive Patent License Agreement—Feb. 2, 2012, http://worldnetdaily.com.uk/markets/news/read/20671060/etview_medical, Jul. 5, 2012.

* cited by examiner

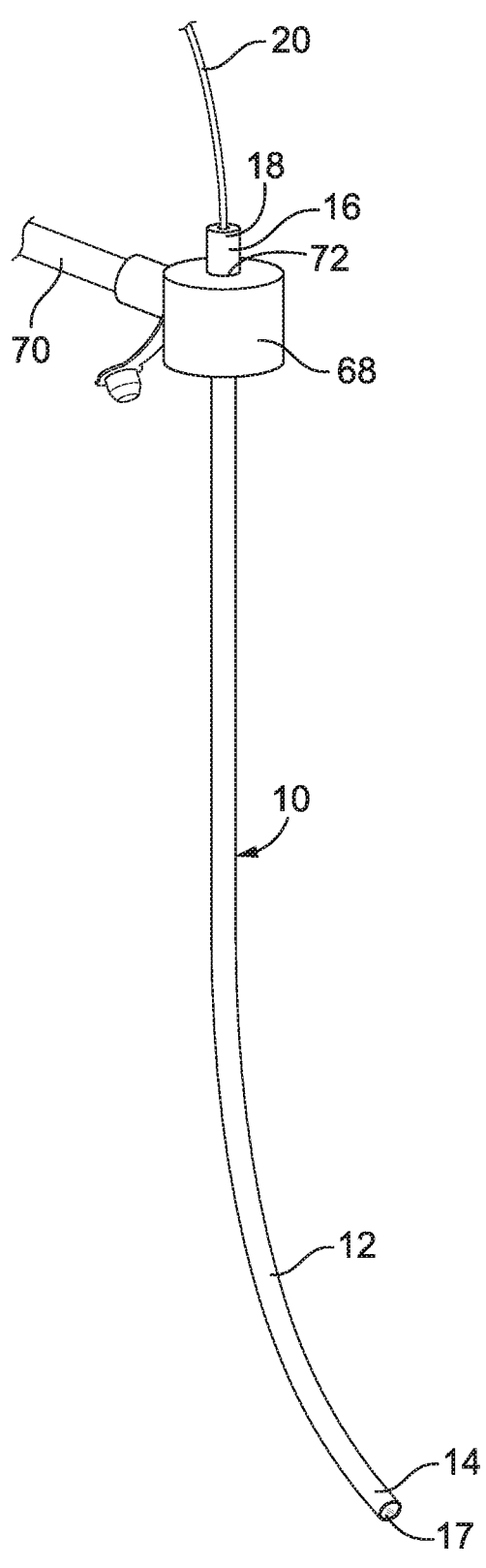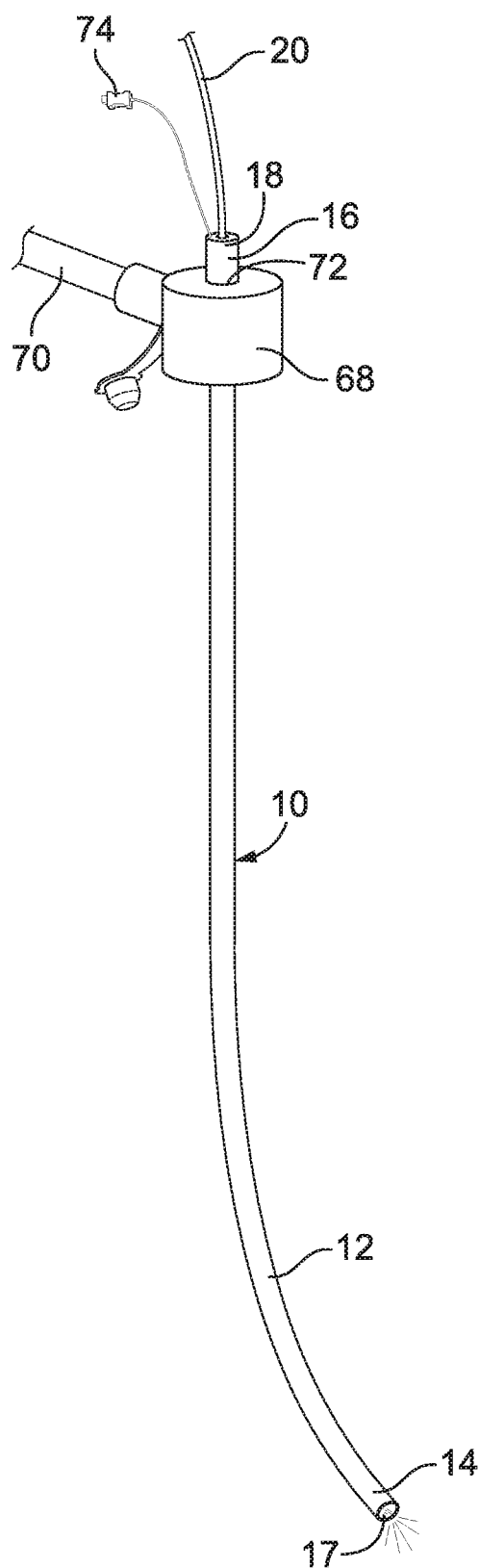
FIG. 4A
FIG. 4B

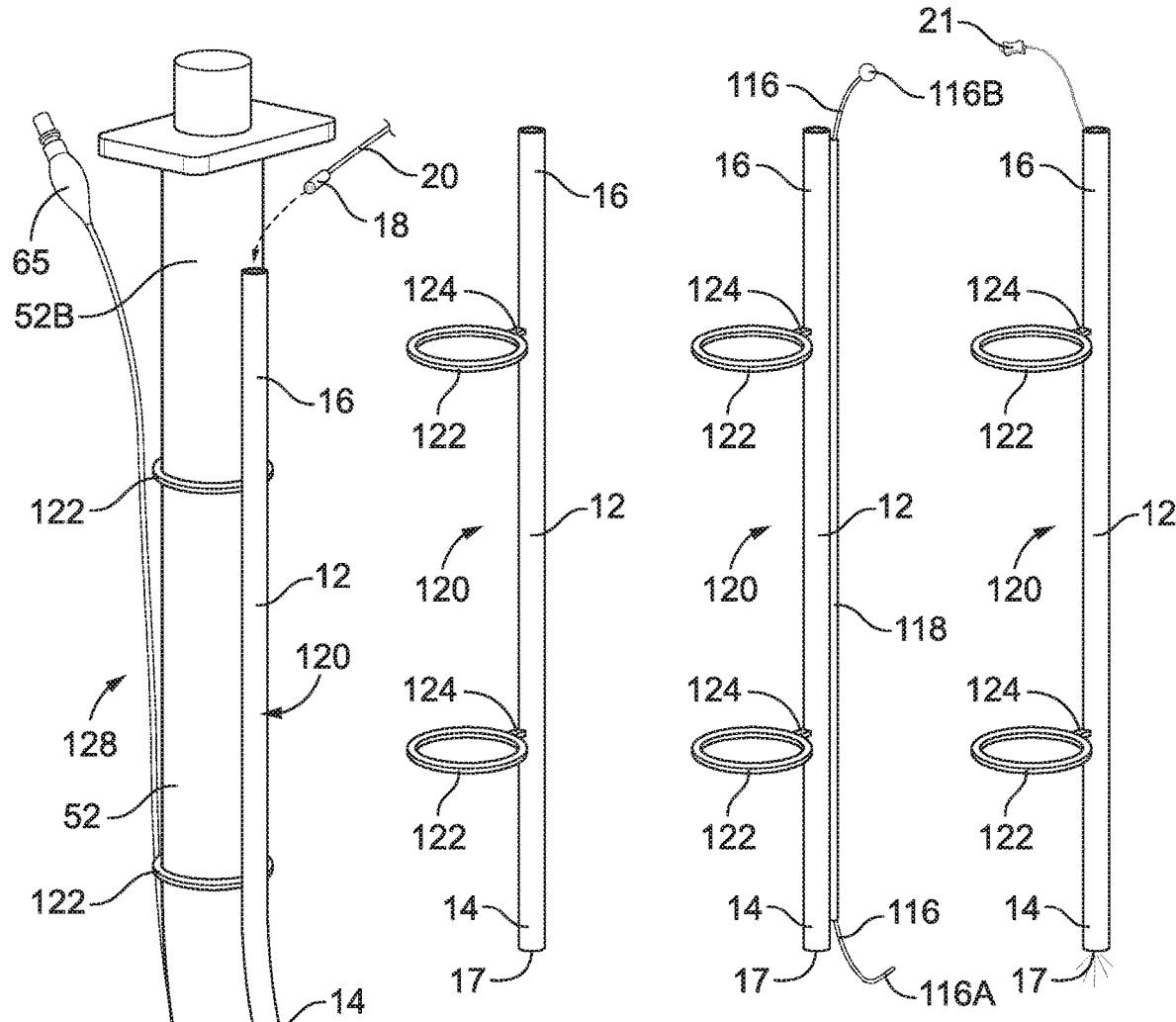
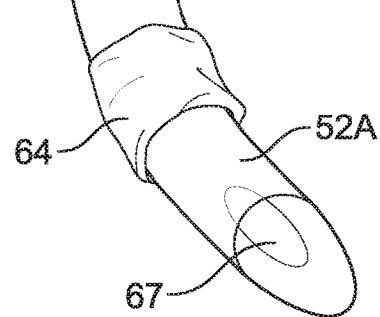
FIG. 9F
FIG. 9A     FIG. 9B     FIG. 9C
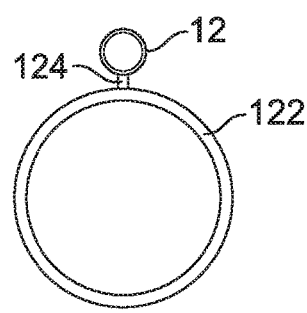
FIG. 9D
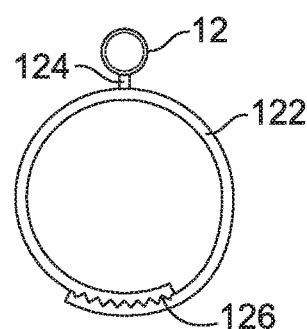
FIG. 9E

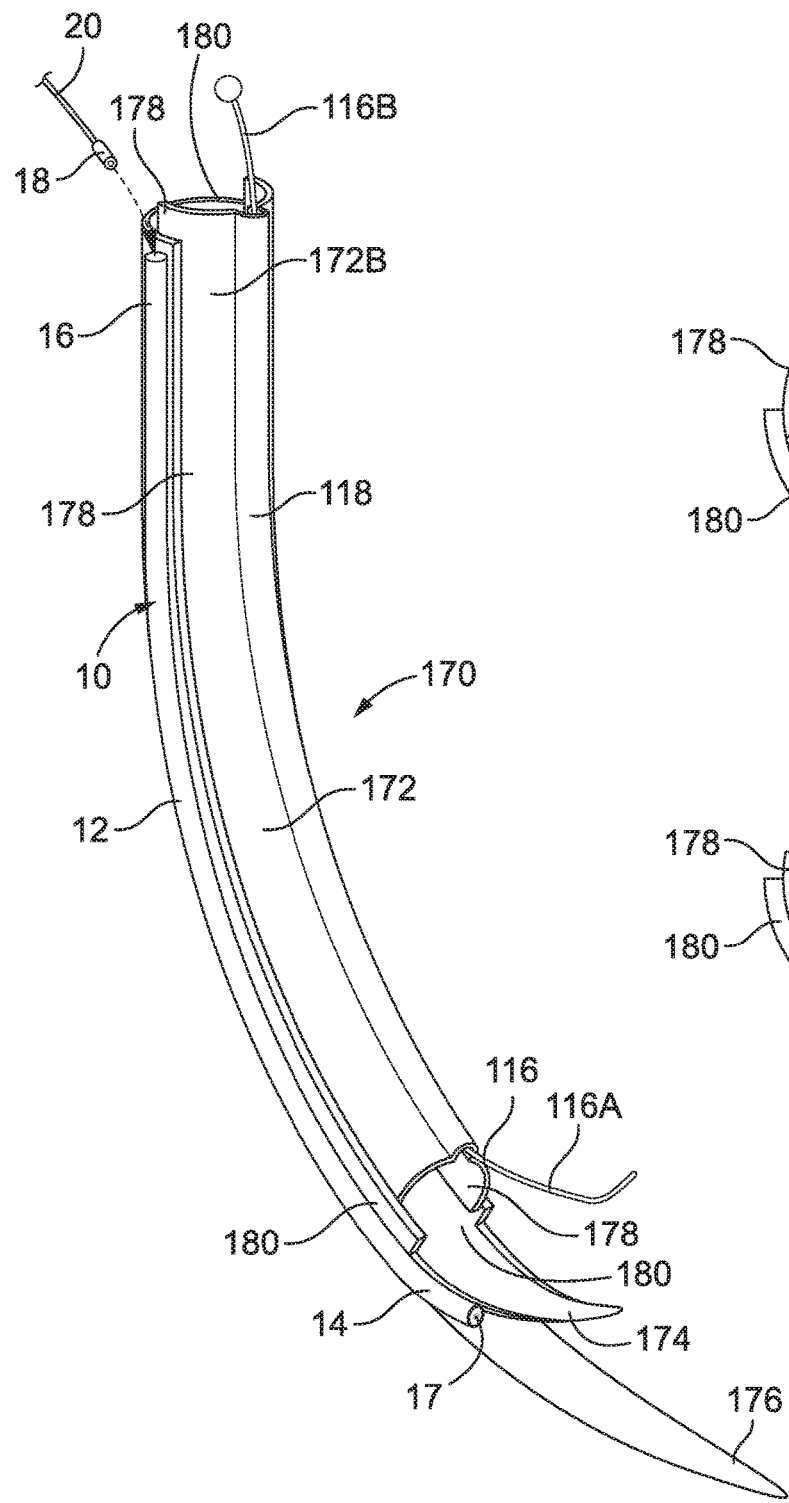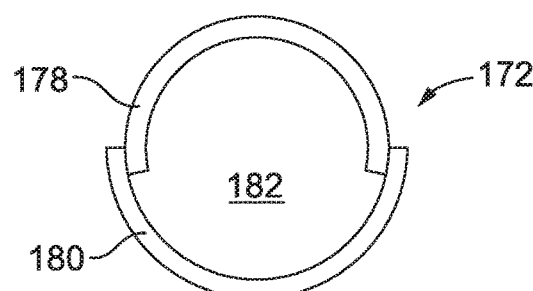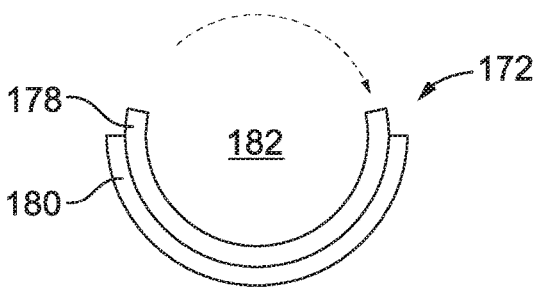
FIG. 12A
FIG. 12B
FIG. 12C

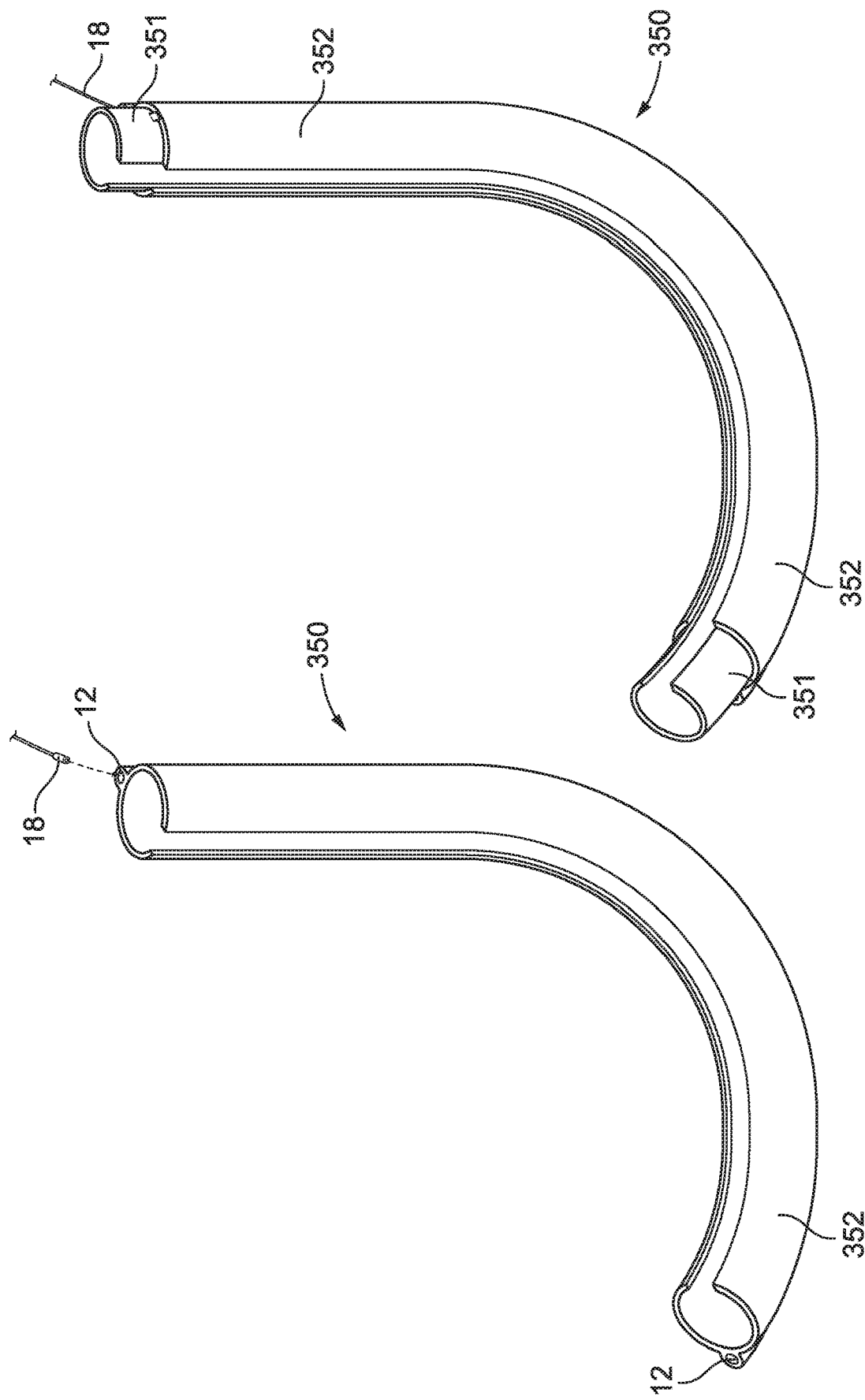

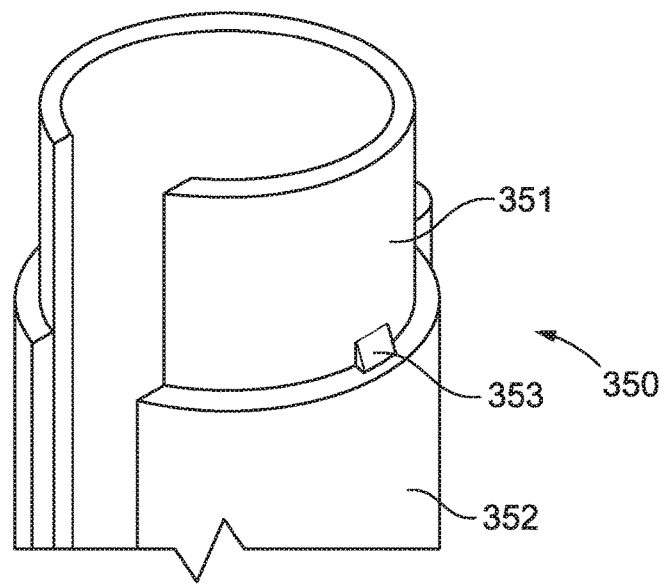
FIG. 16L
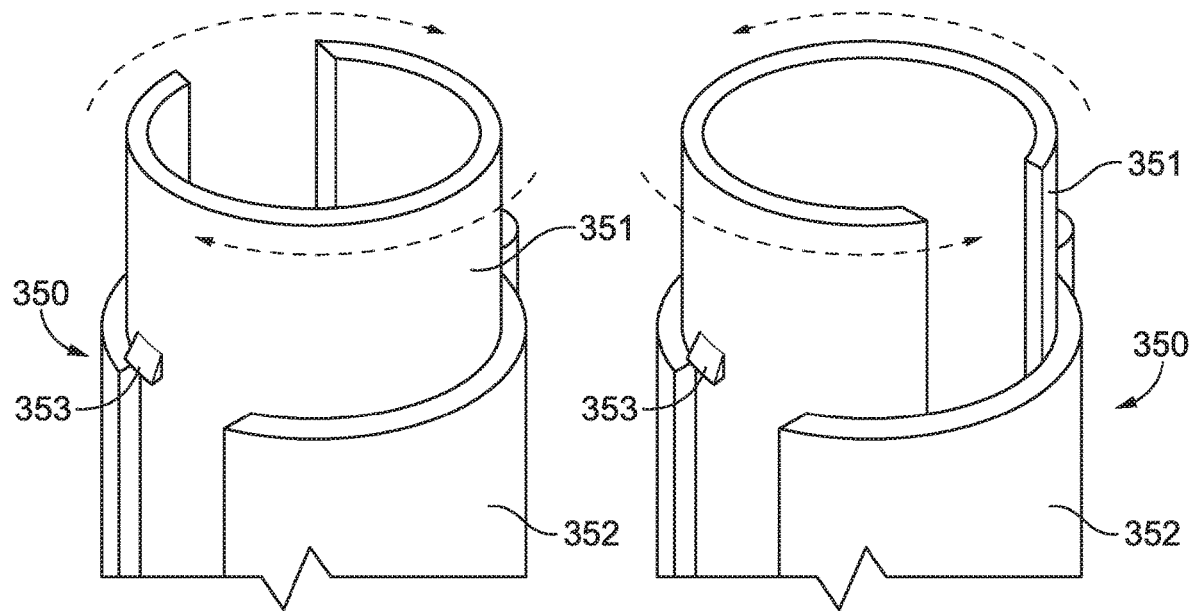
FIG. 16M
FIG. 16N

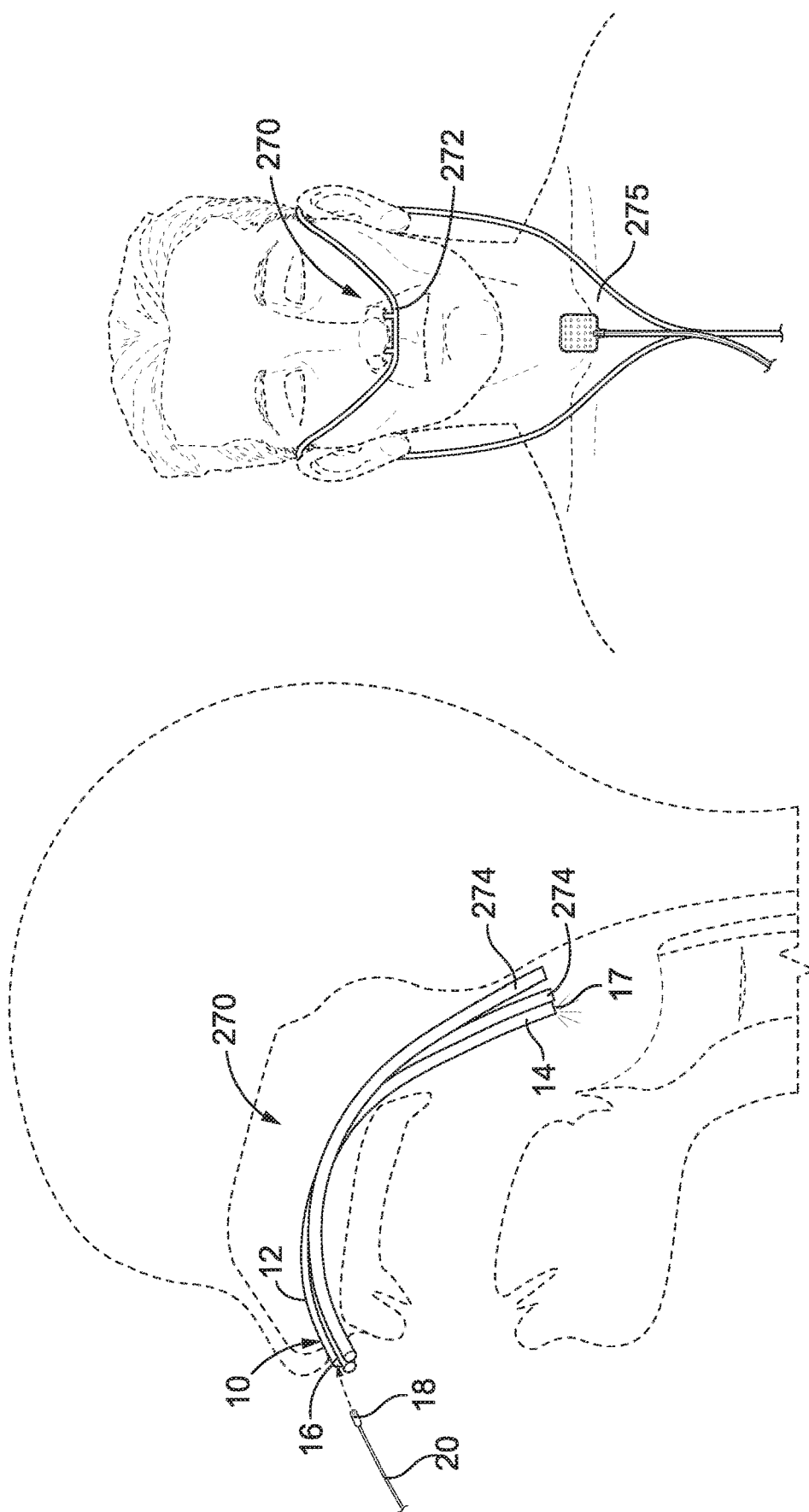

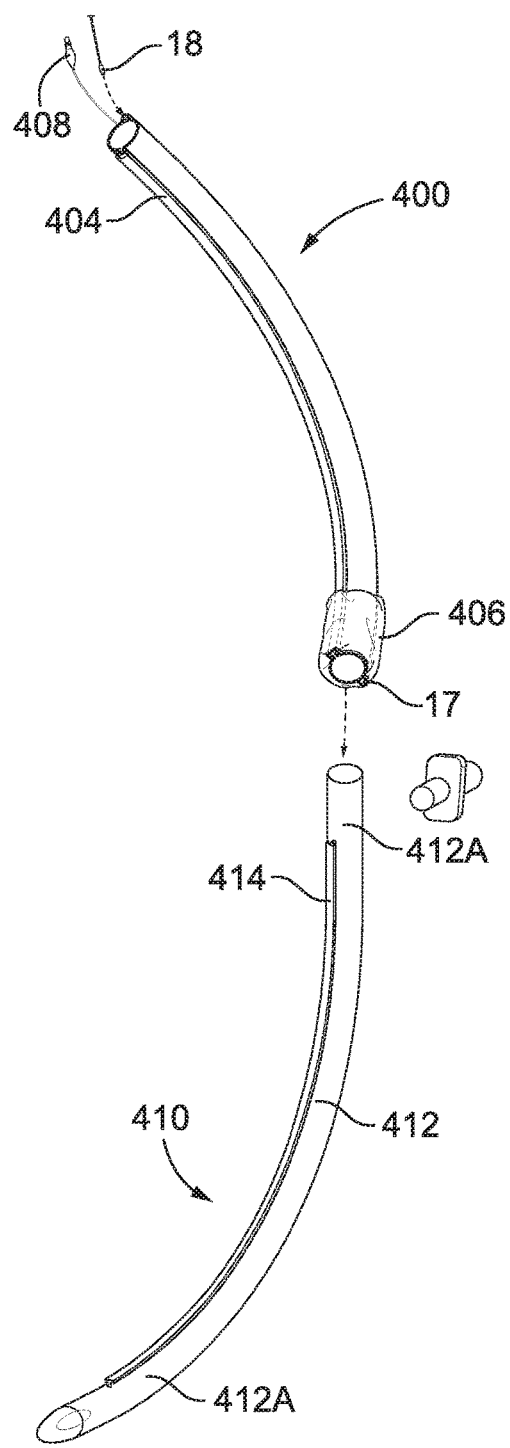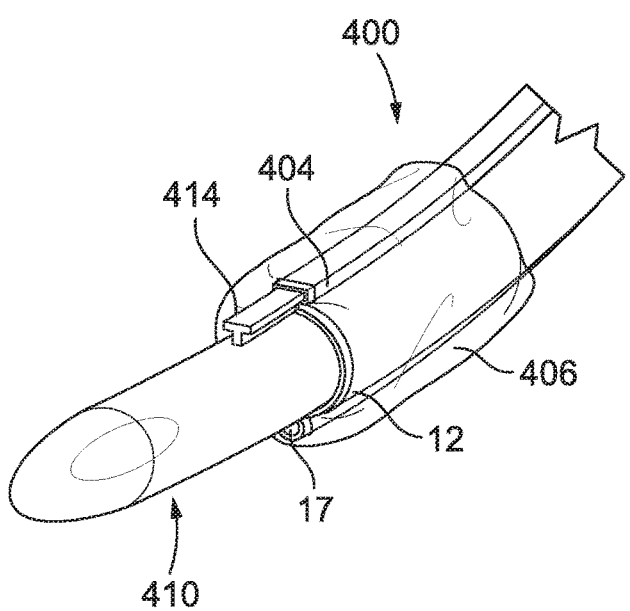
FIG. 27A
FIG. 27B

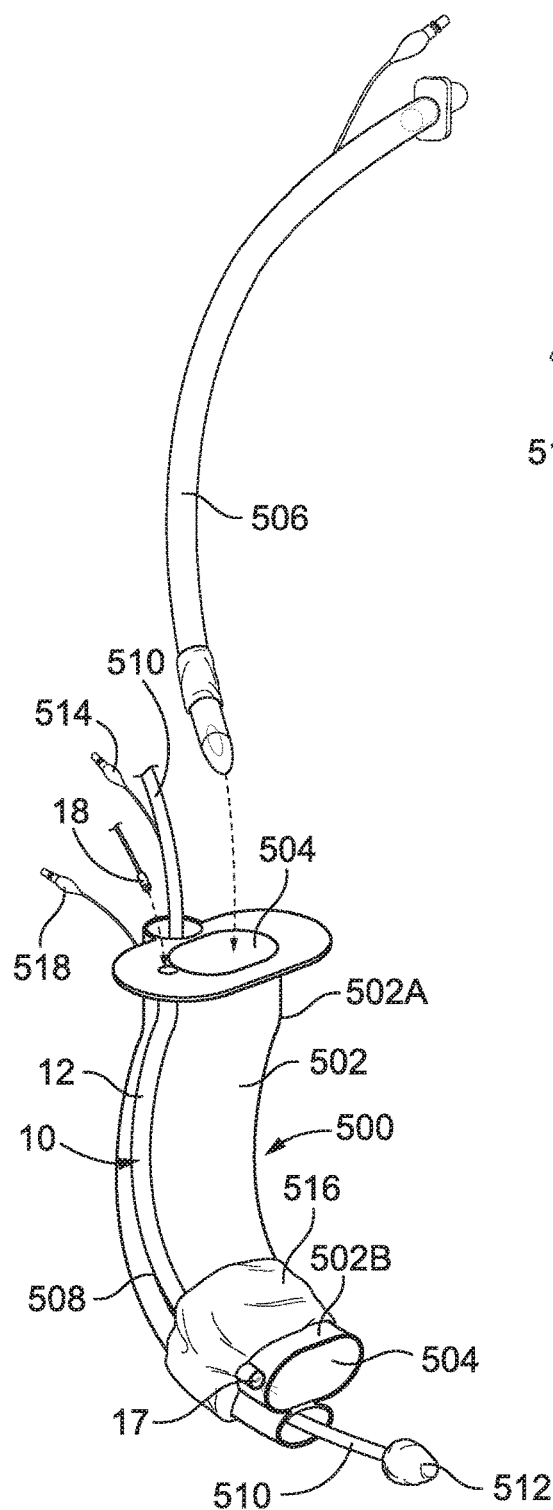
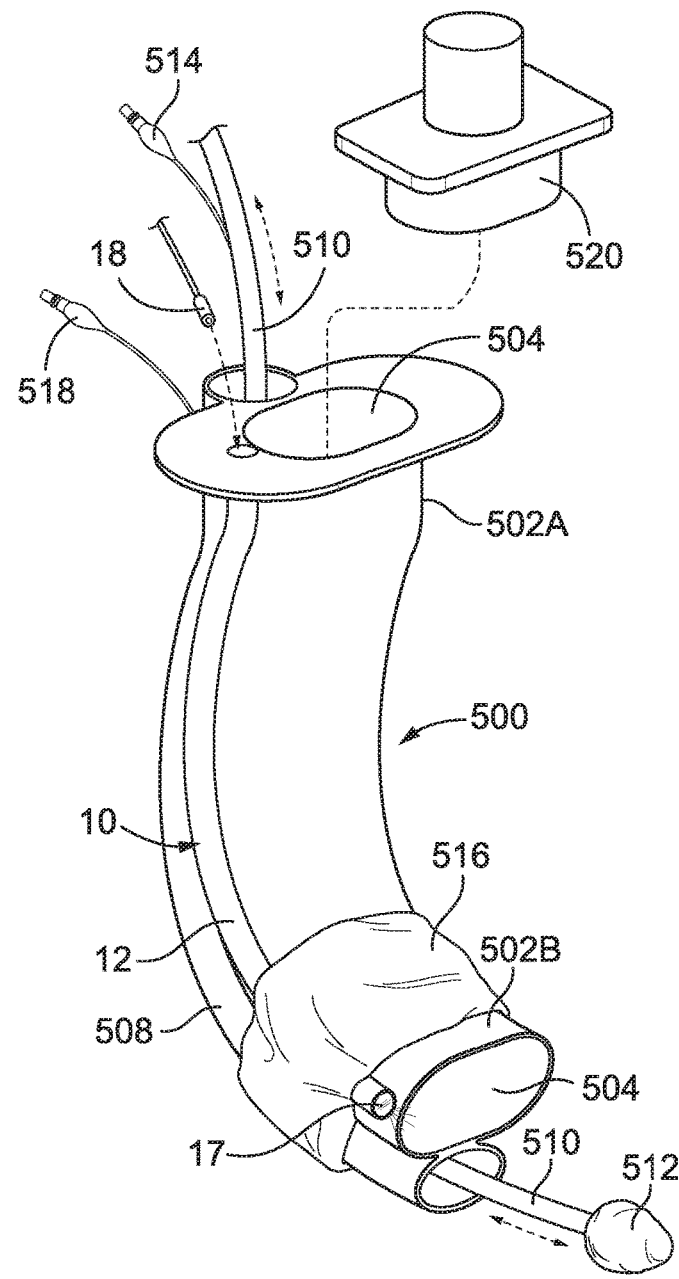
FIG. 34A
FIG. 34B

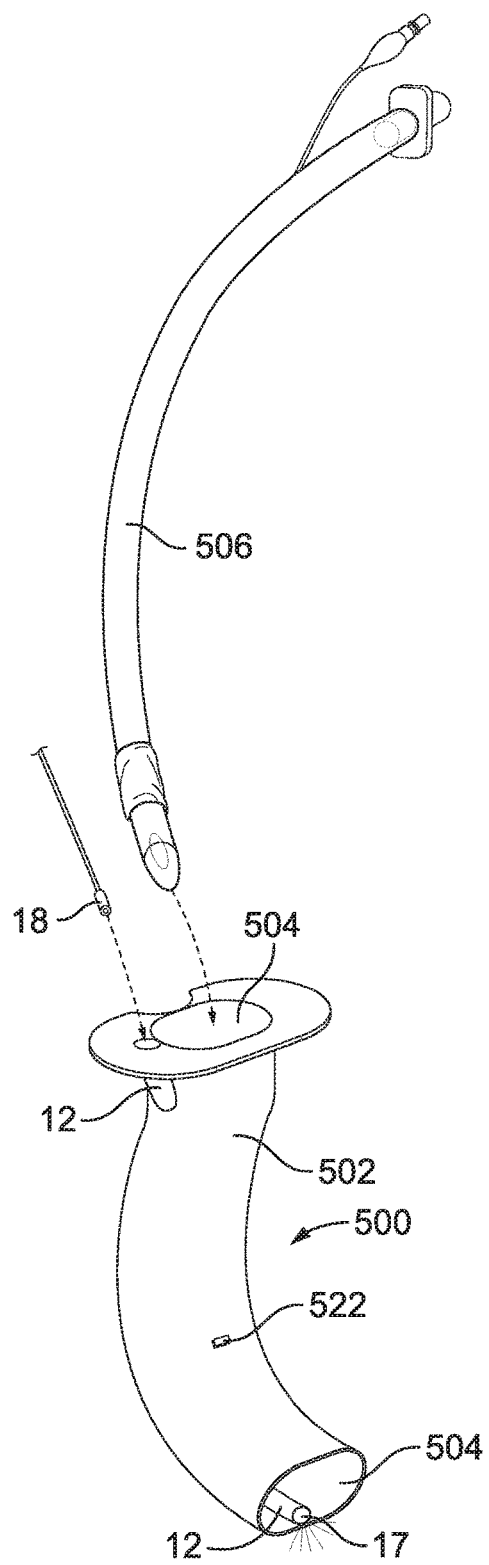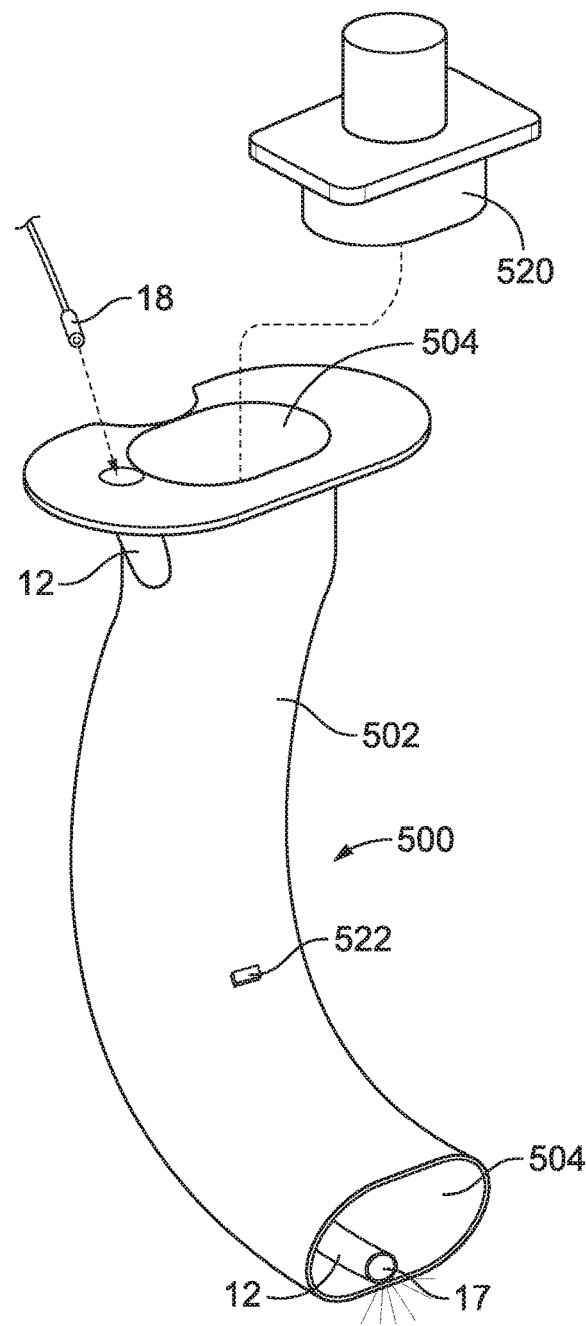
FIG. 34C
FIG. 34D

MEDICAL DEVICES AND METHODS OF PLACEMENT

CROSS-REFERENCE TO RELATED APPLICATIONS

This application is a continuation-in part of U.S. patent application Ser. No. 14/798,751 filed on Jul. 14, 2015, which is a continuation-in-part of U.S. patent application Ser. No. 14/455,470 filed Aug. 8, 2014, the entire disclosures of which are incorporated herein.

FIELD OF THE INVENTION

The invention provides various medical devices, each with a camera placed in a camera tube, which allows for one camera to provide continuous visualization for each device during and after placement in a patient. A sound device, such as a microphone, is incorporated in many devices and provides continuous monitoring of breath and heart sounds in a patient. The camera and microphone do not contact the patient's tissues and thus, do not require sterilization. The continuous visualization and sound monitoring of the patient are in real time and enable remote monitoring as well. Methods for rapid and accurate placement of a medical device in a patient are provided as well.

BACKGROUND

Various devices are available to stabilize a patient and facilitate his breathing, feeding and medication delivery. Such devices are used in patients during surgical procedures, after certain traumas including spinal cord injuries, and in patients suffering from certain medical conditions including advanced Alzheimer disease. These devices include endotracheal tubes, airway devices, feeding tubes, oral airways, nasal cannulas and the like.

Because human anatomy varies significantly from a patient to a patient, properly placing a medical device in a patient's trachea requires a significant skill and is a task laced with inherent risk. The task becomes even more complicated because the insertion procedure may have to be performed immediately at an accident site, on pediatric patients, in a nursing home, on a battlefield or at a natural disaster site where many patients have to be attended at the same time.

The process of placing a breathing tube in a patient is called intubation. Devices such as laryngoscopes, videolaryngoscopes, fiberoptic scopes, as well as other proprietary videoscopes have been developed. These devices provide accuracy for initial placement, but do not provide continuous visualization or mobility of the image after a medical device has been placed in a patient. Newer devices, such as Vivasight SL or DL endotracheal tubes, provide continuous visualization, but are costly because they depend on a single use of disposable cameras and they are not transferrable from one medical device to another. The Totaltrack VLM supraglottic airway has a proprietary reusable camera for only its one device, and it cannot be transferred to other medical devices.

Thus, there remains the need for improved devices which can be easily monitored remotely by a qualified personal during placement and after placement for an adverse reaction. After a medical device has been placed in a patient, the need remains to monitor in real time the patient's possible adverse reactions such as for example, aspiration, airway secretion, apnea, etc.

SUMMARY OF THE INVENTION

At least some of these needs are addressed by present medical devices which are equipped with a portable universal visualization device in which a camera is contained within a separate camera tube and which transmits information that can be accessed and monitored remotely and simultaneously from several patients in real time.

One embodiment provides a medical visualization device which comprises a camera tube with a distal end and a proximal end. The distal end is sealed with a transparent material and a proximal end has an opening. A camera with a wire is placed inside of the camera tube. The camera can be placed inside of the camera tube and it can be retracted from the camera tube on demand. The camera can be reused in various devices without sterilization. The camera can transmit images to a remote location wirelessly. In some embodiments, the camera tube comprises a fiber optic material. The visualization device can be equipped with at least one of the following: a light source, a stylet, a bougie and a sound- and temperature-monitoring device which can transmit the information to a remote location wirelessly. The visualization device can transmit images, sounds and other data to any number of remotely located monitoring devices and/or data storage devices. Such devices include, but are not limited to, a wireless portable device, smart phone, tablet, watch, cell phone, hand-held wireless device, computer, remote data server, radio, television, walkie-talkie and the like.

A further embodiment provides a method of continuous monitoring of a patient's at least one internal organ, the method comprising placing in the patient the visualization device with the camera in the sealed camera tube, causing the camera to transmit images of the internal organ in real time through the transparent material at the distal end of the camera tube, and analyzing the transmitted images. In some embodiments, the images are transmitted wirelessly to at least one remote location.

Various internal organs can be monitored by this method, including nasopharynx, pharynx, hypopharynx, supraglottic structures, airway, trachea, vocal cords, stomach, and vagina.

In some embodiments, the length of the camera tube in the visualization device is adjustable and it can be adjusted to the length of at least one of the following devices: an endotracheal tube, a supraglottic airway, airway device, oral airway, dilator, tracheostomy device, intubating oral airway, esophageal stethoscope, nasal cannula, feeding tube, suction tube and endotracheal changing tube.

Further embodiments provide a method for placing a medical device in a patient in which the medical device is equipped with the visualization device and a bougie. The medical device is inserted in the patient and the placement of the device is guided with the bougie under continuous visualization.

A kit for monitoring a patient's internal organ in real time is also provided. The kit comprises a camera tube with the adjustable length and with at least one ring attached externally to the camera tube, wherein the camera tube has a distal end and a proximal end and wherein the distal end of the camera tube is sealed with a transparent material; and a reusable camera which can be placed and removed from the camera tube and which can transmit images wirelessly to at least one remote location. This real time information obtained with the visualization device can be transferred or stored to multiple distant monitoring sites.

Also provided is a medical device comprising a visualization device sealed to, attached to or otherwise combined with at least one of the following second devices: an endotracheal tube, a supraglottic airway device, a ventilator adaptive cap, a dilator, a tracheostomy device, a nasal trumpet, a an oral airway, an esophageal stethoscope, a laryngoscope, a speculum, a nasal cannula, a feeding tube, a suction tube, a suction catheter, and an endotracheal changing tube; and wherein the visualization device comprises a camera tube with a distal end and proximal end, the distal end being sealed with a transparent material and a camera being placed inside of the camera tube through an opening at the proximal end. These medical devices can be further equipped with at least one of the following a bougie, a flexible stylet and a sound- and temperature-monitoring device. In some embodiments, the visualization device is sealed, attached or otherwise connected externally to the second device. In other embodiments, the visualization device can be placed inside of the second device. Various endotracheal tubes equipped with the visualization device are contemplated as well, including an endotracheal tube which comprises a sleeve through which the visualization device can be inserted, an endotracheal tube into which the visualization device is placed internally through a ventilator adaptive cap and an endotracheal tube to which the visualization device is attached externally.

Further embodiments provide an oral airway device comprising a tubal body with a central lumen and a visualization device attached to the tubal body, wherein the diameter of the lumen is such that an endotracheal tube can be placed insider the lumen and wherein the visualization device comprises a camera tube sealed at the distal end with a transparent material and a camera placed inside the tube through the opening at the proximal end, end wherein the camera tube is positioned along the tubal body. The visualization device can be attached to the tubal body either internally or externally. The oral airway device can further comprise a removable handle which can be connected to the oral airway device with a holder.

Further embodiments provide an oral airway device with a rotating central passageway made of two half-cylinders, a first external half-cylinder and second internal half-cylinder, wherein the second half-cylinder fits inside the first half-cylinder and can glide inside the first half-cylinder along the proximal-distal axis of the first half-cylinder and wherein the second half-cylinder can also rotate inside the first half-cylinder and thereby create a completely enclosed central passageway or only partially enclosed central passageway with a lateral opening, and wherein the first half-cylinder and the second half-cylinder can be completely separated from each other.

Other embodiments provide a supraglottic ventilating tube with camera, comprising a ventilating tube with the distal end and the proximal end and equipped with a visualization device comprising a camera tube attached externally along the ventilating tube, and a camera which can be placed inside the camera tube, wherein an inflatable cuff which wraps around the ventilating tube and the camera tube being positioned under the cuff.

Methods for intubating and extubating a patient are also provided in which an endotracheal tube or ventilating tube is loaded onto the second half-cylinder of the oral airway device which is then assembled with the first half-cylinder of the oral airway device and the assembly is inserted into a patient under continuous visualization and monitoring.

Another embodiment provides a tubeless intubating device, comprising an ellipsoid body attached to a handle and a visualization device attached to the intubating device, wherein the visualization device comprises a camera tube and a camera which can be placed and removed from the camera tube and wherein the ellipsoid body comprises a lumen and canal which opens beneath the handle.

Other embodiments provide a sliding endotracheal cuff device, comprising a tube with the distal end and the proximal end, a rail attached externally on the tube along the proximal-distal axis, wherein the rail has a groove which opens inside the tube, wherein the device further comprises a cuff which wraps around the tube externally at the distal portion of the tube, and wherein the device further comprises a camera tube attached externally to the tube along the proximal-distal axis, and a camera which can be positioned inside and removed from the camera tube.

Further embodiments include an assembly in which an oral airway device is inserted inside of a carrier which comprises a tubal body with a lumen and a first balloon which caps the distal end of the carrier. The carrier has a lumen opening proximal to the first balloon and the carrier has a second balloon circumventing the tubal body of the carrier proximally to the lumen. The carrier may further optionally comprise a third balloon circumventing the body of the carrier proximally to the second balloon. The balloons can be inflated with an inflating means. Methods of intubating and extubating a patient with the carrier assembly are provided as well.

Further embodiments provide an oral airway device comprising a two-part tubal body of adjustable length, with a lumen and open proximal and distal ends, wherein the two-part tubal body is made from an inner cylindrical tube at least partially inserted into an outer cylindrical tube, wherein the device further comprises a bougie and a visualization device comprising a camera tube, and a camera placed in the camera tube, wherein the distal end of the camera tube is sealed with a transparent material which creates a sealed distal transparent window. The inner cylindrical tube can rotate around inside the outer cylindrical tube. In some embodiments, the inner cylindrical tube can be extended out from the outer cylindrical tube at least partially and retracted back into the outer cylindrical tube. In some embodiments, the bougie is incorporated in at least one of the inner cylindrical tube wall and the outer cylindrical tube wall. The bougie can slide proximally and distally, and the bougie can rotate inside the wall. The camera tube in the device may be incorporated in at least one of the inner cylindrical tube wall and the outer cylindrical tube wall. In some embodiments, the camera tube is incorporated in the inner cylindrical tube wall stationary. In other embodiments, the camera tube is incorporated in the inner cylindrical tube wall, and the camera tube can slide distally along the wall and is extendable from the distal end of the inner cylindrical tube. The oral airway device can be assembled together with an endotracheal tube. In further embodiments, the oral airway device can be assembled with a double-lumen device comprising an anterior tube and a posterior tube aligned in the anterior/posterior position, wherein the oral airway device is inserted in the anterior tube, and wherein a cuff is wrapped around the double lumen device. At least one of the following devices can be inserted in the posterior tube: an esophageal blocker or a suction tube. An endotracheal tube can be then further inserted into the oral airway device. The assembly can be used for supraglottic ventilation and occlusion of esophagus.

Further embodiments provide a method of intubating a patient with an oral airway device comprising a two-part tubal body of adjustable length. This method comprises a step of sliding a bougie of the oral airway device distally from the two-part tubal body of the oral airway device; followed by placing the bougie of the oral airway device through the vocal cords of the patient under direct vision from the camera; and then sliding the inner cylindrical tube of the oral airway device over the bougie; and placing the inner cylindrical tube of the oral airway device at one of the two locations: through the vocal cords or just proximal to the vocal cords.

Other embodiments include a kit comprising an outer cylindrical tube, an inner cylindrical tube which can be inserted in the outer cylindrical tube, a visualization device comprising a camera tube, and a camera placed in the camera tube, wherein the distal end of the camera tube is sealed with a transparent material which creates a sealed distal transparent window; and a bougie.

Other embodiments include a visualization device comprising a camera tube, and a camera placed in the camera tube, wherein the distal end of the camera tube is sealed with a transparent material which creates a sealed distal transparent window; a bougie; and a cuff with at least two lumens and at least two passages through the cuff body, a first passage and the second passage; wherein the camera tube is inserted in the first passage and the bougie is inserted in the second passage.

BRIEF DESCRIPTION OF THE DRAWINGS

FIGS. 4A and 4B depict two embodiments showing a visualization device attached to a built-in ventilator adaptive cap. FIG. 4A is an embodiment without a light source and FIG. 4B is an embodiment with a light source.

FIGS. 9A, 9B and 9C are a side view of a visualization device equipped with rings. FIG. 9A is a side view of a visualization device equipped with two rings. FIG. 9B is a side view of the visualization device as shown in FIG. 9A, but equipped further with a bougie. FIG. 9C is a side view of the visualization device as shown in FIG. 9A, but equipped further with a light source. FIG. 9D is a cross-sectional view through the visualization device of FIG. 9A showing a ring connected to the camera tube. FIG. 9E is a cross-sectional view through the visualization device of FIG. 9A showing an adjustable sliding ring with a clasp connected to the camera tube. FIG. 9F is a side view of an endotracheal tube to which the visualization device of FIG. 9A is connected with two sliding rings.

FIG. 11A is a side view of the airway device and FIG. 11B is the device as shown in FIG. 11A, but with a ventilator adaptive cap.

FIGS. 12A, 12B and 12C depict an oral airway intubating device with a visualization device. FIG. 12A is a side view of the oral airway device, while FIGS. 12B and 12C are cross-sections through the airway device in its full cylinder form (FIG. 12B) and in its half-cylinder form in which one half-cylinder is retracted into the other half-cylinder (FIG. 12C).

FIG. 14A depicts an embodiment in which the visualization device is attached externally to a tracheostomy tube, while FIG. 14B depicts an embodiment in which the visualization device is attached inside of the tracheostomy tube.

FIG. 16A shows a visualization device being positioned inside of the oral airway. FIG. 16B is the same as FIG. 16A, but includes a light source for the visualization device. FIG. 16C is the same as FIG. 16A, but includes a whistle. FIG. 16D is an intubating oral airway device with a main lumen into which an endotracheal tube can be placed.

FIGS. 16H, and 16J-16P depict an intubating/extubating oral airway device with a rotating central passageway. FIGS. 16H and 16J depict the capacity of intubating/extubating oral airway device with a rotating central passageway to extend distally. The embodiment of FIGS. 16H and 16J has a camera tube with camera placed externally on the intubating/extubating oral airway, while the embodiment of FIG. 16K provides the intubating/extubating oral airway in which the camera tube is placed inside of the rotating central passageway. FIGS. 16L-16N demonstrate further how the inner half-cylinder can rotate in the intubating/extubating oral airway to create a fully enclosed central passageway. FIGS. 16O-16P depict insertion of an endotracheal tube inside the rotating central passageway of the intubating/extubating oral airway.

FIG. 18A shows a laryngoscope with a visualization device, and FIG. 18B is the same, except it is further equipped with a bougie and the visualization device is equipped with a light source.

FIGS. 20A-F depict a nasal cannula with a visualization device. FIG. 20A depict positioning of the cannula on a patient's head and FIG. 20B is the same as in FIG. 20A, except the visualization device is equipped with a light source. FIG. 20C is a side view of the cannula of FIG. 20A, and FIG. 20D is a side view of the cannula of FIG. 20B. FIG. 20E is a cross-sectional view of a patient's head with the cannula of FIG. 20A inserted. FIG. 20F is a further embodiment in which a nasal cannula with a visualization device as shown in FIG. 20A is further combined with an external stethoscope.

FIG. 22A depicts a visualization device positioned inside of the suction tube. FIG. 22B the same as in 22A, but equipped further with a bougie, and FIG. 22C is the same as FIG. 22B, but showing the bougie protruding from the distal end of the suction tube.

FIG. 25A is a side view of the supraglottic ventilating tube with camera. FIG. 25B is an enlarged view of the supraglottic ventilating tube distal tip with a cuff. FIGS. 25C and 25D depict insertion of the supraglottic ventilating tube into an intubating/extubating oral airway.

FIG. 26A depicts the upper surface of the tubeless intubating device. FIG. 26B depicts the bottom surface of the tubeless intubating device. FIGS. 26C-26F depict loading the tubeless intubating device with an endotracheal tube for insertion into a patient. FIG. 26G depicts the upper surface of the tubeless intubating device without a cuff, while FIG. 26H depicts the bottom surface of the tubeless intubating device of FIG. 26G. FIGS. 26I and 26J depict loading of the device FIG. 26G with a supraglottic airway.

FIGS. 27A-27G depict a sliding endotracheal cuff (FIGS. 27A, 27C-27G) and loading an endotracheal tube into the sliding cuff (FIG. 27B).

FIG. 33A depicts an embodiment with a suction tube, FIG. 33B with a medication dispensing device and FIG. 33C with biopsy forceps.

FIGS. 34A-34H depict various embodiments for an oral airway device. FIG. 34A depicts an embodiment with a separate lumen for an esophageal blocker. An endotracheal tube which can be placed into the oral airway device is also shown. FIG. 34B is the same embodiment as in 34A, but with a ventilator cap instead of an endotracheal tube. FIG. 34C is an oral airway device without a balloon with an endotracheal tube also shown. FIG. 34D is the same embodiment as in 34C, but with a ventilator cap instead of an endotracheal tube. FIGS. 34E-34H depict an expendable oral airway device with a carrier. FIG. 34E shows placement of an oral airway device into a carrier. FIG. 34F is an enlarged view of the carrier from FIG. 34E. FIGS. 34G and 34H depict an oral airway device positioned inside of the carrier, with FIG. 34G showing the oral airway device positioned fully inside the carrier, while FIG. 34H showing the oral airway device expending from the carrier.

FIG. 35A depicts an oral airway device positioned in a patient, while FIG. 35B provides an embodiment of an oral airway device with a side opening.

FIG. 36A is an embodiment with two balloons, while FIG. 36B is an embodiment with three balloons. FIG. 36C shows positioning of the three balloon nasopharyngeal airway device in a patient.

FIG. 37A is a side view of the device, FIGS. 37B and 37C are zoomed in views of a cuff region. In the embodiment of FIG. 37B, the camera tube is sealed and is not mobile. In the embodiment of FIG. 37C, the camera tube can slide to advance or retract distally to the cuff.

FIG. 45A depicts the visualization device straight, while FIG. 45B depicts the visualization device curved.

DETAILED DESCRIPTION

The present invention provides improved medical devices equipped with a visualization device for intubation, ventilation, feeding and monitoring of a patient. The present invention also provides methods for rapid and accurate placement of a medical device in a patient and remote continuous real-time monitoring of the patient after the placement.

These medical devices are equipped with a visualization device in which a camera is placed in a separate sealed camera tube. As the camera does not come in contact with a patient, there is no need to sterilize the camera and the same camera can be reused in many applications. Thus, the same camera can be switched between different medical devices which monitor internal organs such as medical devices that are placed in patient's airway, larynx, gastrointestinal tract, chest or vaginal cavity. In some embodiments, the camera is disposable.

Figure 1A:
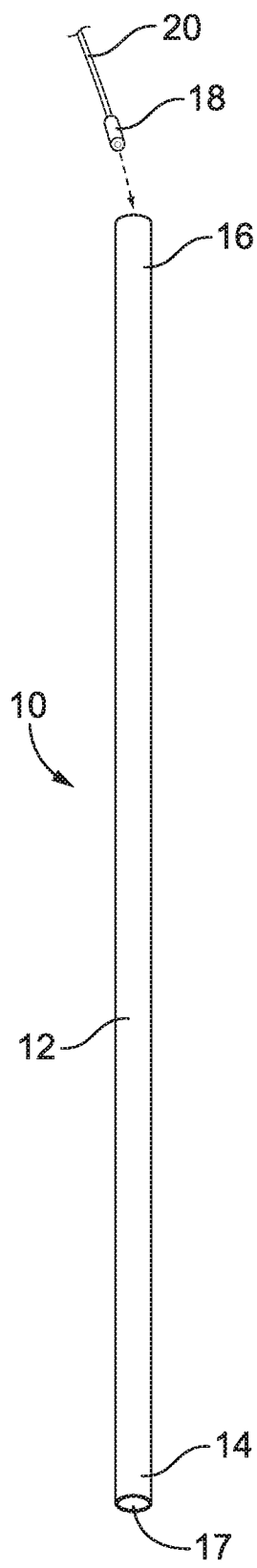
FIGS. 1A, 1B and 1C depict a side view of an embodiment for a visualization device as shown in FIG. 1A which can be further equipped with a stylet as shown in FIGS. 1B and 1C.
Figure 1B:
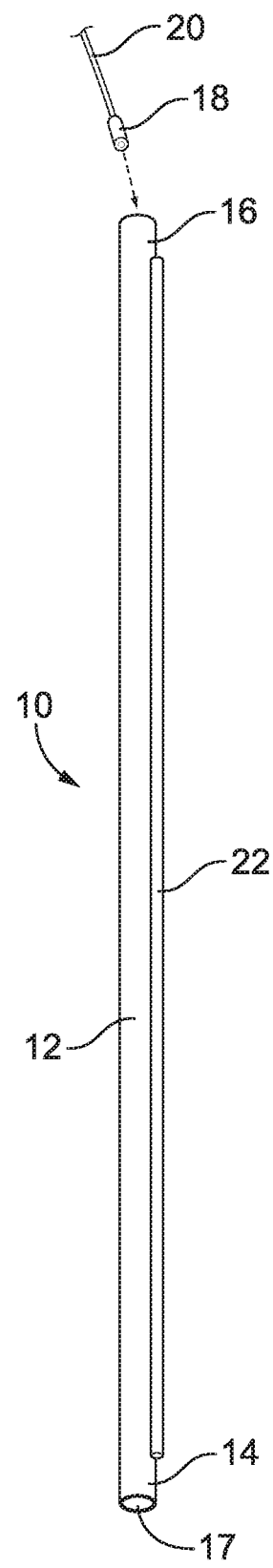
Figure 1C:
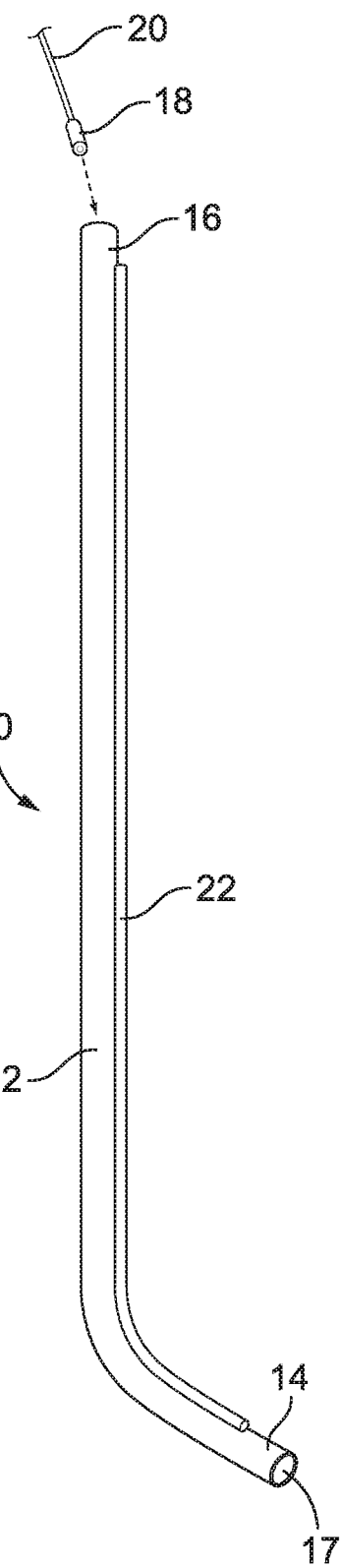

One embodiment provides a visualization device as shown in FIG. 1A and its further embodiments as shown in FIGS. 1B and 1C. A visualization device, generally 10, in FIG. 1A comprises a camera tube 12 with a distal end 14 and a proximal end 16. The camera tube 12 can be a plastic tubing. In some embodiments, the camera tube 12 may comprise a fiber-optic material. The camera tube 12 is sealed at the distal end 14 with a transparent material 17. The diameter of camera tube 12 is designed in such a way that a camera 18 with wire 20 can be inserted inside of the camera tube 12 through an opening at the proximal end 16 and moved down the camera tube 12 toward the distal end 14, so that the camera 18 transmits continuously images obtained through the transparent material 17. The length of the camera tube 12 can vary and it can be adjusted dependent on the length of a medical device with which the visualization device is to be used. For example, the length of the camera tube 12 may be longer when the visualization device 10 is used with a feeding tube in comparison to the length of the camera tube 12 when the visualization device 10 is used with an endotracheal tube. In some embodiments, the visualization device obtains images and transmits wirelessly, broadcasts or records this information to at least one device positioned at a remote location.

Because the camera tube 12 is sealed at the distal end 14 with the transparent material 17, the camera 18 does not come in contact with patient's tissues or fluids and therefore, the camera 18 does not have to be sterilized or to be disposable, and it can be reused in further applications. However, the camera 18 can be disposable in some applications. The camera 18 can be loaded with a chip and equipped to obtain and transmit digital images in real time. The camera 18 is further connected by an electric wire 20 to an image receiving and processing device (not shown) such as a computer equipped with a monitor or a computer network. The camera 18 may also be in communication wirelessly with an image-receiving device located at any location, including multiple locations and remote locations. Because the length and diameter of the camera tube 12 can be adjusted based on patient's needs, the visualization device 10 is suitable for a broad variety of patients, including pediatric patients and adult patients with abnormal anatomy or trauma.

As the visualization device 10 is bendable and flexible, the visualization device 10 is easy to insert in a patient and remove from the patient. The camera 18 may have its own light source. As the visualization device 10 transmits images from a patient in real time, it can be used for guiding a medical device for proper placement. Thus, some embodiments are concerned with methods for rapid and accurate placement of a medical device inside of a patient, including a method for guided and rapid placement into patient's airway, larynx, gastrointestinal tract, chest or vaginal cavity under continuous visualization.

As shown in embodiment of FIG. 1B, the visualization device 10 can be further equipped with a stylet 22 which can be sealed onto or otherwise attached to the camera tube 12 externally on at least one side of the camera tube 12 along the proximal-to-distal (16-14) axis of the camera tube 12. The stylet 22 can be made of metal wire or some other sturdy material with the purpose to keep the otherwise flexible visualization device 10 in a particular shape. In some embodiments, the stylet 22 can be of the same length as the camera tube 12. In other embodiments, the stylet 22 is shorter than the camera tube 12 such that at a least a portion of the camera tube 12 on either the proximal end 16 or distal end 14, or on the both ends 16 and 14 is not in contact with the stylet 22. As shown in FIG. 1C, the stylet 22 can be bent into various shapes and it retains the shape into which it has been bent, which permits for visualization device 10, which is otherwise flexible, to retain a particular shape.

In alternative embodiments, the visualization device 10 can be equipped with a bougie which can be attached to the camera tube 12 externally on at least one side of the camera lumen 12 along the proximal-distal (16-14) axis of the visualization device 10.

The bougie can be made of various materials, including plastic material which is bendable. As the bougie is bendable, but keeps a shape into which it is bent, the bougie is suitable for guiding the visualization device 10 inside of a patient. In some embodiments, the bougie can be of the same length as the camera tube 12. In other embodiments, the bougie can be made shorter or longer than the camera tube 12 such that only a portion of the camera tube 12 is in contact with the bougie. In some embodiments, the bougie protrudes on at least the distal end 14.

The visualization device 10 can be further equipped with a portable light source (not shown) which can be either built-in the camera 18 or it can be built-in the camera tube 12. In alternative, a light source can remain outside the camera tube 12 on the proximal end 16, but still be placed such that the light source sheds light inside of the camera tube 12.

In embodiments of FIGS. 1A-1C, the camera tube 12 can be disposable, while the camera 18 is reusable without the need of sterilization. However, the camera 18 can be also disposable in at least some embodiments.

During placement in a patient, a visualization device 10 either alone or in combination with another medical device is positioned such that it is inserted with its distal end 14 in the patient under continuous visualization with the camera 18.

Any of the visualization devices 10 described above can be attached, sealed or otherwise connected to a disposable or non-disposable medical device either externally or internally and as described in more detail below. Various medical devices for pediatric and adult patients can be built such that the camera device tube 12 is sealed or attached to the medical device during manufacturing. In some embodiments, the visualization device 10 can slide or glide along the medical device to which the visualization device 10 is attached. For example, the camera tube 12 of the visualization device 10 can be equipped with a set of rings, a rail or a half-cylinder which will allow the camera tube 12 to slide or glide along the medical device to which the visualization device 10 is attached.

In other embodiments, the visualization device 10 can be sold as a kit which can be attached by a medical practitioner to a pre-made medical device for pediatric and adult patients, based on a particular patient's individual needs. The length of the camera tube 12 can vary such that the camera tube 12 is of the same or similar length with a medical device to which the visualization device 10 is sealed, attached or otherwise connected to.

Having the ability to verify placement for a medical device in real time from near and far allows several experts to assist and verify placement. This is accomplished by equipping the medical device with the visualization device 10. In some embodiments, a method is provided in which the visualization device 10 is used for placing a medical device in a patient in ambulances, on battlefields, in nursing homes or hospitals. The visualization device 10 provides the ability to monitor in real time a patient. Because the visualization device 10 may interact with a plethora of devices disposable and otherwise, the use of the device 10 on various medical devices provides for a method in which a medical practitioner can customize a proper device for each patient or situation. Having the same camera equipment that can interact with various medical devices provides economy of scale such that even the smallest of organizations can have all the proper vigilance and technology.

At least in some embodiments the visualization device 10 can be used in assembly with at least one medical device as described in more detail below. A method in which the visualization device 10 is used on an airway device allows continuous visualization of any of the following in a patient in real time: nasopharynx, pharynx/hypo pharynx, supraglottic structures, airway, internal organ anatomy, vocal cords during normal and abnormal ventilation. This method also allows detection of abnormal anatomy and abnormal vocal cord movements.

Figure 2:
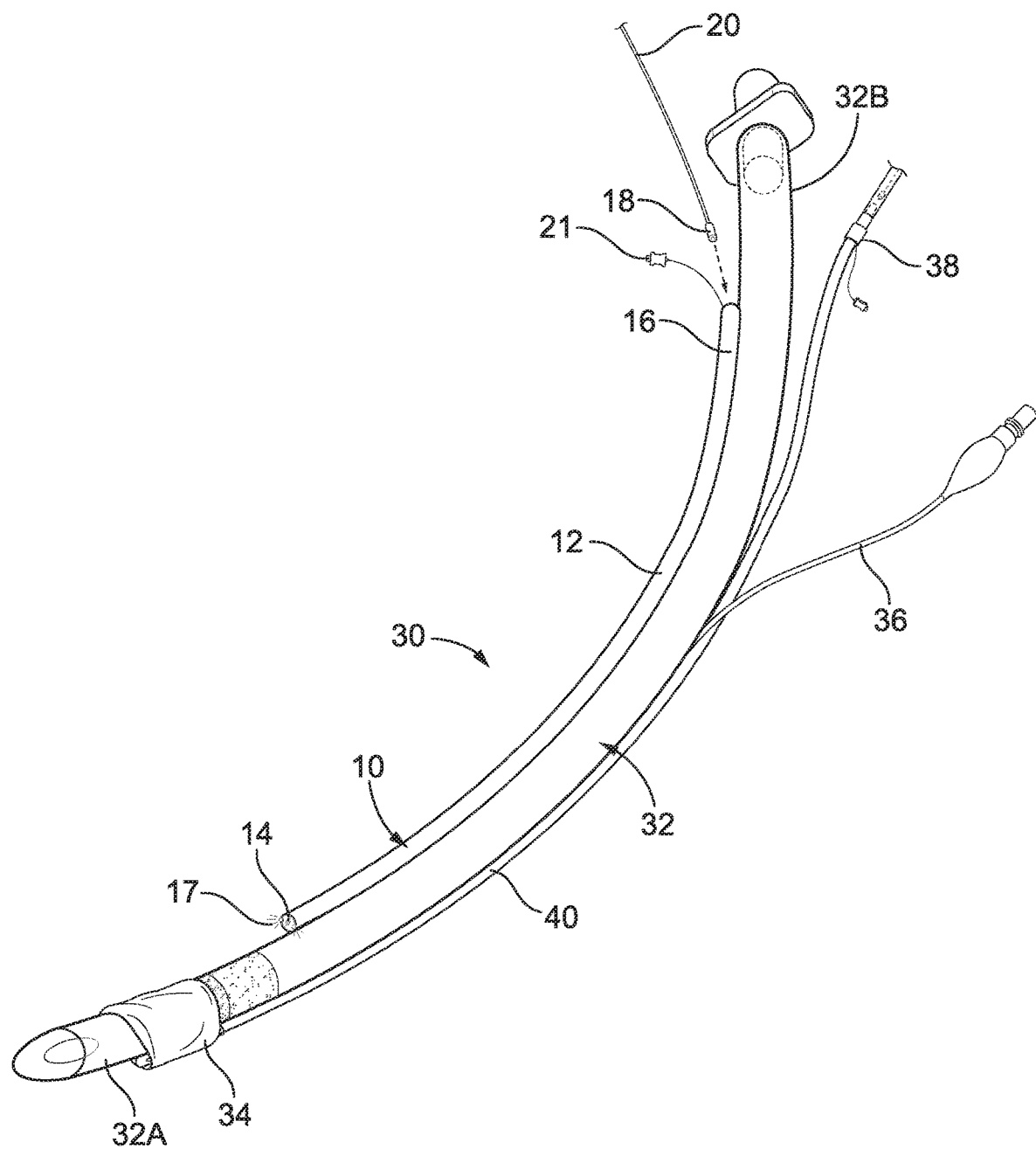
FIG. 2 depicts a side view of an embodiment for an endotracheal device equipped with a visualization device.

Referring to FIG. 2, this embodiment provides an endotracheal device, generally 30. The endotracheal device 30 comprises an endotracheal tube 32 with a distal end 32A and a proximal end 32B. The visualization device 10 is sealed or otherwise attached externally on at least one side of the endotracheal tube 32, along the proximal-distal (32B-32A) axis of the endotracheal tube 32. The visualization device 10 comprises essentially of all elements as shown in FIG. 1A, with the camera 18 inserted inside of the camera tube 12 through an opening at the proximal end 16 of the camera tube 12, all the way down to the distal end 14 and the opening of the distal end 14 being sealed with the transparent material 17. Because the camera 18 is positioned inside of the sealed camera tube 12, the camera 18 does not come into contact with a patient and the camera 18 does not need to be sterilized and can be reused in multiple applications. Thus, the camera 12 does not have to be disposable or to be sterilized before further applications. However, the camera 18 can be disposable in at least some applications.

As the camera 18 is contained inside of the separate camera tube 12 which is positioned externally on the endotracheal tube 32, a diameter of the camera tube 12 is not limited by a diameter of the endotracheal tube 32. Thus, the diameter of the camera tube 12 can be larger or smaller than the diameter of the endotracheal tube 32.

Thus, the visualization device 10 can be used on endotracheal devices for pediatric patients and patients with abnormal anatomy. In some embodiments, the visualization device 10 has a diameter larger than that of the endotracheal tube 32.

The camera 18 is connected by electric wire 20 to an external device such as a computer and monitor (not shown). At least in some embodiments, the visualization device 10 is further equipped with a light source 21. The light source 21 can be kept outside of the camera tube 12, but in proximity with the proximal end 16 of the visualization tube 12 so that the light source 21 sheds light inside of the camera tube 12. In alternative embodiments, the light source 21 can be built-in the camera tube 12 or in further embodiments, the light source 21 can be built-in the camera 18.

At least in some applications, the camera 18 is a digital camera equipped with a chip and it collects and transmits images continuously. The camera 18 can be connected wirelessly or hard-wired with a computer network (not shown) which collects and analyzes images obtained by the camera 18. This arrangement permits for remote, continuous and real time monitoring of the endotracheal device 30 during placement and after-placement in a patient. Thus, an accurate and rapid placement of the endotracheal device 30 can be achieved. Further and because the visualization device 10 continues to acquire images after the endotracheal device 30 is placed inside of a patient, the patient can be monitored in real time for adverse reactions such as bleeding, airway obstruction, shifting or malfunctioning, etc. of the endotracheal device 30 and other reactions. The endotracheal device 30 may continue to transmit images and information for as long as it remains in a patient.

In some embodiments, the endotracheal tube 32 is further fitted with a cuff 34 at its distal end 32A. In other embodiments, the endotracheal tube 32 is not fitted with the cuff 34. The cuff 34 can be inflated with a device 36 after the endotracheal device 30 is placed in a patient and its proper positioning inside of the patient is verified by images obtained with the visualization device 10.

The endotracheal device 30 can be further equipped with a sound-monitoring device 38 which is sealed onto or otherwise attached externally on one side of the endotracheal tube 32 along the proximal-distal axis (32B-32A) of the endotracheal tube 32. The sound-monitoring device 38 can be a microphone placed inside of a plastic tube 40. It monitors heart beats and breathing tones and can be connected by wire or wirelessly to a remote device which collects and monitors patient's vital signals. In the embodiment of FIG. 2, the visualization device 10 is placed proximally to the cuff 34 and externally to the endotracheal tube 32. It will be understood that the endotracheal device 30 can be built with any endotracheal tube 32, including single-lumen and double-lumen tubes. The endotracheal device 30 can be used for either pediatric or adult patients. The endotracheal device 30 can be made in various sizes.

Figure 3:
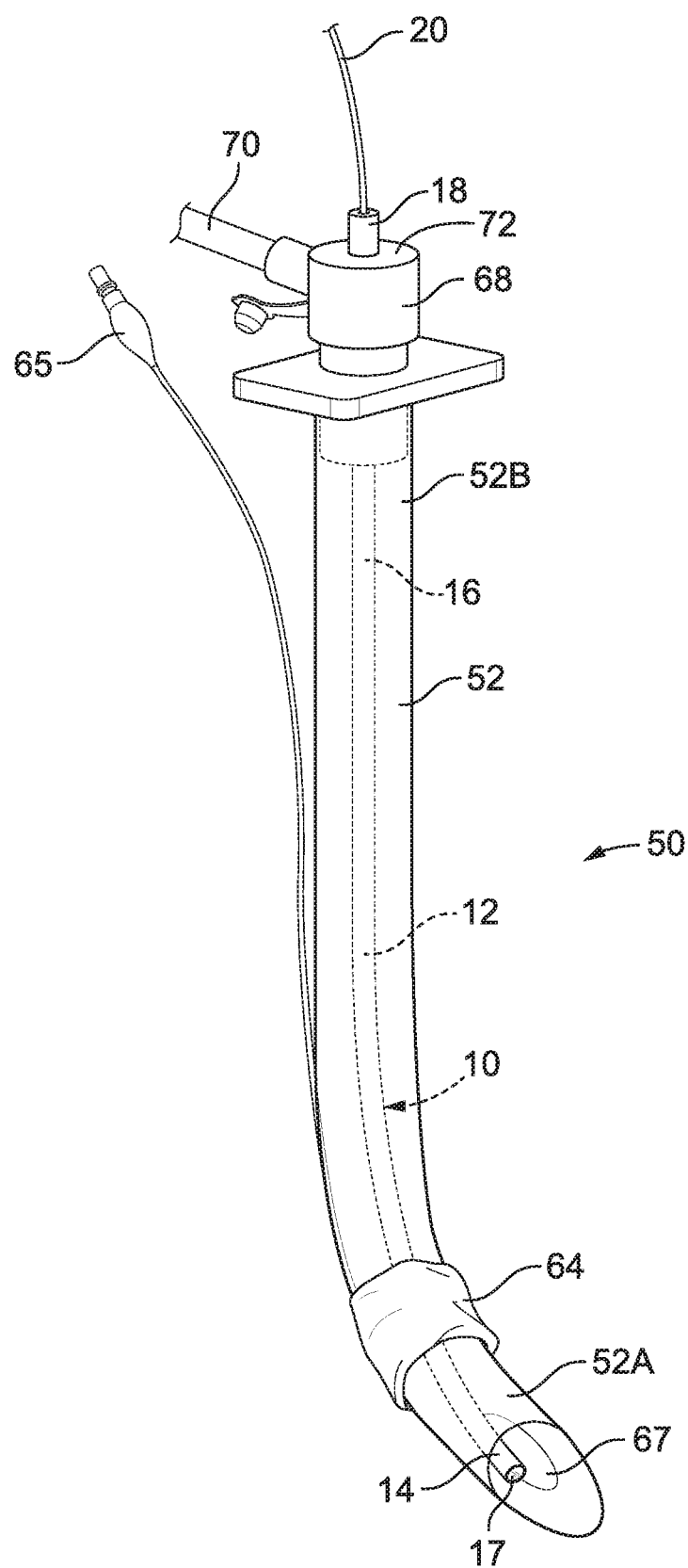
FIG. 3 depicts a side view of an alternative embodiment for an endotracheal device equipped with a visualization device.

In another embodiment and as shown in FIG. 3, an endotracheal device, generally 50, comprises an endotracheal tube 52 with a distal end 52A and a proximal end 52B, and a visualization device 10 placed inside of the endotracheal tube 52 through an opening in the proximal end 52B. In this embodiment, the visualization device 10 is attached to a built-in ventilator adaptable cap 68 which connects the endotracheal device 50 to a ventilator (not shown) through an outlet 70. The built-in ventilator adaptable cap 68 comprises an opening 72 through the cap 68. The visualization device 10 is passed through the opening 72 and is placed inside of the endotracheal tube 52. The built-in ventilator adaptable cap 68 is then connected with the endotracheal tube 52 at the proximal end 52B of the endotracheal tube 52.

The visualization device 10 is the same as the visualization device 10 of FIGS. 1A and 1t comprises a camera tube 12 with a sealed distal end 14 and an open proximal end 16. A camera 18 is placed inside of the camera tube 12 through the proximal end 16 of the camera tube 12. The camera 18 is connected by electrical wire 20 to an image-monitoring device (not shown). In some embodiments, the camera 18 is connected wireless to an image-monitoring device (not shown). The camera 18 collects images continuously and in real time through a transparent material 17 with which the distal end 14 of the camera tube 12 is sealed. The images can be transmitted to a remote location.

The endotracheal tube 52 can be optionally equipped with a cuff 64 at the distal end 52A such that the cuff 64 wraps around the endotracheal tube 52 and the cuff 64 can be inflated with a device 65, once the endotracheal device 50 is properly placed inside of a patient's airway. As can be seen from FIG. 3, the distal end 14 of the visualization device 10 extends distally from the distal end 52A of the endotracheal tube 52 and below the cuff 64 such that even when the cuff 64 is inflated with a device 65 after placement in a patient, the visualization device 10 can still record images inside of a patient's body and below the cuff 64. Further, the endotracheal device 50 may have an elliptical opening 67 at the distal end 52A and the visualization device 10 can be positioned inside of the endotracheal tube 52 such that the distal end 14 of the visualization device 10 aligns with or is in close proximity with the elliptical opening 67 of the endotracheal tube 52.

Referring to FIGS. 4A and 4B, further embodiments provide a visualization device 10 assembled with a built-in ventilator adaptable cap 68 which connects to a ventilator (not shown) by an outlet 70. The visualization device 10 is inserted through an opening 72 in the built-in ventilator adaptable cap 68 as shown in FIGS. 4A and 4B. As shown in FIG. 4B, the visualization device 10 can be further equipped with a light source 74 which can be a part of the camera tube 12 or it can be built in the camera 18, or it can remain outside the built-in ventilator adaptable cap 68. The visualization device 10 is assembled with the built-in ventilator adaptable cap 68 as shown in FIGS. 4A and 4B and can be then used in an endotracheal tube as described in connection with FIG. 3 or in a supraglottic device or with a laryngeal mask or with any other medical device to which a built-in ventilator adaptable cap 68 can be attached. As shown in FIGS. 4A and 4B, the camera tube 12 has a distal end 14 and a proximal end 16. The camera 18 is placed inside of the tube 12 through an opening in the proximal end 16 and moved all the way down to the distal end 14 which is sealed with a transparent material 17. The camera 18 collects images through the transparent material 17 and transmits the images in real time to a monitoring device which can be located remotely.

Figure 5A:
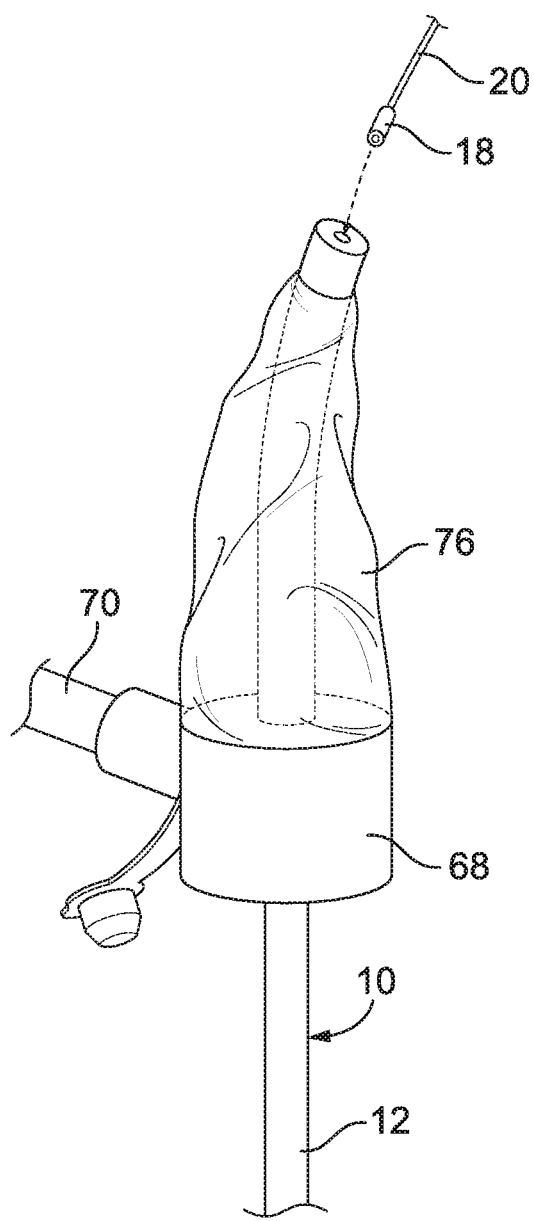
FIGS. 5A, 5B and 5C depict side views of further embodiments of a visualization device attached to a built-in ventilator adaptive cap and delivered through a sliding sleeve (FIGS. 5A and 5B), with further embodiment in FIG. 5C which includes a bougie or a flexible stylet as shown in the insert.
Figure 5B:
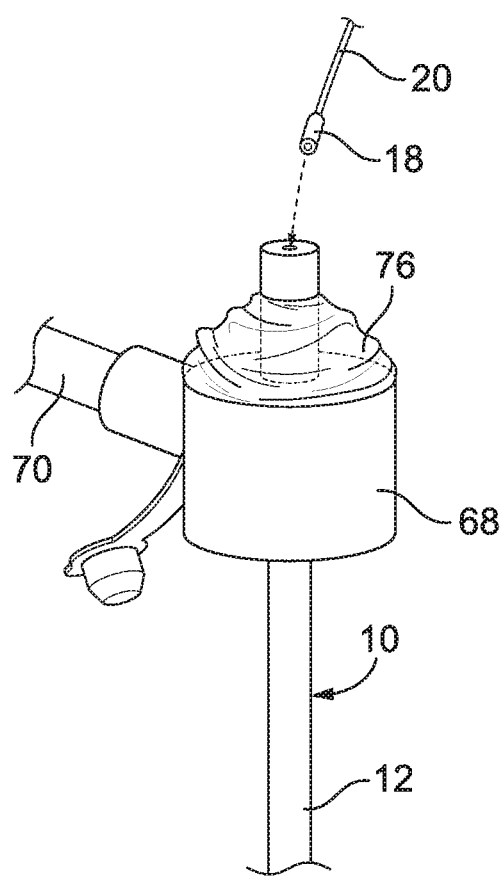
Figure 5C:
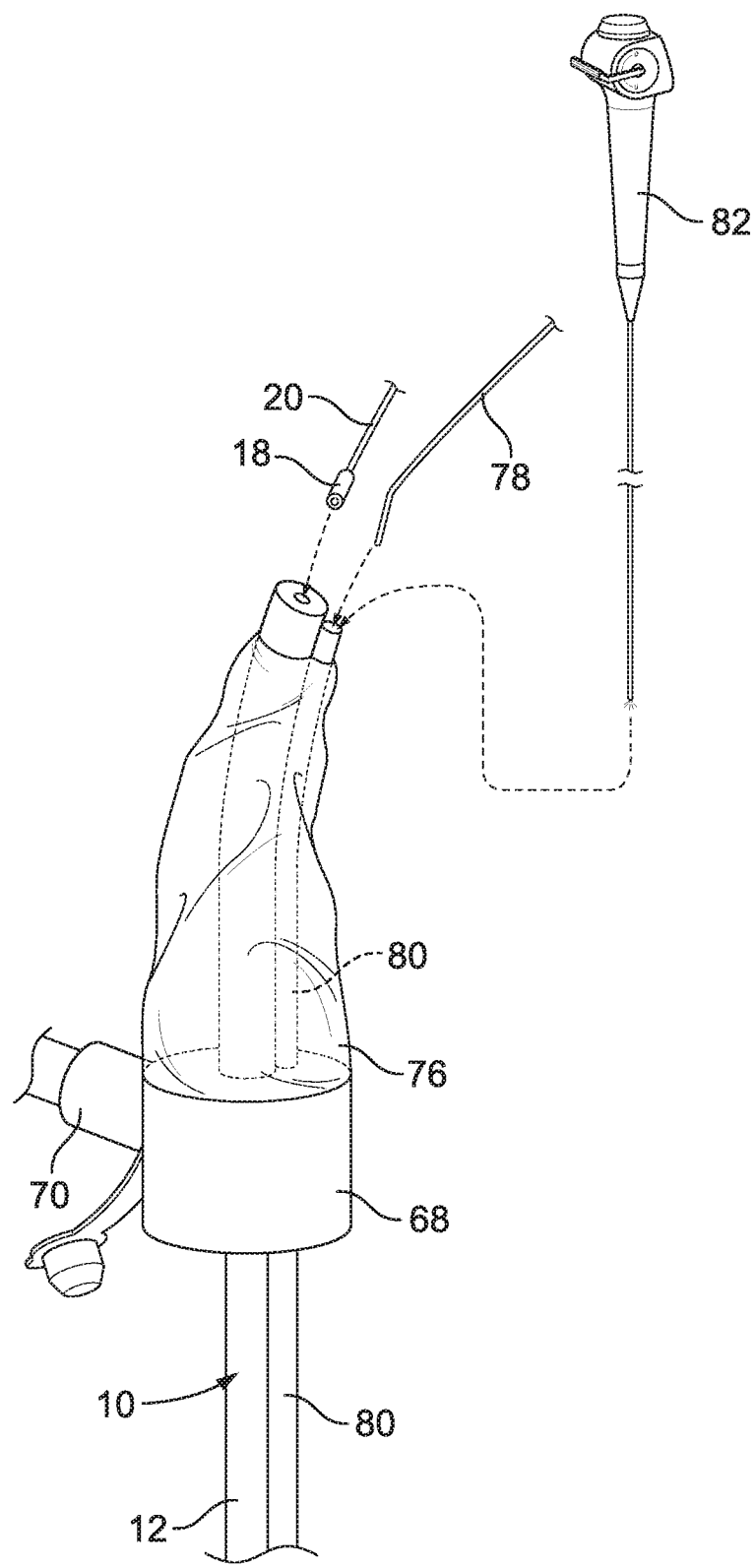

Further embodiments for a built-in ventilator adaptable cap 68 equipped with a visualization device 10 are shown in FIGS. 5A, 5B and 5C. As can be appreciated from FIG. 5A, the visualization device 10 comprises the camera 18 inside of the camera tube 12. The visualization device 10 is inserted through the ventilator adaptable cap 68. As shown in the embodiment of FIG. 5A, a plastic clear sleeve 76 can be attached over the adaptable cap 68 such that the sleeve 76 can slide up and down as shown in FIGS. 5A and 5B in the proximal-distal direction, which allows the visualization device 10 to remain sterile during insertion and removal. As the visualization device 10 is inserted and removed through the sleeve 76, the visualization device 10 remains sterile and free of contamination. The sleeve 76 is long enough to maintain the whole visualization device 10 outside the ventilation cap and remain sterile. A further embodiment is shown in FIG. 5C in which the visualization device 10 is inserted through the sleeve 76 as shown in FIGS. 5A and 5B, except a bougie 78 is added through a bougie tube 80.

The bougie 78 can be replaced with a flexible guided stylet 82 as shown in the insert to FIG. 5C which rotates and guides a stylet inside of a patient, which is protected from patient's tissues. If the tube 80 is used with a stylet, then the tube 80 has to be sealed at the distal end. Additional tubes can be attached and placed through the sleeve 76. Such tubes include, but are not limited to a suctions tube and a tool tube which can be used for delivering biopsy forceps and other tools. The assembly of the built-in ventilator adaptable cap 68 and visualization device 10 with the sleeve 76 can be used with any medical device to which a built-in ventilator adaptable cap can be attached, including an endotracheal tube as described in connection with FIG. 3, a supraglottic device or with a laryngeal mask airway. If an embodiment with a bougie or stylet is used as described in connection with FIG. 5C, the bougie 78 can protrude distally or slide independently from a medical device and guide the medical device movement inside of a patient during placement under visualization with the visualization device 10.

Figures 6A, 6B:
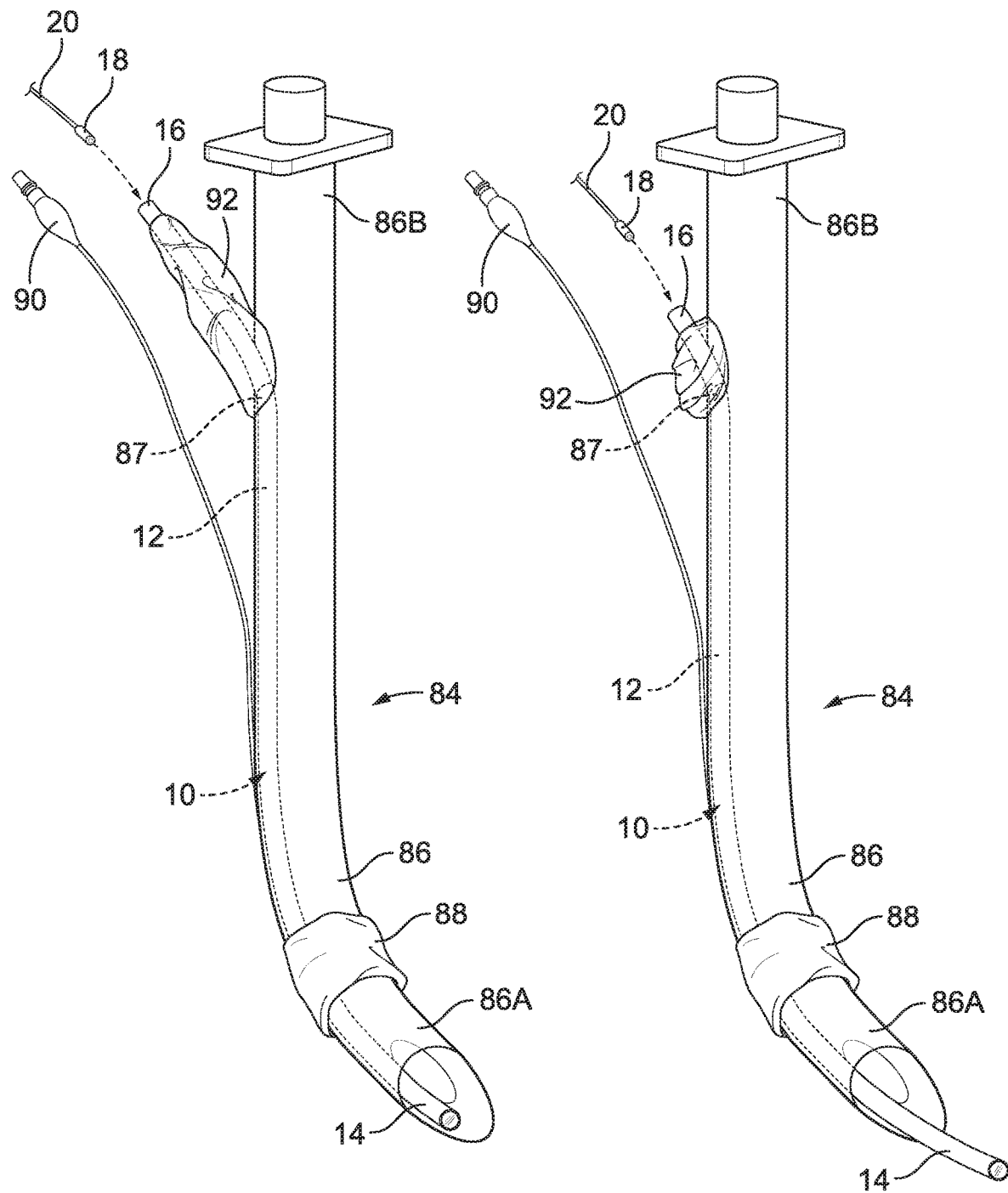
FIGS. 6A and 6B depict side views of an embodiment for an endotracheal device equipped with a visualization device delivered through a sliding sleeve.

Further embodiments for an endotracheal device equipped with a visualization device, generally 84, are shown in FIGS. 6A and 6B. As can be appreciated from FIG. 6A, the visualization device 10 which comprises the camera 18 inside of the camera tube 12 can be inserted inside of an endotracheal tube 86 through an opening 87 on one side of the endotracheal tube 86. As shown in the embodiment of FIG. 6A, a plastic sleeve 92 can be attached over the opening 87 such that the sleeve 92 can slide up and down as shown in FIGS. 6A and 6B, which facilitates keeping the visualization device 10 sterile while it is moved in or out of the endotracheal tube 86. As the visualization device 10 is inserted and removed from the endotracheal tube 86 through the sleeve 92, the visualization device 10 remains sterile and free of contamination. The visualization device 10 can be removed entirely from the endotracheal tube 86 through the sleeve 92 and remain sterile. The endotracheal tube 86 may be equipped with a cuff 88 positioned near the distal end 86A. The visualization device 10 can move inside the endotracheal tube 86 along the proximal-distal (86B-86A) axis such that the visualization device 10 is distal to the cuff 88 or the visualization device 10 can protrude outside the endotracheal tube 86 distally as shown in FIG. 6B. This permits for obtaining images from a patient with the visualization device 10 after the cuff 88 is inflated with a device 90 and obtaining the images from the area in a patient's body which is distal to the cuff 88. This distal to the cuff 88 area is available for monitoring after the cuff 88 is inflated because of the visualization device 10 in which the camera 18 collects images through the transparent material 17 at the distal end 14.

In this embodiment, the visualization device can slide up and down inside of an endotracheal tube, which permits advancement and retraction of the camera tube 12 while maintaining sterility of an endotracheal tube into which the visualization device 10 can be inserted as described above. The camera 18 can be easily advanced inside of the camera tube 12 and provide inspection of the endotracheal tube through its length as well as distal to the tip of the endotracheal tube.

Figure 7A:
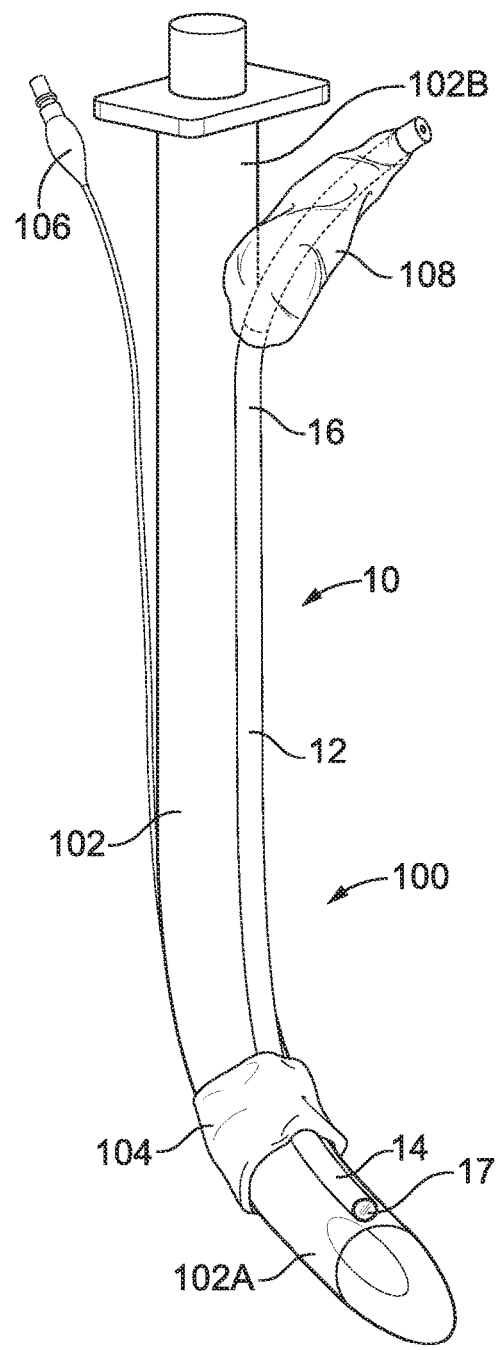
FIGS. 7A and 7B depict side views of an alternative embodiment for an endotracheal device equipped with a visualization device and delivered through a sliding sleeve.
Figure 7B:
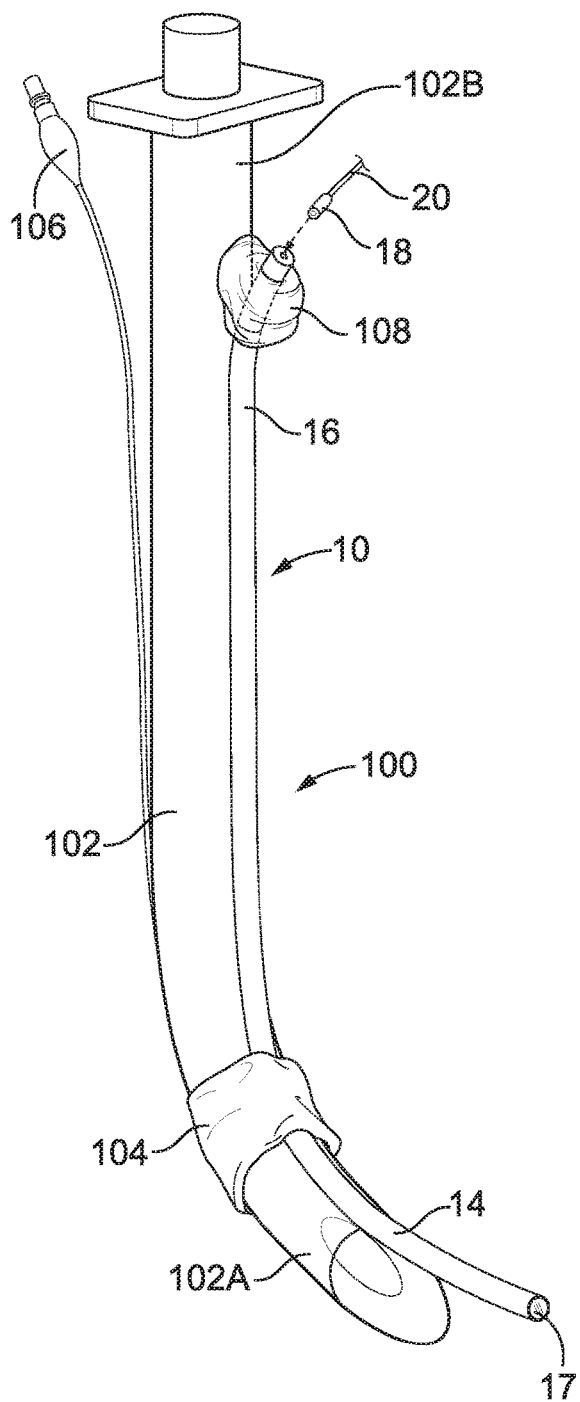

Further embodiments for an endotracheal device, generally 100, equipped with a visualization device 10 are shown in FIGS. 7A and 7B. Additional tubes can be attached to the tube 10 or be placed adjacent to the tube 10. Such tubes include, but are not limited to a suction tube, a tube for delivering instruments such as forceps, a bougie or flexible stylet. As can be appreciated from FIG. 7A, the visualization device 10 comprises the camera 18 inside of the camera tube 12 positioned externally on the endotracheal tube 102 and along the proximal-distal (102B-102A) axis. As shown in the embodiment of FIG. 7A, a plastic sleeve 108 can be attached to the endotracheal tube 102 such that the sleeve 108 can slide up and down outside the endotracheal tube 102 as shown in FIGS. 7A and 7B, which facilitates the movement of the visualization device 10 along the proximal-distal (102B-102A) axis of the endotracheal tube 102. As the visualization device 10 is inserted and removed through the sleeve 108, the visualization device 10 remains sterile and free of contamination. The endotracheal tube 102 may be equipped with a cuff 104 wrapped around the endotracheal tube 102 near its distal end 102A. The visualization device 10 moves outside the endotracheal tube 102 along the proximal-distal axis 102B-102A such that the visualization device 10 can be proximal to the cuff 104. This also permits for obtaining images from a patient with the visualization device 10 after the cuff 88 is inflated with a device 106. The camera tube 12 can slide proximal or distal of the cuff 104. Thus, at least in some embodiments, the camera tube 12 would be into a sealed tunnel.

Figure 8:
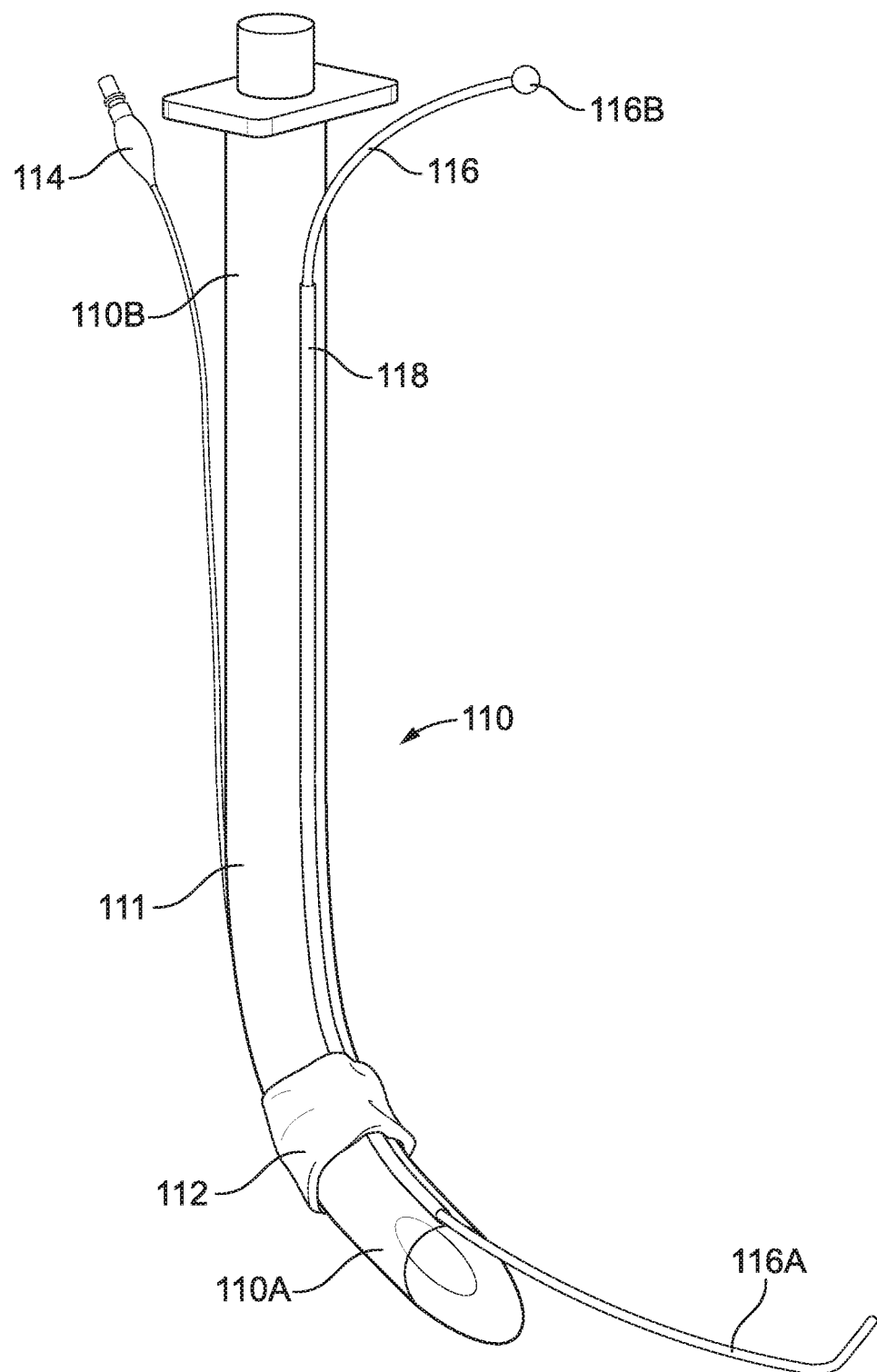
FIG. 8 is a side view of an embodiment for an endotracheal device equipped with a bougie.

FIG. 8 depicts a further embodiment of an endotracheal device, generally 110. The device 110 can be equipped with the visualization device 10 and the sound tube 40 described in connection with FIG. 2 (not shown). The endotracheal device is further equipped with a bougie 116 which can slide up and down along the proximal-distal (116B-116A) axis inside of a tube 118 which is attached externally to the endotracheal tube 111. The endotracheal tube 111 is equipped with a cuff 112 located in proximity to a distal end 110A of the tube. The cuff 112 can be inflated with a device 114 after the endotracheal device 110 is placed inside of a patient. The visualization device 10 can be sealed or attached to the endotracheal tube 111 either outside or inside as described above in connection with embodiments provided by FIGS. 2, 3, 4A, 4B, 5A, 5B, 6A, 6B, 7A and 7B. The bougie 116 guides the movement of the endotracheal device 111 during placement in a patient under visualization with the visualization device 10 and permits guided sliding down the medical device over the bougie 116 inside of the patient's airway.

Further embodiments of a visualization device, generally 120, are shown in FIGS. 9A-9C. As shown in FIG. 9A, the camera tube 12 can be equipped with at least one, and preferably two external rings 122 which are sealed or otherwise connected by means 124 to the camera tube 12. In some embodiments, one ring 122 is positioned at about ⅓ of the camera tube length from the proximal end 16 and the other ring is positioned at about ⅔ of the camera tube length from the proximal end. While in the embodiment of FIG. 9A, the camera tube 12 is equipped with two rings 122, other embodiments include those in which more than 2 rings are used or only one ring is used. The positioning of the rings along the proximal-distal (16-14) axis of the camera tube 12 can also vary. Other modalities include a clasp or a plastic band to hold the camera tube 12.

As in all other embodiments, the camera tube 12 has a distal end 14 sealed with a transparent material 17 and a proximal end 16 with an opening through which a camera 18 is inserted into the camera tube 12. As shown in FIG. 9B, the visualization device 120 can be further equipped with a tube 118 sealed or otherwise attached externally along the proximal-distal (16-14) axis of the camera tube 12. A bougie 116 is placed inside of the tube 118 such that a distal end 116A of the bougie 116 protrudes distally over the camera tube 12, while its proximal end 116B extends outside the visualization device 120 proximally and can be used by a medical provider to rotate the distal end 116A and in this way guide the movement of the visualization device 120 along with a medical device to which it is attached.

As shown in FIG. 9C, the visualization device 120 can be further equipped with a light source 21 which can be either built in the camera tube 12, built in the camera 18 or it can be kept outside the visualization device 120 and outside the patient's body. The visualization device 120 is attached to a medical device with the rings 122, and this permits for customized positioning of the visualization device 120 as it can slide up and down along a proximal-distal axis of a medical device.

As shown in a cross-sectional view in FIG. 9D, the ring 122 can be of any diameter in order to fit on a medical device of choice. As shown further in FIG. 9E, at least in some embodiments the ring 122 may have a clasp 126 such that the diameter of the ring 122 can be adjusted according to a diameter of a medical device to which the visualization device 120 is attached with the rings 122.

An embodiment as shown in FIG. 9F provides an assembly, generally 128, in which the visualization device 120 is attached with the rings 122 to an endotracheal tube 52. The rings 122 can slide up and down along the proximal-distal (52B-52A) axis of the endotracheal tube 52, and in this way the position of the visualization device 120 can be adjusted with respect to the endotracheal tube 52. Further, the rings 122 can rotate around the endotracheal tube 52, which permits altering the positioning of the camera device 120 if images are needed from a different area inside of a patient.

Because the rings 122 can be adjustable, the visualization device 120 can be used with an endotracheal tube of any size, including those for pediatric patients. Further, the visualization device 120 with at least two rings connected externally to the camera tube 12 can be provided as a kit, and a medical practitioner can assemble the visualization device with any conventional endotracheal tube or any other conventional medical device for which visualization and monitoring are needed at the time of treatment.

Further embodiments provide an intubation method in which an endotracheal tube, including any of the endotracheal tubes described above and equipped with the visualization device as described above, is placed in patient's airway and positioned under the patient's vocal cords under constant visualization by the visualization device 10.

Figure 10:
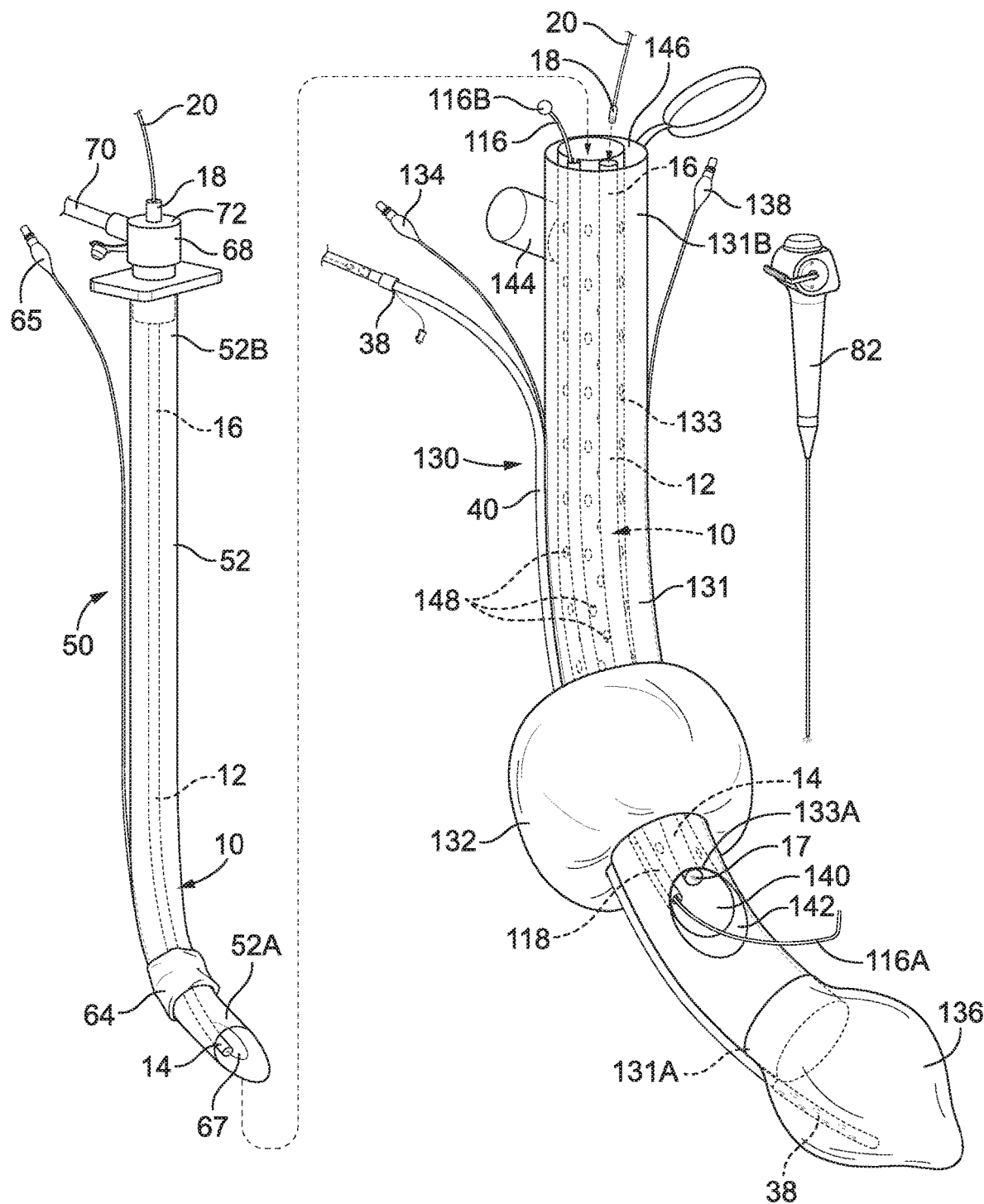
FIG. 10 is a side view of a supraglottic airway device equipped with a visualization device. An endotracheal device of FIG. 3 is shown as an insert on the left and a flexible guided stylet is shown as an insert on the right.

Referring to FIG. 10, it depicts a side view of a supraglottic airway device, generally 130. Any standard endotracheal tube known in the art and an endotracheal device of FIG. 3 is shown in the insert on the left of FIG. 10 can be used in combination with the supraglottic airway device 130.

The supraglottic airway device 130 comprises a supraglottic tubal body 131 with a distal end 131A and a proximal end 131B and a lumen 146. The supraglottic airway device 130 includes a designated intubation tube 133 which is inserted into the lumen 146 and into which an endotracheal device 50 can be placed as shown in FIG. 10. The distal end 133A of the intubation tube 133 ends with an elliptical opening 140 which is located distally from a cuff 132 which can be inflated with a device 134. The intubation tube 133 has a plurality of holes 148 distributed throughout its body to allow ventilation from outlet 144 through tubal body 131.

While a standard endotracheal device, including an endotracheal device 50, may be equipped with a visualization device, the supraglottic airway device 130 comprises its own visualization device 10 which is placed in the lumen 146. The visualization device 10 comprises a camera tube 12 with a distal end 14 and a proximal end 16. The distal end 14 is sealed with a transparent material 17. The camera tube 12 is sealed or otherwise attached externally to the intubation tube 133 along the proximal-distal (131B-131A) axis. The supraglottic device 130 can be further equipped with a bougie 116 which is located inside of the tube 118. The tube 118 is placed inside of the lumen 146 and such that the distal end 116A of the bougie 116 protrudes from the tube 118 and outside the supraglottic tubal body 131 through an elliptical opening 142 which is located on the supraglottic tubal body 131 slightly proximally from the distal end 131A. The elliptic opening 142 of the supraglottic tubal body 131 overlaps partially with the elliptic opening 140 of the intubation tube 133. The bougie tube has its own opening through 140.

At the distal end 131A, the tubal body 131 is capped with a balloon 136 which can be inflated with a device 138. In some embodiments, the bougie 116 can be replaced with a flexible guided stylet 82 shown on the right of FIG. 10.

In addition to the visualization device 10, the supraglottic device 130 can be also equipped with a sound- and temperature-monitoring device 38 which is located inside a tube 40 which is sealed or otherwise attached externally to the tubal body 131 along the proximal-distal (131B-131A) axis. The sound device 38 can monitor patient's heart beat and breathing after the supraglottic device 130 is placed inside of the patient. On its proximal end 131B, the tubal body 131 may be connected to a ventilator (not shown) though an outlet 144. Because the supraglottic device 130 can ventilate in a closed circuit through the tubal body 131, an endotracheal tube 50 can be placed inside of the intubation tube 133 without the need to stop ventilation and therefore, the supraglottic device 130 provides continuous ventilation, continuous visualization in real time through the visualization device 10 and continuous sound and temperature monitoring by the sound monitoring device 38 with a temperature probe. This real time information can be transferred or stored to multiple distant monitoring sites.

Other advantages for the supraglottic airway device include the ability to intubate, extubate and to easily reintubate if needed under continuous ventilation and the ability to continuously visualize vocal cords and supraglottic structures. The device 130 is suitable for applications in children and adults. Further, the device 130 is equipped with the cuff 132 for blocking the pharynx and the balloon 136 which blocks the esophagus after the device 130 is placed in a patient. Furthermore, an endotracheal tube can be placed just proximal to the vocal cords in the tubal body 133. This permits ventilation through 144 and tubal body 131 uninterrupted.

Figure 11A:
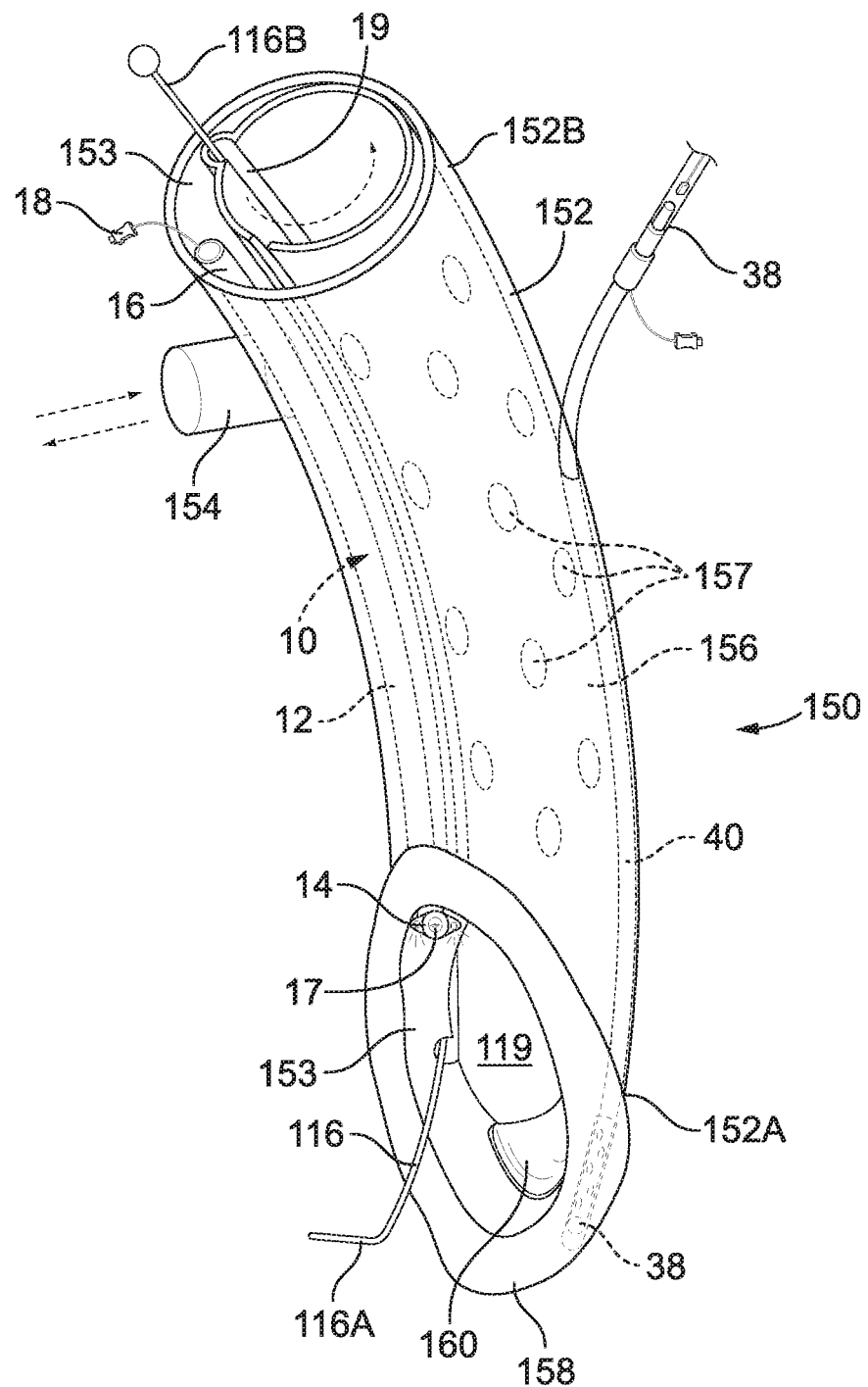
FIGS. 11A and 11B depict a side view of an alternative airway device with a visualization device.
Figure 11B:
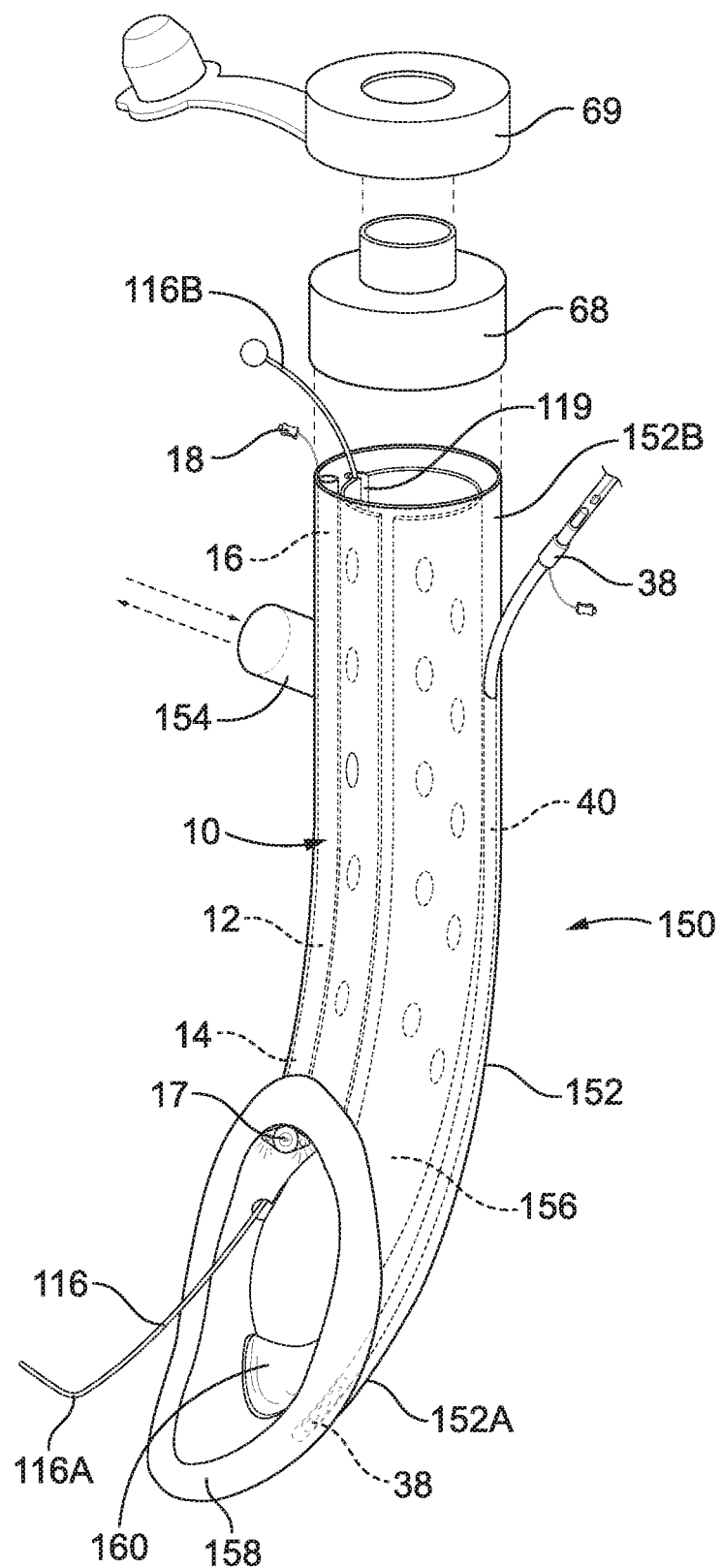

Referring to FIGS. 11A and 11B, an alternative embodiment for an airway device, generally 150, is provided. This device can be used in pediatric and adult patients as it is adoptable to different sizes. It provides continuous visualization of supraglottic structures and it can be advanced, retracted, or rotated, side to side to provide direct visualization of vocal cords. As can be appreciated from FIGS. 11A and 11B, the airway device 150 comprises a tubal body 152 with a distal end 152A and a proximal end 152B and a lumen 153. The tubal body 152 may be connected to a ventilator through an outlet 154. A visualization device 10 is sealed or otherwise attached inside of the tubal body 152 along the proximal-distal (152B-152A) axis on at least one side. The visualization device 10 comprises a camera tube 12 with a distal end 14 and a proximal end 16. The camera tube 12 is sealed at the distal end 14 with a transparent material 17. The proximal end 16 of the camera tube 12 remains open and a camera 18 is inserted in the camera tube 12 through the proximal end 16. The camera 18 does not come in contact with a patient's body and it does not have to be sterilized, it does not have to be disposable, although it may be disposable in at least some applications. The visualization device 10 can be further equipped with a light source which can be built in the camera tube 12 or be a part of the camera 18. In alternative, a light source may be left outside the camera tube 12, but still shed enough light inside of the camera tube 12 for the camera 18 to obtain images inside of a patient's body.

An intubation tube 156 is placed inside of the lumen 153 of the tubal body 152 along the proximal-distal (152B-152A) axis. The intubation tube 156 shares a lumen 119 with a bougie 116 which is inserted inside the lumen 119 along the proximal-distal (152B-152A) axis such that a distal end 116A of the bougie 116 may protrude outside the tubal body 152 at the distal end 152A and proximal end 116*b* may protrude outside the tubal body 152 and the proximal end 152*b* can be used by a medical practitioner to guide the movement of the airway device 150 with the bougie 116 during placement in a patient, including advancing the bougie 116 through patient's vocal cords under direct visualization by camera 18. The intubation tube 156 has a plurality of holes 157 distributed along the intubation tube 156.

At least in some embodiments, the airway device 150 is further equipped with a sound- and temperature-monitoring device 38 which can be inserted in a tube 40 which is sealed or otherwise attached inside of the tubal body 152 along the proximal-distal (152B-152A) axis such as the distal end of the sound-monitoring device 38 is positioned at or near the distal end 152A of the tubal body 152, which is also equipped with a cuff 158 along the perimeter of the tubal body 152 at the distal end 152A. The intubation tube 156 is designed such that at least in some embodiments the intubation tube 156 has a ramp 160 at the distal end 152A of the airway device 150. A standard endotracheal tube, including those described in various embodiments above, can be placed inside of the lumen 119 in the intubation tube 156 for positioning in a patient.

As shown in FIG. 11B, a ventilator adaptable cap 68 and a lid 69 are attached to the tubal body 152 at the proximal end 152B. The endotracheal tube is inserted into the device 150 through the cap 68. Using the cap 68 with the lid 69 on the airway device 150 is preferred when ventilation is accomplished through an outlet 154.

Yet another embodiment for an oral airway device, generally 170, is provided as shown in FIGS. 12A, 12B and 12C. As can be appreciated from FIG. 12A, the airway device 170 comprises a tubal body 172 with a distal end 172A and a proximal end 172B. The tubal body 172 ends with two ramps 174 and 176 at the distal end 172B. As can be appreciated from a side view in FIG. 12A and cross-sectional views of the tubal body 172 in FIGS. 12B and 12C, the tubal body 172 is made of two half-cylinders 178 and 180. The half-cylinder 178 is slightly smaller in diameter than the half-cylinder 180. The tubal body 172 can be present in one of the two forms: as a full cylinder shown in FIG. 12B or as a half-cylinder as shown in FIG. 12C. The half-cylinder 178 and the half-cylinder 180 are connected by means such that the half-cylinder 178 can rotate and retract into the half-cylinder 180. The half-cylinder form of FIG. 12C is achieved by the half-cylinder 178 rotating at about 180 degrees and aligning with the half-cylinder 180 such that the half-cylinder 178 is located inside of the half-cylinder 180 as shown in FIG. 12C.

A visualization device, generally 10, is sealed or otherwise attached externally to the half-cylinder 180 along the proximal-distal (172B-172A) axis. The visualization device 10 comprises of a camera tube 12 with a distal end 14 and a proximal end 16. The distal end 14 is sealed with a transparent material 17. A camera 18 is placed through an opening at the proximal end 16 into the camera tube 12 and is moved inside the camera tube 12 to the distal end 14. Similarly to all other embodiments, the camera 18 does not come in contact with a patient's body, and it does not have to be disposable, does not have to be sterilized and it can be reused in multiple devices. The camera 18 is connected with wire 20 to at least one monitoring device and it transmits images in real time. The camera 18 can be connected wirelessly to at least one monitoring device which can be positioned at some remote location. A light source can be added as described in connection with the visualization device in other applications.

The half-cylinder 180 ends in two ramps 174 and 176 at the distal end 172A. The ramp 174 is smaller in size than the ramp 176 and the two ramps are superimposed over each other such as the smaller ramp 174 is proximal to a lumen 182 created by half-cylinders 178 and 180 when they are in the full-cylinder form as shown in FIG. 12B, while the ramp 176 is distal to the lumen 182. The ramps 174 and 176 are flexible and absorb the shock from sliding and releasing an endotracheal tube which can be delivered into a patient by the oral airway device 170. The ramps also facilitate the removal of the oral airway device 170 after the endotracheal tube is placed inside of the patient.

As shown in FIG. 12A, the oral airway intubating device 170 can be further equipped with a bougie 160 which can be inserted into a tube 118 along the proximal-distal (172B-172A) axis such that a distal end 116A of the bougie 116 protrudes distally from the oral airway device 170 and a proximal end 116B protrudes outside the oral airway device proximately and can be used to manipulate the distal end 116A of the bougie 116 such that it guides the movement of the airway device 170 during placement in a patient. The bougie tube 118 is located on the smaller half-cylinder 178 and it shares the lumen 182 with the tubal body 172.

Figure 13:
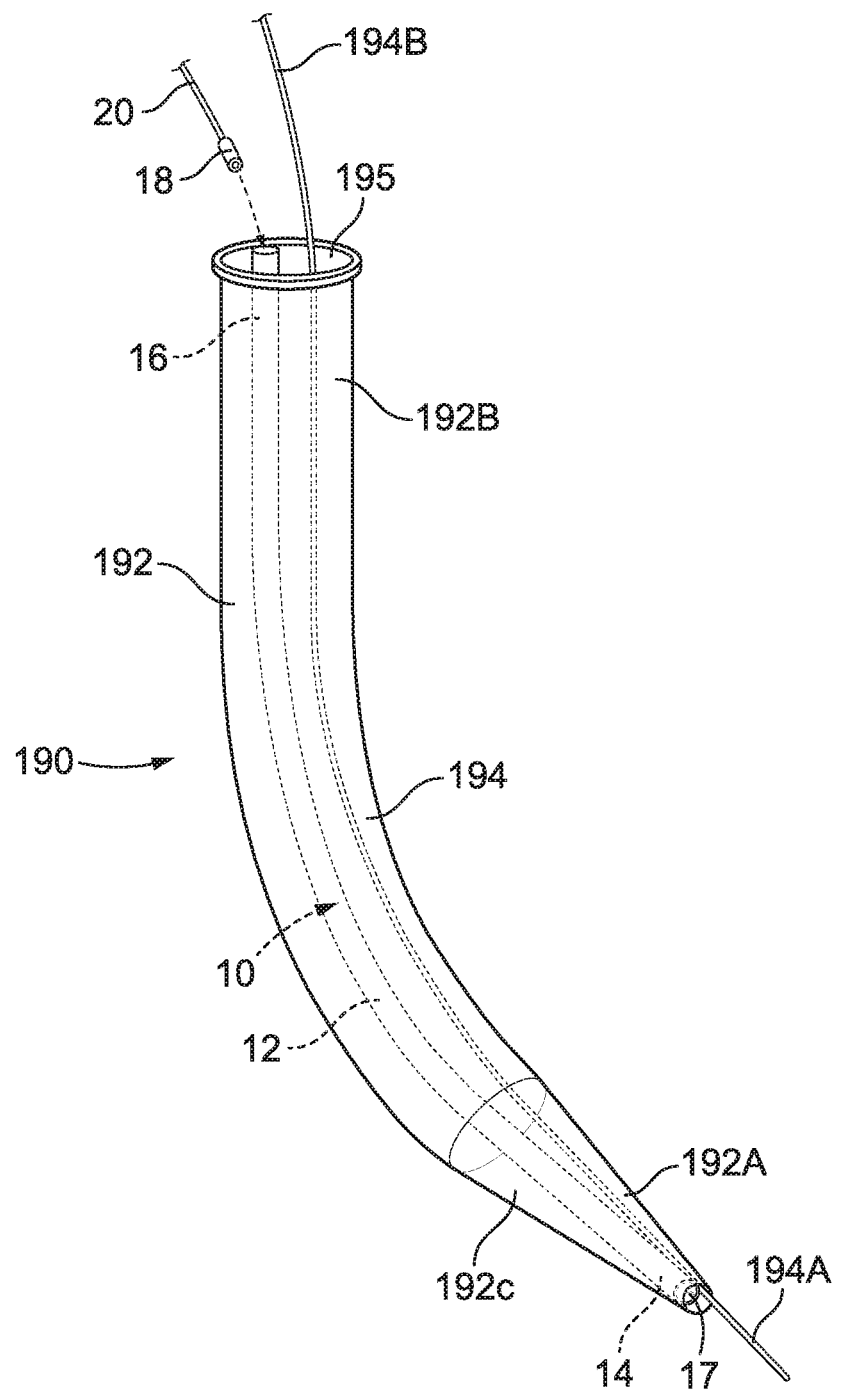
FIG. 13 depicts a side view of a dilator with a visualization device.

A further embodiment provides a dilator with a visualization device, generally 190 in FIG. 13. As can be appreciated from FIG. 13, the dilator 190 comprises a tubal body 192 with a proximal end 192B and a distal end 192A. A certain distal portion of the tubal body 192 is tapered into a conical shape 192C such that the opening at the distal end 192A of the tubal body 192 is significantly smaller in diameter in comparison to an opening at the proximal end 192B. A visualization device 10 is positioned inside of a lumen 195 of the tubal body 192 and along the proximal-distal (192B-192A) axis. The visualization device 10 may be sealed or otherwise attached inside of the tubal body 192. The visualization device 10 is essentially the same device as shown in FIG. 1A, and it comprises a camera tube 12 with a proximal end 16 and a distal end 14. The distal end 14 of the camera tube 12 is in close proximity with the distal end 192A of the tubal body 192. A camera 18 which can be either disposable or reusable is placed inside of the camera tube 12 through an opening at the proximal end 16 and all the way down to the distal end 14 of the camera tube 12, which is sealed with a transparent material 17. Just like other embodiments, the visualization device 10 can be equipped with a light source located outside of the dilator 194 or built in the camera tube 12. In some embodiments, the light source can be built in the camera 18.

As shown in FIG. 13, the camera 18 is connected by electrical wire 20 to a monitoring device (not shown). In some embodiments, the camera 18 can be in communication with a monitoring device wirelessly. A guide wire at the proximal end 194A is positioned inside of the lumen 195 of the tubal body 192. A proximate end 194b of the guide wire 194 protrudes outside of the tubal body 192 at the proximal end 192b. The visualization device 10 verifies appropriate placement of the dilator device 190 and allows mobility of continuous visualization as dilation proceeds. The dilator device 190 is especially well suited for use with the Seldinger technique.

Figure 14A:
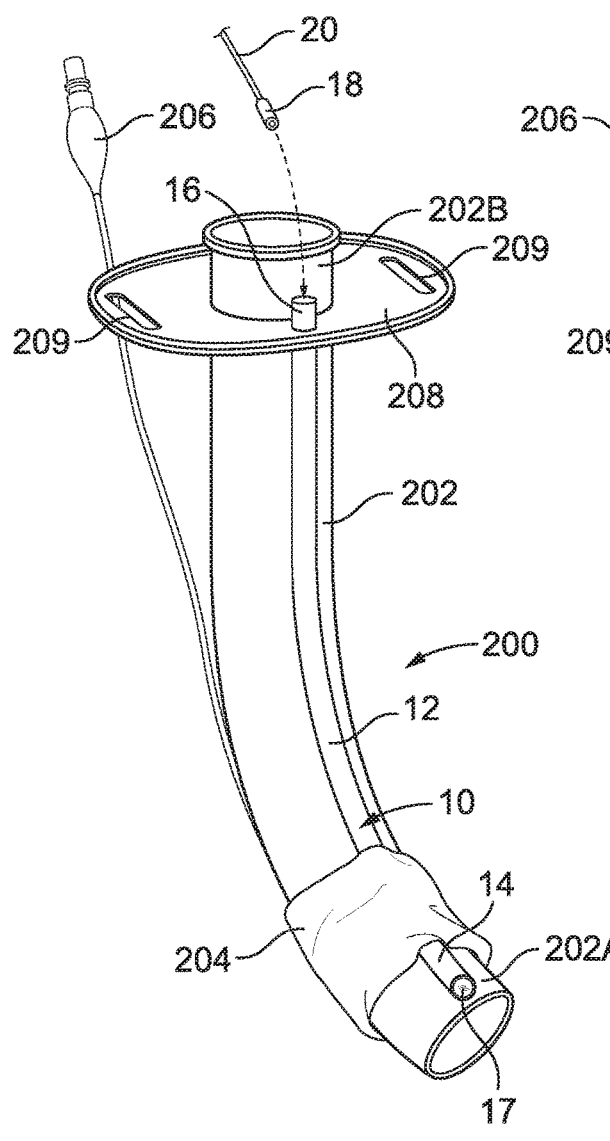
FIGS. 14A and 14B depict a side view of a tracheostomy device with a visualization device.

Further embodiments provide various tracheostomy tubes equipped with a visualization device. FIG. 14A depicts a side view of an embodiment for a tracheostomy device, generally 200. The device 200 comprises a tubal body 202 with a distal end 202A and a proximal end 202B. An inflatable cuff 204 is wrapped around the tubal body 200 in some proximity to the distal end 202A, but never at the very distal end 202A. The cuff 204 can be inflated with a device 206 after proper placement of the device 200 in a patient. At the proximal end 202B, the tubal body 202 protrudes through a plastic plate 208 such that some portion of the tubal body 202 is proximal to the plastic plate and will remain outside of a patient's neck after the device 202 is positioned in the patient. The plastic plate 208 may be oval in shape with the tubal body 202 protruding from the plate in the middle of the oval plastic plate 208. The plastic plate 208 may have two openings 209, one on each side of the plate such that the device 200 can be secured around patient's neck with some bandage by tying the device 200 through the openings 209 around patient's neck.

In the embodiment of FIG. 14A, the visualization device 10 is sealed or otherwise attached to the tubal body 202 externally. The visualization device 10 comprises a camera tube 12 which is sealed or otherwise attached externally along the proximal-distal (202B-202A) axis to the tubal body 202. The camera tube 12 is placed under the cuff 204 such that the cuff 204 wraps over the camera tube 12 and a distal end 14 of the camera tube 12 is distal to the cuff 204. The distal end 14 is sealed with a transparent material 17. A proximal end 16 of the camera tube 12 protrudes through the plastic plate 208 and remains outside of patient's neck. A camera 18 can be placed inside of the camera tube 12 through an opening in the proximal end 16. The camera 18 is not disposable, does not need to be sterilized and can be easily removed from the camera tube 12. The camera 18 is connected by electrical wire 20 to a monitoring device. In further embodiments, the camera 18 can be in communication with a monitoring device wirelessly. A light source can be added to the visualization device 10 as was described in other embodiments above.

Figure 14B:
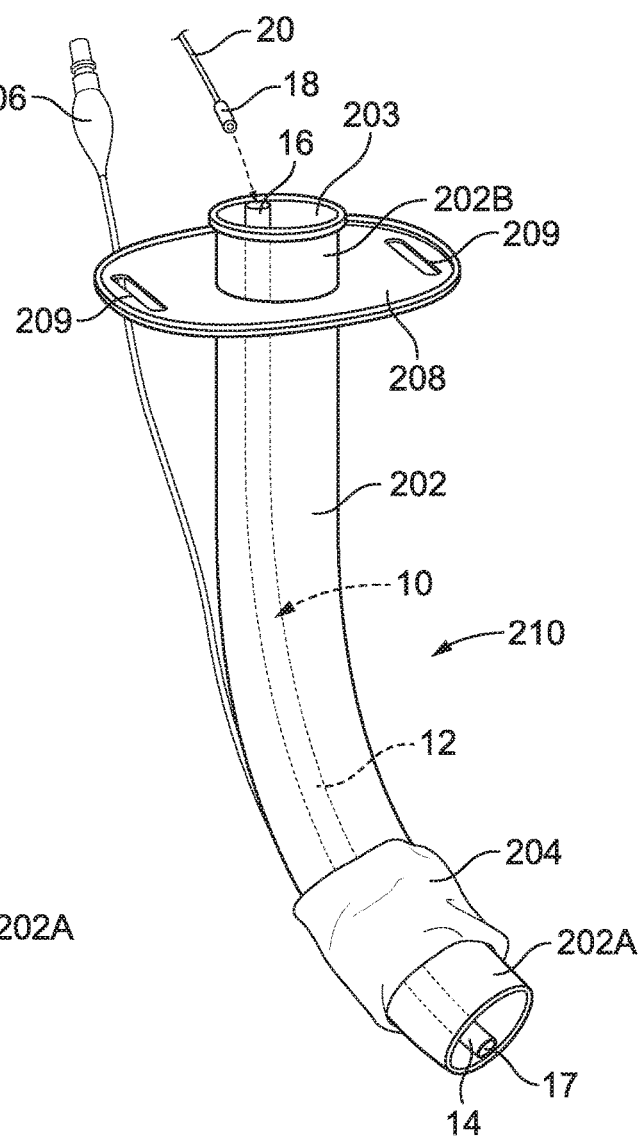

FIG. 14B depicts another embodiment for a tracheosomy device, generally 210. In this embodiment, the device 210 comprises of the same tubal body 202, cuff 204, plate 208 and other components as was discussed in connection with the device 200. However, unlike the device 200, a visualization device 10 is placed inside of a lumen 203 of the tubal body 202. The visualization device 10 comprises a camera tube 12 with a distal end 14 and a proximal end 16. The camera tube 12 may be sealed or otherwise attached internally to the tubal body 202 along the proximal-distal (202B-202A) axis such as the distal end 14 of the camera tube 12 is in close proximity with the distal end 202A of the tubal body 202. The distal end 14 is sealed with a transparent material 17. A camera 18 is placed inside of the camera tube 12 through an opening at the proximal end 16 which remains outside of the patient's neck after the device 210 is placed in the patient. The camera 18 is connected by electrical wire 20 to a monitoring device. In other embodiments, the camera 18 communicates with a monitoring device wirelessly. In some embodiments, the visualization device 10 comprises a light source.

Figure 15:
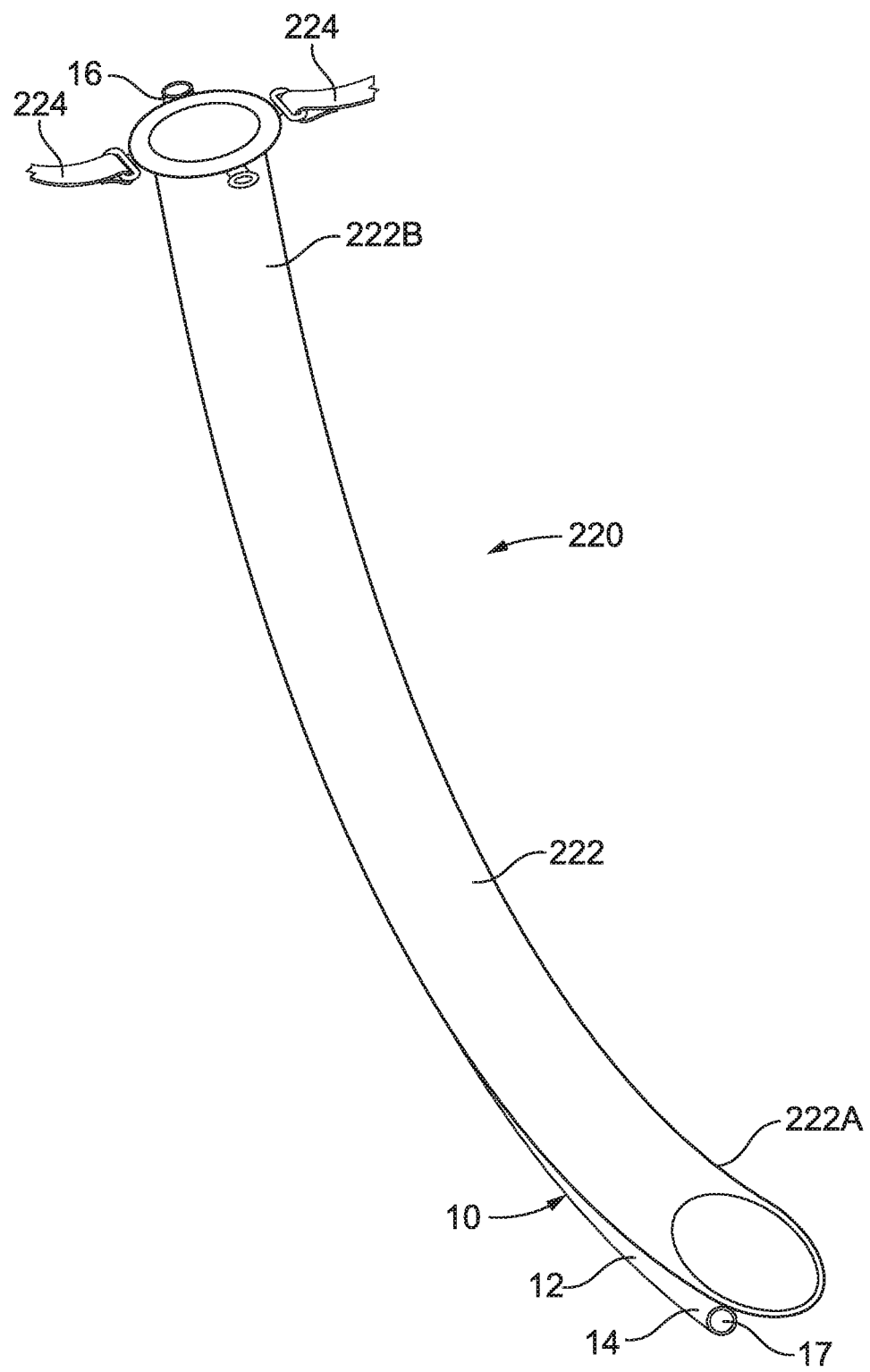
FIG. 15 depicts a side view of a nasal trumpet with a visualization device.

A further embodiment provides a nasal trumpet with a visualization device, generally 220 in FIG. 15. The trumpet 220 comprises a tubal body 222 with a proximal end 222B and a distal end 222A. Two fasteners 224 are attached at the proximal end 222B of the tubal body 222. After placing the trumpet 220 in a patient, the proximal portion of the tubal body 222 with the fasteners 224 remains outside of the patient, and the fasteners 224 can be used to secure the trumpet 220 around the patient's head.

A visualization device 10 is sealed or otherwise attached to the tubal body 222 externally along the proximal-distal (222B-222A) axis. The visualization device 10 comprises a camera tube 12 with a proximal end 16 and a distal end 14. The distal end is in near proximity with the distal end 222A of the tubal body 222. The distal end 14 is sealed with a transparent material 17. A camera 18 is placed inside of the camera tube 12 through an opening at the proximal end 16. The camera 18 is moved all the way to the distal end 14 and collects images in real time inside of a patient's body during placement of the device 220 as well as after the device 220 has been properly placed and secured. As in other embodiments, the camera 18 does not come in contact with patient's body, does not have to be sterilized and can be reused in multiple devices or in different patients. The camera 18 communicates with a monitoring device (not shown) either with electrical wire 20 or wirelessly, or both.

Figure 16C:
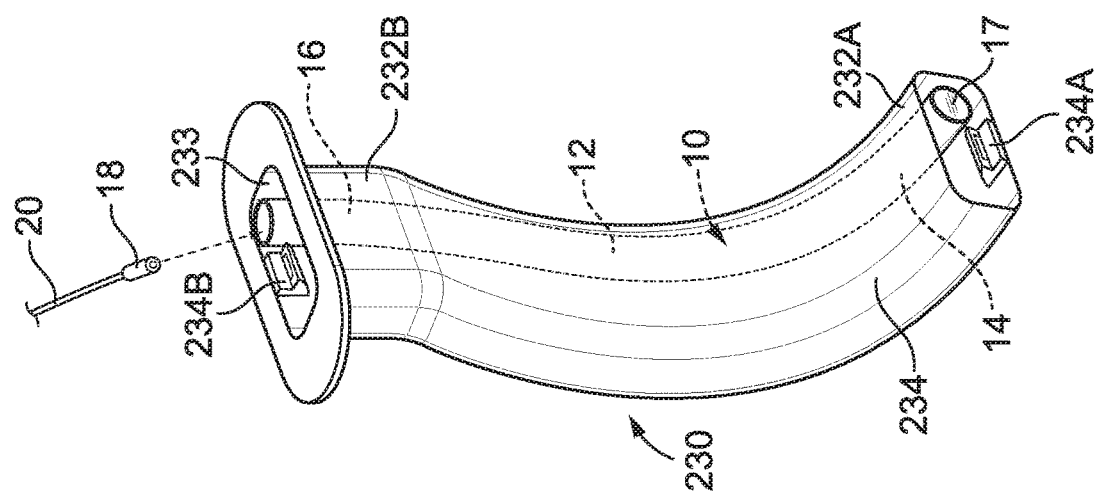
FIGS. 16A-16C depict a side view of an oral airway equipped with a visualization device and FIG. 16D depicts an intubating oral airway also equipped with a visualization device.
Figure 16B:
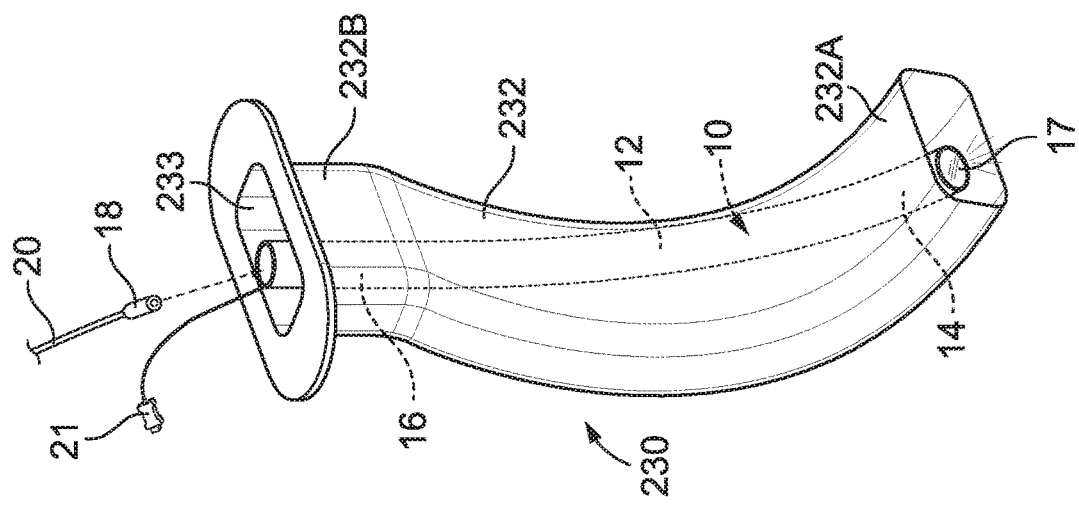
Figure 16A:
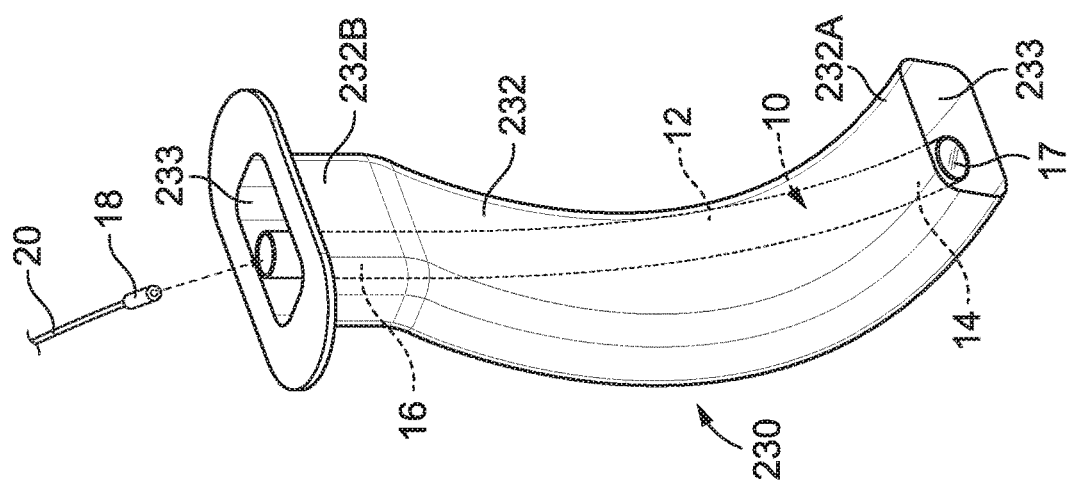

Further embodiments provide various oral airways as shown in FIGS. 16A, 16B, 16C, and 16D. Referring to FIG. 16A, an oral airway with a visualization device, generally 230, comprises a tubal body 232 with a lumen 233. The tubal body is slightly curved in a hook-like shape along the proximal-distal (232B-232A) axis. A visualization device 10 is placed inside of the lumen 233 of the tubal body 232. The visualization device 10 comprises a camera tube 12 and a camera 18. The camera tube 12 may be sealed or otherwise attached internally to the tubal body 232 inside of the lumen 233 and along the proximal-distal (232B-232A) axis. The camera tube 12 has a proximal end 16 and a distal end 14. The distal end 14 is in close proximity with the distal end 232A of the tubal body 232. The distal end 14 is sealed with a transparent material 17.

The camera tube 12 has an opening at the proximal end 16 through which the camera 18 is inserted into the camera tube 12 all the way to the distal end 14. The camera 18 communicates with a monitoring device either wirelessly or by electrical wire 20. The embodiment shown in FIG. 16B is the same as in FIG. 16A, except a light source 21 is added to the visualization device 10. The light source 21 may remain outside of the camera tube 12 or it may be built in the camera tube 12 or it may be a part of the camera 18.

The embodiment shown in FIG. 16C is the same as that of the FIG. 16A, except two whistles 234A and 234B are added inside of the lumen 233 of the tubal body 232. The whistle 234B is located at the proximal end of the tubal body 232 and it produces a sound when a patient breathes in. The whistle 234A is located at the distal end of the tubal body 232 and it produces a sound when the patient breathes out.

Further embodiments include an oral airway as shown in FIGS. 16A-16C, but further equipped with a sound and temperature monitoring device which is also placed inside of the lumen 233 and transmits information to a monitoring device which can be positioned at a remote location.

Figure 16D:
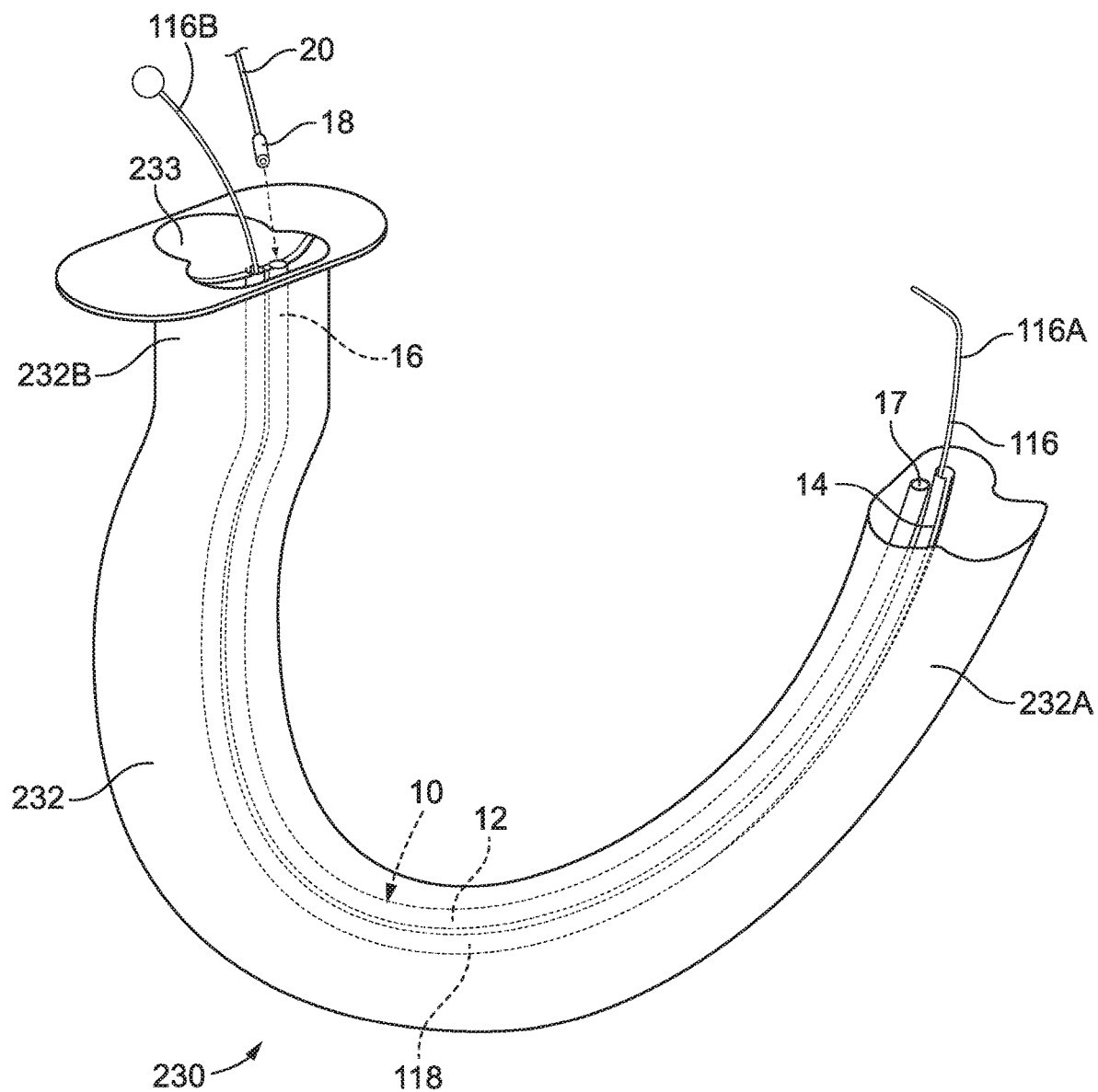

The embodiment of FIG. 16D is an intubating airway device with a visualization device, generally 230. The intubating airway device 230 comprises a tubal body 232 with a lumen 233 in which an endotracheal tube can be placed. A visualization device 10 comprises a camera tube 12 with a distal end 14 and a proximal end 16. The distal end 14 is sealed with a transparent material 17. A camera 18 is placed inside of the camera tube 12 through an opening at the proximal end 16. The camera tube 12 is placed inside the lumen 233 of the tubal body 232.

A bougie 116 is added inside of the tubal body 232 such that the bougie 116 is inserted in a tube 118 which shares the lumen with the lumen 233 along the proximal-distal (232B-232A) axis. A portion 116A of the bougie 116 protrudes outside the distal end 232A of the tubal body 232. A portion 116б of the bougie 116 protrudes outside the tubal body 232 from the proximal end 232B and over vocal cords. An endotracheal tube can be positioned inside the lumen 233 and the bougie 116 is used under constant visualization from the camera 10 to guide the placement of the endotracheal tube through patient's vocal cords. The distal end 14 of the camera tube 12 is in proximity with the distal portion 116A of the bougie 116 and therefore, the guided placement takes place under constant visualization.

Figure 16E:
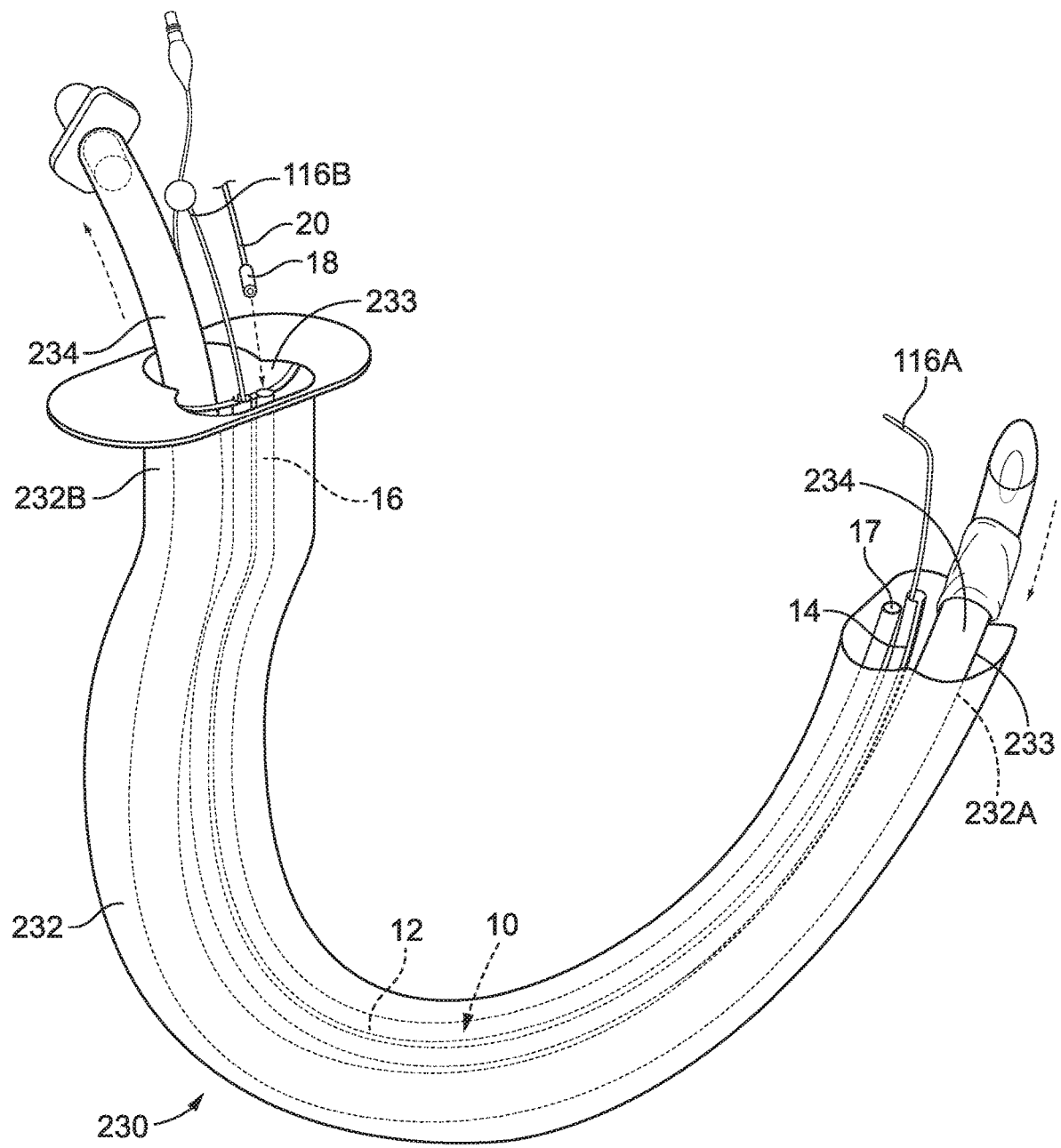
FIG. 16E is an intubating/extubating oral airway device with a main lumen as shown in FIG. 16D and into which an endotracheal tube has been placed.

FIG. 16E is the same intubating airway device with a visualization device, 230 of FIG. 16D, but with an endotracheal tube 234 inserted inside of the lumen 233 of the tubal body 232 of the intubating airway device 230. As can be appreciated from FIG. 16E, any endotracheal device can be easily inserted and removed by sliding through the lumen 233. Thus, the intubating airway device 230 can be used to intubate, extubate and reintubate under continuous visualization. The device provides continued visualization during intubation and extubation as well as during ventilation via the camera 18 in the camera tube 12. Thus, the device 230 can be used for intubating and extubating without lifting the patient's mandible, tongue or soft tissues of the oral airways and this method is one of the embodiments.

Figure 16F:
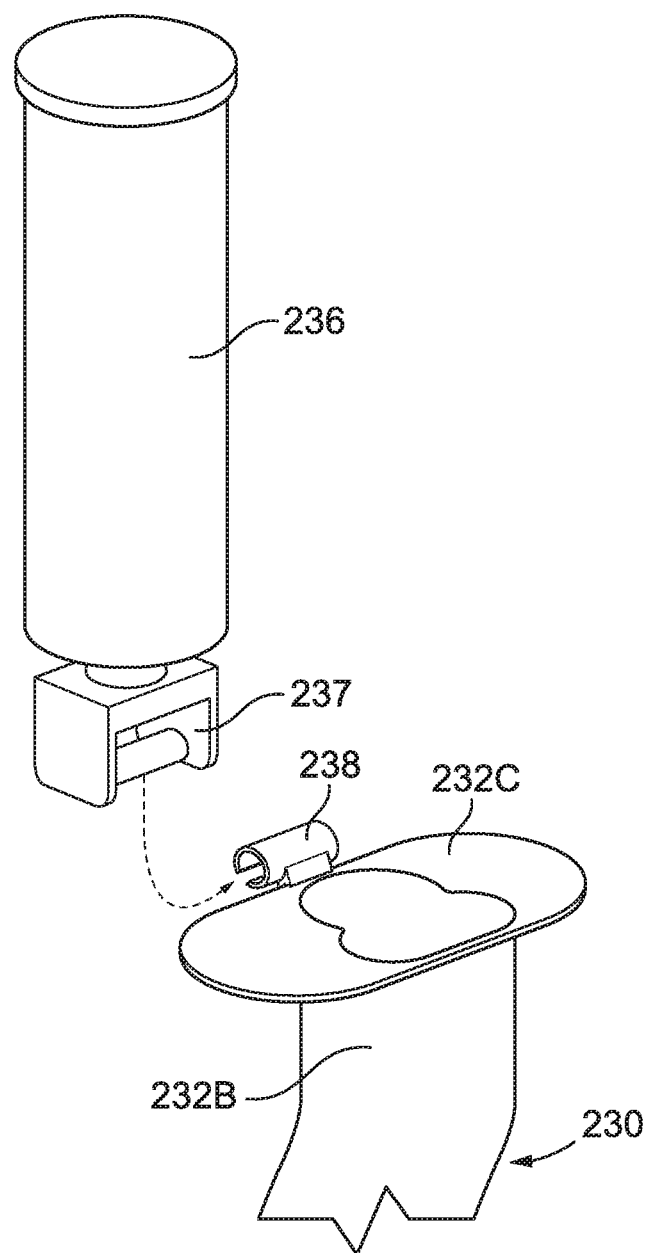
FIGS. 16F and 16G are embodiments showing a portion of an intubating/extubating oral airway device with a detachable handle which can be attached to a holder on an intubating/extubating oral airway device.
Figure 16G:
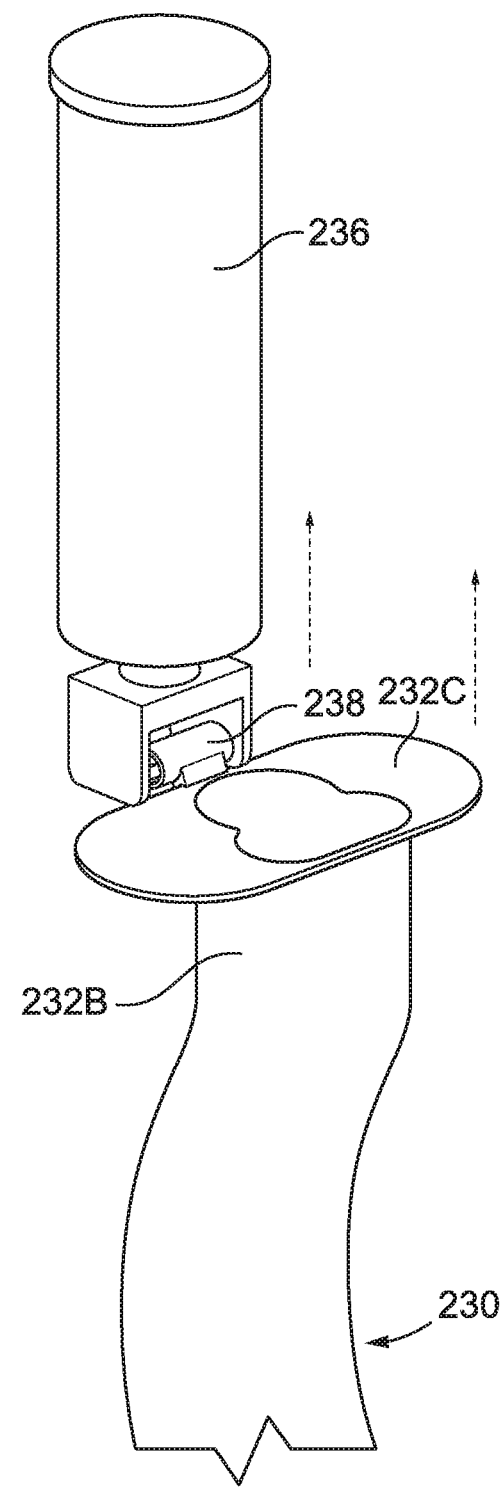

FIGS. 16F and 16G provide a further embodiment for an oral airway intubating/extubating device. As can be seen from the figures, a handle 236 can be connected to the proximal end 232B of the oral airway intubating/extubating device 230. The handle 236 can be made of any suitable sturdy material such as for example, plastic, wood or metal. The handle 236 can be of any shape and size that would provide a sufficient grip for a hand of a medical provider. In some embodiments, the handle 236 is a cylinder. In other embodiments, it can be made in any other shape suitable for gripping by a hand. On one end, the handle 236 has a means 237 for attaching to a holder 238 which is connected the proximal surface 232C of the oral airway intubating/extubating device 230, as shown in FIG. 16G. The means 237 can be made in any shape suitable for connection to the holder 238. In some embodiments, the means 237 can be in a shape of a cylinder as shown in FIG. 16F. In some embodiments, the holder 238 can be in a shape of a half-cylinder slightly bigger in diameter than the means 237 as shown in FIG. 16F such as that the means 237 fits tightly inside the holder 238.

When the handle 236 is connected to the holder 238, a medical service provider can use the handle 236 to lift the patient's mandible and tongue. Thus, intubation/extubation can be easily accomplished on any patient, including patients who are unconscious and by any medical service provider, including those who are of small physical statute. Because the handle 236 can be disconnected from the holder 238, the handle 236 can be removed after it is no longer in use. It can be reconnected with the holder 238 later if needed for further manipulations of the patient's lower jaw and/or tongue.

FIGS. 16H, and 16J-16P provide a further embodiment for an oral airway intubating/extubating device with a rotating central passageway, generally 350. The oral airway intubating/extubating device with a rotating central passageway comprises of two half-cylinders, an inner half-cylinder 351 and outer half-cylinder 352. The half-cylinder 351 is smaller in diameter and fits inside the larger half-cylinder 352 such as the inner half-cylinder 351 can slide proximally and distally inside the outer half-cylinder 352, as shown in FIG. 16J. At least in some applications, the inner half-cylinder 351 can be removed completely from the device 350, such as only the outer half-cylinder 352 remains inserted in a patient, as shown in FIG. 16H.

As can be appreciated from FIG. 16J, the inner half-cylinder 351 may be longer than the outer half-cylinder 352 and the inner half-cylinder 351 can slide distally and proximally inside the outer half-cylinder 352. As can be appreciated from FIGS. 16H and 16J, a camera tube 12 can be attached externally along the outer half-cylinder 352 in some embodiments and a camera 18 can be placed inside the camera tube 12 and provide continuous visualization during intubation and extubation.

Figure 16K:
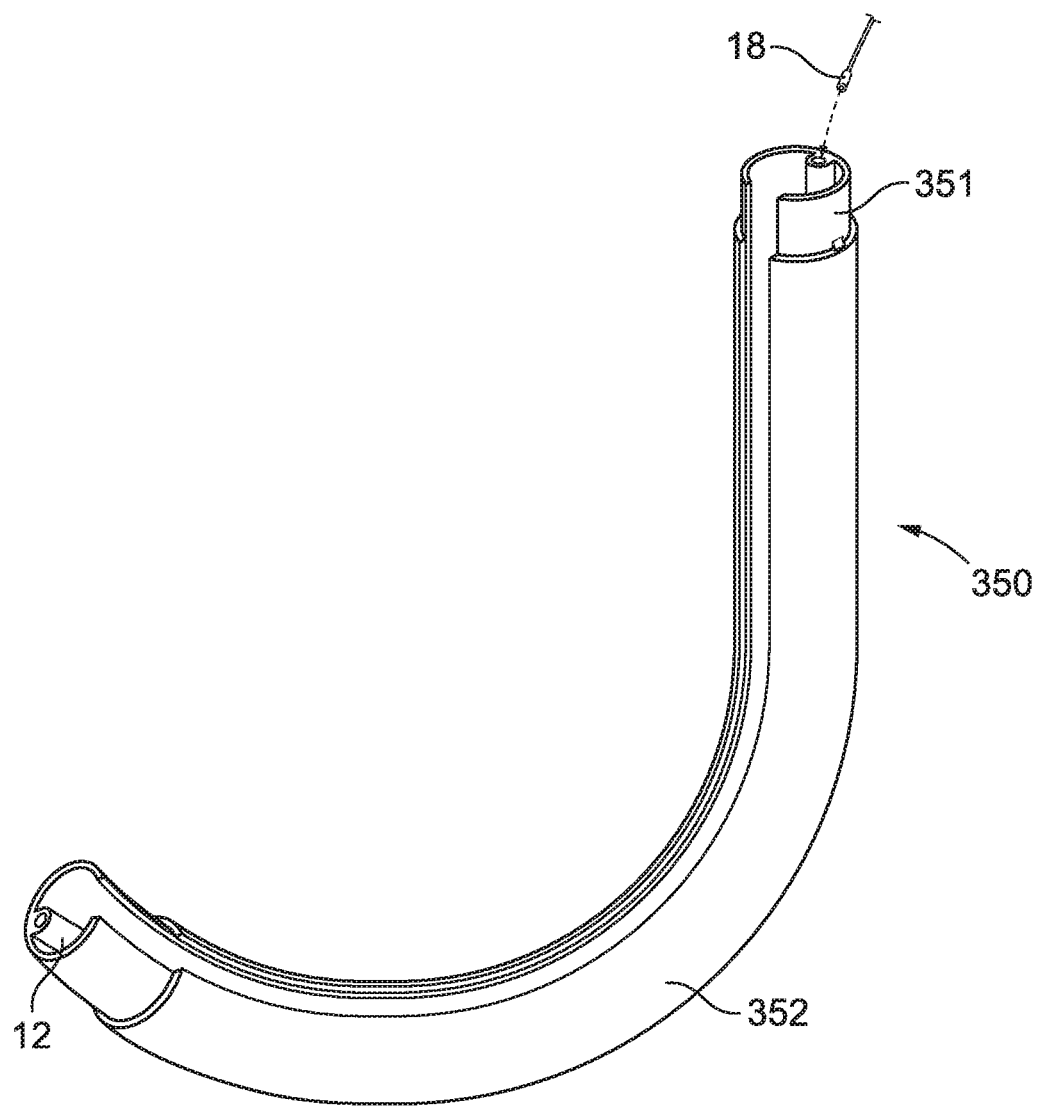

In other embodiments, the camera tube 12 can be positioned inside the inner half-cylinder 351, as shown in FIG. 16K such that the camera 18 provides continuous visualization during intubation and extubation.

As can be appreciated from FIGS. 16L-16N, the inner half-cylinder 351 can rotate inside the outer half-cylinder 352 such that the two half-cylinders may create a completely enclosed passageway as shown in FIG. 16N or the half-cylinders may create a passageway which is not fully enclosed and remains open on at least one side as shown in FIG. 16L. In some embodiments, the inner half-cylinder 351 may have at least one retractable extension 353 which when extended outside the half-cylinder 351 locks the half-cylinder 351 in a position on the half-cylinder 352 and prevents the half-cylinder 351 from sliding further distally along the outer half-cylinder 352.

Figure 16O:
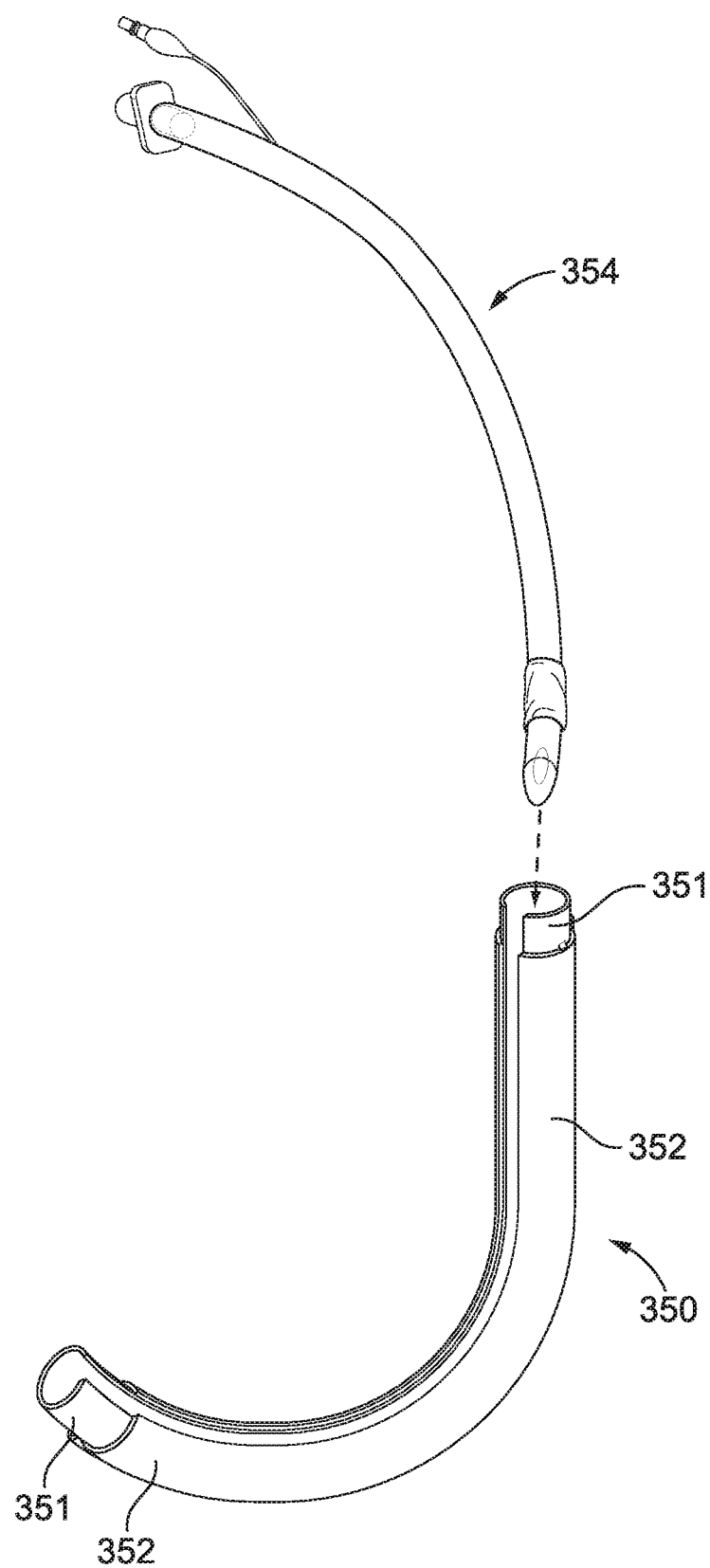
Figure 16P:
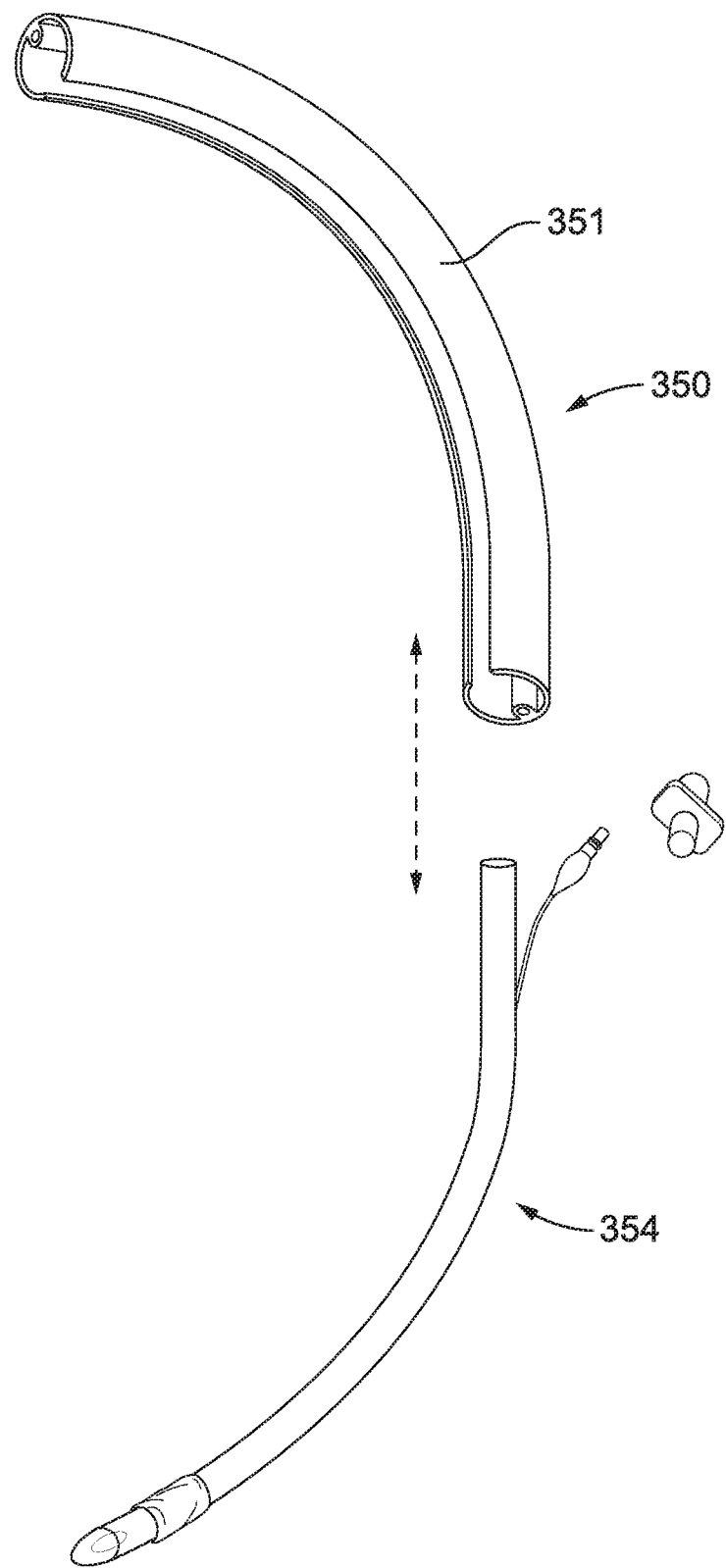

FIGS. 16O and 16P depict two different ways of inserting an endotracheal tube 354 inside the oral airway intubating/extubating device with a rotating central passageway 350. As shown in FIG. 16O, the endotracheal tube 354 can be conveniently placed inside the rotating central passageway of the oral airway intubating/extubating device 350. In alternative and as shown in FIG. 16P, the endotracheal tube 354 can be first placed inside the inner half-cylinder 351 which is then inserted insider the outer cylinder 352. This assembly permits flexibility and makes insertion of endotracheal tubes of various sizes, including small pediatric endotracheal tubes, very accurate and under constant visualization of a camera. Further and because the inner half-cylinder 351 can slide along the proximal-distal axis, the intubation can be accurate and customized for a particular patient to fit the patient's size and anatomy. Alternatively, the device 250 may be placed over the endotracheal tube 354 which is already in place in a patient in order to provide constant visualization and a conduit for extubation and possible reintubation.

Figure 17A:
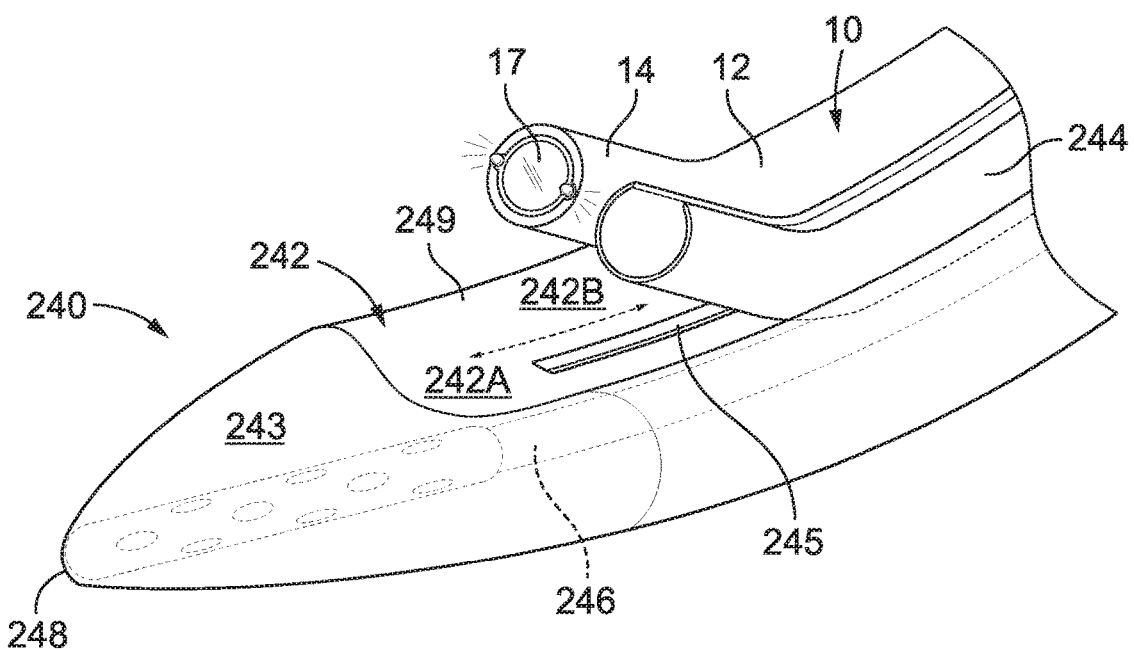
FIGS. 17A and 17B depict a side view for a supraglottic airway device equipped with a visualization device and working tube and bougie tube.

Further embodiments provide a supraglottic airway device with a visualization device. Referring to FIG. 17A, it depicts a supraglottic airway device with a visualization device, generally 240. It comprises a body 242 with a lumen 243 into which a sound-monitoring device 246 is placed. The body 242 may have a cylinder-like shape tapered at the distal end, and with the distal end the body 242 protruding with a tongue-like tip 248. At least a portion of the body 242 surface is slightly curved toward the lumen 243 and creates a surface 249. The visualization device, generally 10, comprises a camera tube 12 with a distal end 14 which is sealed with a transparent material 17, and a camera 18 which is placed inside of the camera tube 12 through an opening at the proximal end of the camera tube 12. The camera tube is positioned externally on surface 249 along the distal-proximal axis of the body 242. The camera tube 12 is connected with the surface 249 by a sliding means 245 such that the camera tube 12 can slide along the 242A-242B axis on the surface 249.

The camera 18 is placed inside of the camera tube 12 and because the camera tube 12 is sealed at the distal end 14, the camera 18 does not come in contact with a patient and the camera 18 does not need to be sterilized and it can be reused in other applications. The camera 18 is connected by electric wire 20 or wirelessly to a monitoring device. The camera 18 is not disposable and can be reused in other applications.

Figure 17B:
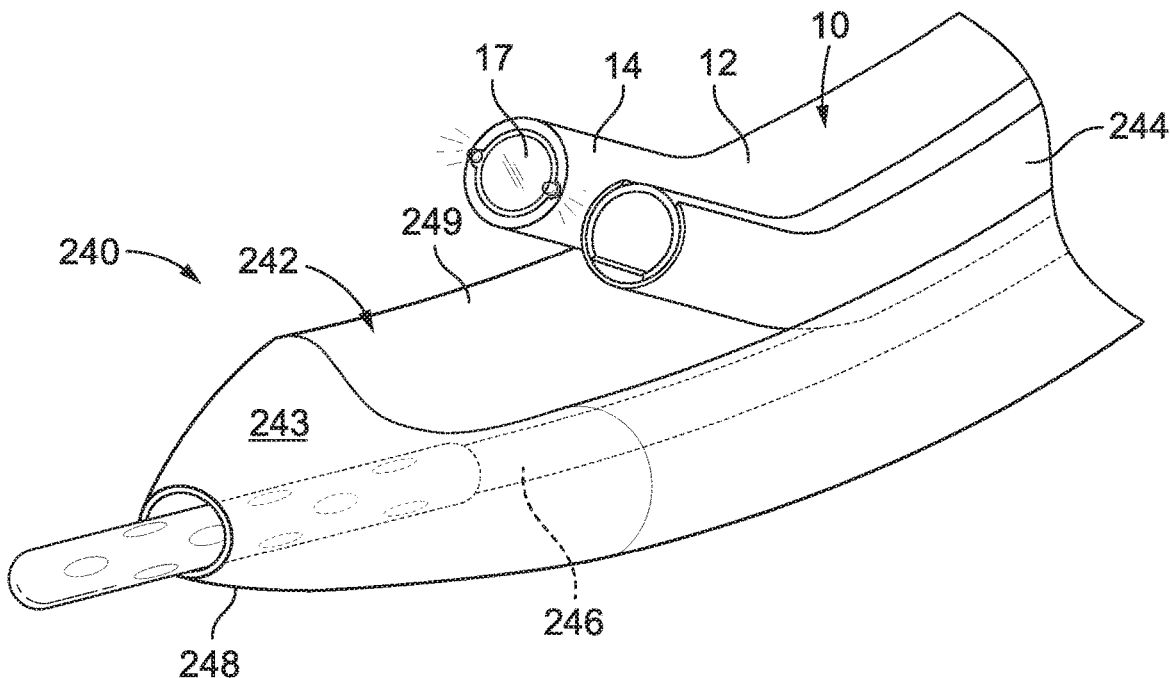

The device 240 is further equipped with a bougie tube 244 which is also located on the surface 249 and is connected to the surface 249 with a sliding means 245 such that the bougie tube 244 can slide along the 242A-242B axis. FIG. 17B provides an alternative embodiment for the device 240, in which the sound and temperature monitoring device 246 can protrude through an opening at the 248 tip.

Figure 18A:
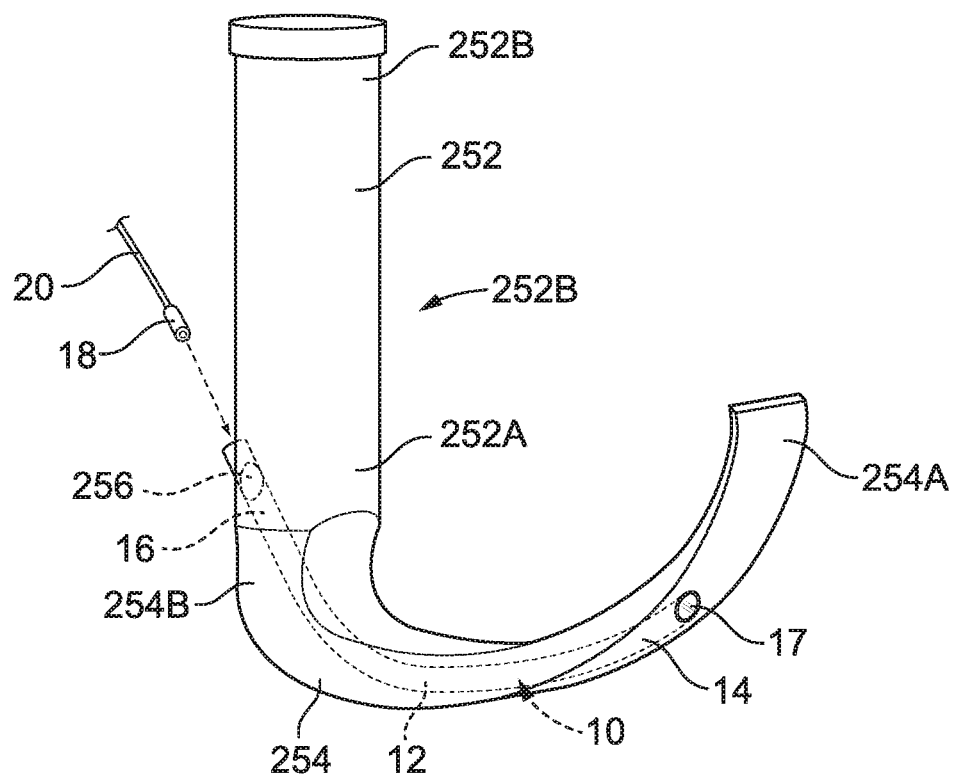
FIGS. 18A-18B depict a side view for a one-piece laryngoscope with a visualization device.
Figure 18B:
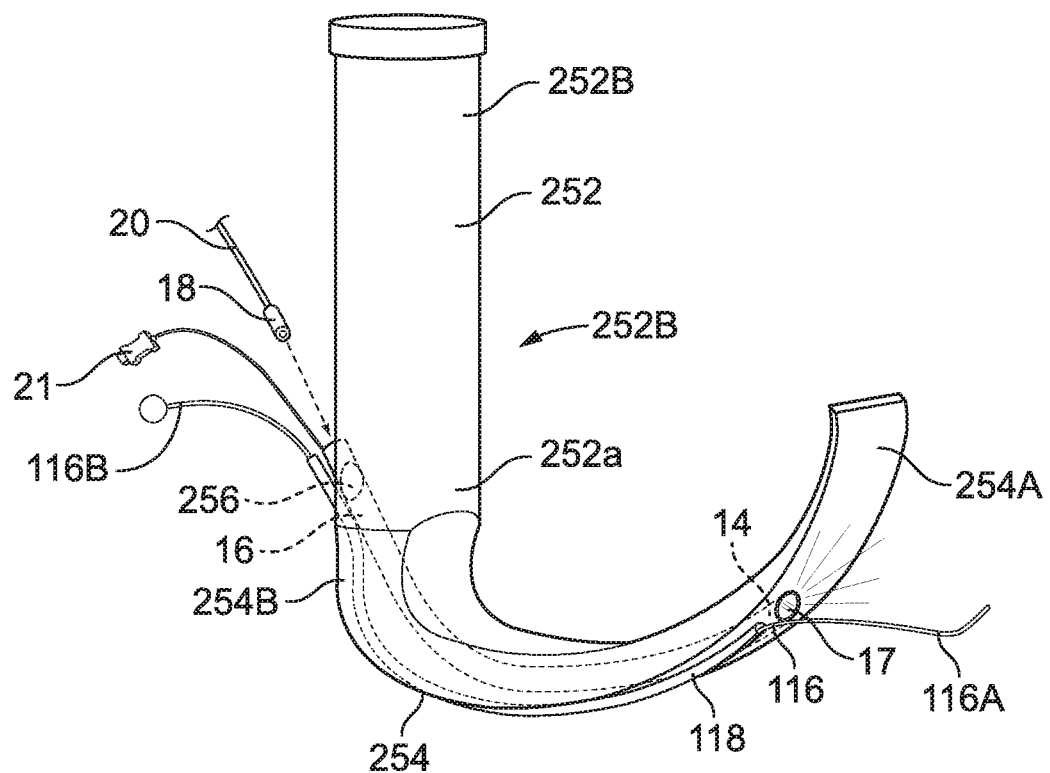

A further embodiment provides a one-piece video-laryngoscope with a visualization device, generally 250, as shown in FIGS. 18A and 18B. The video-laryngoscope 250 comprises a tubal body 252 which has a proximal end 252B and a distal end 252A. The tubal body 252 extends with a scoop-like portion 254 at the distal end 252A. The scoop-like portion 254 curves horizontally such that the distal end 254A of the scoop-like portion 254 is nearly parallel to the proximal end 254B of the scoop-like portion. The tubal body 252 has an opening 256 near its distal end 252A. A visualization device 10 which comprises a camera 18 placed inside of a camera tube 12 is placed through the opening 256 such that the distal end 14 of the camera tube 12 may be in proximity with the proximal end 254A of the scoop-like portion 254. The device can be easily inserted to an upper esophagus and visualize vocal cords.

However, the position of the distal end 14 can be adjusted as needed by sliding the camera tube 12 through the opening 256. The distal end 14 is sealed with a transparent material 17 such that the camera 18 does not come in contact with a patient's body and therefore, the camera 18 does not need to be sterilized and it can be reused in multiple applications. The camera 18 is inserted into the camera tube 12 through an opening at the proximal end 16. The camera 18 is connected to at least one monitoring device either by electrical wire 20 or wirelessly.

The embodiment of FIG. 18B is the same as that of FIG. 18A, except a light source 21 is added to the visualization device 10 as described in connection with the light source 21 in other medical devices above. A bougie 116 in a tube 118 is also added through the opening 256, and the distal end 116A of the bougie 116 can be manipulated at the proximal end 116B such that the placement of the device 250 is guided under continuous visualization with the camera 18.

Figure 19:
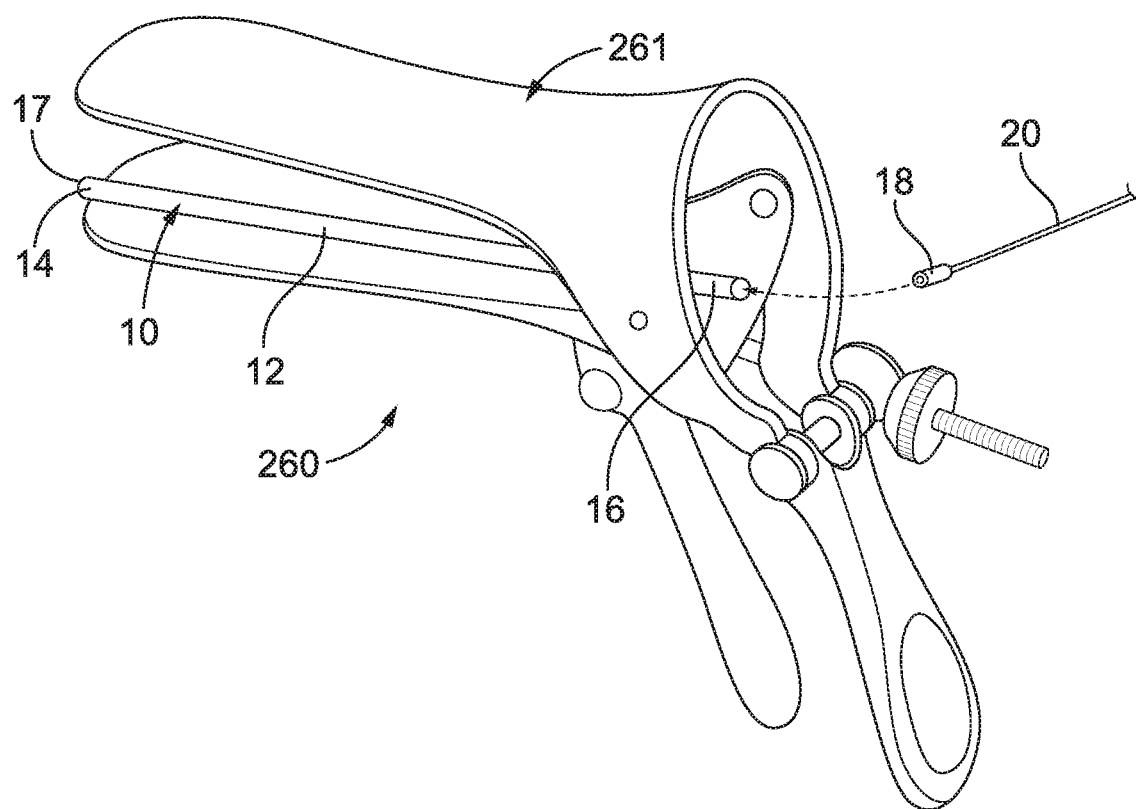
FIG. 19 depicts a side view of a speculum with a visualization device.

A further embodiment includes a vaginal speculum with visualization device, generally 260 as shown in FIG. 19. Any speculum 261, including disposable, generally known and used for a pelvic exam can be equipped with a visualization device, generally 10, which comprises a camera 18 placed inside of a camera tube 12. The camera tube 12 can be attached to the speculum 261 or to some other instrument. The camera 18 is placed in the camera tube 12 through an opening at a proximal end 16 and is moved all the way toward the distal end 14 which is sealed with a transparent material 17. The camera 18 connected to at least one monitoring device by electric wire 20 or the camera 18 can be connected wirelessly.

Further embodiments relate to various tubing equipped with a visualization device shown in FIG. 1A and as described in more detail below.

Figure 20A:
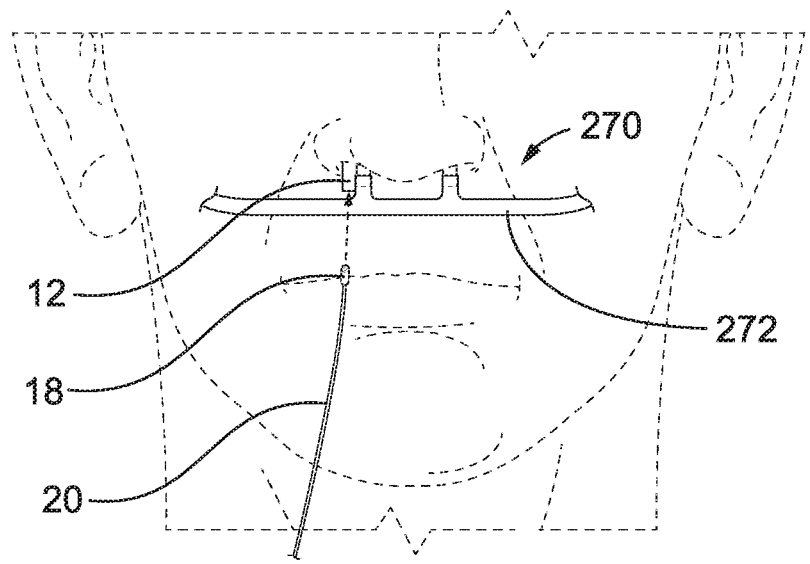

FIGS. 20A-20F refer to various embodiments for a nasal cannula with a visualization device, generally 270. FIG. 20A shows the positioning of a nasal cannula 272 on patient's head with a visualization device 10 added to one of the two nostril tubes. The nasal cannula 272 can be any nasal cannula known in the art and used by medical practitioners. The visualization device 10 is as described in connection with FIG. 1A and comprises a camera 18 inserted inside of a camera tube 12. The camera tube 12 is sealed or otherwise attached externally along at least one nostril tube 274 of the nasal cannula 272 as shown in more detail in FIG. 20C. This nasal cannula with the visualization device 10 provides continuous visualization of vocal cords, upper esophagus. The cannula can be used to determine whether vocal cords are moving correctly, if there is any abnormal anatomy and the color of the patient's tissues.

As shown in FIG. 20E, the nasal cannula with the visualization device can be properly positioned through patient's nostrils as the positioning is guided and constantly visualized with the camera device 10. The distal end 14 of the camera tube 12 aligns with the distal end of at least one nostril tube 274. As shown in FIG. 20F, the nasal cannula with the visualization device can be further equipped with an external stethoscope 275, which can be placed on patient's chest externally and monitors breathing and heart-beat sounds.

Figure 20B:
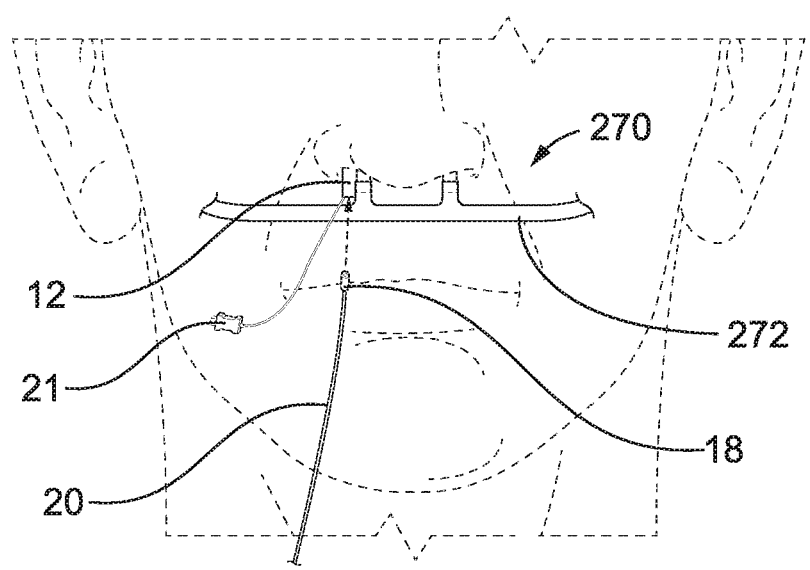
Figure 20C:
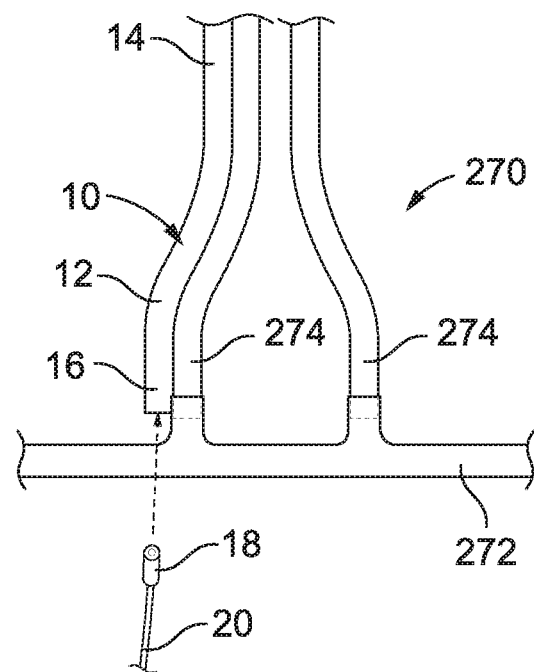
Figure 20D:
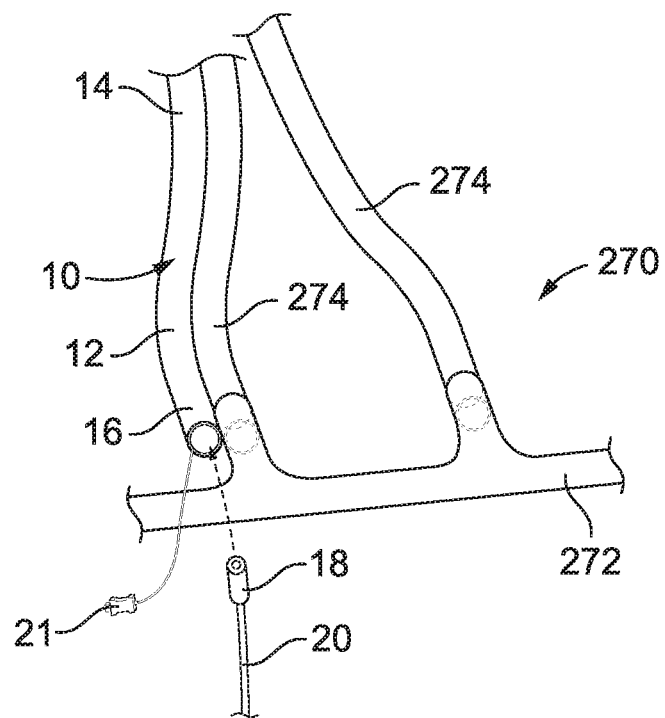

FIGS. 20B and 20D show the same embodiment as in FIGS. 20A and 20C, except the visualization device 10 is equipped with a light source 21 as was described in connection with the light source 21 in other embodiments.

Figure 21:
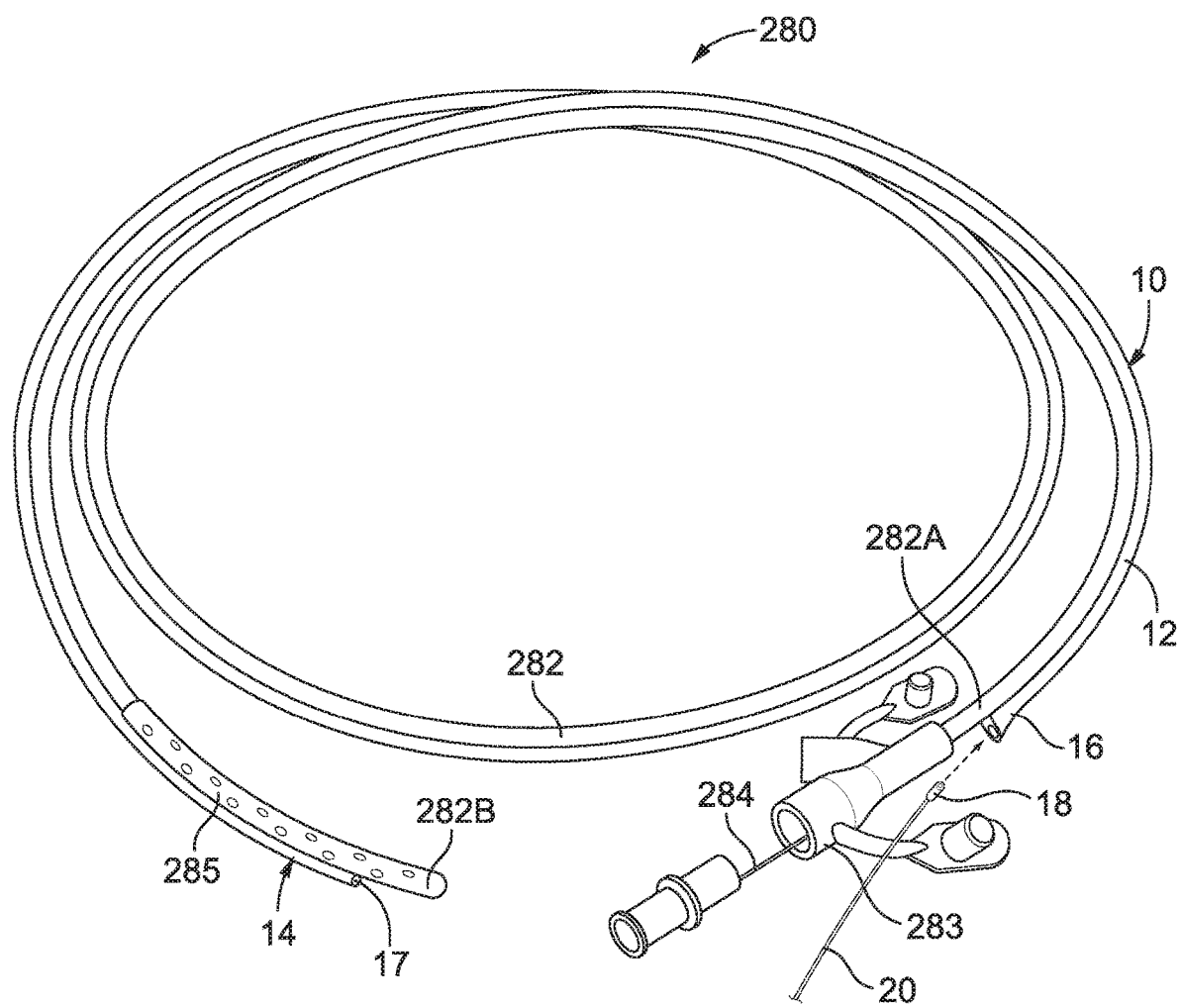
FIG. 21 is a feeding tube equipped with a visualization device.

A further embodiment includes a feeding tube with a visualization device, generally 280, as shown in FIG. 21. A visualization device, generally 10, is sealed or otherwise attached externally along the proximal-distal (282A-282B) axis of a feeding tube 282. The visualization device 10 is essentially the same as described in connection with FIG. 1A and other embodiments above. It comprises a camera tube 12 with a proximal end 16 and a distal end 14. A camera 18 with wire 20 is inserted into the camera tube 12 through an opening at the proximal end 16 and is slid all the way to the distal end 14 which is sealed with a transparent material 17. The camera 18 does not come in contact with a patient's body and can be reused in multiple devices. Any feeding tubes known in the art can be used in this embodiment, including a feeding tube with a stylet 284 as shown in FIG. 21. The feeding tube 282 can be equipped with an adaptor 283 at the proximal end 282A. The feeding tube 282 may further comprise a plurality of holes 285 at the distal end 282B for food distribution.

Figure 22A:
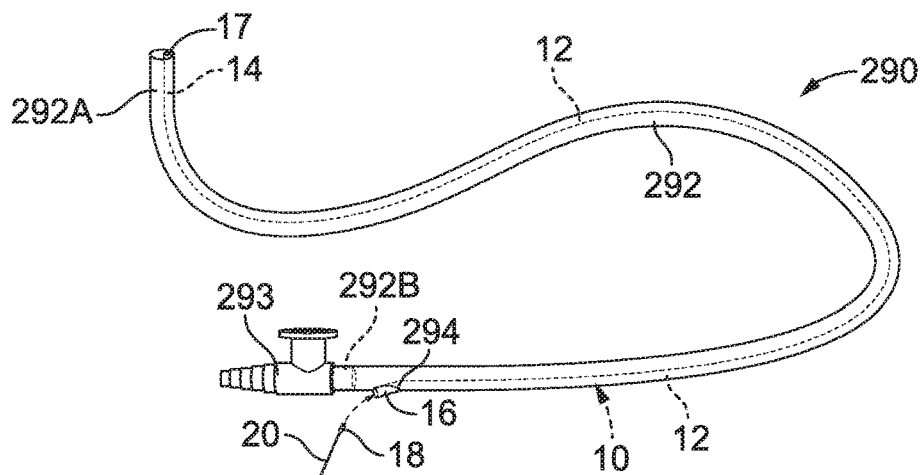
FIG. 22A, 22B, 22C depict various embodiments of a suction tube equipped with a visualization device.
Figure 22B:
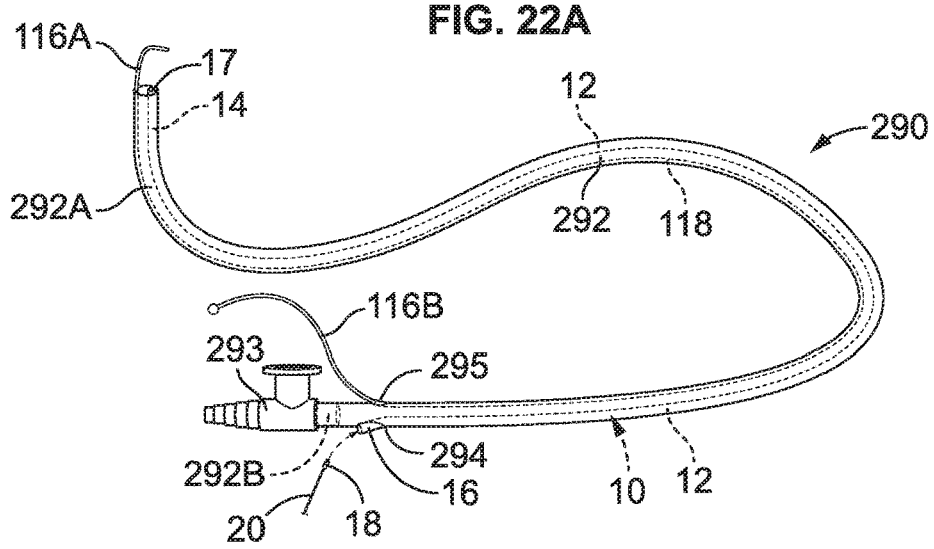
Figure 22C:
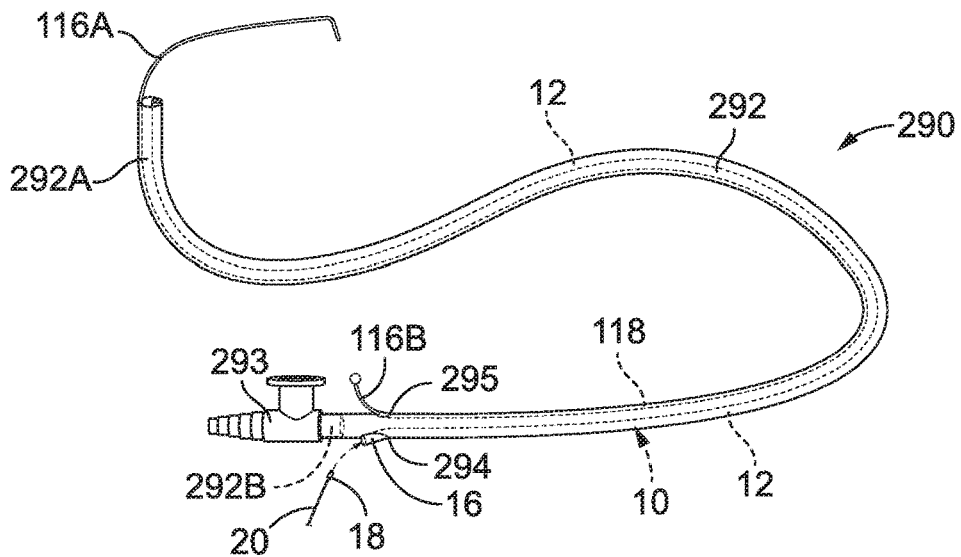

Further embodiments provide various suction tubes equipped with a visualization device, generally 290, as shown in FIGS. 22A, 22B and 22C. Any suction tube including but not limited to the nasal gastric tubes known in the art can be used and in general a suction tube 292 with an adaptor 293 at a proximal end 292B is suitable, as shown in FIG. 22A. A visualization device, generally 10, comprises a camera tube 12 and a camera 18 with wire 20. The camera 18 is inserted into the camera tube 12 through an opening at a proximal end 16 and is slid all the way to the distal end 14 of the camera tube 12. The distal end 14 is sealed with a transparent material 17. The camera 18 can transmit information to a remote location.

The camera tube 12 is placed inside of the suction tube 292 through an opening 294 at the proximal end 292B of the suction tube 292. The camera tube 12 is then aligned with the length of the suction tube 292 such that the distal end 14 of the camera tube 12 is in close proximity with the distal end 292A of the suction tube 292.

FIGS. 22B and 22C is a further embodiment of a suction tube with a visualization device, generally 290 as shown in FIG. 22A, but it is further equipped with a bougie 116 placed inside of a tube 118 which is placed inside of the suction tube 292 through an opening 295. A distal end 116A of the bougie 116 can protrude outside the distal end 292A of the suction tube 292 and can be manipulated by a medical practitioner with a proximal end 116B which protrudes outside a patient such as the placement of the suction tube 292 is guided under constant visualization with the camera 18 through the distal end 14 of the camera tube 12. The bougie 116 under constant visualization from the camera 12 permits rapid and accurate placement of the device 290 in a patient. The bougie 116 can be used to guide the placement of the device 290 and moving it left or right in the trachea.

Figure 23:
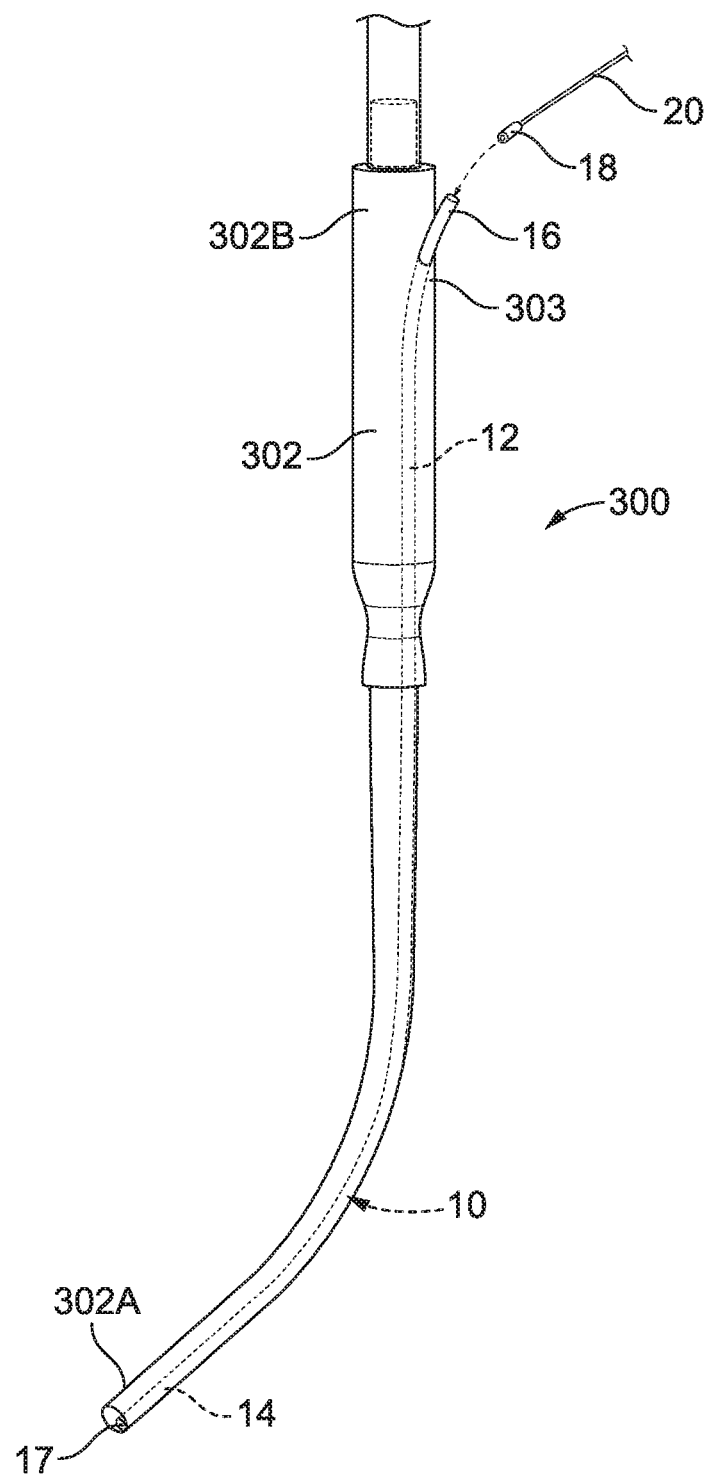
FIG. 23 depicts a suction catheter equipped with a visualization device.

Referring to FIG. 23, this embodiment provides a suction catheter with a visualization device, generally 300. The suction catheter 302 is not flexible and can be any suction catheter known in the art. A visualization device, generally 10, is positioned inside the suction catheter 302 through an opening 303 which is in near proximity with a proximal end 302B of the suction catheter 302. The visualization device 10 comprises a camera 18 with wire 20 which is placed inside of a camera tube 12 through an opening at a proximal end 16 of the camera tube 12 and then the camera 18 is slid to the distal end 14 which is sealed with a transparent material 17. The distal end 14 of the camera tube 12 is aligned with the distal end 302A of the suction catheter 302, while the proximal end 16 of the camera tube 12 protrudes outside the patient's body such as the camera 18 can be pulled out from the camera tube 12 as needed. In other embodiments, the suction tube is placed externally and this combination can work with suction caps.

Figure 24:
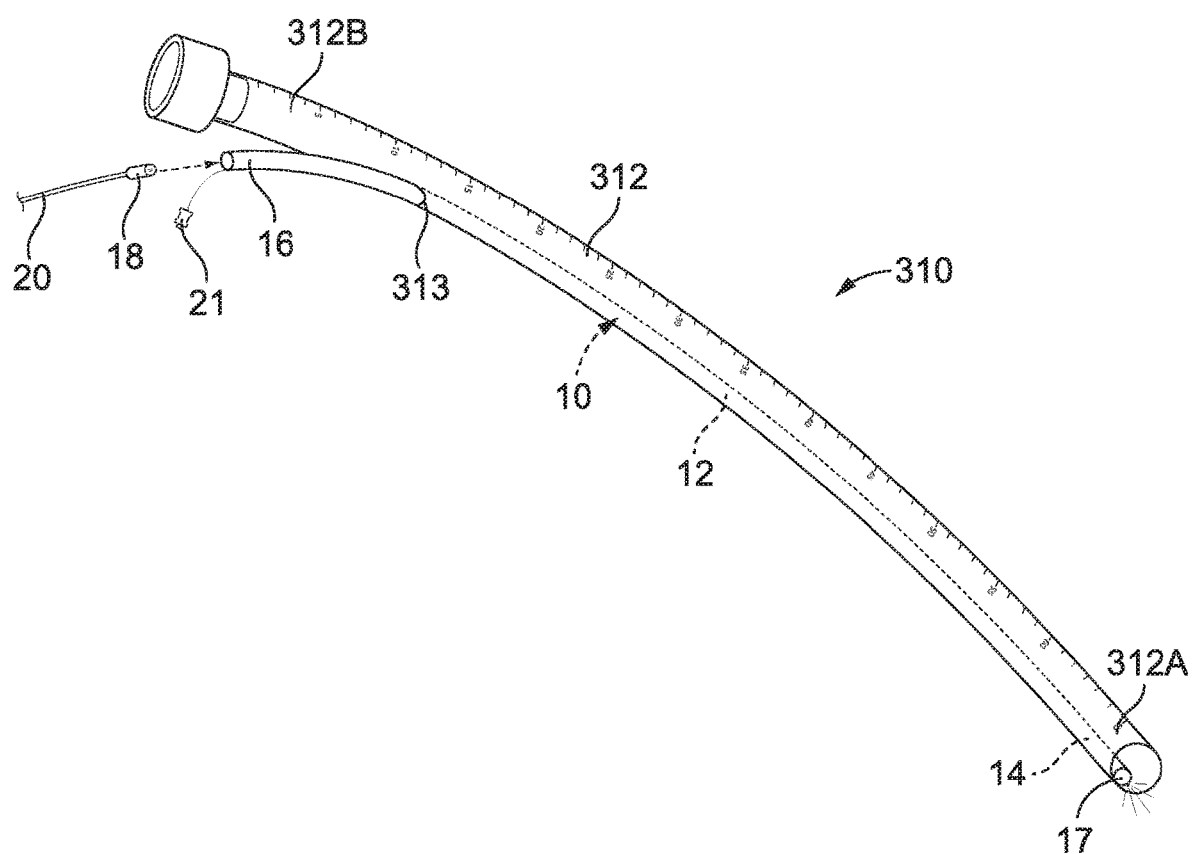
FIG. 24 depicts an endotracheal changing tube equipped with a visualization device.

Referring to FIG. 24, this embodiment provides an endotracheal changing tube with a visualization device, generally 310. An endotracheal changing tube can be any endotracheal changing tube as known in the art. A visualization device, generally 10, comprises a camera 18 with wire 20 which is placed inside of a camera tube 12 through an opening at a proximal end 16 of the camera tube 12 and slid all the way to a distal end 14 of the camera tube 12. The distal end 14 is sealed with a transparent material 17. The visualization device 10 is placed inside of the endotracheal changing tube 312 through an opening 313 in the changing tube 312 such as the camera tube 12 is aligned with the changing tube 312 along the proximal-distal (312B-312A) axis, and the distal end 14 of the camera tube 12 is in close proximity with the distal end 312A of the changing tube 312. In other embodiments, the camera tube 12 can be placed outside of the endotracheal changing tube or it can be fitted externally onto an endotracheal changing tube known in the art.

Further embodiments include a supraglottic ventilating tube with camera, generally 360 as shown in FIGS. 25A-25D. As can be appreciated from FIG. 25A, the device 360 comprises a tube 361 with the distal end 361A and the proximal end 361B. The device 360 is equipped with a visualization device 10 as described in connection with FIGS. 1A, 1B and 1C and which comprises a camera tube 12 attached externally to the device 360. A disposable camera 18 can be inserted into the camera tube 12 along with a light source 362. In proximity to the distal end 361A, the device 360 comprises an inflatable cuff 364 which wraps around the tube 361. The cuff 364 can be inflated with a means 366 after the esophageal camera tube is positioned in a patient.

Figures 25A, 25B:
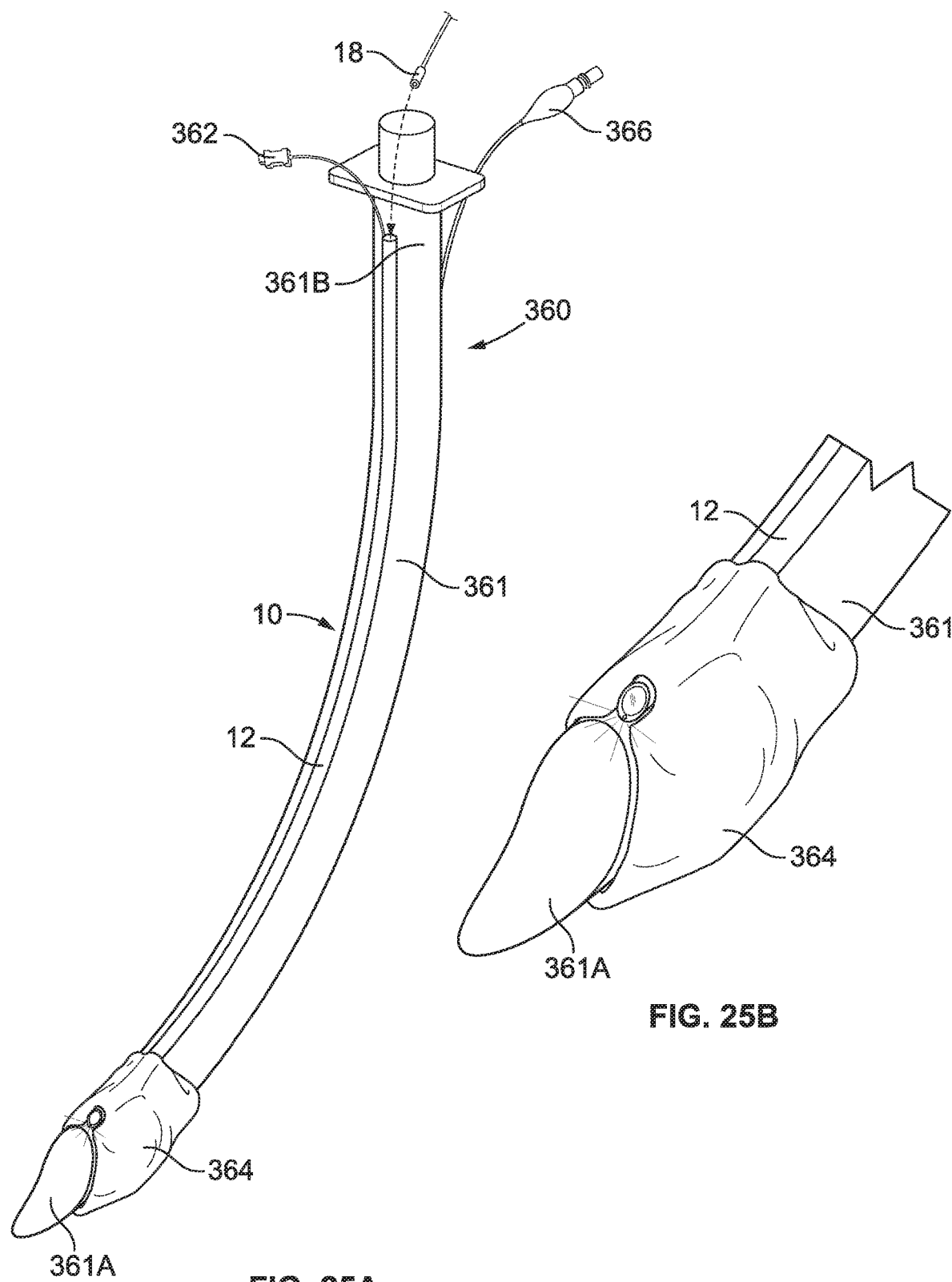
FIGS. 25A-25D depict a supraglottic ventilating tube with camera.

As can be appreciated from FIG. 25B, the camera tube 18 is positioned under the cuff 364 such that the cuff 364 wraps over the camera tube 12. The camera tube 12 can slide along the tube 361 such that images with the camera 18 can be taken either proximally or distally from the cuff 364 after the cuff 364 is inflated in the patient.

Figure 25C:
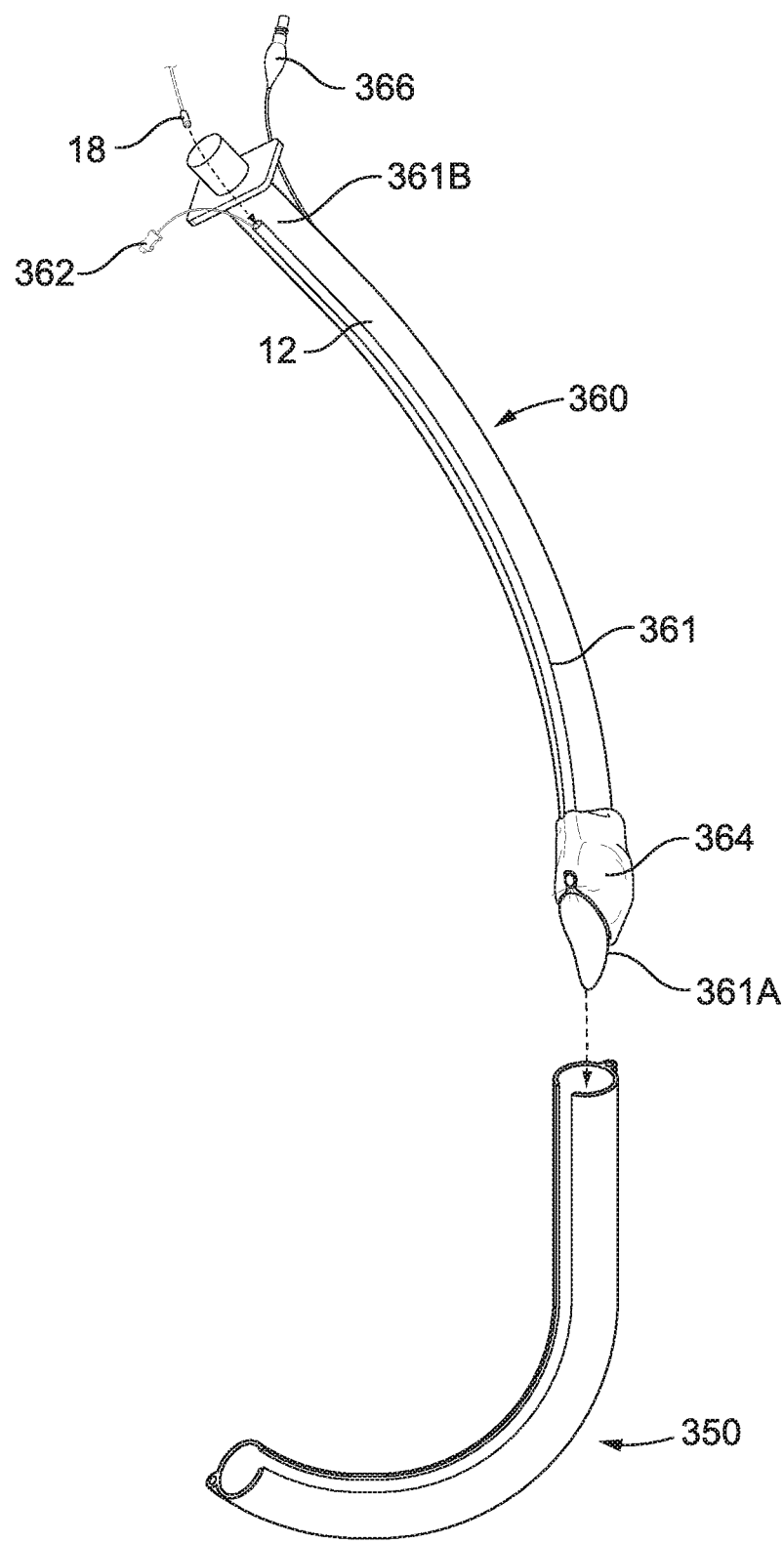
Figure 25D:
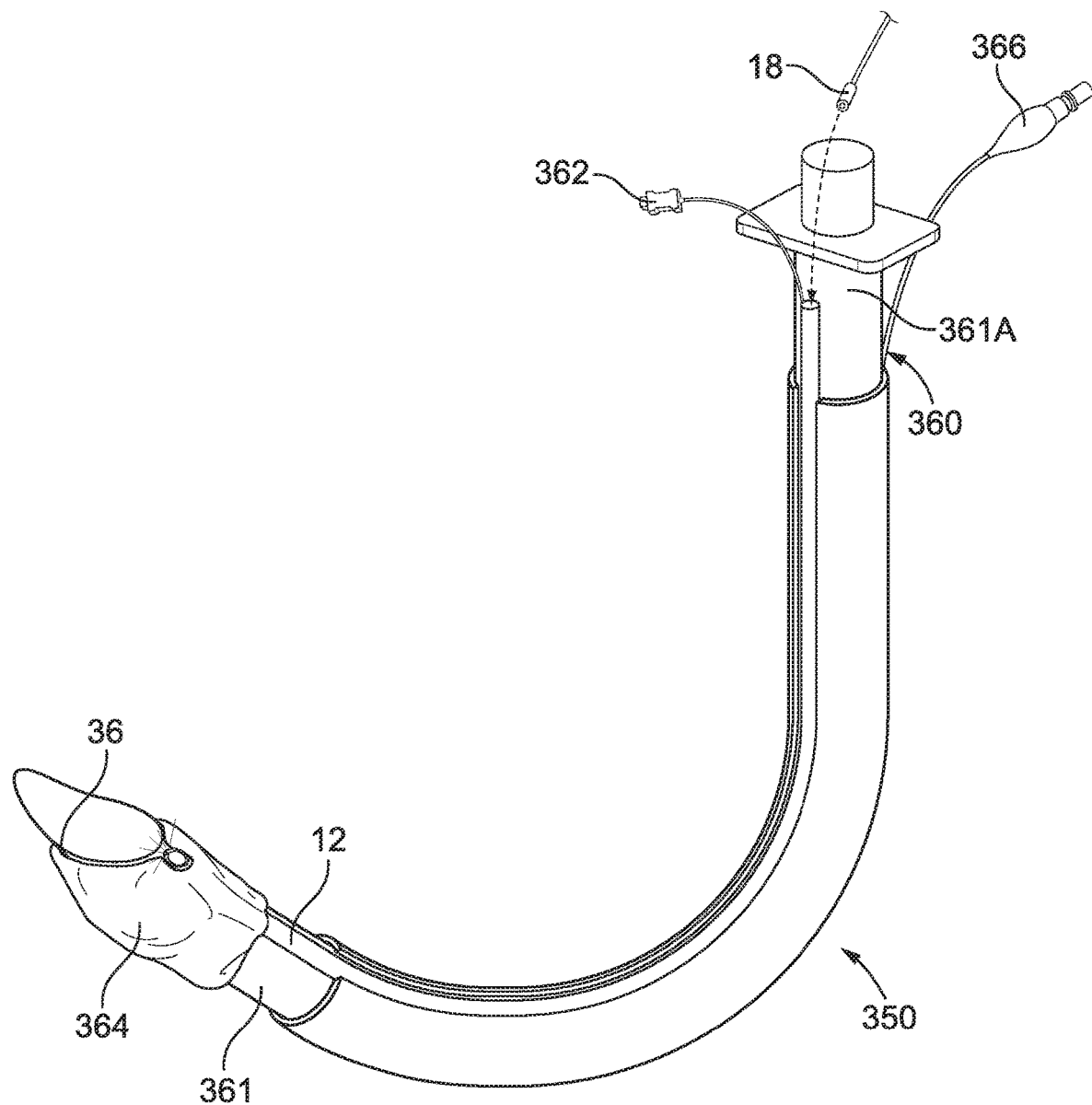

As shown in FIGS. 25C and 25D, the device 360 can be placed inside the intubating/extubating oral airway device 350, including the intubating/extubating oral airway device 350 shown in FIGS. 16H, and 16J-16K. As can be appreciated from FIG. 25D, the device 360 can be easily inserted into a patient with help of the intubating/extubating oral airway device 350. Supraglottic ventilating tube can be positioned under the direct and continuous visualization into patient's hypopharynx. The device 350 can be removed after the insertion is completed.

Figure 26A:
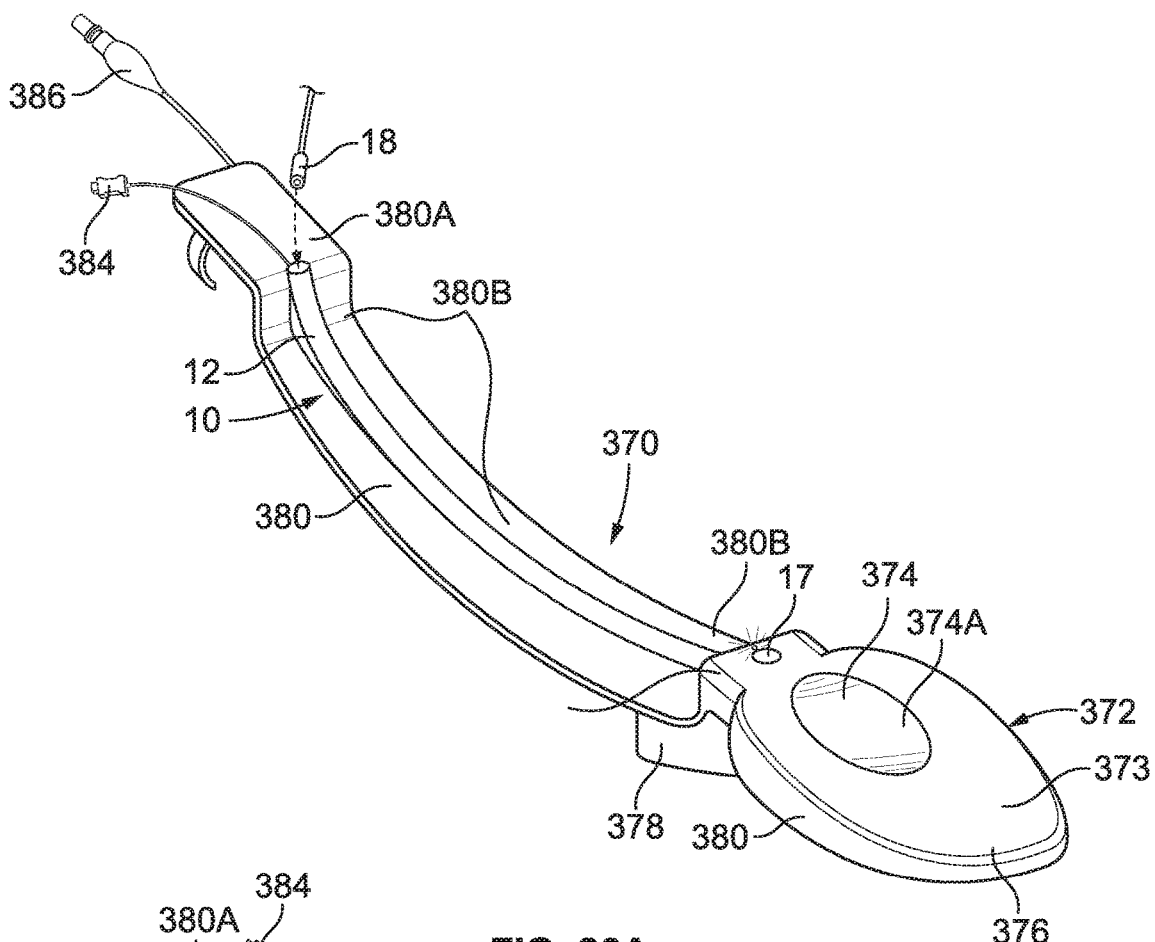
FIGS. 26A-26J depict a tubeless intubating device.
Figure 26B:
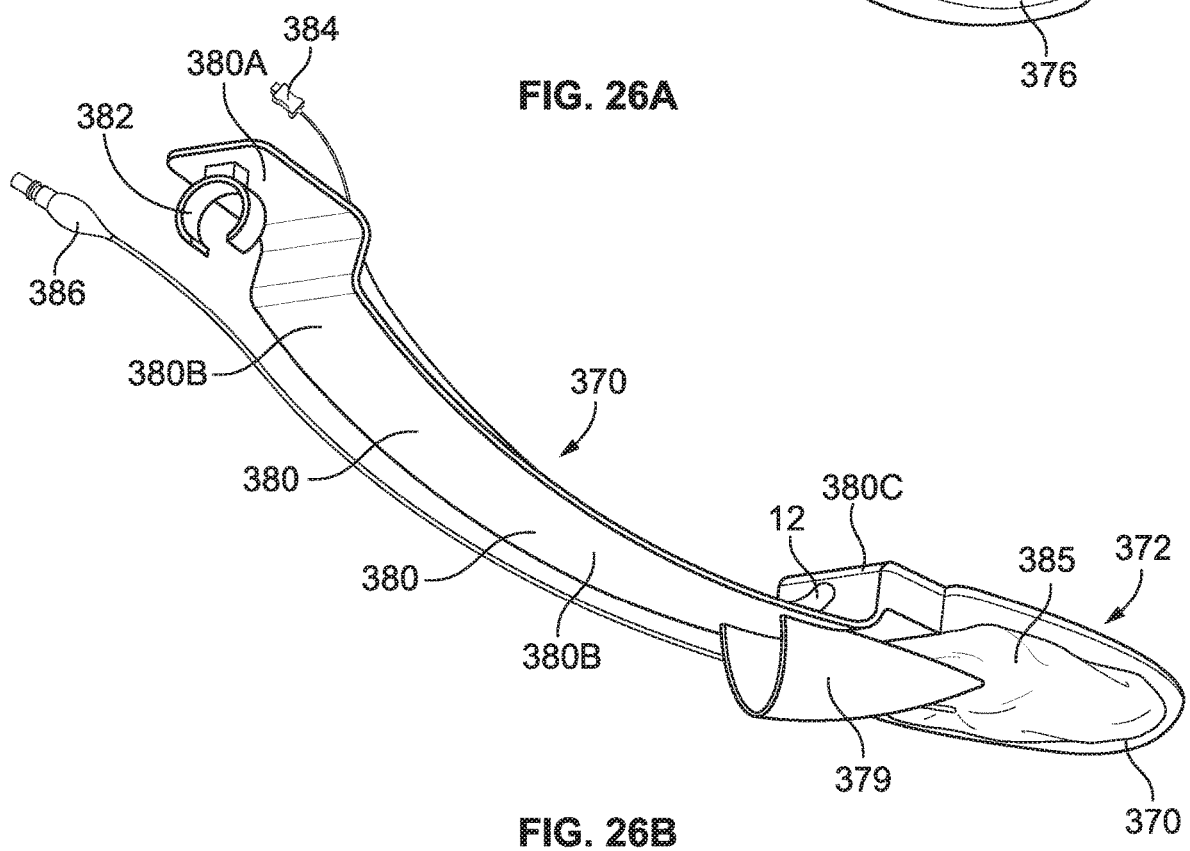

Further embodiments provide a tubeless intubating device shown in FIGS. 26A-26J, generally 370. The tubeless intubating device 370 has the upper surface shown in FIG. 26A and the bottom surface shown in FIG. 26B. The tubeless intubating device 370 comprises an ellipsoid body 372 which has an upper oval surface 373 with a lumen opening 374A on the upper oval surface 373 of the ellipsoid body 372 as shown in FIG. 26A. The upper oval surface 373 is connected to the bottom half-ellipsoid surface 378 as shown in FIG. 26A and FIG. 26B such that the distal end 376 of the ellipsoid body 372 is tapered because the bottom half-ellipsoid surface 378 is tapered at the distal end 376. The ellipsoid body 372 encloses a lumen 374 which opens onto the upper oval surface 373 with the lumen opening 374A. The lumen 374 opens on the proximal side of the bottom half-ellipsoid surface 378 with a canal 379 which connects to the bottom half-ellipsoid surface 378 and extends beneath the bottom half-ellipsoid surface 378. The bottom half-ellipsoid surface 378 also connects to a handle 380.

The handle 380 comprises three parts connected together: the proximal part 380A, the middle part 380B and the distal part 380C. The proximal part 380A may be made in flat rectangle shape with a ring-holder 382 attached on the bottom surface of the proximal part 380A. The 380A part bends down at about a 90 degree angle at its distal part where it connects to the middle part 380B. The middle part 380B is also of flat rectangle shape and may vary in length. As can be seen from FIG. 26B, the canal 379 is connected to the bottom surface of the middle part 380B at the distal portion of the middle part 380B. The middle part 380B connects to the distal part 380C at its distal end. The middle part 380B bends up at about a 90-degree angle at the distal part and connects to the distal part 380C. The distal part 380C connects by its distal end to the oval upper surface 373 of the ellipsoid body 372.

A visualization device, generally 10, comprising the camera tube 12 and camera 18 which can be inserted into the camera tube 12, is attached to the handle 380 on its upper surface such as the visualization device 10 extends along the handle 380 from its proximal end 380A at which the camera 18 is inserted insider the camera tube 12 and all the way into the distal portion 380C. Just like in other embodiments, the camera tube 12 is sealed with a transparent material 17 at its distal end such as the camera 18 does not come into direct contact with the patient's body and can be reused. Just like in other embodiments, the camera tube 18 can slide along the proximal-distal axis of the handle 380. The visualization device 10 may further comprise a light source 384 which can be inserted into the camera tube 12 along with the camera 18. In some embodiments the ellipsoid body 372 can comprise an inflatable cuff 385 which can be inflated with a means 386.

In some embodiments, the handle 380 can be made of flexible material. In other embodiments, the tubeless intubating device 370 can be designed without the cuff 385. In some embodiments, the camera tube 12 is fixed to the handle 380. In some embodiments, the camera tube 12 includes a light source. In other embodiments, the camera tube 12 has no additional light source.

The tubeless intubating device 370 can be used for intubating a patient with an endotracheal tube of any size under continuous visualization of the camera 18. The tubeless intubating device 370 can be also used for extubation and for reintubation of a patient. It can also act as a supraglottic device with an endotracheal tube inflated with the cuff 385.

Figure 26C:
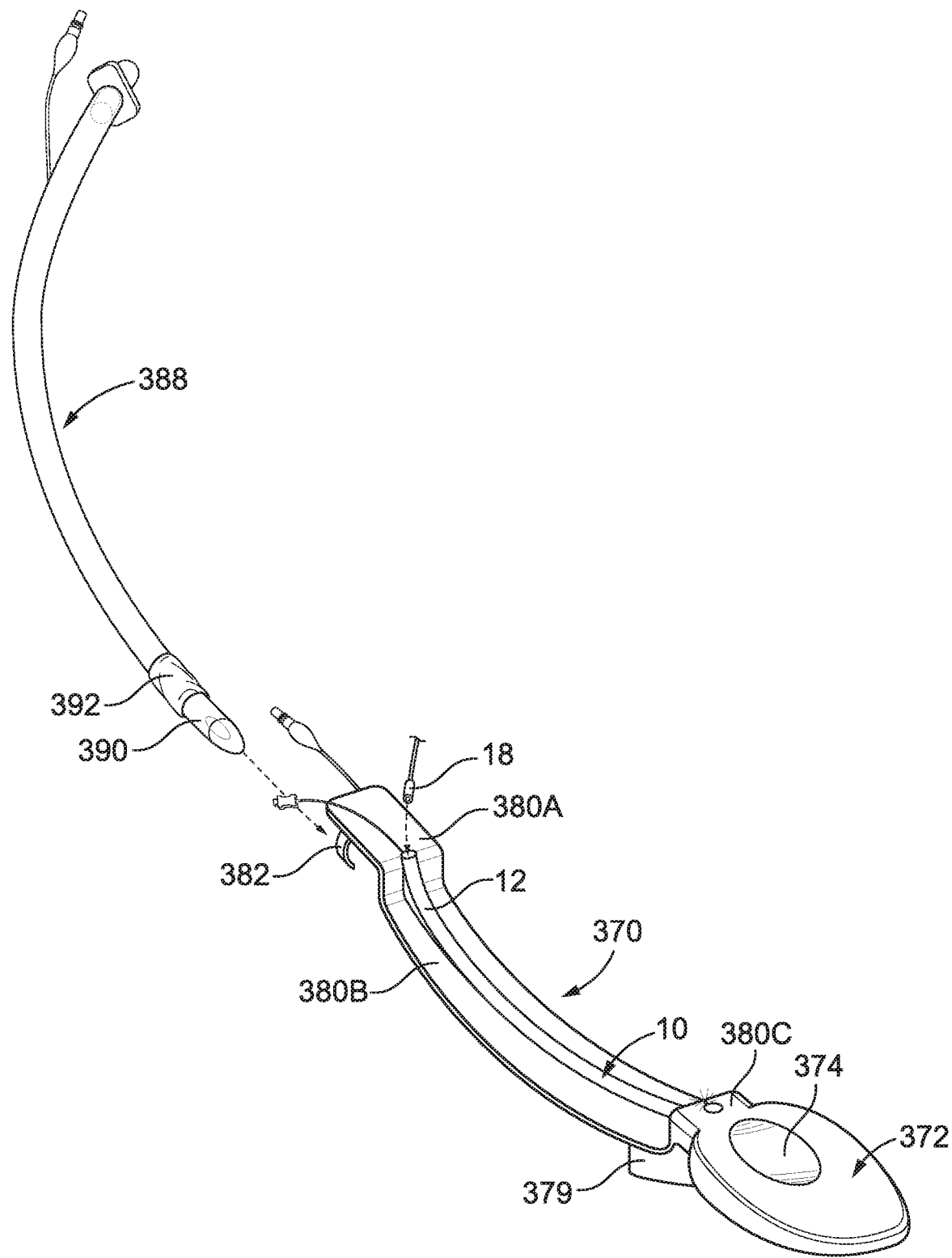

As shown in FIG. 26C, an endotracheal tube 388 can be loaded onto the tubeless intubating device 370 such that the proximal end of the endotracheal tube 388 is secured on the tubeless intubating device 370 with the ring holder 382. It will be appreciated that any endotracheal tube can be loaded into the device 370 and inserted into a patient. As can be seen in FIG. 26C, the endotracheal tube 388 in this embodiment is equipped with a cuff 390. The endotracheal tube cuff 390 can be inflated after it is loaded into the device 370 and secured in place with the ring holder 382. It will be appreciated that the embodiments of the device 370 shown in FIGS. 26A-26C are equipped with the cuff 385 and the cuff 385 of the structure can be inflated in the hypopharynx.

Figure 26D:
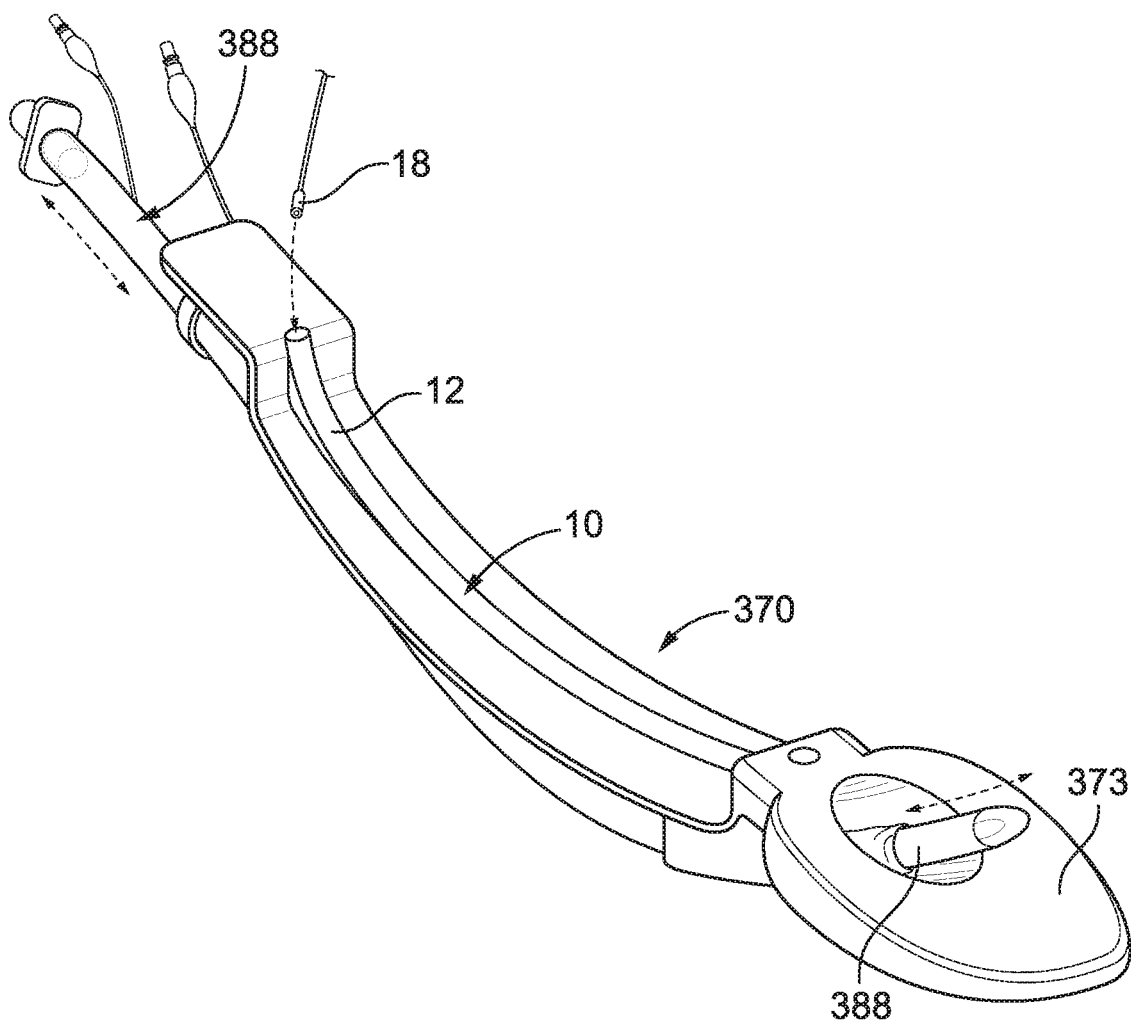
Figure 26E:
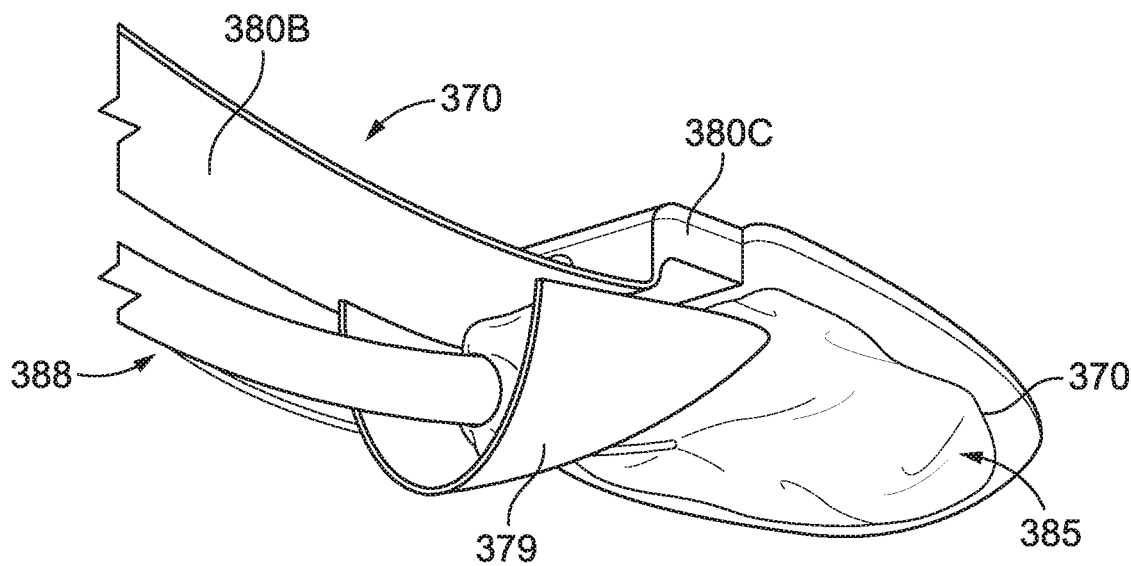

The distal end of the endotracheal tube 388 is then passed through the canal 379 and through the lumen 374 such that the distal end of the endotracheal tube 388 protrudes from the lumen opening 374A on the upper oval surface of the ellipsoid body 372, as shown in FIGS. 26D and 26E. The endotracheal tube 388 can slide along the proximal-dorsal axis of the tubeless intubating device 370 such that a longer or shorter portion of the endotracheal tube 388 protrudes from the lumen opening 374A.

Figure 26F:
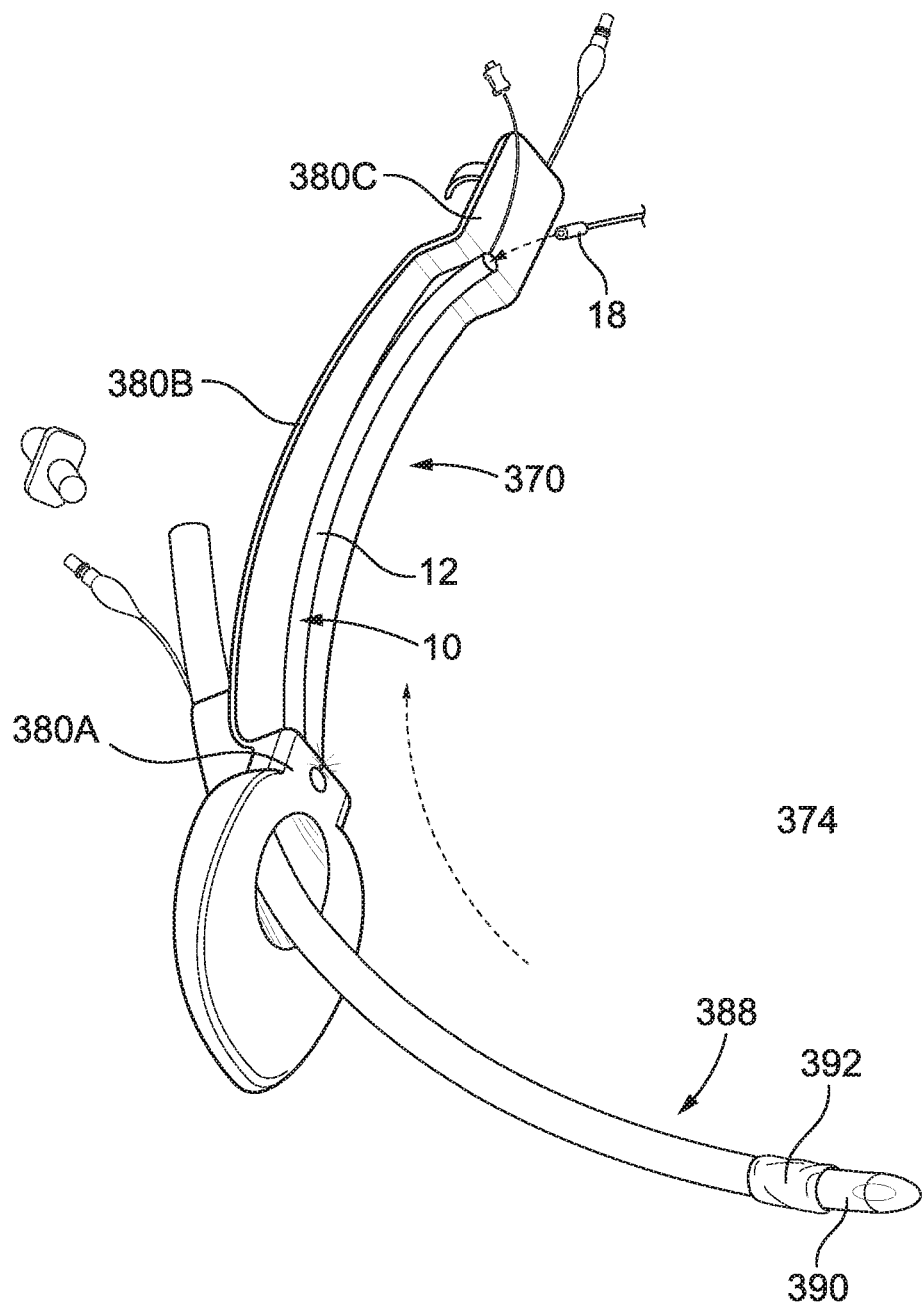

As can be further appreciated from FIG. 26F, after the tubeless intubating device 370 delivers and assists in placing the endotracheal tube 388 in the patient under direct and continuous visualization, the tubeless intubating device 370 can be easily removed from the patient while the endotracheal tube 388 remains safely in place under continual vision. Thus, the tubeless device 370 can be used with a standard endotracheal tube to intubate and extubate a patient. The device 370 can be also used as a supraglottic device.

Figure 26G:
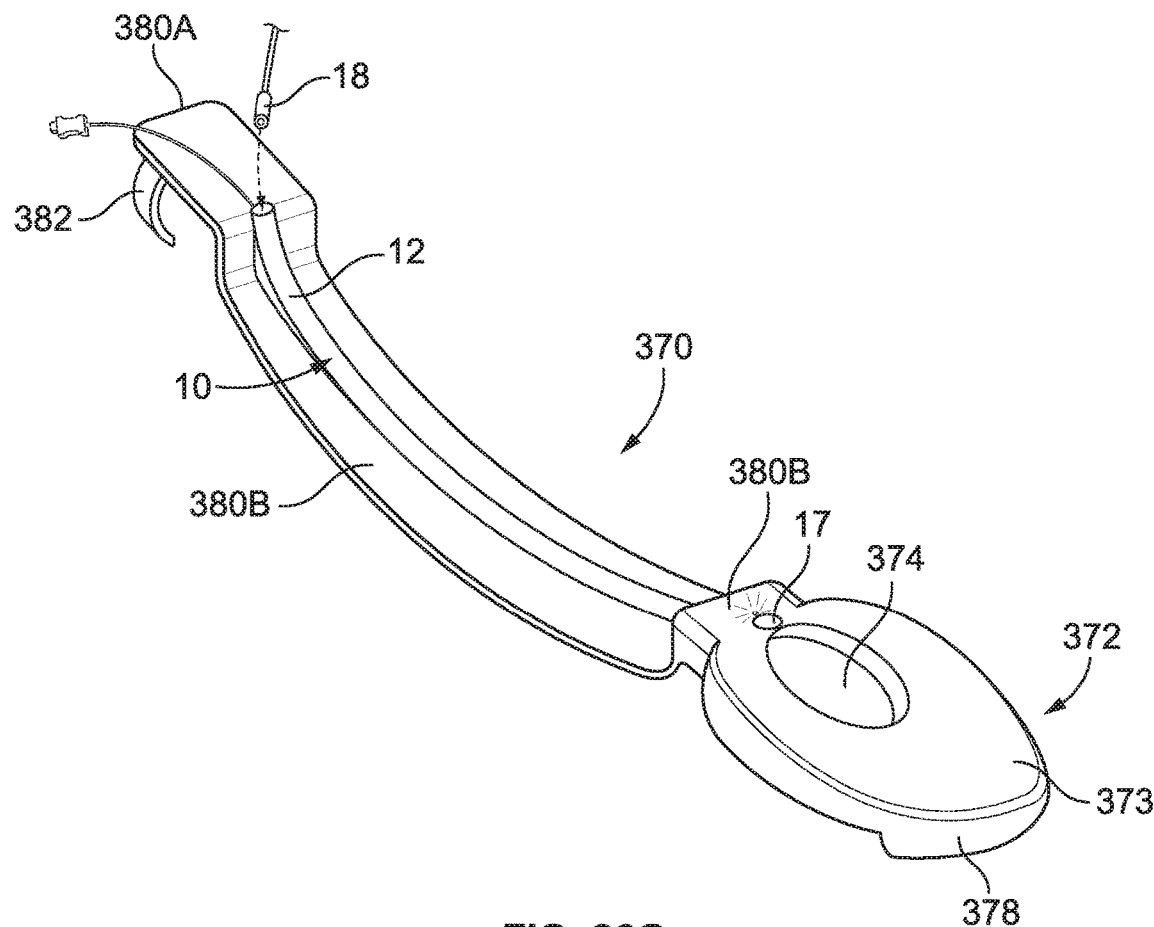
Figure 26H:
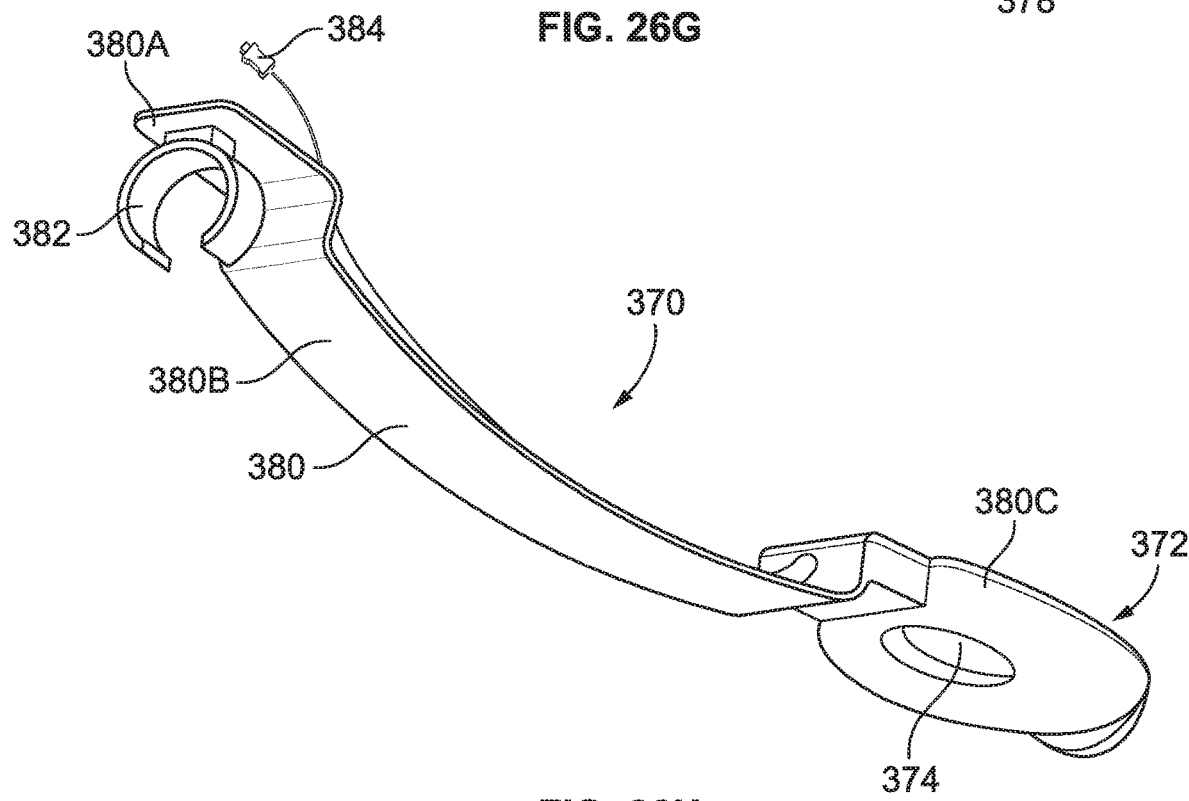

Further embodiments of the tubeless intubating device 370 are shown in FIGS. 26G-26J. As shown in FIG. 26G and can be particularly appreciated from FIG. 26H, the tubeless intubating device 370 in these embodiments does not comprise a cuff. Nevertheless and just like the tubeless intubating device 370 of FIG. 26A, the device 370 of FIG. 26G has the upper surface shown in FIG. 26G and the bottom surface shown in FIG. 26H. The tubeless intubating device 370 comprises an ellipsoid body 372 which has an upper oval surface 373 with a lumen opening 374A on the upper oval surface 373 of the ellipsoid body 372 as shown in FIG. 26G. The upper oval surface 373 is connected to the bottom half-ellipsoid surface 378 as shown in FIG. 26G and FIG. 26H such that the distal end 376 of the ellipsoid body 372 is tapered because the bottom half-ellipsoid surface 378 is tapered at the distal end 376. The ellipsoid body 372 encloses a lumen 374 which opens onto the upper oval surface 373 with the lumen opening 374A. The lumen 374 opens on the proximal side of the bottom half-ellipsoid surface 378 as shown in FIG. 26H. The bottom half-ellipsoid surface 378 also connects to a handle 380. This embodiment of the device 370 does not comprise a canal.

The handle 380 comprises three parts connected together: the proximal part 380A, the middle part 380B and the distal part 380C. The proximal part 380A may be made in flat rectangle shape with a ring-holder 382 attached on the bottom surface of the proximal part 380A. The 380A part bends down at about a 90-degree angle at its distal part where it connects to the middle part 380B. The middle part 380B is also of flat rectangle shape and may vary in length. As can be seen from FIG. 26B, the canal 379 is connected to the bottom surface of the middle part 380B at the distal portion of the middle part 380B. The middle part 380B connects to the distal part 380C at its distal end. The middle part 380B bends up at about a 90-degree angle at the distal part and connects to the distal part 380C. The distal part 380C connects by its distal end to the oval upper surface 373 of the ellipsoid body 372.

A visualization device, generally 10, comprising the camera tube 12 and camera 18 which can be inserted into the camera tube 12, is attached to the handle 380 on its upper surface such as the visualization device 10 extends along the handle 380 from its proximal end 380A at which the camera 18 is inserted insider the camera tube 12 and all the way into the distal portion 380C. Just like in other embodiments, the camera tube 12 is sealed with a transparent material 17 at its distal end such as the camera 18 does not come into direct contact with the patient's body and can be reused. Just like in other embodiments, the camera tube 12 can slide along the proximal-distal axis of the handle 380. The visualization device 10 may further comprise a light source 384 which can be inserted into the camera tube 12 along with the camera 18.

Figure 26I:
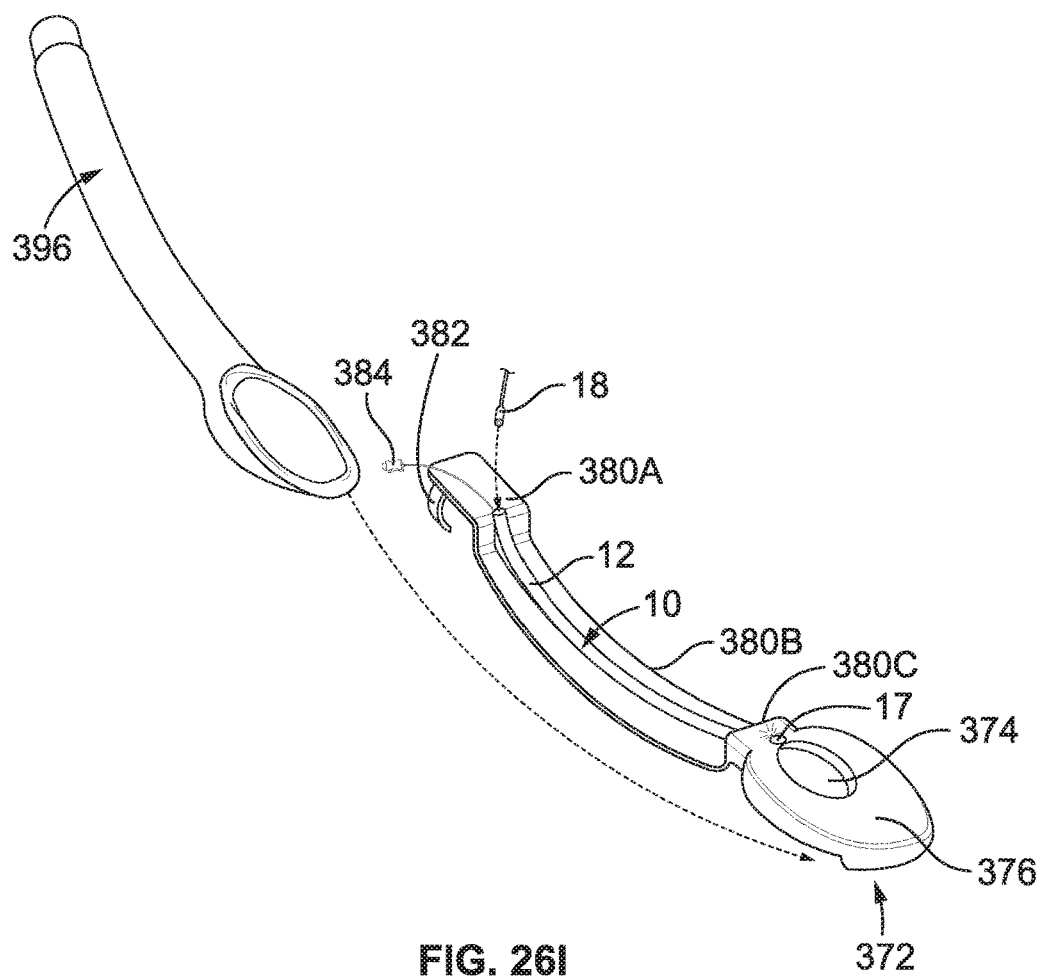
Figure 26J:
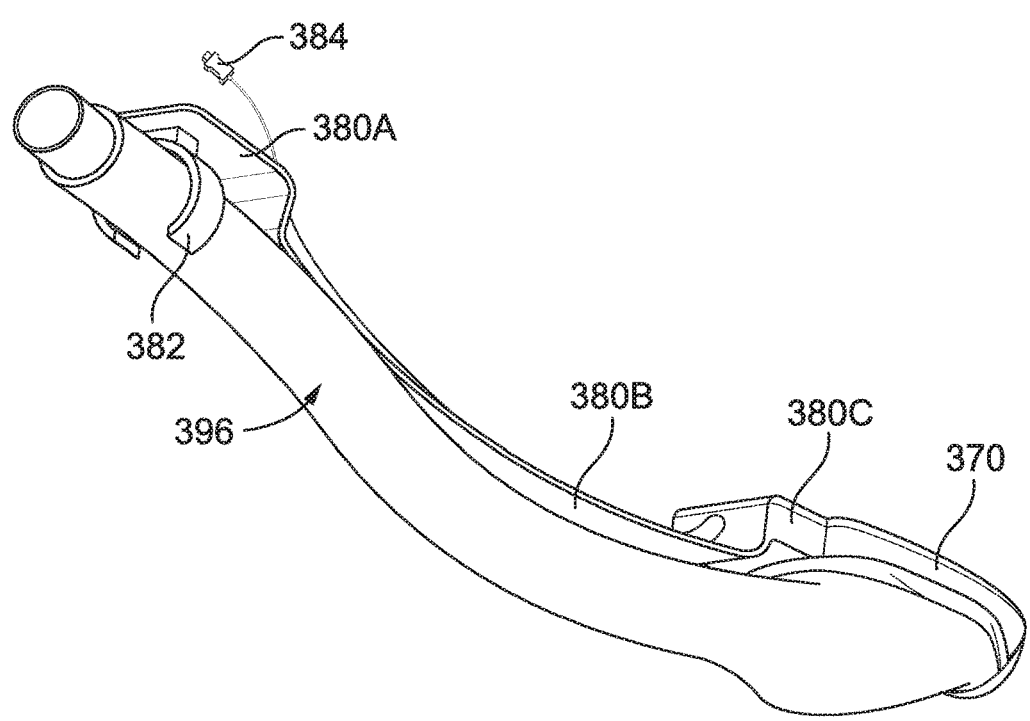

As shown in FIGS. 26I and 26J, the device 370 can be used for intubation and extubation of a patient with a supraglottic airway, generally 392 in FIGS. 26I and 26J. The device 370 can also be used for placement of a laryngeal mask airway. As shown in FIG. 26J, the supraglottic airway 392 is secured in the device 370 with the ring holder 382 such that the distal end of the device 392 is aligned with the distal end of the device 370 and the lumen 394 of the device 392 is aligned with the lumen 374 of the device 370 and secured. Because the assembly of the devices 370 and 392 is equipped with the camera device 10, it provides continuous visualization of patient's supraglottic structure during placement.

Figure 27C:
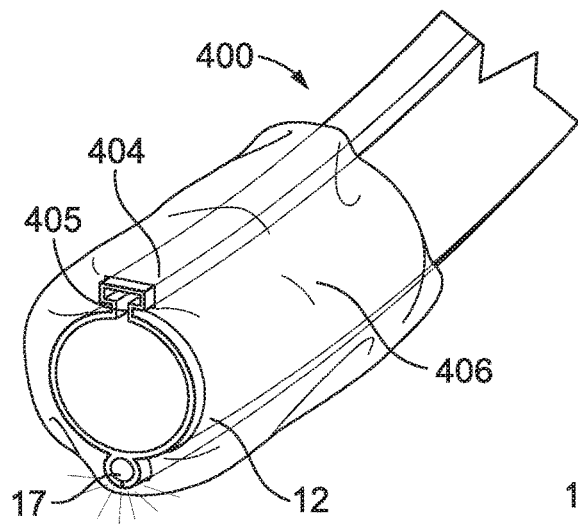

Further embodiments provide a sliding endotracheal cuff device, generally 400 as shown in FIGS. 27A-27G. As can be appreciated from FIGS. 27A and 27B, an endotracheal tube 410 comprises a tube 412 with a proximal end 412A and a distal end 412B with a rail 414 along the proximal-distal axis (412A-412B) designed such that the endotracheal tube 410 fits inside the device 400 and the rail 414 fits into the rail 404 of the device 400. The device 400 can then slide along the proximal-distal axis 412A-412B on the endotracheal tube 410 as shown in FIG. 27B. The details of the device 400 design are further explained in connection with FIGS. 27C-27F. As can be appreciated from 27C, the rail 404 has a groove 405 facing inside the tube 402. The groove 405 is designed such that the rail 414 of the endotracheal tube 410 fits inside the groove 405 and can slide along the rail 404. The rail design permits to easily remove the endotracheal tube 410 from the device 400 while the device 400 remains in place in a patient. In alternative, the device 400 can be removed, while the endotracheal tube 410 remains in place in the patient. Because the device 400 remains in place, changing from one endotracheal tube 410 to another can be easily accomplished. Further because the cuff 406 is presented on a separate device, an endotracheal component can remain in place if what needs to be replaced is only a cuff. While in drawings of FIG. 27, the device 400 is shown a cylinder, this device can be a half-cylinder in other embodiments.

Figure 27D:
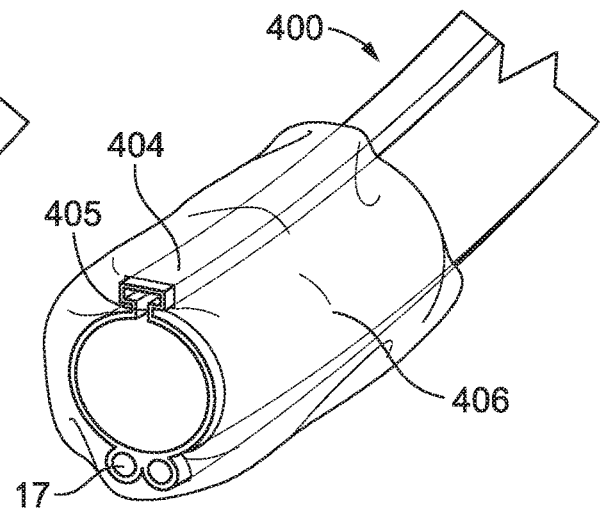
Figure 27E:
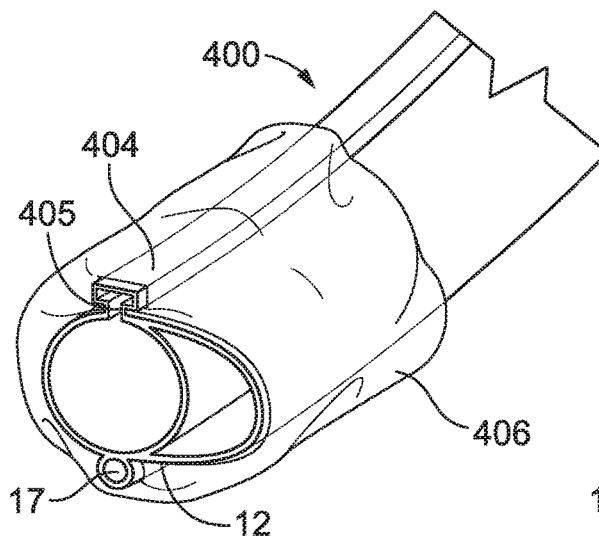
Figure 27F:
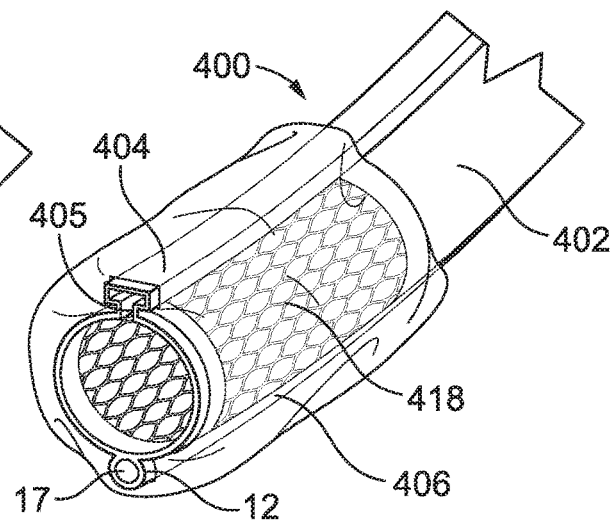

As can be further appreciated from FIG. 27D, some embodiments for the device 400 comprise an additional tube 416 which can be used for delivering drugs, suction and tools such as for example forceps and bougie. Further embodiments for the device 400 include an embodiment of FIG. 27E in which the cuff 406 can move along the rail 404. Yet further embodiments for device 400 include an embodiment of FIG. 27F, where the distal portion 402A of the tube 402 comprises mesh 418. As can be further appreciated from FIG. 27F, the cuff 406 can inflate over the mesh 418.

Figure 27G:
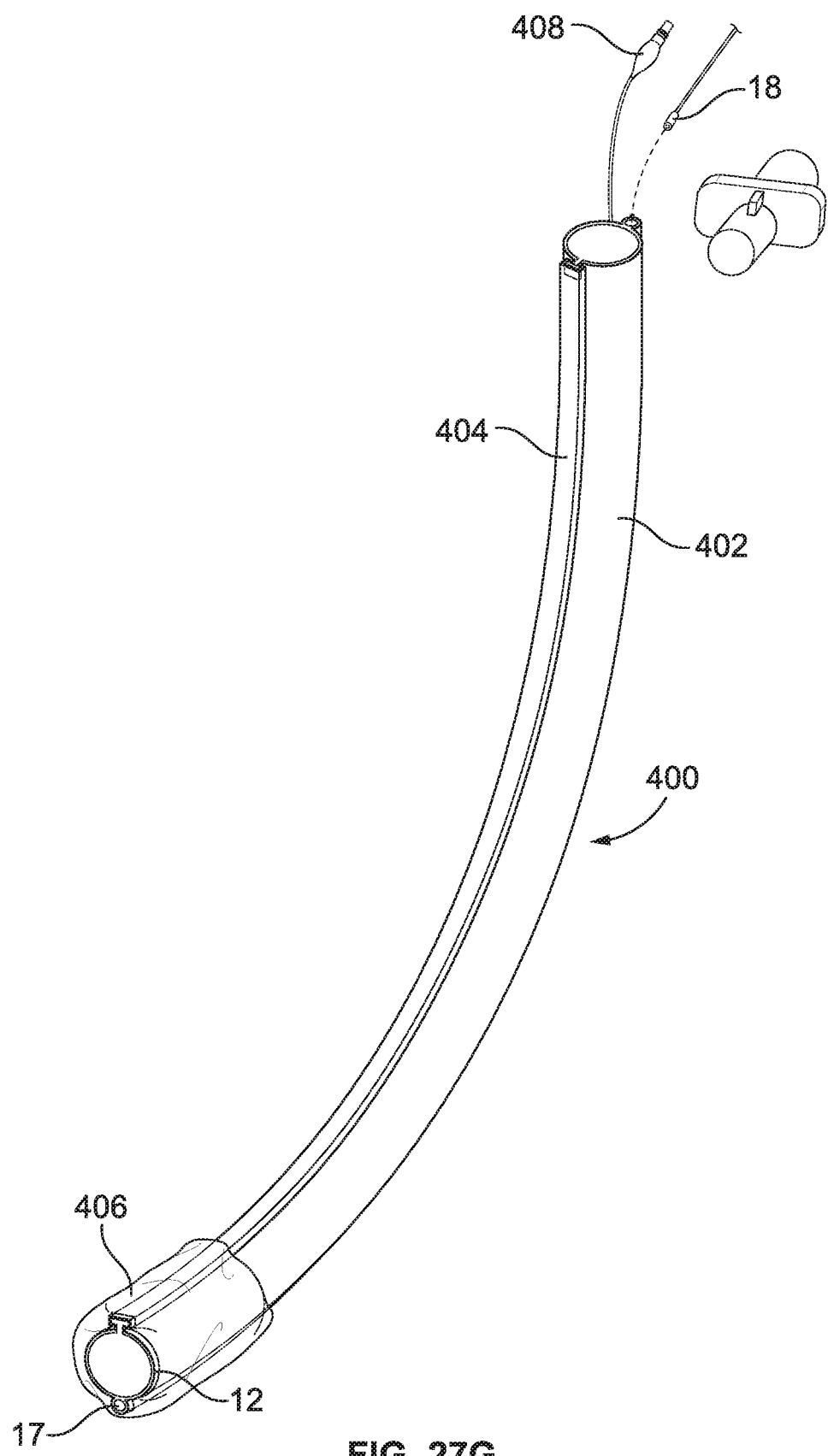

As can be appreciated from FIG. 27G, the camera tube 12 may be fixed along the body 402 or it can slide proximally and distally along the body 402. Overall, the device 400 prevents a problem of broken seal after the device has been in place in a patient for a period of time.

Figures 28A, 28B:
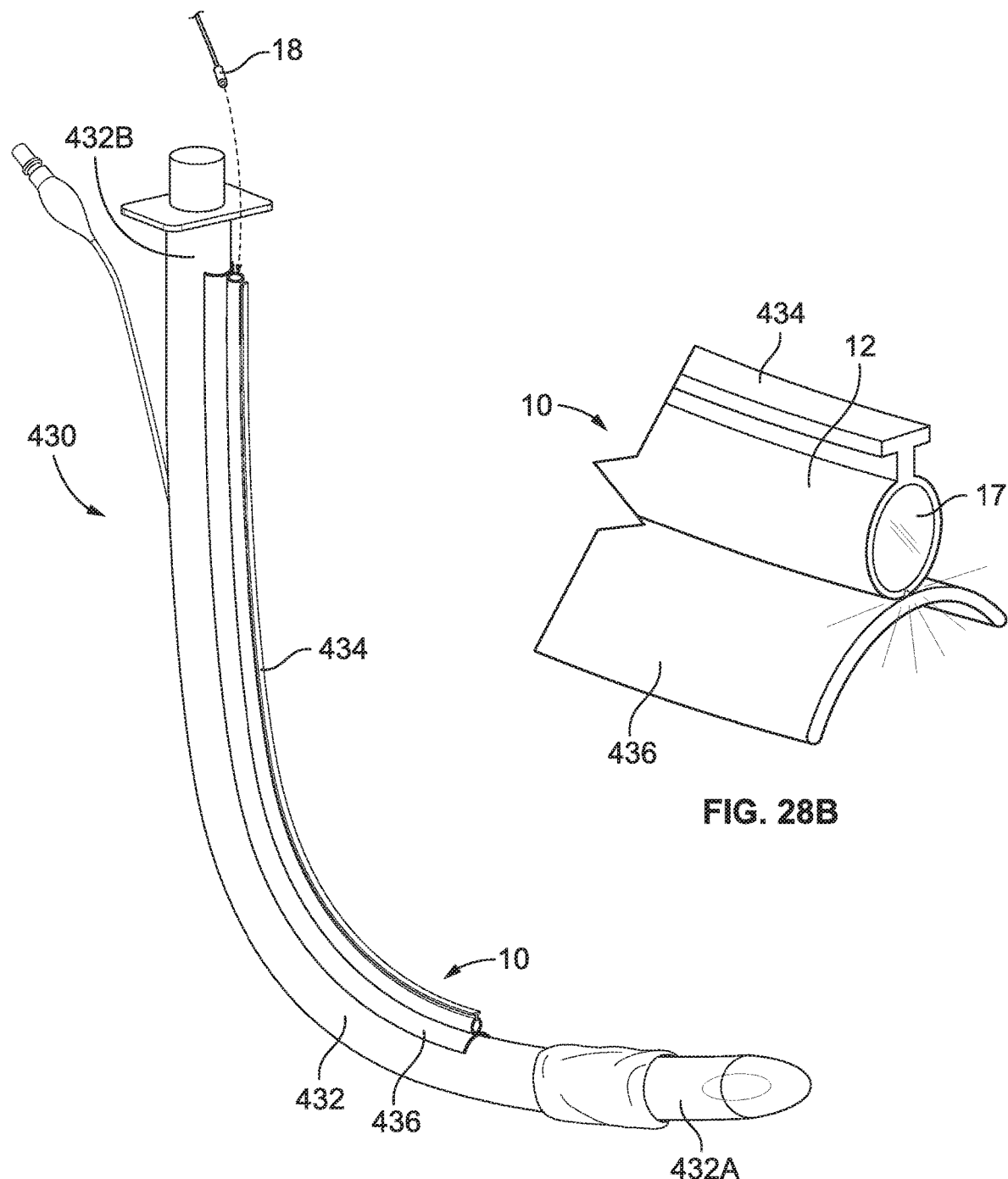
FIGS. 28A-28B depict an endotracheal tube with a visualization device which can slide along the endotracheal tube and be removed from the endotracheal tube.

Further embodiments provide an endotracheal tube, generally 430, as shown in FIGS. 28A and 28B. The device 430 comprises a tube 432 with the proximal end 432A and the distal end 432B. A visualization device 10 is positioned along the proximal-distal axis (432A-432B) of the tube 432. As can be appreciated from FIG. 28B, the visualization device 10 comprises a camera tube 12 sealed with a transparent material 17 at the distal end. A camera 18 can be placed inside the camera tube 12. The camera tube 12 comprises a rail 434 running along the camera tube 12. The tube 12 further comprises a half-cylinder 436 attached on the side opposite to the side of the tube 12 to which the rail 434 is attached. The half-cylinder 436 has a diameter such that the visualization device 10 can be easily snap over the tube 432 of the endotracheal tube 430 with the half-cylinder 436. Thus, the visualization device 10 in this embodiment can be easily assembled with any endotracheal tube and it can also be easily removed from the endotracheal tube when visualization is no longer needed. Importantly, the camera tube can be detached at any time. Thus, this device is similar to a laryngoscope, yet the camera tube can be removed at any time if no longer needed. Thus, one of the advantages of this device is a rail which permits gliding along any other tubal device.

Figure 29A:
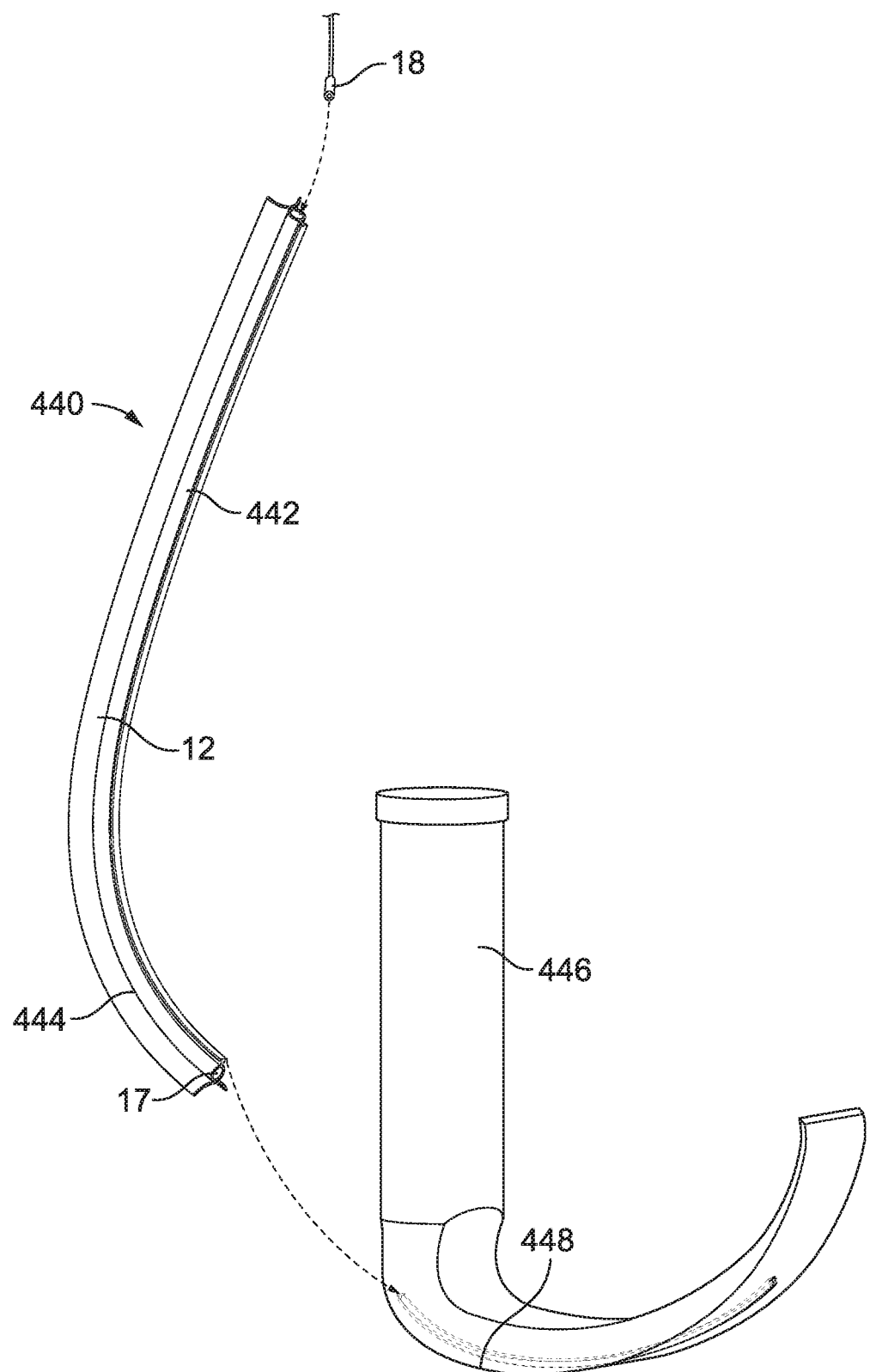
FIGS. 29A-29C depict a sliding camera tube with rail and placing of the camera tube into a laryngoscope.
Figure 29B:
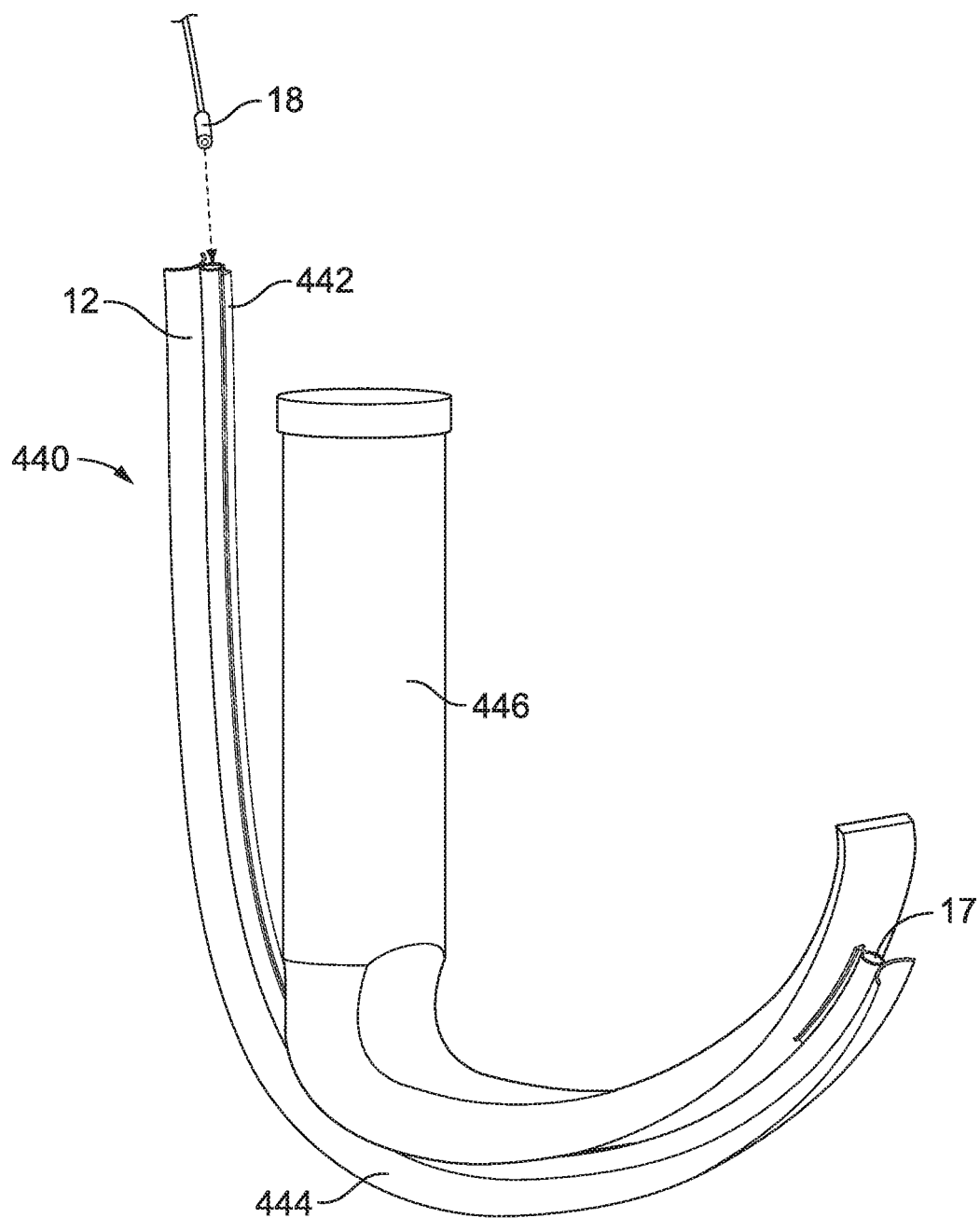
Figure 29C:
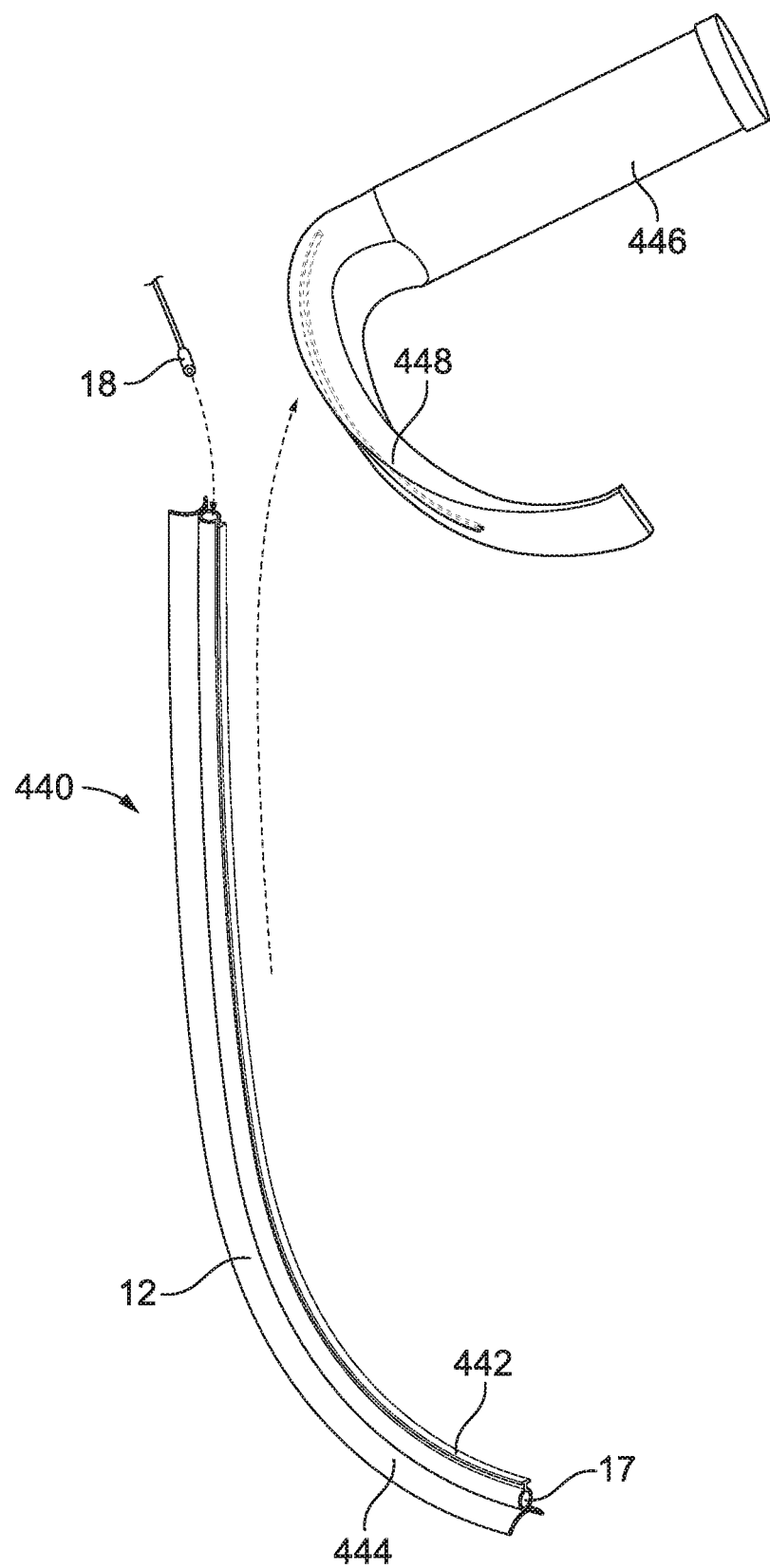

Further embodiments provide a sliding camera tube with rail, generally 440 as shown in FIGS. 29A-29C. As can be appreciated from FIG. 29A, the camera tube 440 comprises a tube into which a camera 18 can be inserted. The tube 12 is sealed at the distal end with transparent material 17. A rail 442 runs along the tube 12. The tube 12 is attached to a half-cylinder 444 which has a diameter such as the camera tube 440 can be easily assembled with an endotracheal tube or any other tube and it can glide along the endotracheal tube or any other tube. As can be appreciated from FIG. 29A, the camera tube 440 can easily slide into a laryngoscope which is equipped with a rail 448 along which the camera tube 440 can slide. As can be appreciated from FIG. 29B, after the camera tube 440 is positioned on the laryngoscope, the camera 18 can be inserted into the tube 12.

As can be further appreciated from FIG. 29C, the camera tube 440 can be easily removed from the laryngoscope and assembled with any other device. For example, the camera tube 440 can be placed on an endotracheal tube as was discussed in connection with FIG. 28. Thus, the device provide intubation during laryngoscopy and after the removal of the device 440 from the device 448.

Figure 30A:
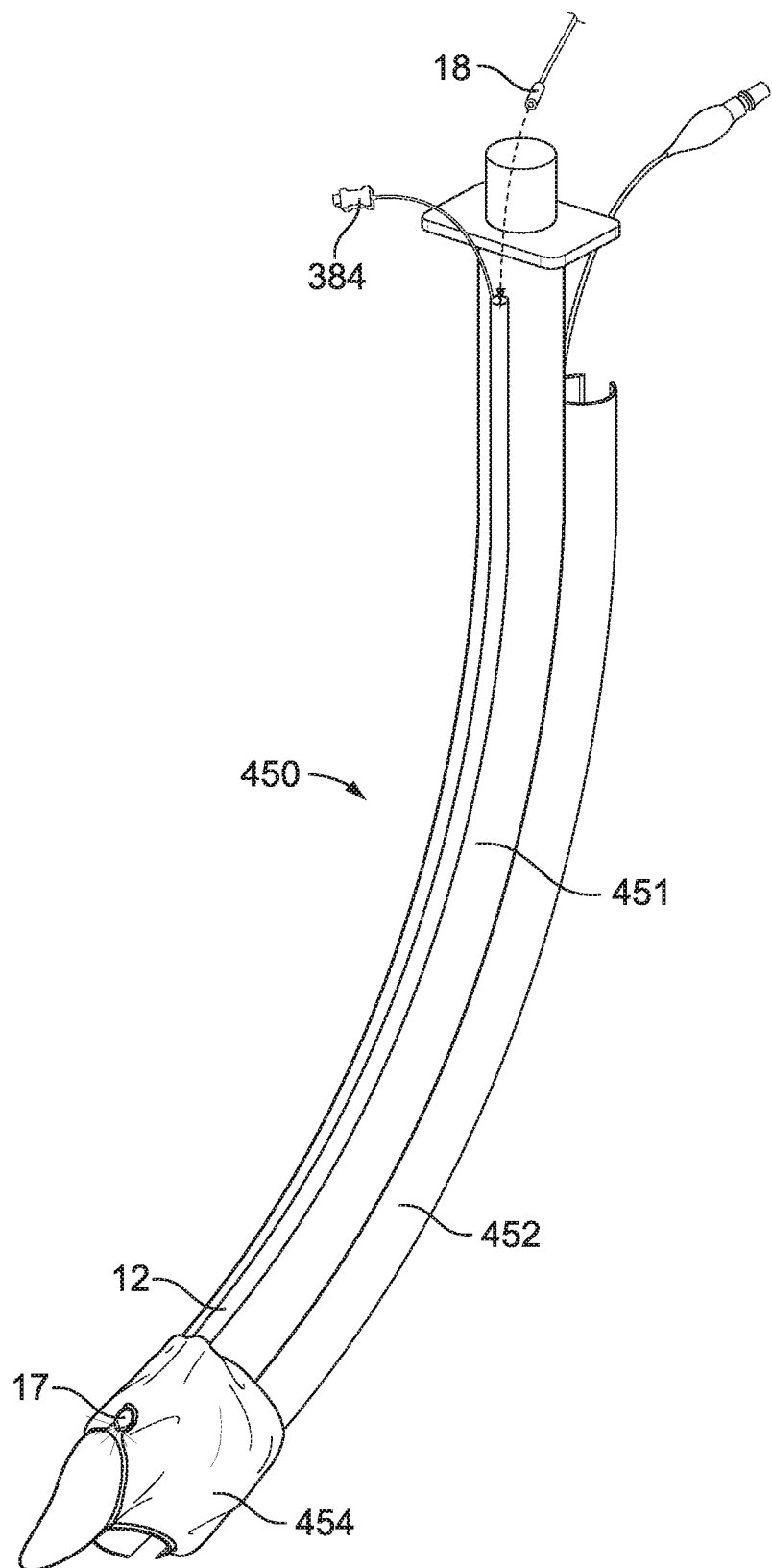
FIGS. 30A-30B depict a supraglottic airway device with built in endoscope guide (FIG. 30A) and insertion of the device into a patient (FIG. 30B).
Figure 30B:
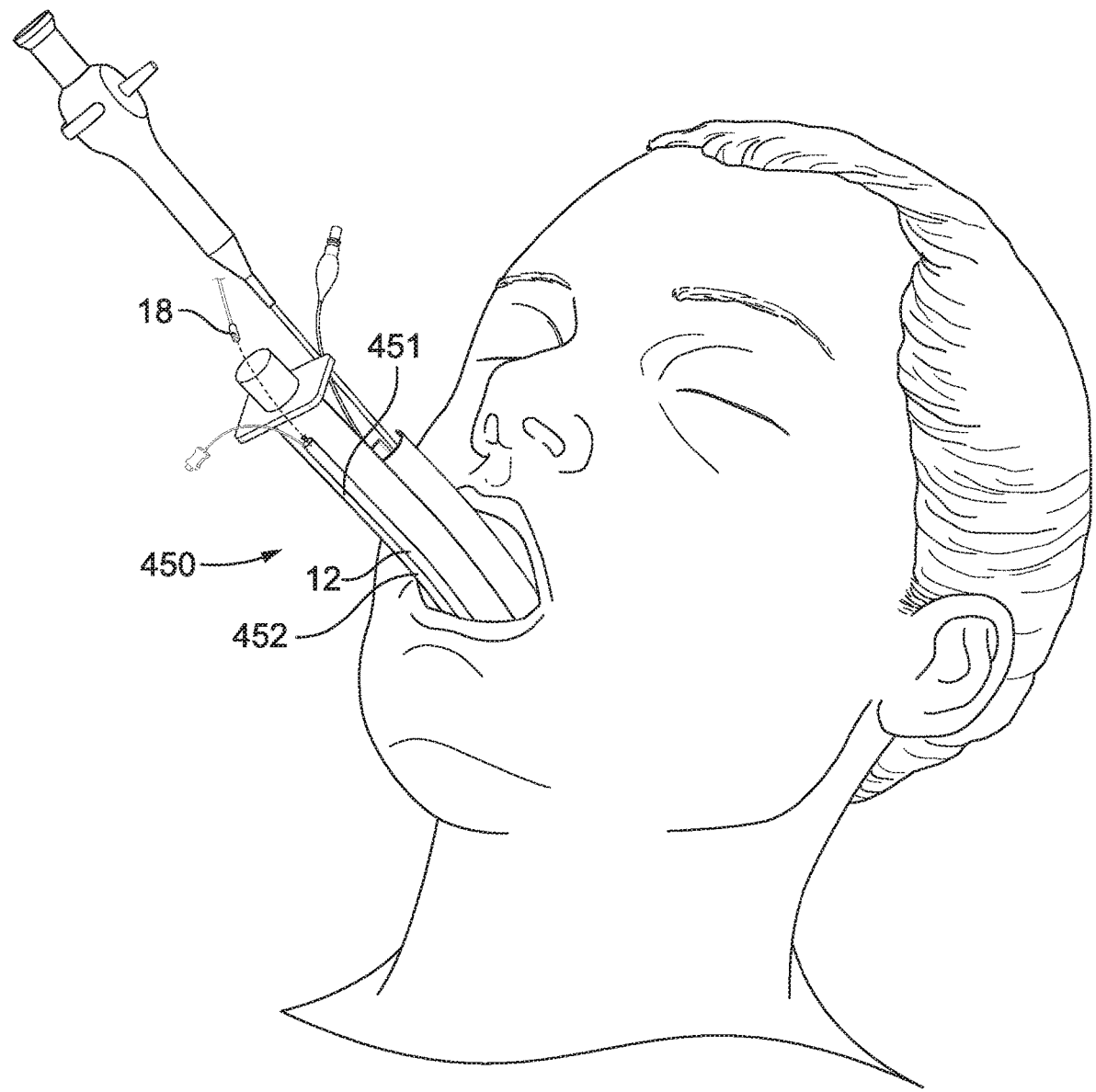

Further embodiments provide a supraglottic airway device with built in endoscope guide, generally 450, as shown in FIGS. 30A and 30B. As can be appreciated from FIG. 30A, the device 450 comprises a camera tube 12 which is positioned externally long the body of the device 450. The device 450 is further equipped with a half-cylinder endoscope guide 452 which runs externally along the body 451 of the device 450, beneath a cuff 454 and creates a semilumen. The device 450 can be used for placing a supraglottic airway with an endoscope in place. The device 450 is adoptable to endoscopes of all sizes. The device 450 can be placed after an endoscope is already inserted in a patient. The device 450 is able to ventilate a patient under continuous visualization during endoscopy. As can be further appreciated from FIG. 30B, the device 450 can be positioned in the patient's oral cavity 456 and then it can be easily removed from the endoscope semi-lumen 452.

Figure 31A:
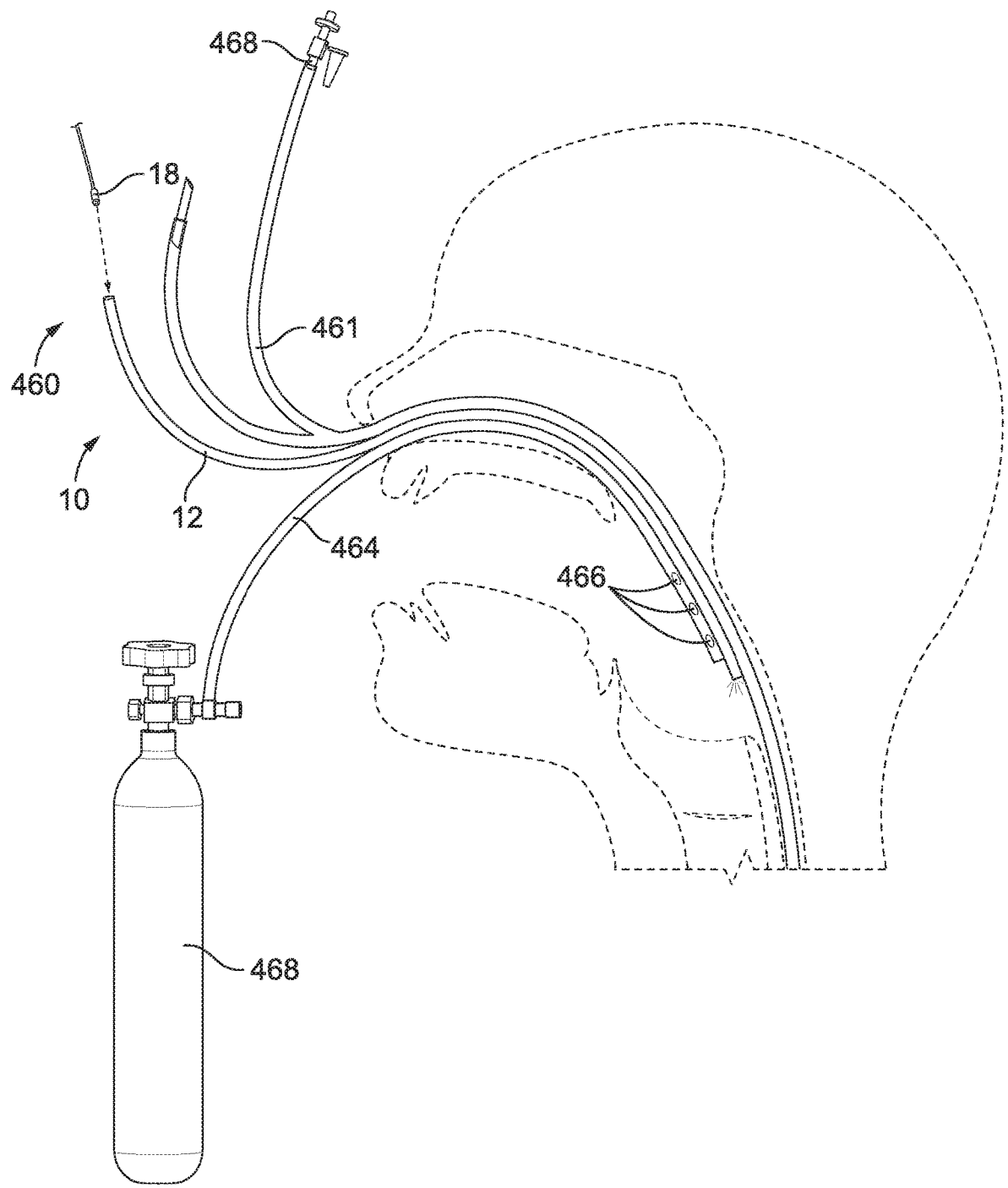
FIGS. 31A and 31B depict an assembly of a naso-gastric tube with a visualization device.
Figure 31B:
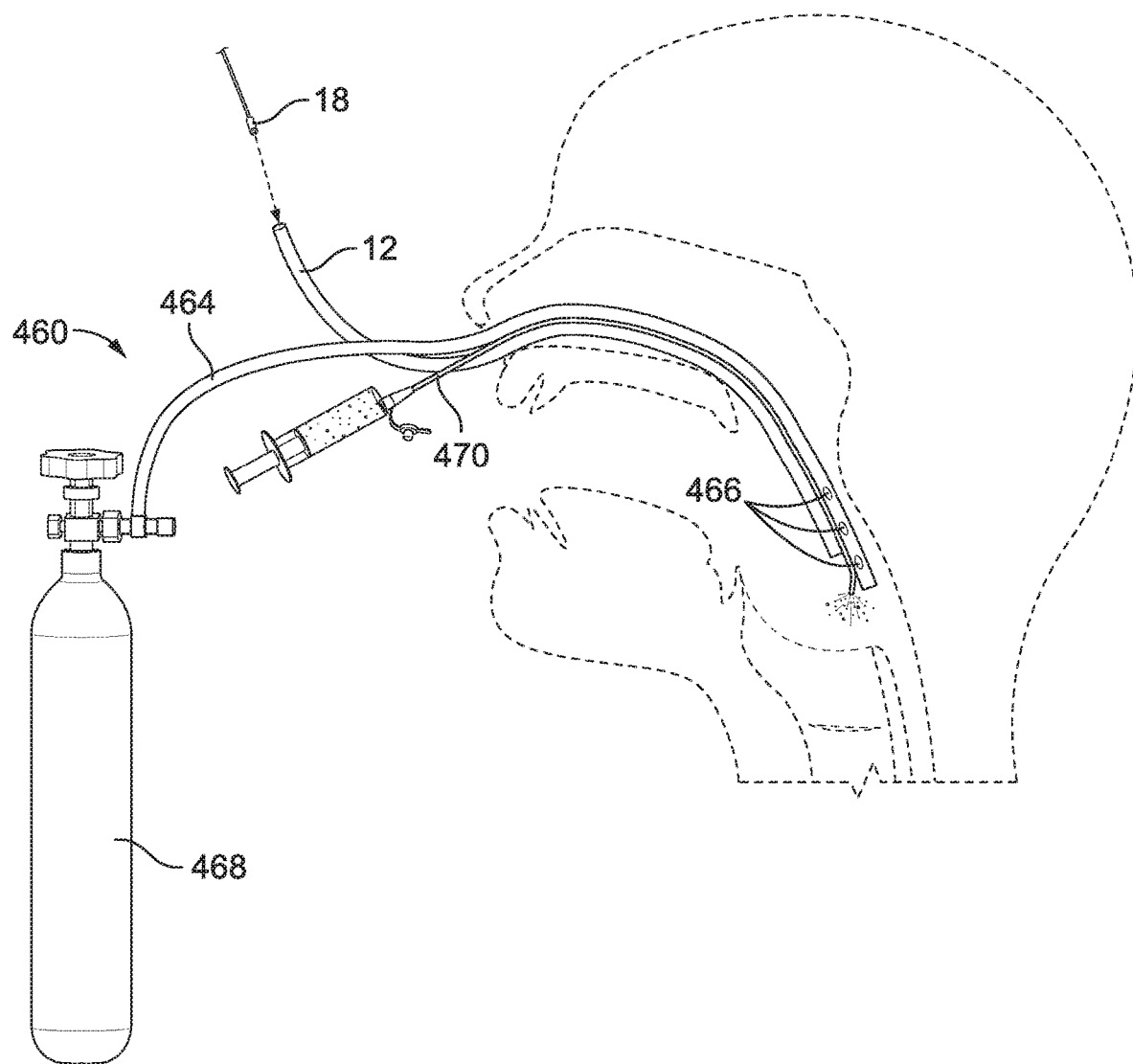

FIGS. 31A and 31B provide further embodiments for an assembly with a naso-gastric tube with a visualization device 10, generally 460. The visualization device 10 comprises a camera tube 12 with a camera 18 which can be inserted inside the camera tube 12. The naso-gastric tube 461 comprises a valve 462. The assembly 460 further comprises an oxygen tube with perforations, 464, which can be connected to a source of oxygen 468. As can be appreciated from FIGS. 31A and 31B, the perforations 466 are located at the distal end of the tube 464 and this permits localization of the perforations in the mid pharynx to deliver oxygen to a patient as shown in FIG. 31A. The length of the camera tube 12, oxygen tube 462 and naso-gastric tube 461 are calculated such that the assembly is flexible and the camera tube 12 can be located in the mid pharynx. However, the camera tube 12 can slide on the gastric tube 461 to travel to the distal gastric tube 461 providing continuous visualization of patient's gastric organs. A person of skill will appreciate that in some embodiments, the assembly 460 comprises a naso-gastric tube 461 as shown in FIG. 31A, while in other embodiments, the assembly 460 comprises a feeding tube 470 in place of the naso-gastric tube 461.

Figure 32:
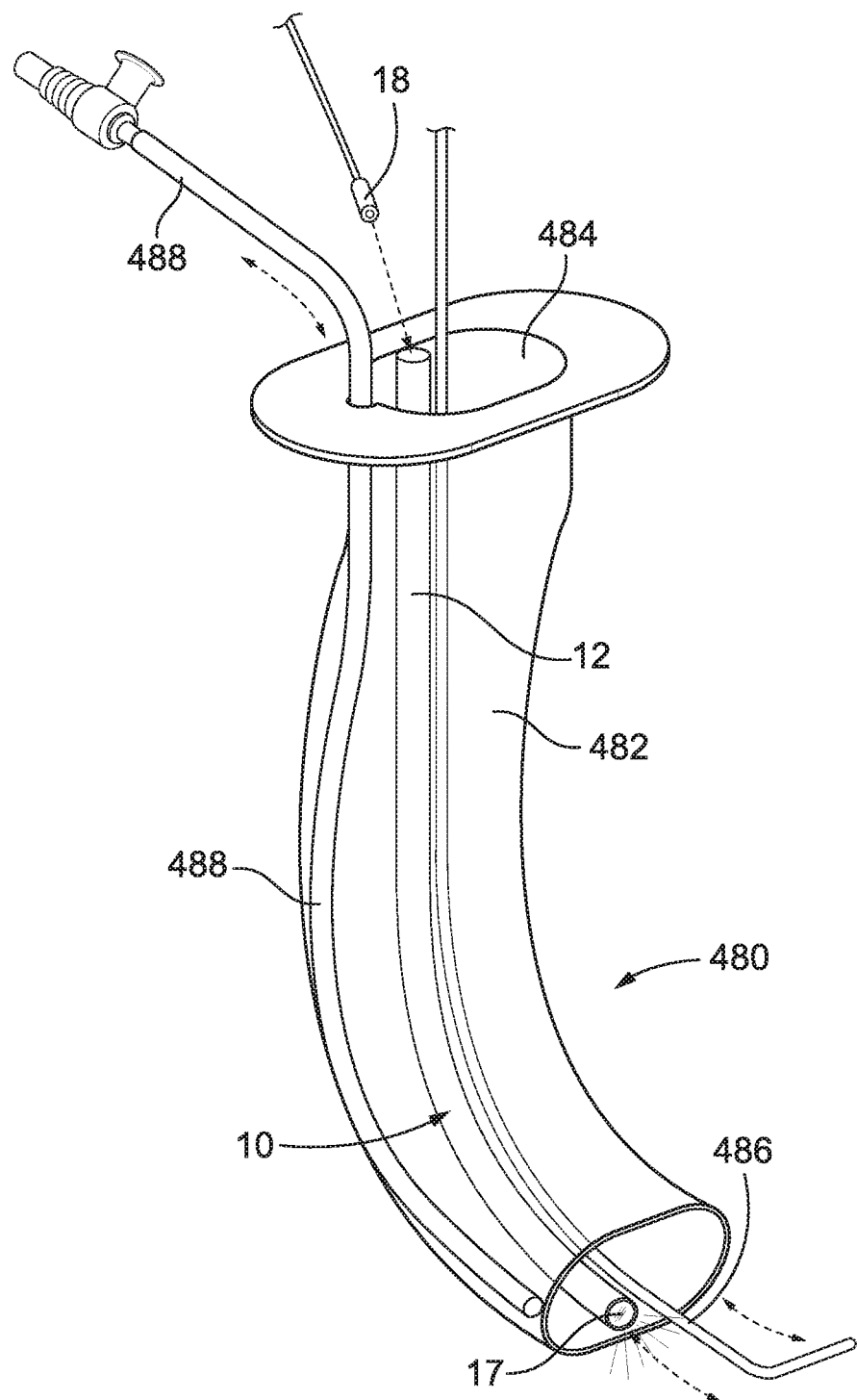
FIG. 32 depicts an oral airway embodiment.

FIG. 32 is a further embodiment of an oral airway with a camera device, generally 480. The oral airway comprises a tubal body 482 with a lumen 484 similar to tubal bodies of other oral airways described in this disclosure. The camera device 10 comprises a camera tube 12 which is sealed at its distal end with transparent material 17 and into which a camera 18 can be placed.

The camera device 10 is placed inside the lumen 484. The oral airway device 480 can provide continuous visualization of patient's supraglottic structure including the vocal cords in patients with positive ventilation pressure and also in patients ventilating spontaneously. The oral intubating device 480 can be used to place an endotracheal tube through the vocal cords without lifting the mandible. As in previous embodiments, the device 480 provides a continuous visualization after the endotracheal tube is placed and during extubation. It should be understood that this camera tube can slide proximal and distal to the tip of the device 480. A bougie 486 is also placed inside the lumen 484 and it can be moved along the proximal-distal axis and guide positioning of the camera device 10 which also can move along the proximal-distal axis. The device 480 further comprises a suction catheter 488 which is also placed inside the lumen 484 and which can move along the proximal-distal axis inside the lumen 484. As can be appreciated by a person of skill, an endotracheal tube can be placed inside the lumen 484 to intubate a patient.

Figure 33C:
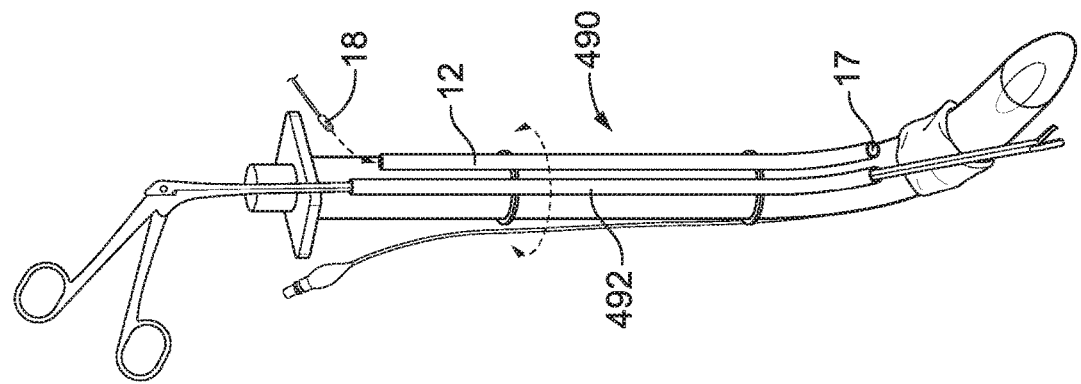
FIGS. 33A-33C depict further embodiments of an endotracheal tube with an externally attached camera tube.
Figure 33B:
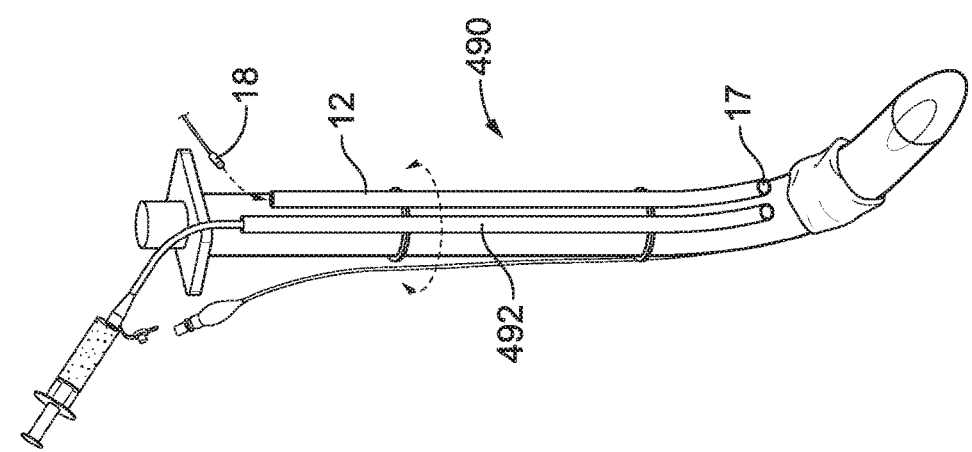
Figure 33A:
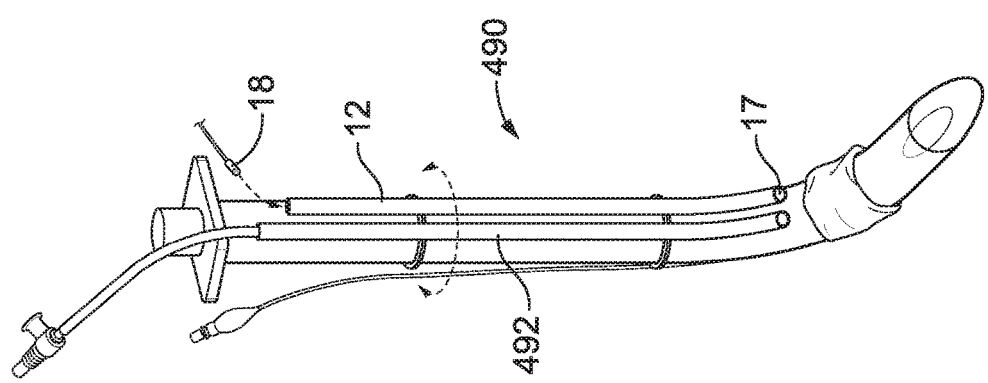

FIGS. 33A-33C are further embodiments of an endotracheal tube 490 with an externally attached camera tube 12 into which a camera 18 can be placed, and a suction tube 492 which is also attached externally to the endotracheal tube 490 as shown in FIG. 33A. As shown in FIG. 33B and FIG. 33C other devices can be externally attached to the endotracheal tube 460, such as a medication dispensing device 494 as shown in FIG. 33B and biopsy forceps 496 as shown in FIG. 33C. Additionally, a ventilating tube can be placed in can be added to the assembly. An additional balloon can be added circumferentially around the camera tube to provide ventilation. This system can be also used to separate ventilation between the left and right bronchus. Because the camera tube 12 and the suction tube 492 are secured on the endotracheal tube 490 with a set of rings, the attachment is flexible and each of the camera tube 12 and suction tube 492 can rotate 360 degrees around the endotracheal tube 490. In addition to be able to rotate around the endotracheal tube 490, the camera tube 12 and suction tube 492 can slide along the proximal-distal axis of the endotracheal tube. The camera tube 12 is sealed at the distal end with transparent material 17 and this allows the camera 18 to visualize the external structures in the airway including but not limited to the vocal cords.

Figure 34E:
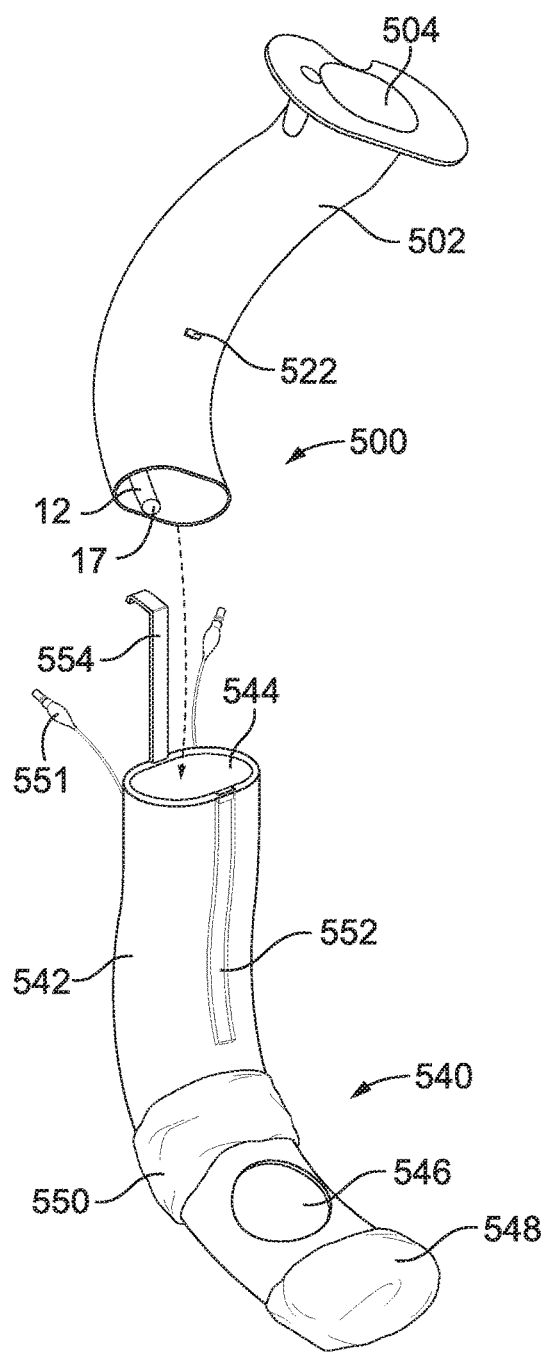

FIGS. 34A-34H are further embodiments of an oral airway device, generally 500, that allows for continuous visualization of the patient's vocal cords. As shown in FIG. 34A, the device comprises a tubal body 502 with a lumen 504 into which an endotracheal tube 506 or any other similar device can be inserted. The tubal body 502 has a proximal end 502A and a distal end 502B. The visualization device 10 is positioned along the tubal body 502 externally and it comprises a camera tube 12 sealed at the distal end with transparent material 17, and a camera 18 which can be used in multiple applications as it does not come into a direct contact with the patient's body. The positioning of the camera device provides for continuous visualization in the anteriorly lumen. An additional tubal body with a lumen 508 is attached along the proximal-distal axis of the tubal body 502. This additional tubal body 508 can be used for positioning an esophageal blocker 510 which can be then placed in the patient's esophagus under direct visualization with the visualization device 10. The esophageal blocker 510 is equipped with a balloon 512 at the distal end. The balloon 512 can be inflated with a means 514 and seal the patient's upper esophagus. In addition, the device 500 is equipped with a second balloon 516 which is circumferential and runs around the bodies 502 and 508, and located proximally to the balloon 512. The balloon 516 can be used to inflate with a means 518 and used for sealing the upper pharynx. Thus, the device 500 may act as a supraglottic airway with the endotracheal tube 506 pulled back proximally in the device 500 with the endotracheal tube 506 inflated.

Alternatively, and as shown in FIG. 34B, the endotracheal tube 506 may be removed and a ventilator cap 520 can be placed proximally in the central oral airway lumen to ventilate the patient as a supraglottic device. The device 500 may allow ventilating as a supraglottic airway under continuous and direct visualization with the visualization device 10. The device may also revert back to place an endotracheal under direct visualization.

FIGS. 34C and 34D provide a further embodiment for an oral airway device, generally 500, but in which the visualization device 10 is positioned internally and inside the lumen 504. FIG. 34C includes an endotracheal tube 506 which can be placed inside the lumen 504, as was discussed in connection with FIG. 34A. Further and as shown in FIG. 34D, the device 500 can be also used a ventilation cap 520.

One of the significant differences between the oral airway device 500 as embodied in FIGS. 34C and 34D versus the embodiments of FIGS. 34A and 34B, the device 500 in of FIGS. 34C and 34D does not comprise a balloon. The body 502 of the device 500 however, comprises at least one retractable extension 522.

Figure 34F:
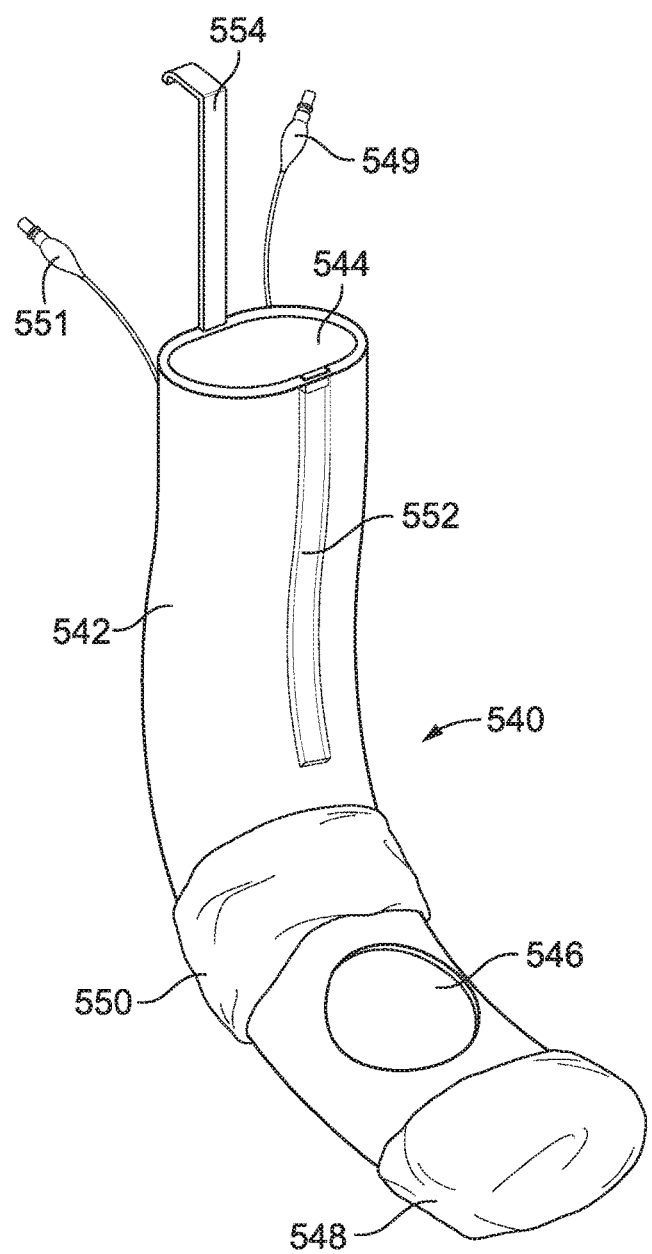
Figure 34H:
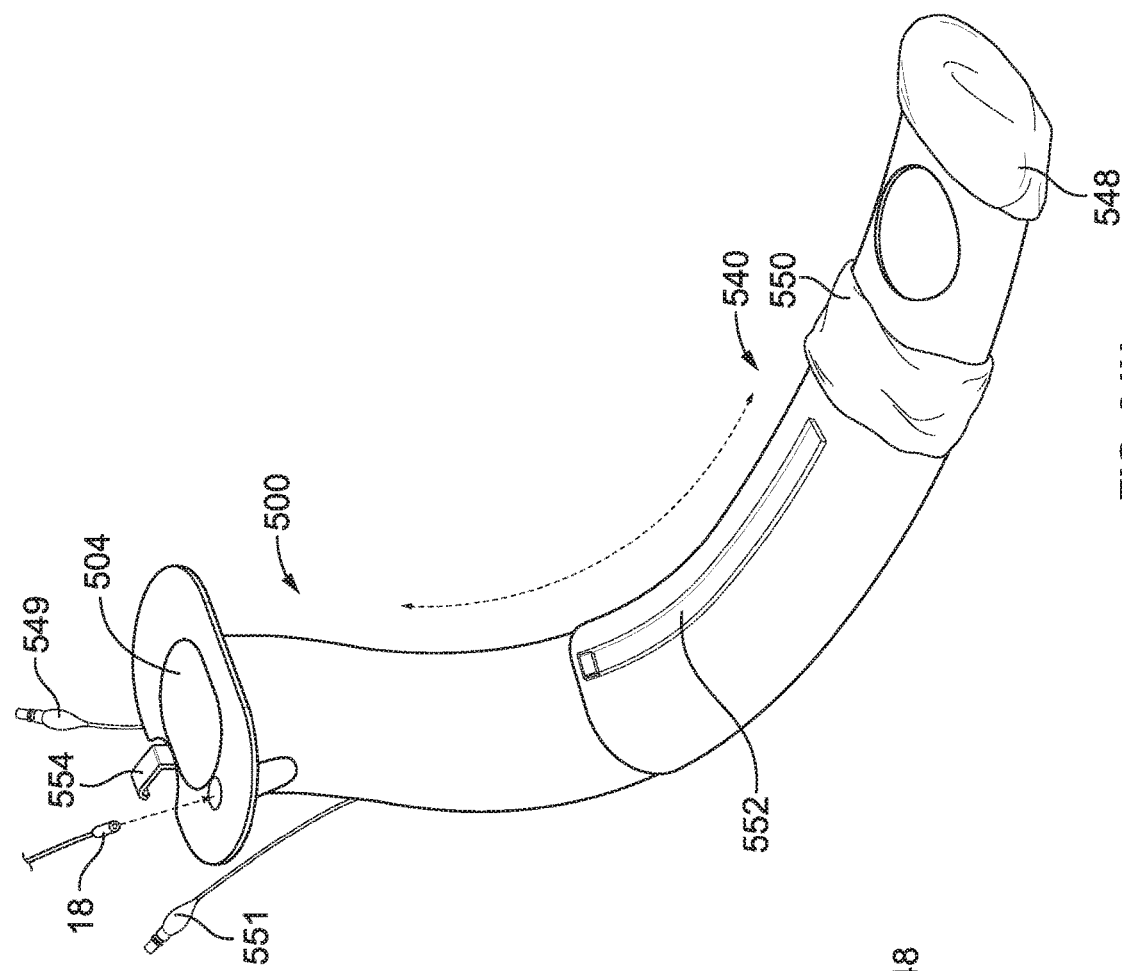
Figure 34G:
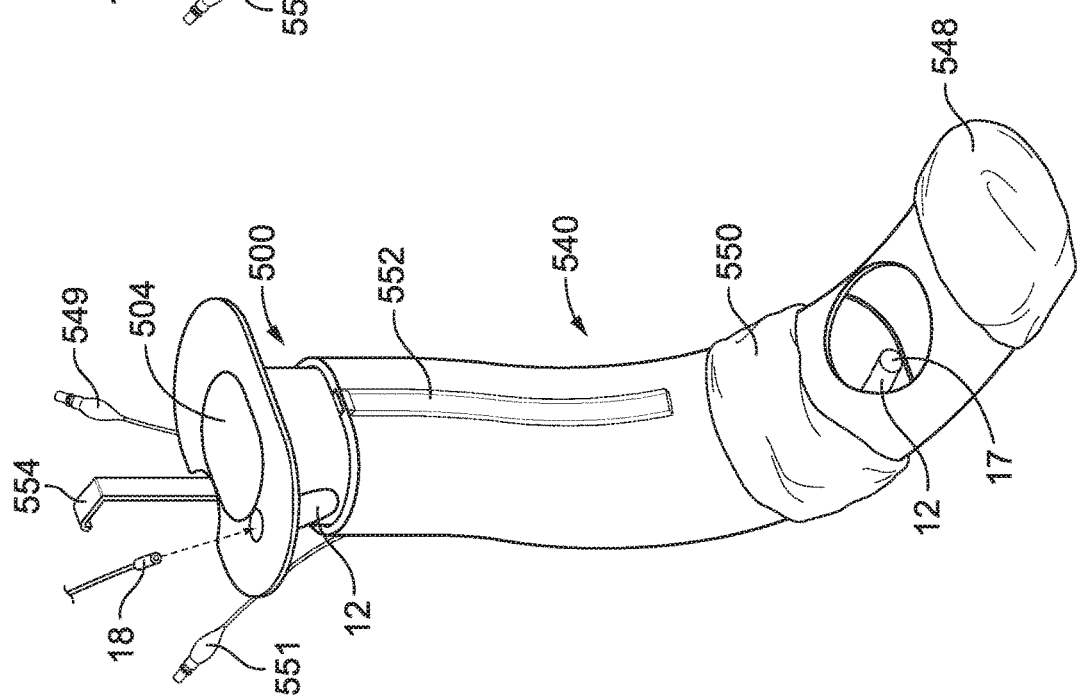

As shown in FIG. 34E, the oral airway device 500 of FIGS. 34C and 34D can be used in a combination with a carrier device 540. As shown in FIGS. 34E and 34F, the carrier device 540 comprises a tubal body 542 with a lumen 544. Two balloons are sealed to the carrier body 542. The first balloon, 548, caps the distal end of the carrier body 542. The first balloon 548 can be inflated with a means 549. The second balloon, 550, is proximal to the first balloon 548, and it rounds around the carrier body 542. The second balloon 550 can be inflated with a means 551.

The carrier body 542 comprises an opening 546 which is located on the carrier body 542 between the first balloon 548 and the second balloon 550. Thus, the lumen 544 opens with the opening 546 on the carrier body 542. The carrier body 542 is equipped with a glide rail 552 which runs along at least a part of the carrier body 542. The carrier body 542 is further equipped with a handle 554 which allows the carrier device 540 to be pushed, pulled and or turned from side to side.

As can be appreciated from FIG. 34E, the oral airway device 500 can be inserted into the lumen 544 of the carrier device 540. The extension 522 of the body 502 can glide along the glide rail 552 until the device 500 is positioned inside the lumen 544. As can be appreciated from FIGS. 34G and 34H, the device 500 can glide up and down inside the carrier 540, this allows an endotracheal tube to be placed proximally in its central lumen 544.

As shown in previous embodiments, the device 500 as a whole maybe advanced distally or brought proximally to align the central lumen between the two balloons 548 and 550 to visualize the vocal cords. An endotracheal tube thus can be advanced under direct and continuous visualization by the camera device 10. If needed, the endotracheal tube can be withdrawn from the trachea altogether or partially within the proximal lumen 504 (balloon on endotracheal tube inflated) to be converted to a supraglottic device.

The balloons 548 and 550 can be inflated and thus occluding the upper esophagus distally and pharynx proximally. This can be accomplished under direct and continuous vision of both the vocal cords, glottic structures and upper esophagus and hypo pharynx by the visualization device 10. The ventilating cap 520 can be placed in the central proximal lumen 504 if an endotracheal tube is absent.

Figure 35A:
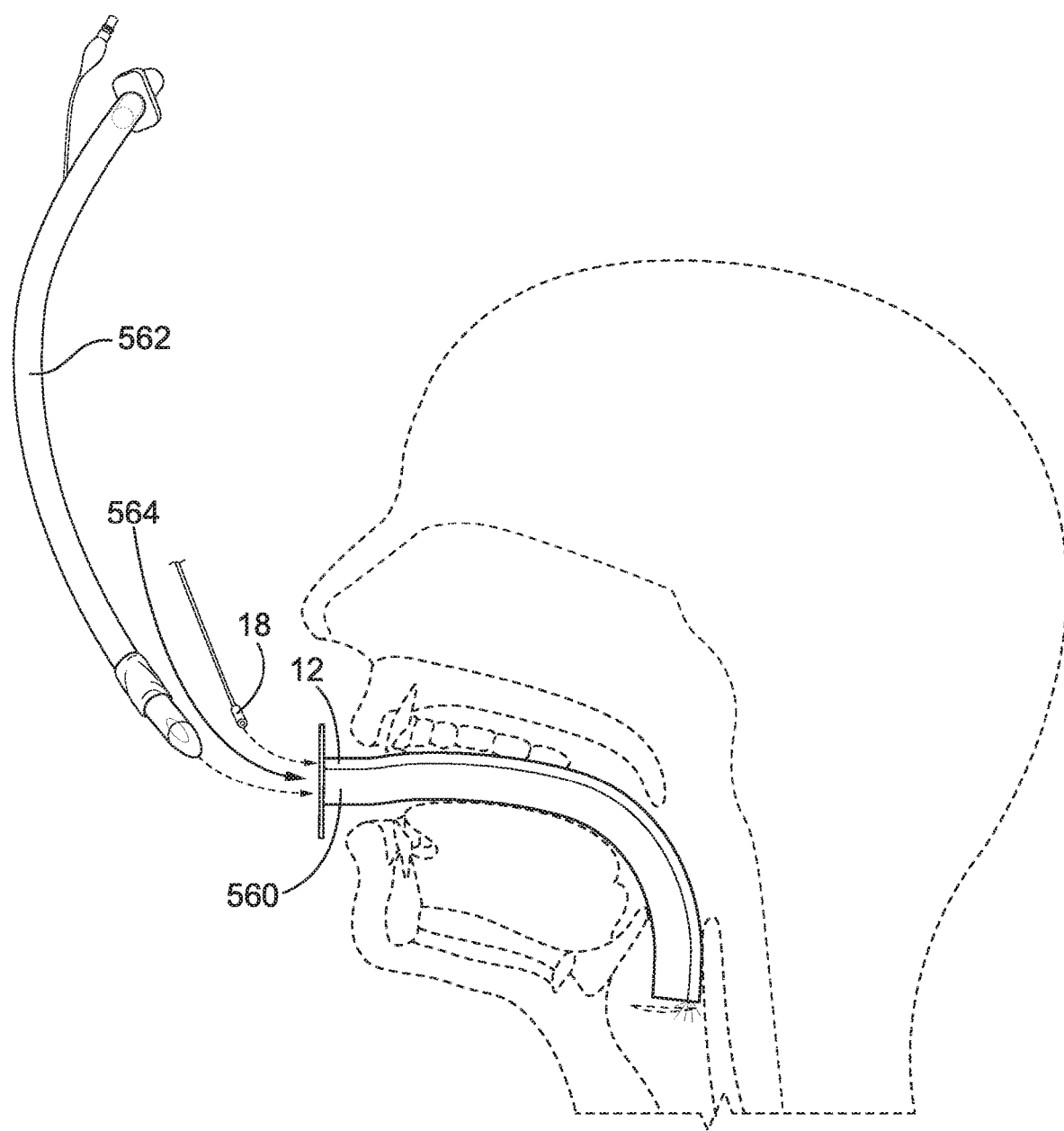
FIGS. 35A-35B are further embodiments of an oral airway device.

FIG. 35A depicts an oral airway device 560 with a camera tube 12 positioned in the patient's mouth. The camera tube 12 is as in prior embodiments with sealed distal end and open proximal end. The oral airway device 560 has a central lumen 564 to allow an endotracheal tube 562 to enter and slide down distally. The oral airway device 560 has a curvature and length to allow the oral airway device 560 to go under the epiglottis and actually touch the patient's vocal cords. Thus, no lifting of the mandible or tissue is needed. This new methodology of intubation allows greater ease and less skill to master then all the other forms of intubation such as laryngoscopy, videolaryngoscopy or fiberoptic intubation.

Once the distal end of the oral airway device 650 is touching or just proximal to the patient's vocal cord, the endotracheal tube 562 can slide proximal to distal in the central lumen 564 through the vocal cords under direct and continuous visualization by the camera 18. Once the endotracheal tube 562 is placed and secured the oral airway device 560 still maintains direct and continuous visualization of the endotracheal tube 562 and the patient's vocal cords.

Figure 35B:
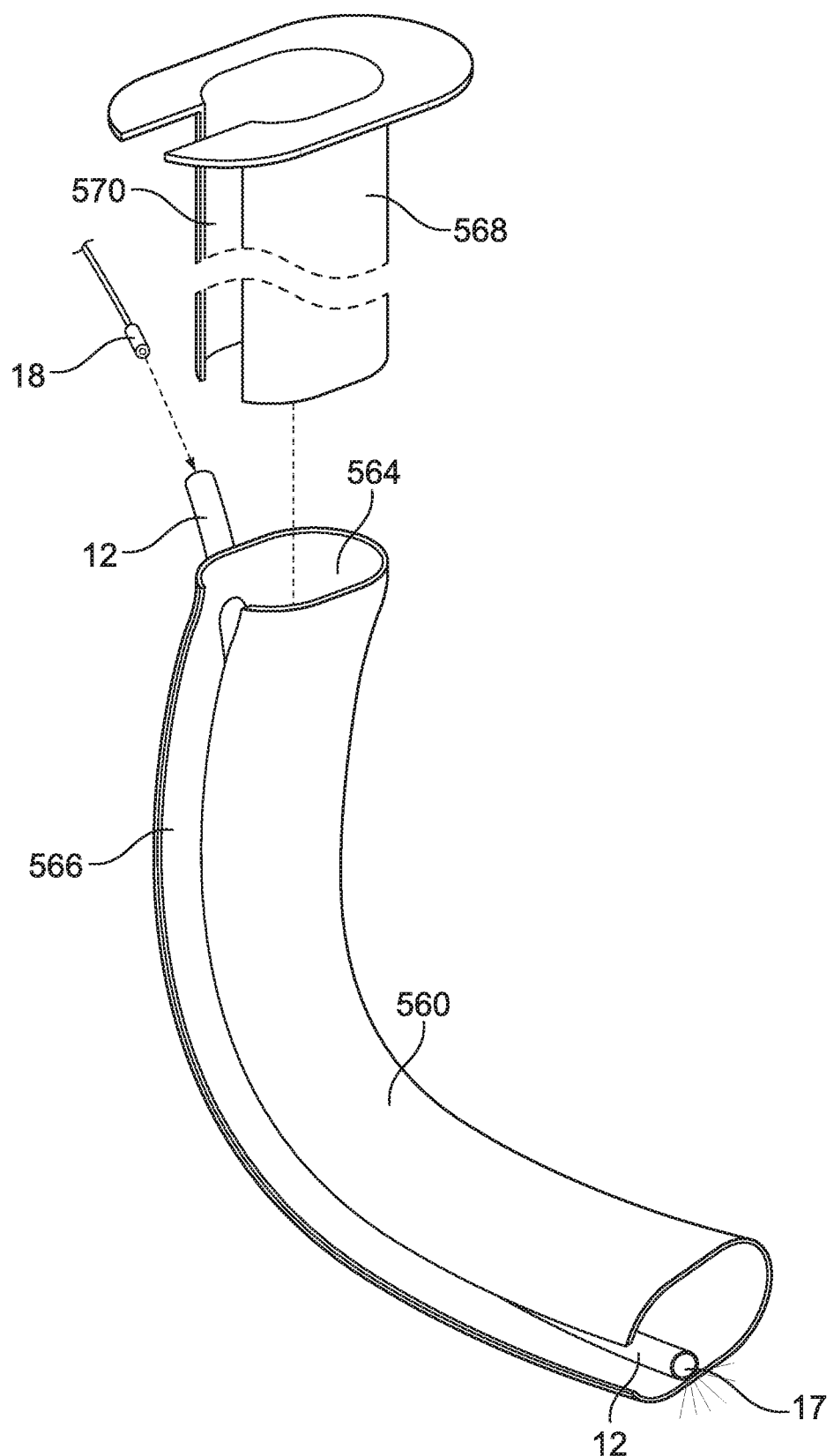

The further details of the oral airway device 560 can be appreciated from FIG. 35B where it is shown that the side 566 of the oral airway device 560 is open to allow the endotracheal tube 562 to be removed laterally from the central lumen 564 of the oral airway device 560 if needed. As can be further appreciated from FIG. 35B, the device 560 can be further equipped with a cap 568 which can be designed in multiple different sizes and can be placed or removed to add or shorten the oral airway device 560 to properly adjust to patients of different sizes. The cap 568 still has a side 570 removed as shown in FIG. 35B to allow an endotracheal tube to be removed from the central portion of the oral airway device 560 laterally. In addition, the cap 568 can be removed and rotated 180 degrees to help hold the endotracheal tube in place.

Figure 36A:
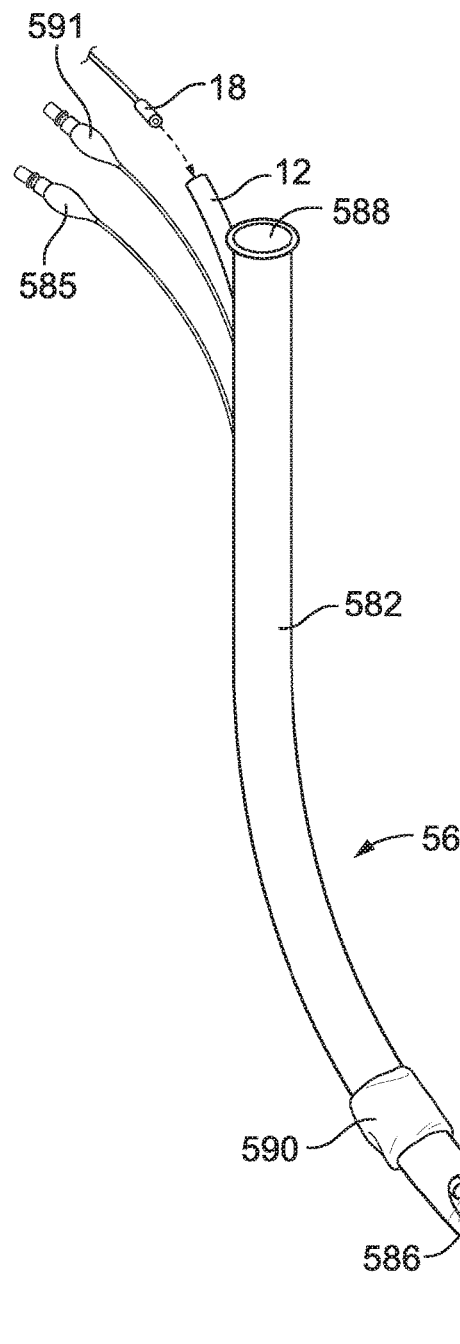
FIGS. 36A, 36B, 36C depict a nasopharyngeal airway device.
Figure 36B:
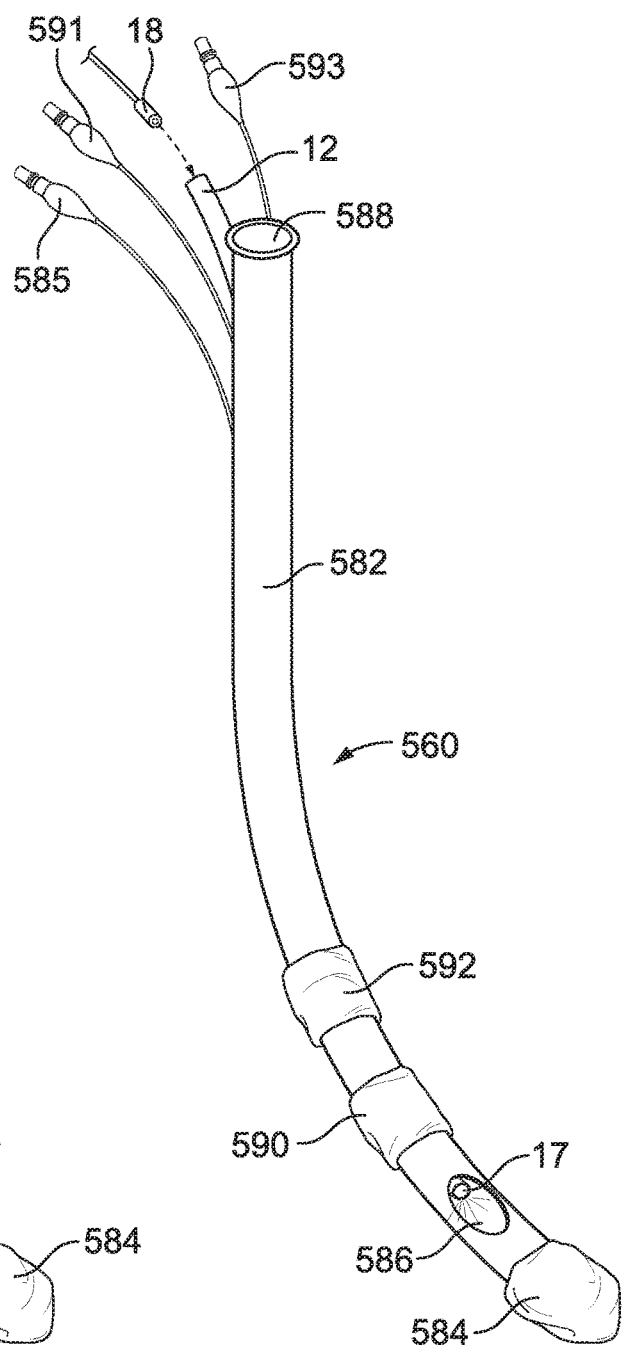
Figure 36C:
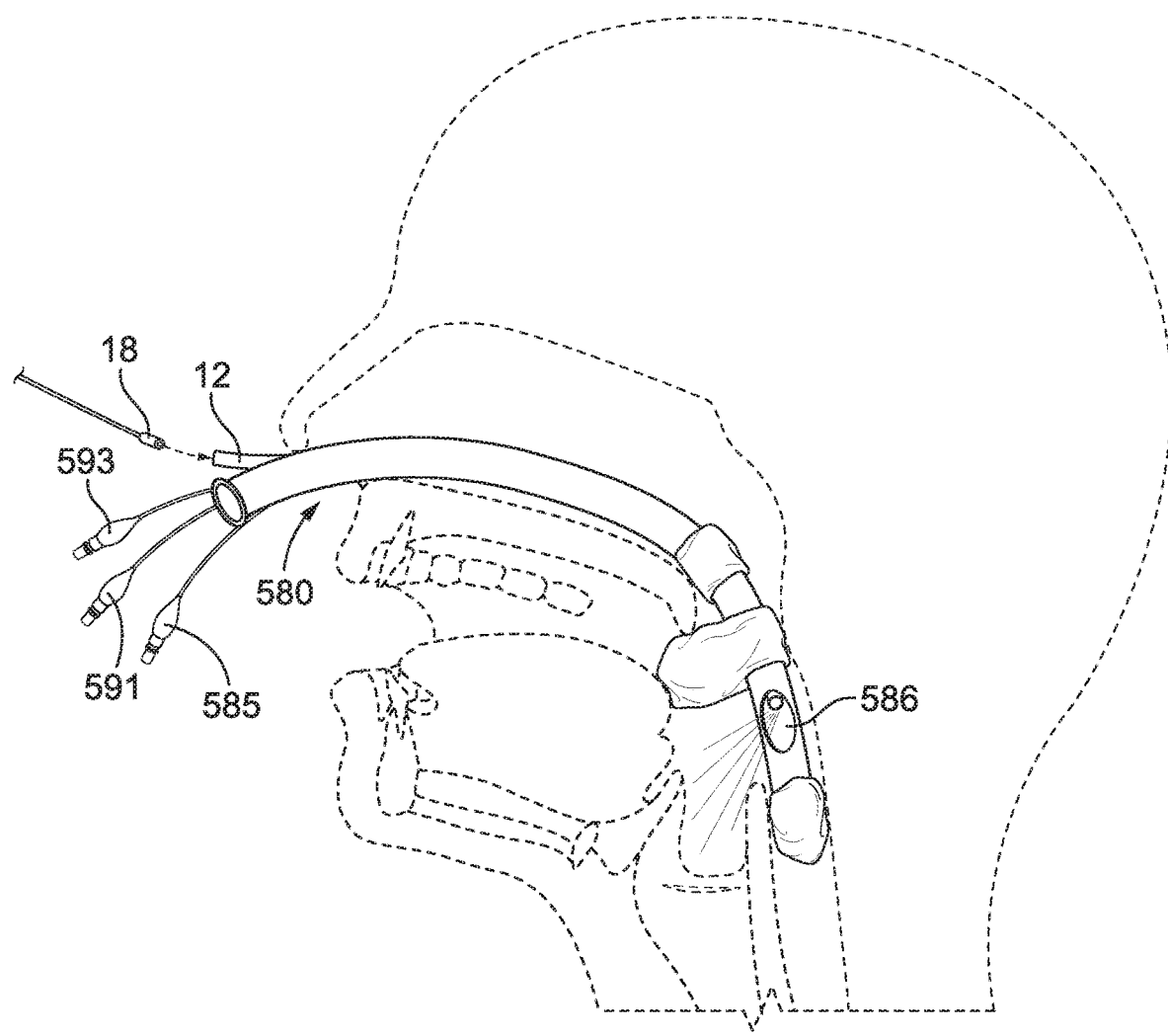

FIGS. 36A, 36B and 36C depict a nasopharyngeal airway device, generally 580. The device comprises a tubal body 582 with a camera tube 12 positioned internally. The distal end of the camera tube 12 is sealed with transparent material 17. A camera 18 is placed inside the camera tube 12. The tubal body 582 has a closed distal end with an occluding soft balloon 584 just proximal to the tip of the body 582. The balloon 584 can be inflated with a means 585. Proximally, to the distal balloon 584 is an open lumen (vocal cord visualization lumen) 586 that has the distal camera tube 12 situated to view anteriorly towards the vocal cords. The vocal cord visualization lumen 586 is proximate to the main lumen 588 in the nasopharyngeal airway tubal body 582. The lumen 588 runs proximally to the distal end merging into the visualization opening 586 that houses the camera tube 12.

A larger balloon 590 maybe placed proximal to the vocal cord visualization camera lumen 586. The balloon 590 may be inflated with a means 591. The balloon 590 may occlude the posterior pharynx. Additionally, another balloon 592 could be situated proximally to the pharyngeal cuff balloon 590, as shown in FIG. 36B. The balloon 592 can be inflated with a means 593.

These balloons ideally occlude the upper esophagus (hypopharynx), pharynx and nasal septum. These balloons may have separate pilot cuffs or share one pilot cuff to one or more balloons. A standard 15 mm cap (not shown) maybe attached to the proximal portion of the nasopharyngeal device to provide positivity pressure ventilation with a sealed hypopharynx and pharynx with the balloons in place and inflated.

As shown in FIG. 36C, the device 580 is placed in a patient and the balloons are inflated in the nasalseptum, pharynx and hypopharynx. The visualization camera lumen 586 can be easily aligned to the vocal cords visualized anteriorly under direct and continuous visualization. A ventilator cap is available to be placed proximally to provide positive pressure ventilation. This device can be a rescue device to provide continual visualization of the vocal cords while maintaining a closed system.

Figures 37A, 37B, 37C:
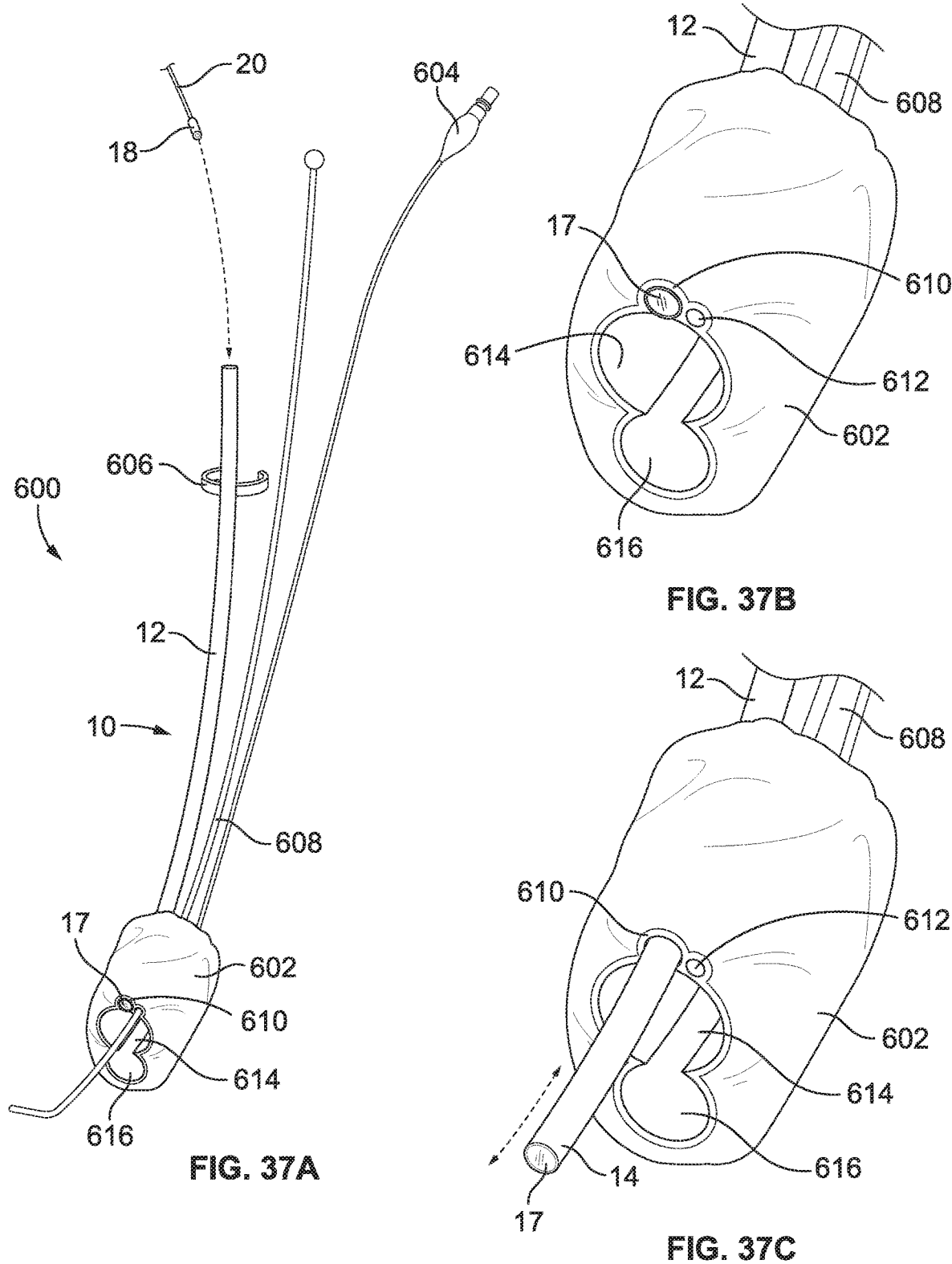
FIGS. 37A, 37B and 37C depict an embodiment of a visualization device equipped with a cuff and a buogie.

As shown in FIGS. 37A, 37B and 37C, a further embodiment provides a visualization device equipped with a cuff, generally 600. As shown in FIG. 37A, the device comprises the visualization device 10, which as shown and described in connection with FIG. 1A, comprises a camera tube 12 with a distal end 14 and a proximal end 16. The camera tube 12 is sealed at the distal end 14. This creates a sealed distal window made of transparent material 17. The diameter of camera tube 12 is designed in such a way that a camera 18 with wire 20 can be inserted inside of the camera tube 12 through an opening at the proximal end 16 and moved down the camera tube 12 toward the distal end 14, so that the camera 18 transmits continuously images obtained through the transparent sealed distal window 17. A cuff 602 wraps around the distal end of the camera tube 12. The cuff 602 has a passage 610 through the cuff body which can be a tube passed through the cuff body such that the cuff 602 can still inflate and creates a closed system after being inserted in a patient and inflated. The camera tube 12 is inserted through the cuff through the passage 610. The cuff 602 can be inflated with means 604. The camera tube 12 is further equipped with at least one holder 606 which can be shaped as a semi-ring or as a ring. The device 600 can be combined with a second device, such as for example an endotracheal tube (not shown) such that the second device is inserted into the holder 606 and is held in place while combined with the camera tube 12. The diameter of the holder 606 can be adopted to an endotracheal tube or any other second device to be combined with the device 600.

The device 600 can be equipped with a bougie 608. As can be seen from FIG. 37A, and can be further appreciated from FIGS. 37B and 37C which are zoom-in images for the cuff-portion of the device 600, the camera tube 12 is inserted through the cuff 602 via the passage 610. The bougie 608 is also inserted through a separate passage 612 in the cuff body. Bougie 608 can be advanced or retracted through the passage 612. In the embodiment of FIG. 37B, the camera tube 12 is sealed to the passage 610 of the cuff 602. In the embodiment of FIG. 37C, the camera tube can slide through the passage 610 and therefore, camera tube 12 can be advanced and retracted through the passage 610. The cuff 602 comprises at least one lumen 614. In some embodiments and as shown in FIGS. 37A, 37B and 37C, the cuff 602 comprises two lumens 614 and 616. The two lumens, 614 and 616, can be of the same diameter of they can be of two different diameters as shown in FIGS. 37A, 37B and 37C.

Figure 38:
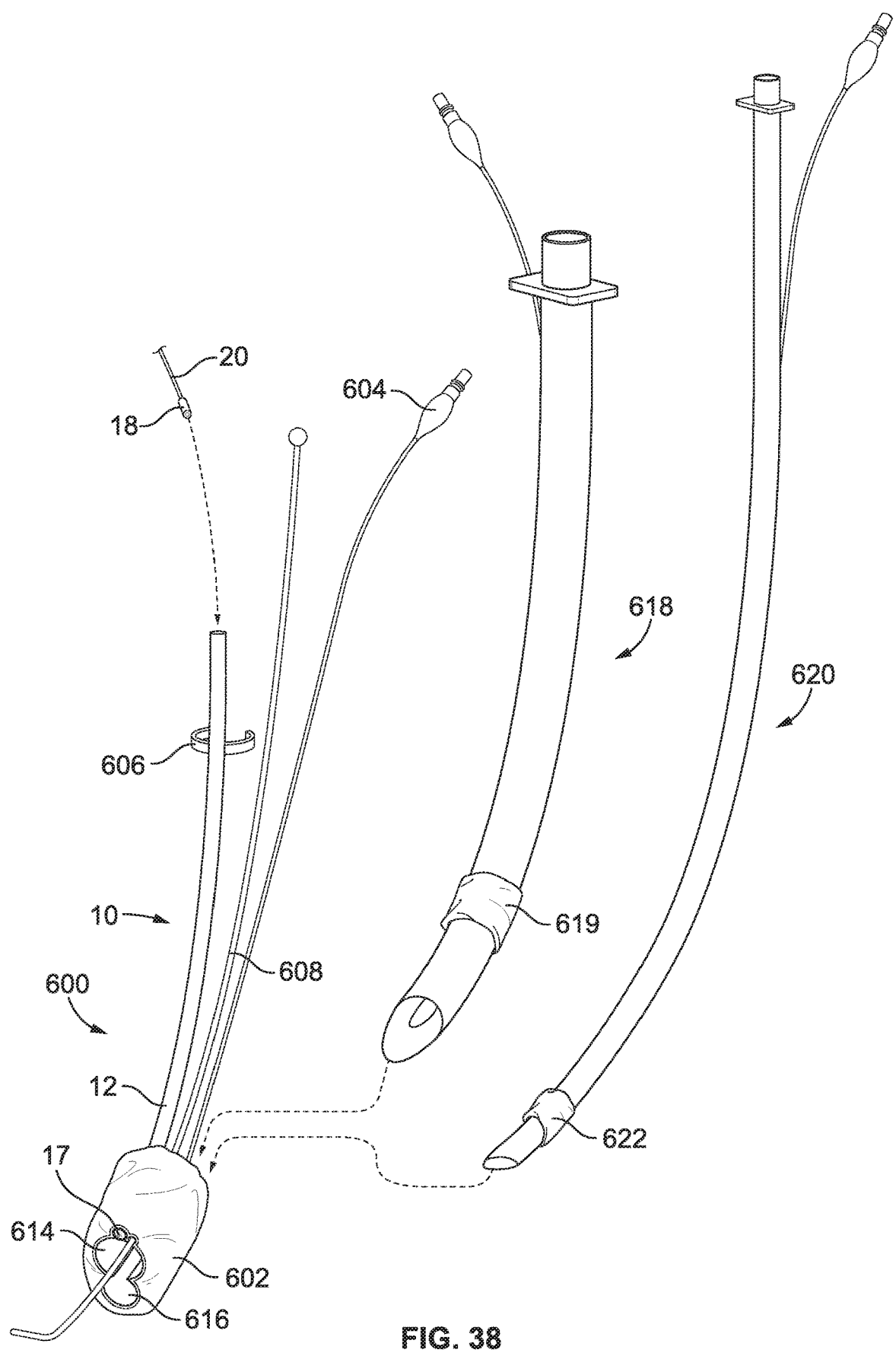
FIG. 38 depicts the device of FIG. 37A as combined with two second devices.

Further embodiments include the cuff 602 with additional lumens which can be of the same or different diameter. The lumens 614 can be used for placing various devices such as for example a tube and or an endotracheal tube through the cuff 602. The device 600 can be used in combination with various second devices, including but not limited to a tube and an endotracheal tube. These devices may be with or without cuffs. This is illustrated in FIG. 38, which shows combining the device 600 with an endotracheal tube 618 and another tube 620. As can be seen from FIG. 38, the endotracheal tube 618 fits through the lumen 614, while the endotracheal tube 620 fits through the lumen 616. The tubes 618 and 620 may be advanced or retracted through the lumens 616.

Figure 39:
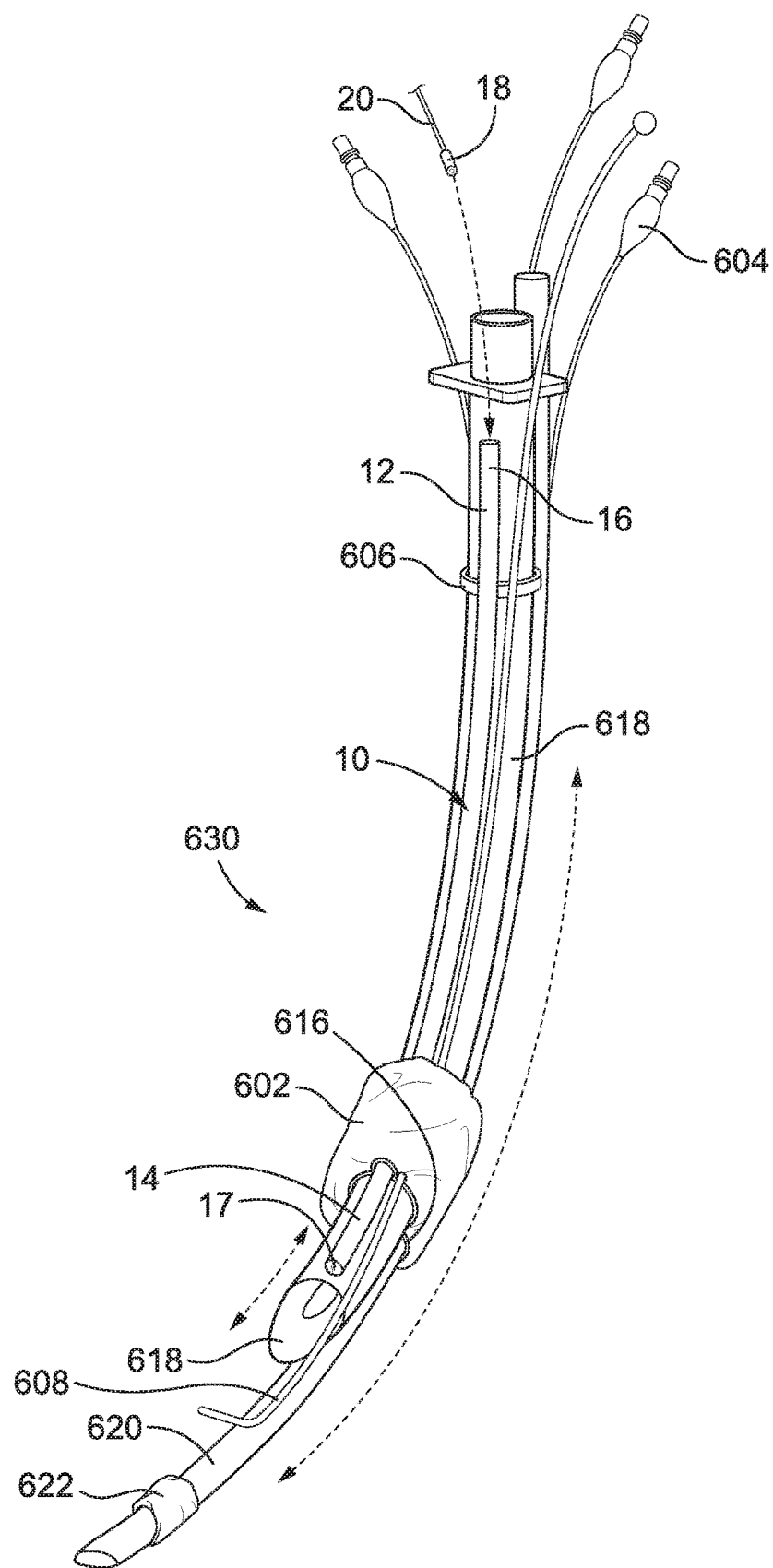
FIG. 39 depicts an embodiment for a supraglottic airway device.

Another embodiment provides a supraglottic airway device as shown in FIG. 39, generally 630. The device 630 comprises the device 600 as described in connection with FIGS. 37A and 37C. The endotracheal tube 618 is combined with the device 600 by being secured with the holder and placed through the cuff lumen. In the embodiment of FIG. 39, the camera tube 12 can slide through the cuff passage 610 and can be advanced distally to the cuff 602 and then retracted proximally to the cuff 602, if needed. A second tube 620 is combined with the device 630 by being placed through the cuff lumen 616. The tube 620 is equipped with a cuff 622 and this tube 620 can slide distally through the cuff lumen 616. Thus, the tube 620 can be advanced and retracted through the lumen 616. When the device 630 is placed in a patient, the cuff 602 can be inflated in the oral pharynx. The distal cuff 622 can be inflated in the upper esophagus. Having the camera 18 monitoring the placement through the transparent window 17 of the camera tube 12 allows the device to be placed under direct visualization proximally to the vocal cords. The bougie can be placed through the vocal cords and can be used a guide for placement of the endotracheal tube 618. In some embodiments, the bougie 608 can be inserted through the same lumen as the tube 620 such that the tube 620 follows the bougie tip to its point. A person of skill will appreciate that in the device 630, each of the tubes 12, 618 and 620 can move independently from each other. The tube 620 can be designed such that it is used for suction. The device 630 can be converted into an intubating device.

Figure 40:
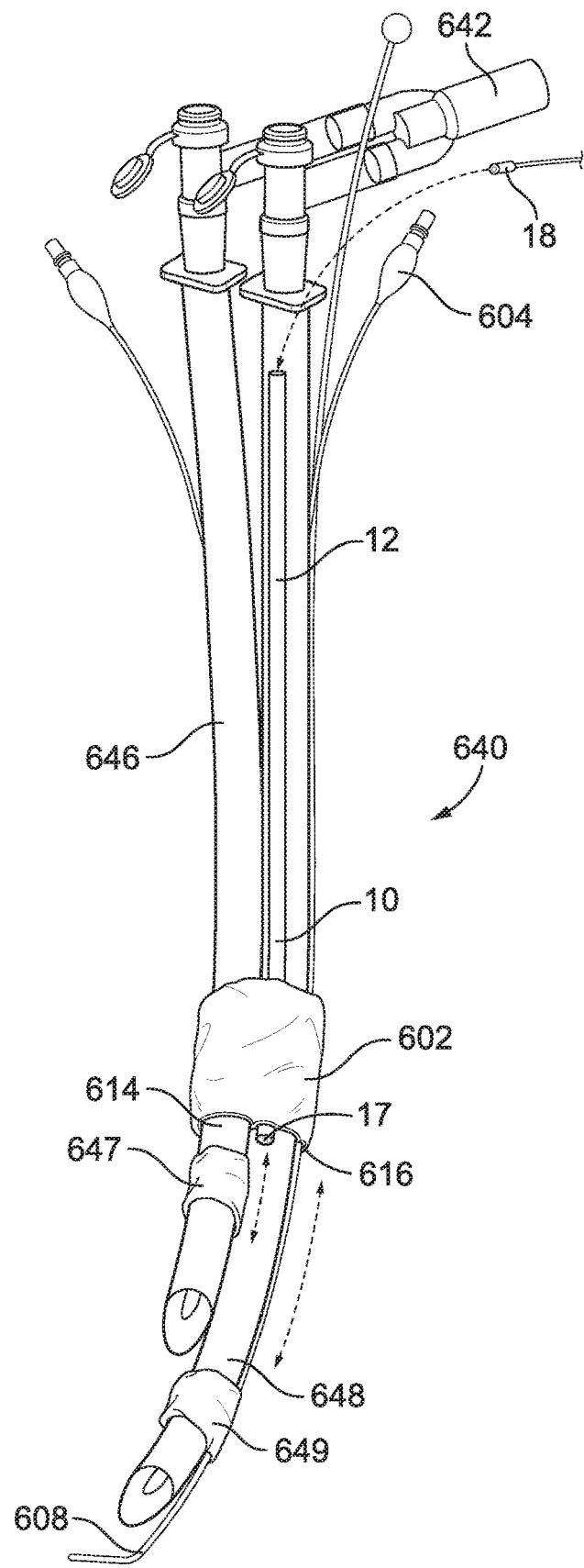
FIG. 40 depicts an embodiment for a double-lumen endotracheal tube convertible to single-lumen endotracheal tube.

Another embodiment of a device is provided in FIG. 40, generally 640. This device comprises the device 600 as described in connection with FIGS. 37A, 37B and 37C and which comprises the visualization device 10 with the inflatable cuff 602 which can be inflated with means 604, and the camera 18 placed inside of the camera tube 12 with the sealed distal transparent window 17. The device 600 further comprises the bougie 608 and two endotracheal tubes 646 and 648. The first endotracheal tube 646 is placed through the cuff lumen 614 and the second endotracheal tube 648 is placed through the cuff lumen 616. In some alternative embodiments, the cuff lumens 614 and 616 can be combined into a single lumen. Each of the two endotracheal tubes 646 and 648, and the camera tube 12 can slide independently of each other distally from the cuff 602. Each of the endotracheal tubes 646 and 648 is connected to a ventilator through an adaptor 642. The device 640 can be placed in the trachea to provide independent ventilation of each bronchus under direct and continual visualization. The bougie 608 can be placed under the distal cuff 649 to guide the endotracheal tube 648 to the proper bronchus under direct vision. The proximal large cuff 602 is placed in the mid-trachea area. The device 640 can be reversibly taken apart by retracting one of the endotracheal tubes 646 or 648, and thus, reverting back to a single remaining lumen endotracheal tube 646 or 648 placed in the mid trachea. Conversely, a single lumen endotracheal tube 648 can be made into a double lumen tube comprising of the two endotracheal tubes 646 and 648. The camera lumen 12 and bougie 608 can slide distally of the cuff 602 independently of the tubes 646 and 648. The device 640 can be also provided in a kit form comprising at least the device 600 and at least two any conventional endotracheal tubes.

Figure 41A:
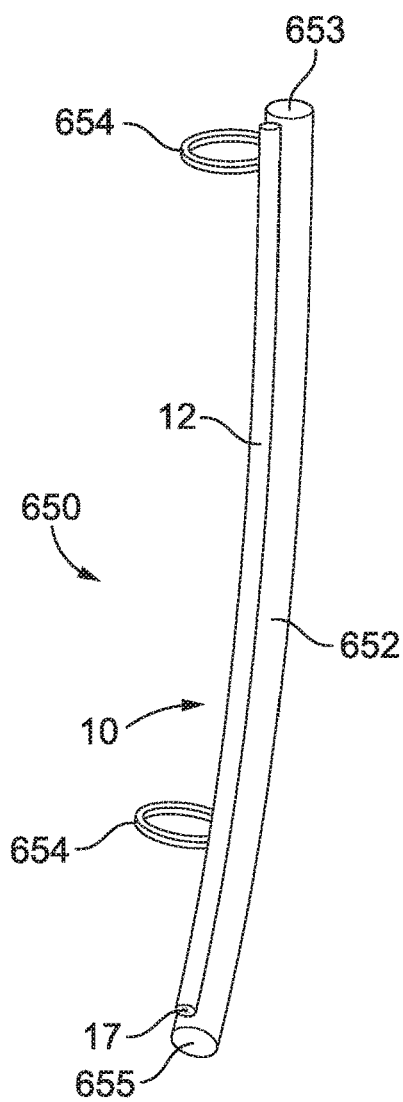
FIG. 41A depicts an embodiment for a visualization device equipped with a tool lumen.
Figure 41B:
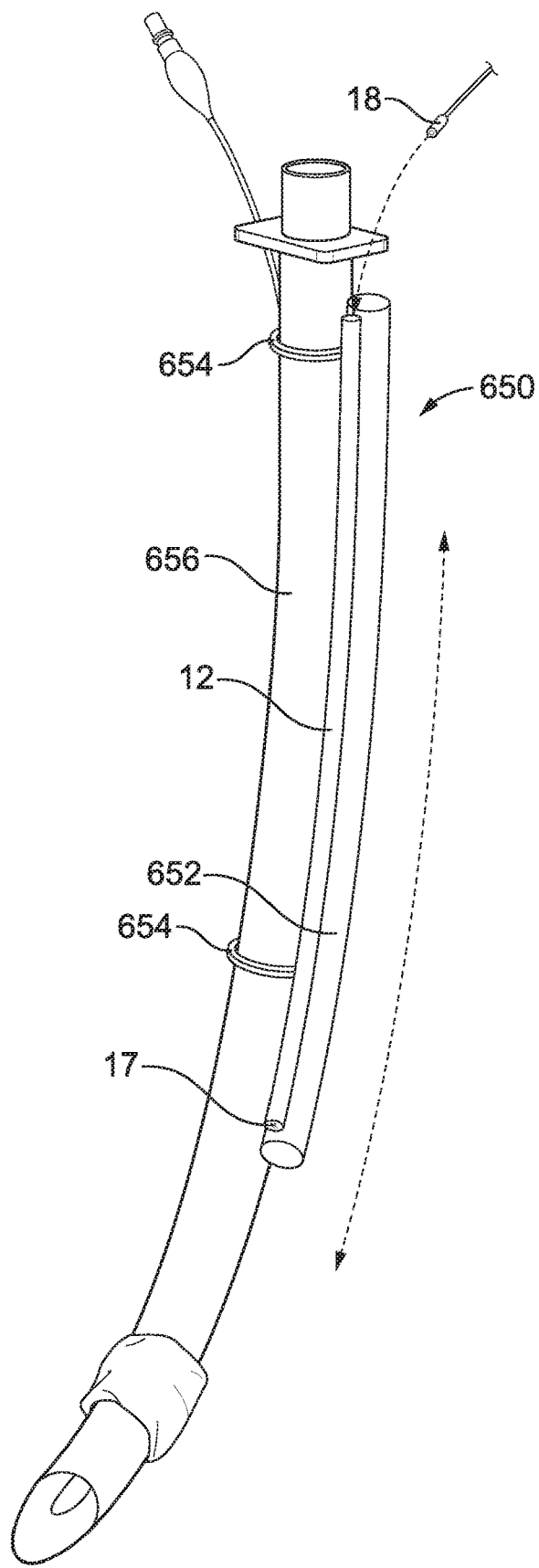
FIG. 41B depicts the device of FIG. 41A combined with an endotracheal tube.
Figure 41C:
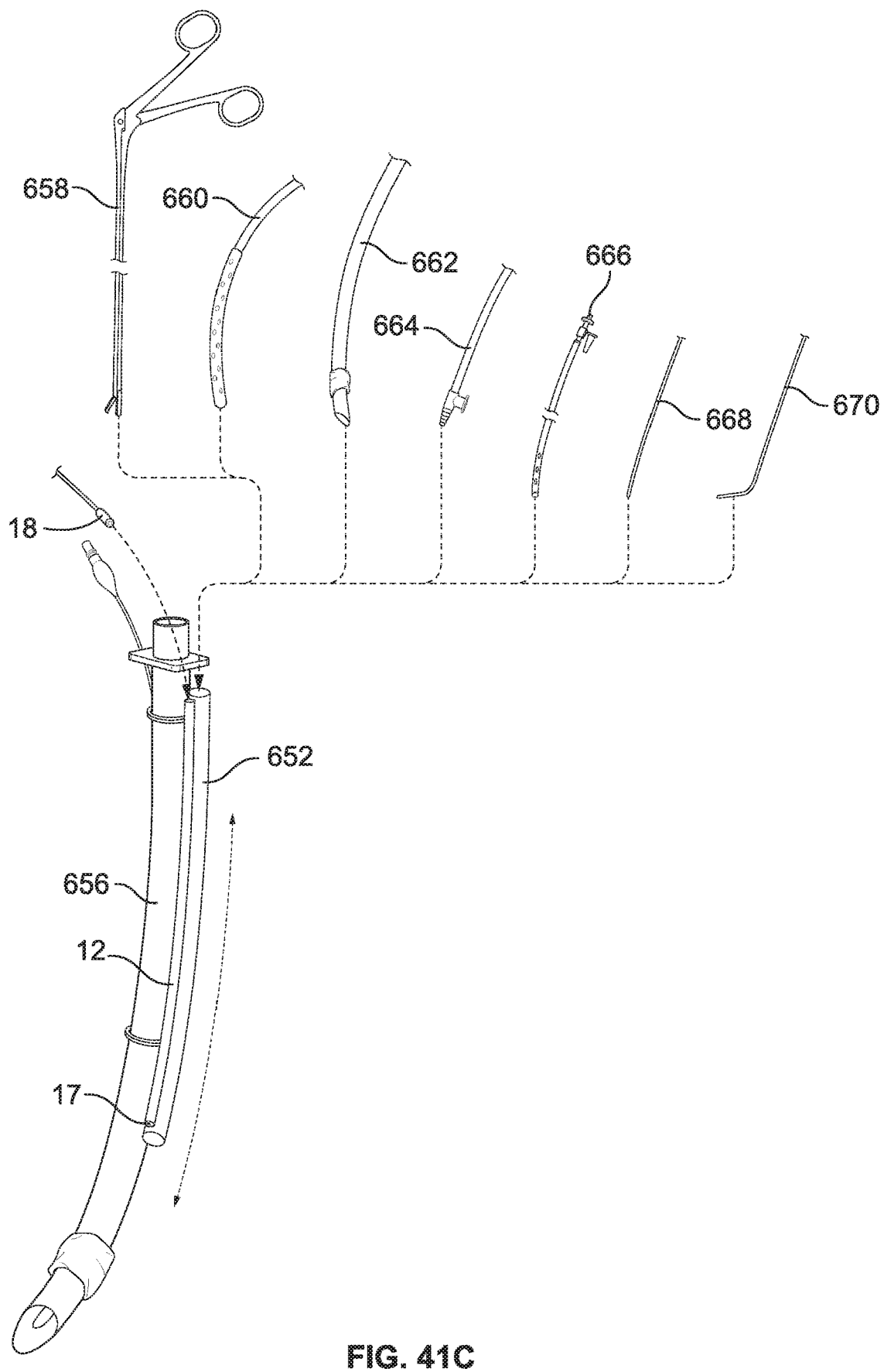
FIG. 41C depicts the device of FIG. 41B and various tools which can be inserted in the tool lumen.

FIG. 41A provides a further embodiment for a visualization device, generally 650. This embodiment comprises the visualization device 10 of FIG. 1A which comprises the camera tube 12, and the camera 18 placed inside of the camera tube 12 with the sealed distal transparent window 17. As shown in FIG. 41A, the visualization device 10 is combined with a tool tube 652 with a lumen with proximal and distal openings, 653 and 655. The tool tube 652 can be sealed, welded or otherwise attached to the camera tube 12. In some embodiments, the device 650 is equipped with at least one and preferably two rings 654 for holding a second device, such as for example an endotracheal tube in combination with the device 650. As shown in FIG. 41B, the device 650 can be assembled with an endotracheal tube 656 through the rings 654. The device 650 can slide along the endotracheal tube 656. As shown in FIG. 41C, various tools, including but not limited to, biopsy forceps 658, esophageal stethoscope 660, cuff tube 662, suction tube 664, nasogastric tube 666, stylet 668 and bougie 670 can be inserted in the tool tube 652 through the proximal opening 653.

As can be appreciated from FIGS. 41A, 41B and 41C, the tool tube 652 has the distal opening 655, and any of the tools 658-670 can be advanced beyond the tool tube distal opening 655. In some embodiments, the camera tube 10, the tube holder 654 and/or the tool tube 652 may have a light source in close proximity or attached to any of the devices or tools. Each of the ring holders 654 is attached to the camera tube 10 and the tool tube 652. The ring holder 654 can be a complete ring or incomplete ring. It is understood that the device 650 can be attached with the ring holder 654 to a tube or an endotracheal tube. The device 650 can then slide on the tube or endotracheal tube proximally or distally, and can also rotate about the tube or endotracheal tube. In other embodiments, the device 650 can be placed internally into an endotracheal tube or supraglottic airway lumen.

Figure 42A:
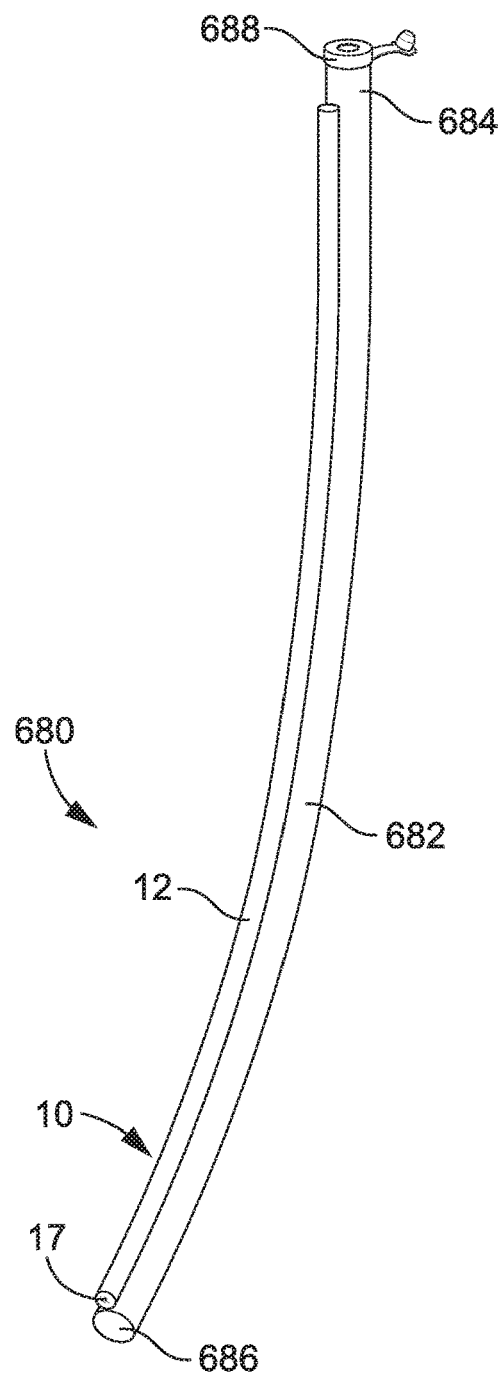
FIG. 42A depicts another embodiment for a visualization device equipped with a tool tube.

FIG. 42A provides another embodiment of a visualization device combined with a tool tube, generally 680. This embodiment comprises the visualization device 10 of FIG. 1A which comprises the camera tube 12, and the camera 18 placed inside of the camera tube 12 with the sealed distal transparent window 17. As shown in FIG. 42A, the visualization device 10 is combined with a tool tube 682 with a lumen with proximal and distal openings, 684 and 686. The proximal opening 684 is sealed if the tool tube 682 is capped with a cap 688. While the embodiment of FIG. 42A does not include ring holders, a person of skill will recognize that in further embodiments, the device 680 can be equipped with at least one ring holder as was discussed in connection with FIGS. 41A, 41B and 41C.

Figure 42B:
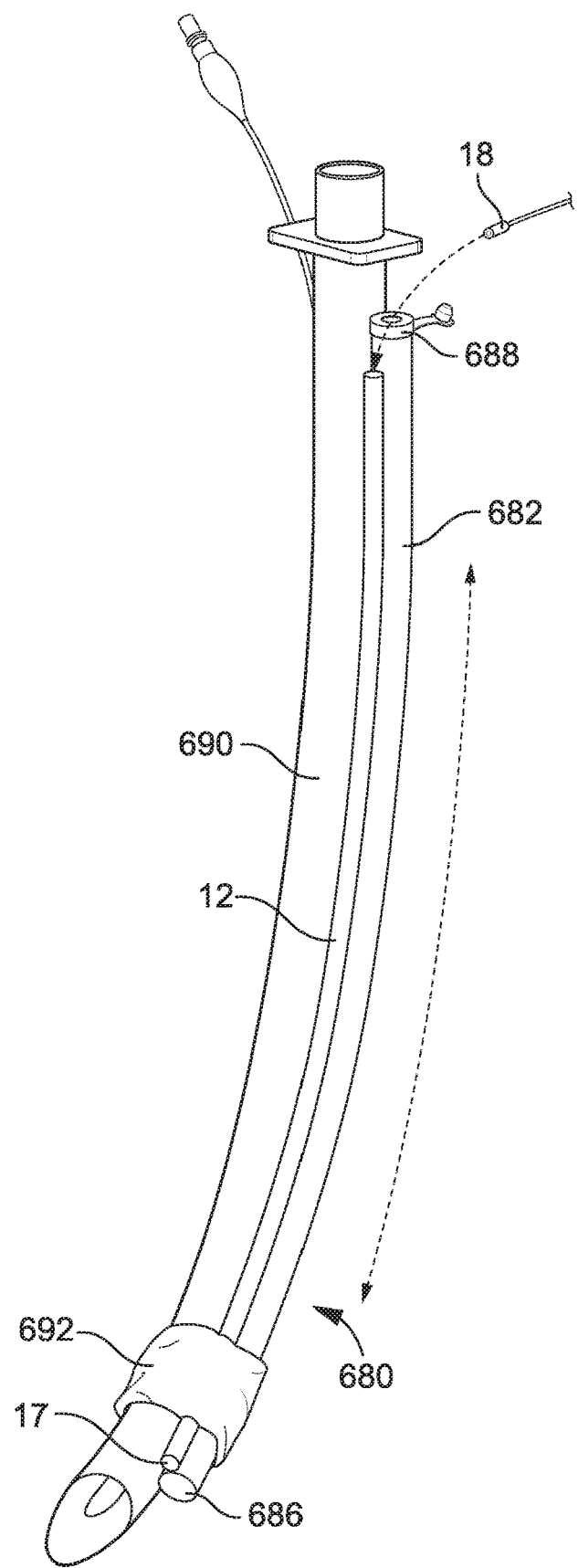
FIG. 42B depicts the device of FIG. 42A combined with an endotracheal tube.
Figure 42C:
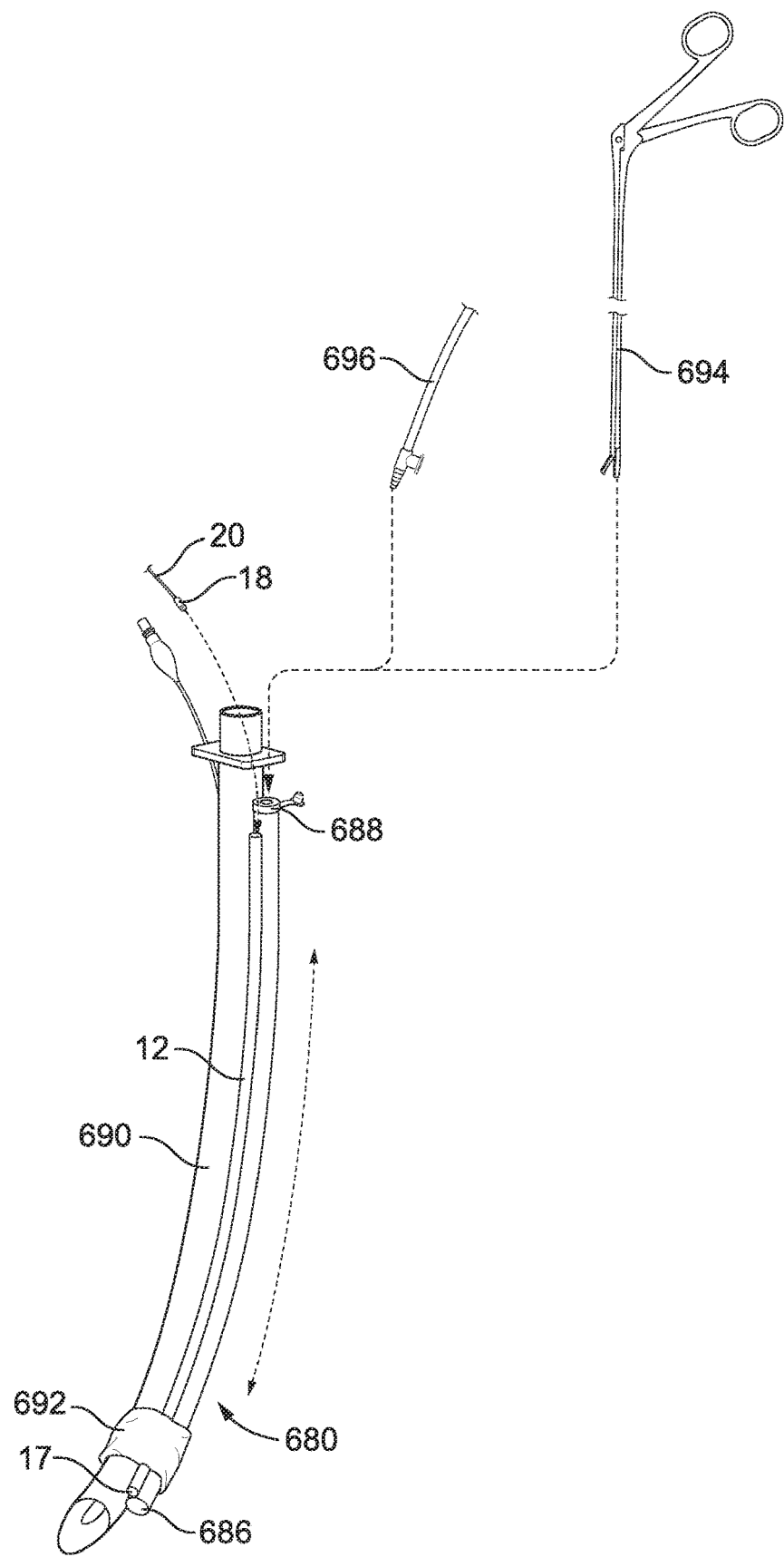
FIG. 42C depicts the device of FIG. 42B and various tools which can be inserted in the tool tube.

As shown in FIG. 42B, the device 680 can be assembled with an endotracheal tube 690 by being placed beneath an endotracheal tube cuff 692. As shown in the embodiment of FIG. 42B, the device 680 can slide proximally or distally under the cuff 692. As shown in FIG. 42C and as was discussed in detail in connection with FIG. 41C, various tools, including but not limited to, biopsy forceps 694 or a suction tube 696 can be placed in the tool tube 682. When the tool tube 682 is not in use or a closed system is to be established for patient's ventilation, the tool tube 682 can be closed with the cap 688 at the proximal end 684.

Figure 43A:
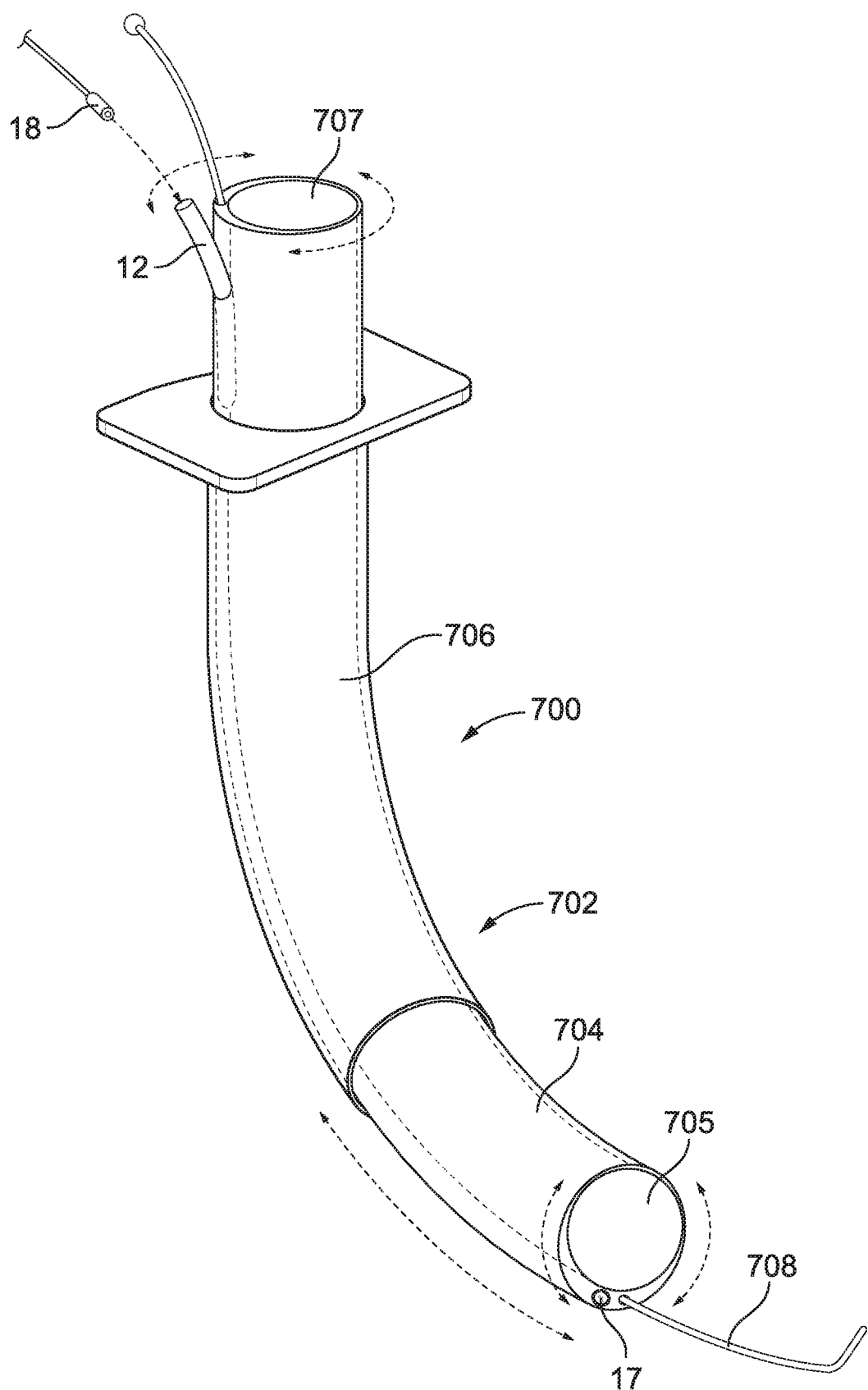
FIG. 43A depicts an expandable oral airway device with adjustable length.

FIG. 43A depicts a further embodiment of an oral airway device with adjustable length for ventilation, continual visualization, and intubation, generally 700. The device 700 comprises a two-part tubal body 702 with a lumen and with open proximal and distal ends. The length of the two-part tubal body 702 can be adjusted because the two-part tubal body 702 is made from an outer cylindrical tube wall 706 and an inner cylindrical tube 704, wherein the inner cylindrical tube 704 at least partially inserted into the outer cylindrical tube 706. The inner cylindrical tube 704 can be extended from the outer cylindrical tube 706, thus increasing the length of the two-part tubal body 702, as needed. The inner cylindrical tube 704 can also retracted back inside of the outer cylindrical tube 706, thus decreasing the length of the two-part tubal body 702, as needed. The diameter of the outer cylindrical tube 706 is larger than the diameter of the inner cylindrical tube 704. Thus, the lumen 707 of the outer cylindrical tube 706 has a diameter larger than the lumen 705 of the inner cylindrical tube 704. The inner cylindrical tube 704 is at least partially inserted inside of the larger outer cylindrical tube 706. The inner cylindrical tube 704 can rotate around inside the outer cylindrical tube 706. The inner cylindrical tube 704 can also move distally and it can be extended distally from the outer cylindrical tube 706, thus the length of the tubal body 702 can be elongated or shorten, as may be needed. In some embodiments, the cylindrical tube 704 can be completely separated and removed from the cylindrical tube 706. FIG. 43E shows in more detail that the device 700 can expand and retract distally. The tube 704 and the tube 706 can rotate around which permits positional flexibility and positioning of the bougie 708 and camera 18 on any side of the patient's body and as needed.

The device 700 comprises a visualization device 10 which comprises the camera tube 12, and the camera 18 placed inside of the camera tube 12 with the sealed distal transparent window 17. The device 700 also comprises a bougie 708. The bougie 708 can be incorporated either inside the wall 703 of the inner cylindrical tube 704 or inside the wall 709 of the outer cylindrical tube 706. The bougie 708 can slide proximally, distally and allow for rotation in its respective cylindrical tubes 704 or 706. The camera tube 12 is nearby inside the wall 703 of the inner cylindrical tube 704 or the wall 709 of the outer cylindrical tube 706. The camera tube 12 can be stationary as shown in FIG. 43C or it can slide independently of the inner cylindrical tube 704 or the bougie 708, as shown in FIG. 43D.

In some embodiments, the camera tube 12 can be associated with the bougie 708 such that they slide together distally from the two-part body 702. The bougie 708 can slide distally and can be placed through the vocal cords under direct vision from the camera 18. After that, the inner cylindrical tube 704 can slide over the bougie 708 to be placed through the vocal cords or just proximal to the vocal cords.

Figure 43B:
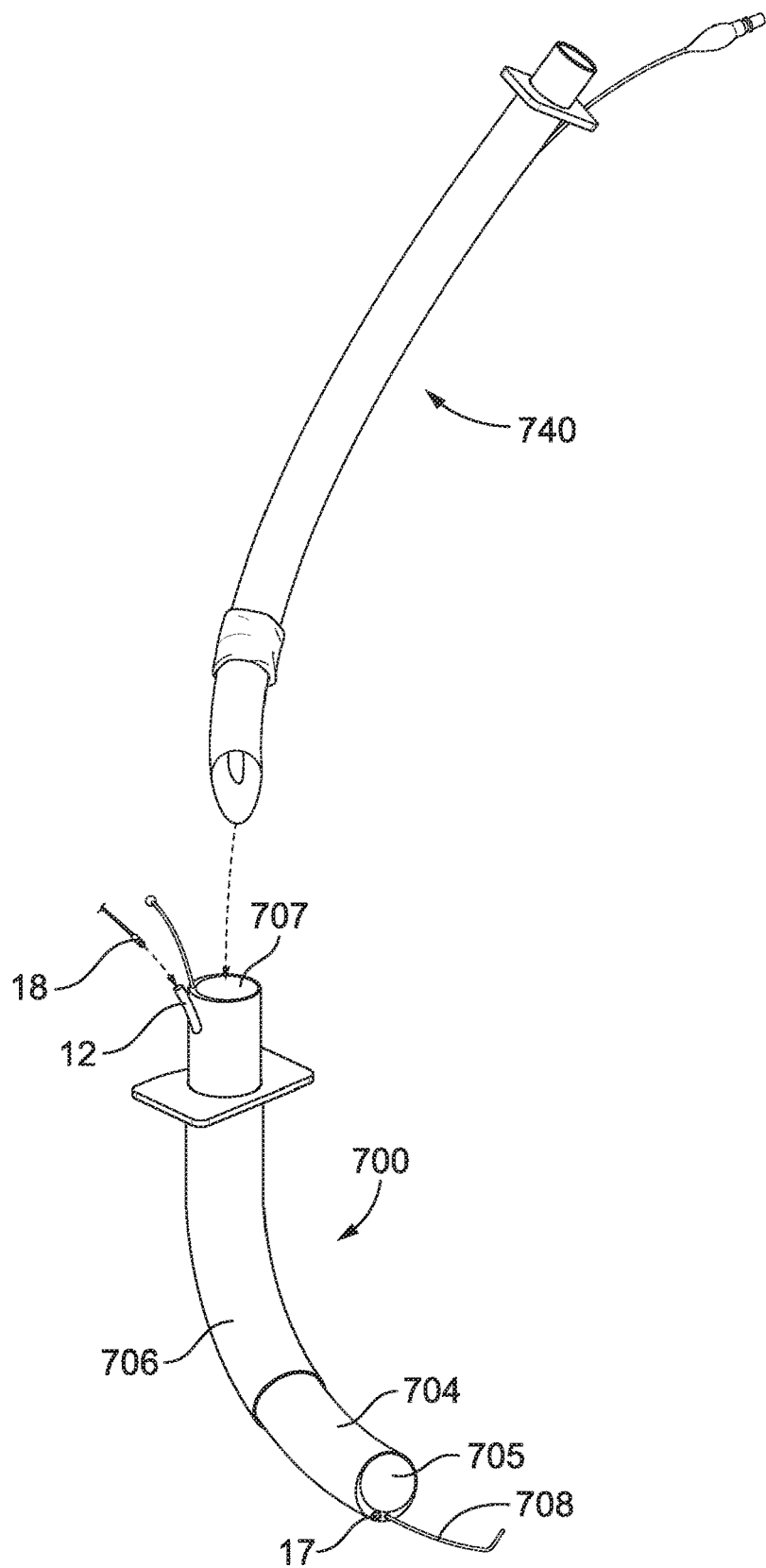
FIG. 43B depicts insertion of an endotracheal tube into the oral airway device of FIG. 43A.
Figure 43C:
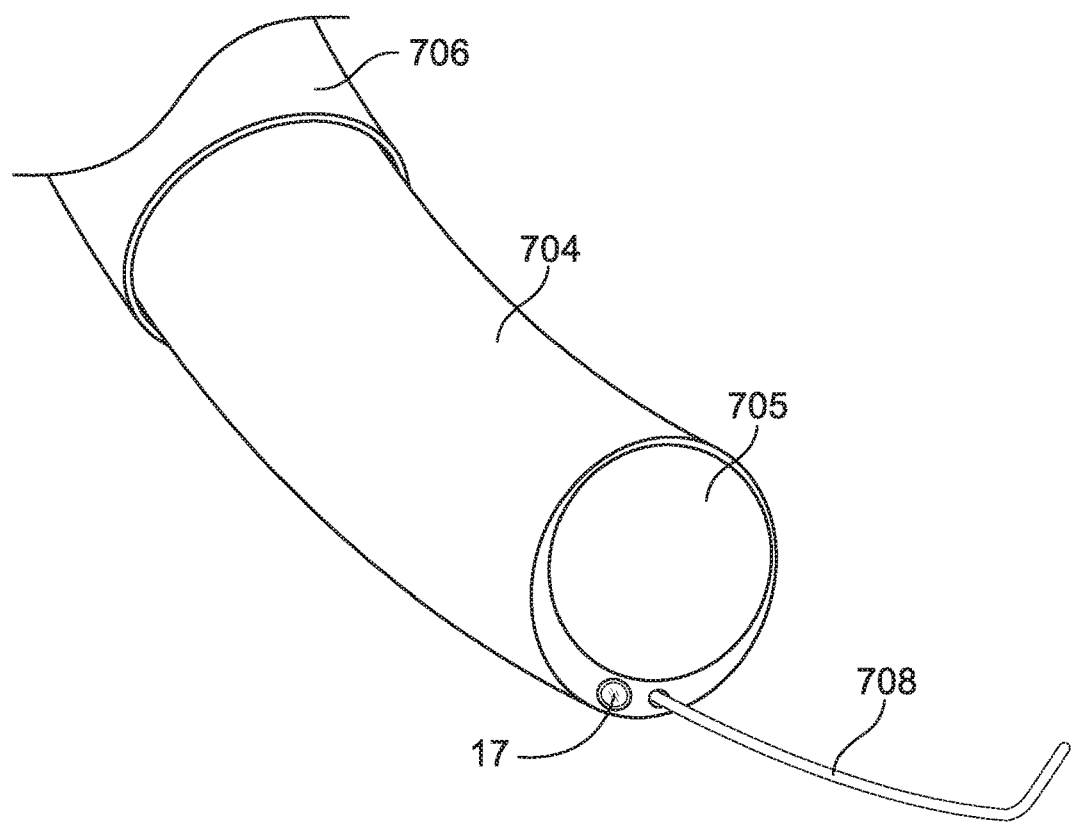
FIG. 43C zooms in on the distal portion of the device of FIG. 43A, in which the camera tube is stationary.
Figure 43D:
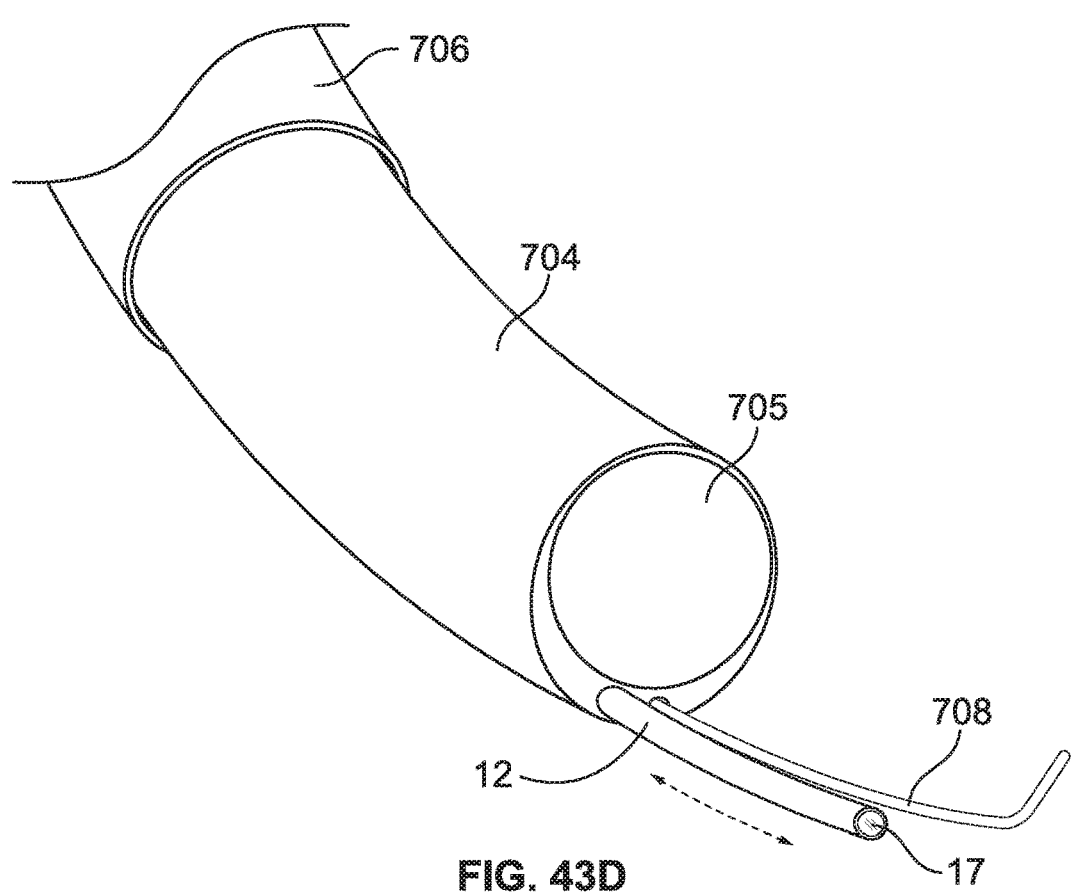
FIG. 43D zooms in on the distal portion of the device of FIG. 43A, in which the camera tube can slide distally from the device of FIG. 43A.
Figure 43E:
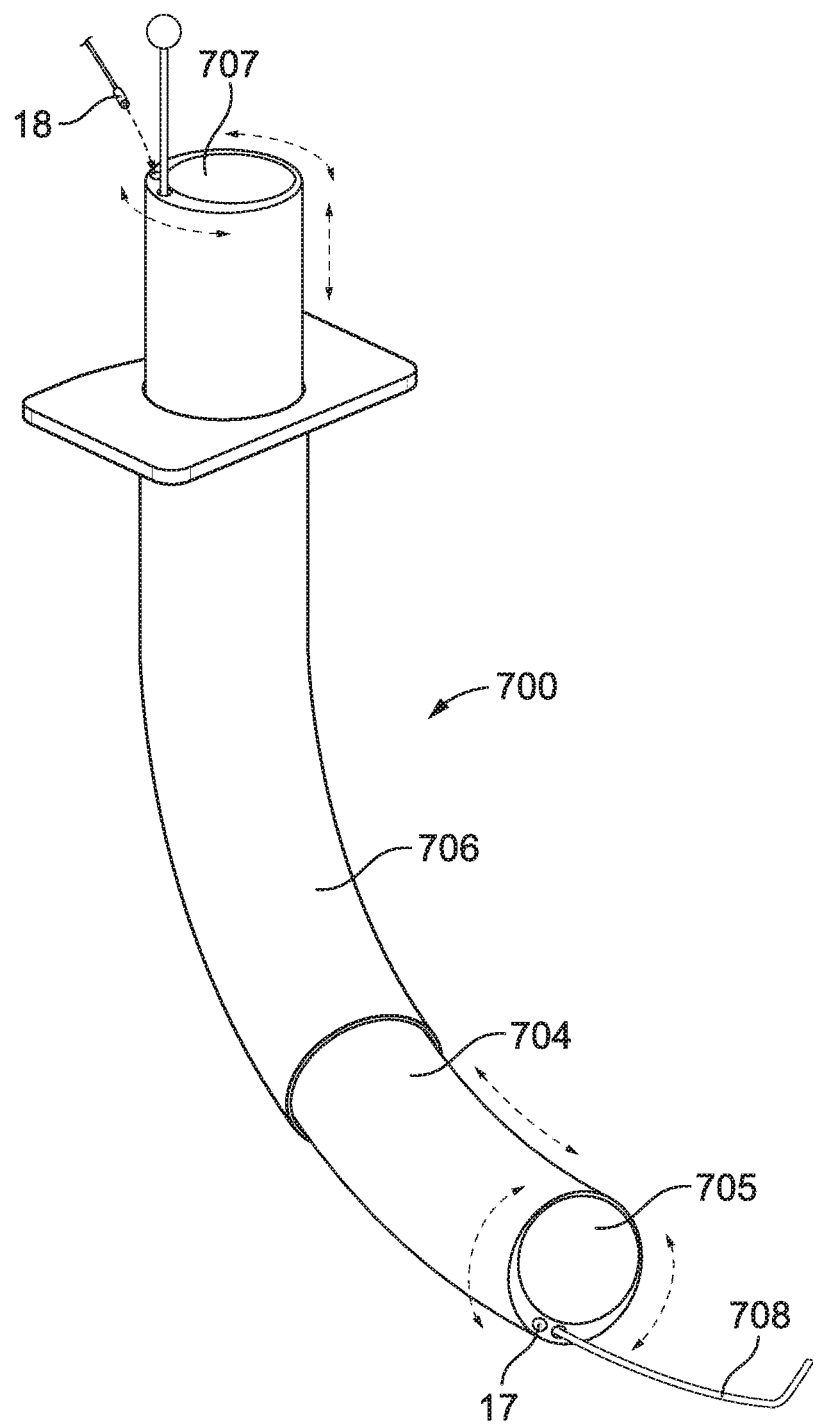
FIG. 43E provides a further embodiment of the expandable oral airway device of FIG. 43A.

As shown in FIG. 43B, an endotracheal tube 710 can be placed inside the lumen 707 of the device 700 under the direct visualization provided by camera 18 placed inside the camera tube 12. Conversely, the device 700 can be placed over the endotracheal tube 710 which has already been placed through the vocal cords of a patient. This allows for continual visualization of extubation with the ability to rapidly reintubate.

In a further embodiment, the outer cylindrical tube 706 can be separated from the inner cylindrical tube 704. In this embodiment, only the outer cylindrical tube 706 is used for inserting into a patient. This outer cylindrical tube 706 is inserted into a patient with the assistance of the bougie 708 and the visualization device 10. Further embodiment, only the inner cylindrical tube 704 is used for inserting into a patient. This inner cylindrical tube 704 is inserted into a patient with the assistance of the bougie 708 and the visualization device 10.

In further embodiments, the device 700 can be further equipped with a tool tube (not shown). The tool tube can be attached along the tubal body 702, or the tool tube can be incorporated in the tube wall 702 and/or the tube wall 704.

Various tools, including but not limited to, biopsy forceps, oxygen tube, carbon dioxide extraction tube or a suction tube can be placed in the tool tube. In some further embodiments, the device 700 can be equipped with a cuff which wraps around the tube 704 at its distal portion or a cuff can wrap around the tube 706 at its distal portion. The cuff can be inflated if a closed system is to be established in order to ventilate a patient.

Further embodiments provide a kit comprising an outer cylindrical tube 706 and the visualization device 10 which comprises the camera tube 12, and the camera 18 placed inside of the camera tube 12 with the sealed distal transparent window 17. In these embodiments, an endotracheal tube which has a bougie can be combined with, placed or attached to the outer cylindrical tube 706. The endotracheal tube can guide by the bougie under direct and continual vision.

Yet further embodiments provide a kit comprising an outer cylindrical tube, an inner cylindrical tube which can be inserted in the outer cylindrical tube, a visualization device comprising a camera tube, and a camera placed in the camera tube, wherein the distal end of the camera tube is sealed with a transparent material which creates a sealed distal transparent window; and a bougie. The bougie and the camera tube can be incorporated in the outer cylindrical tube wall or in the inner cylindrical tube wall.

Figures 44A, 44B:
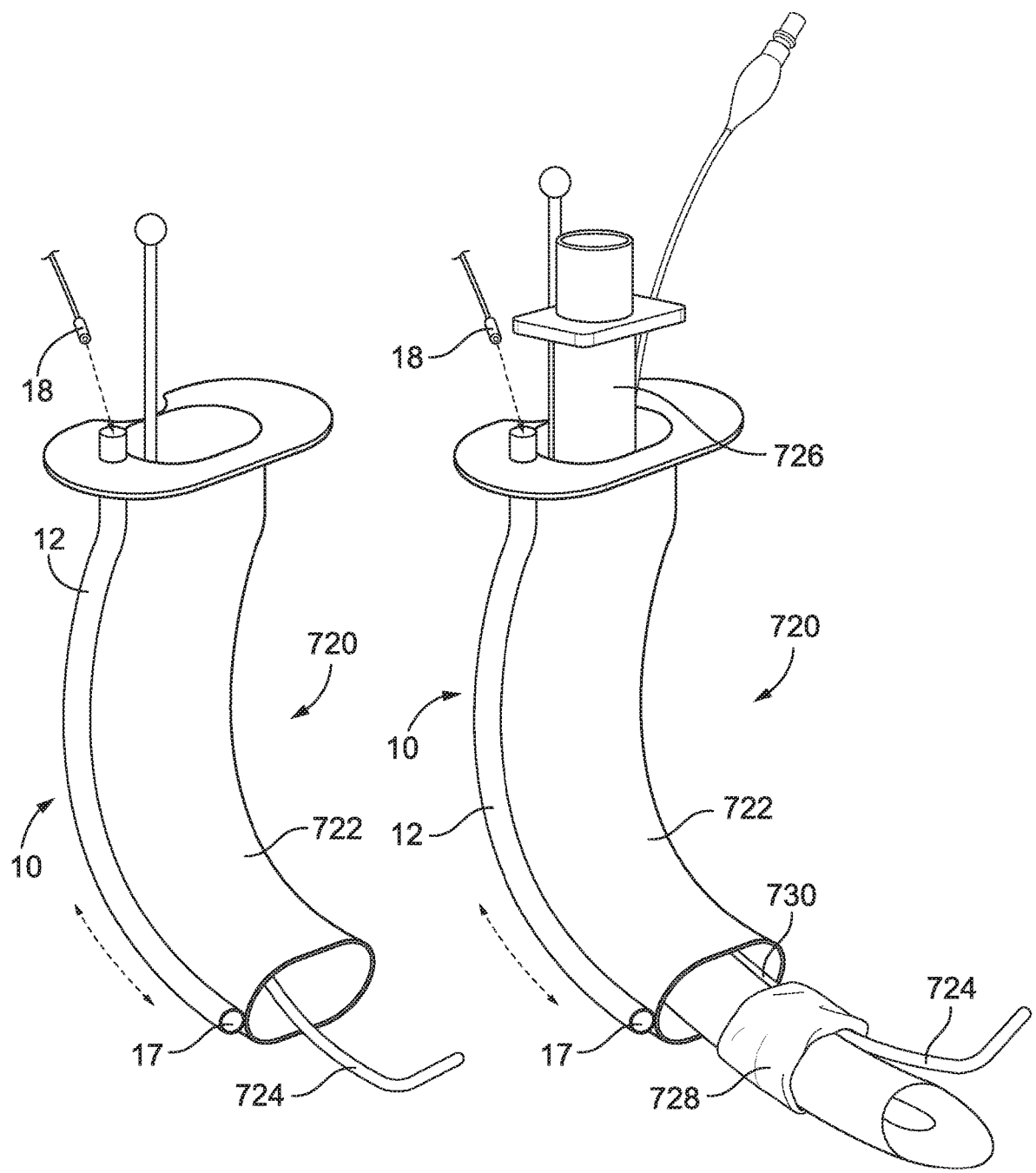
FIG. 44A depicts another embodiment for an oral airway device.
FIG. 44B depicts an assembly of the oral airway device of FIG. 44A with an endotracheal tube.

FIG. 44A provides another embodiment of an oral airway with a visualization device, generally 720. As shown in FIG. 44A, the visualization device 10 comprises the camera tube 12, and the camera 18 placed inside of the camera tube 12 with the sealed distal transparent window 17. In the embodiment of FIG. 44A, the camera tube 12 is affixed externally on a tubal body 722. In the embodiment of FIG. 44A, the camera tube 12 can slide. Thus, the camera tube can extend and retract. In other embodiments, the camera tube 12 can be affixed internally on the tubal body 722. The device 720 is equipped with a bougie 724. In some embodiments, the camera tube 12 can be affixed to the bougie 724 or other lumens and or other tools. The device 720 may have a light source built in the device 720. The bougie 724 can be built in internally or externally of the tubal body 722. The bougie 724 can rotate, extend or retract into the oral airway tubal body 722.

FIG. 44B depicts the assembly of device 720 with an endotracheal tube 726. In this embodiment, the device 720 has a built in endotracheal tube 726 to allow rapid intubation. The endotracheal tube 726 comprises a cuff 728. This cuffed endotracheal tube 726 has a built in bougie tube 730 under the endotracheal tube cuff 728. Thus, the bougie 724 can rotate, extend or retract. The bougie 724 can help direct the endotracheal tube 726 through the vocal cords. Conversely, the camera tube 12 can be placed externally or internally to the endotracheal tube 726. The camera 18 can be disposable or non-disposable. The camera tube 12 could rotate, extend or retract.

Figure 45A:
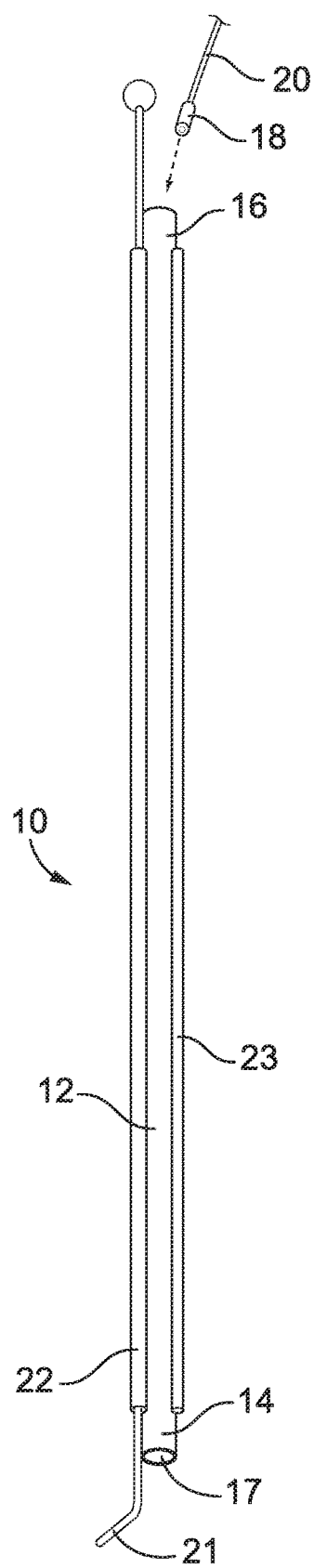
FIGS. 45A and 45B depict a visualization device equipped with a stylet and bougie.
Figure 45B:
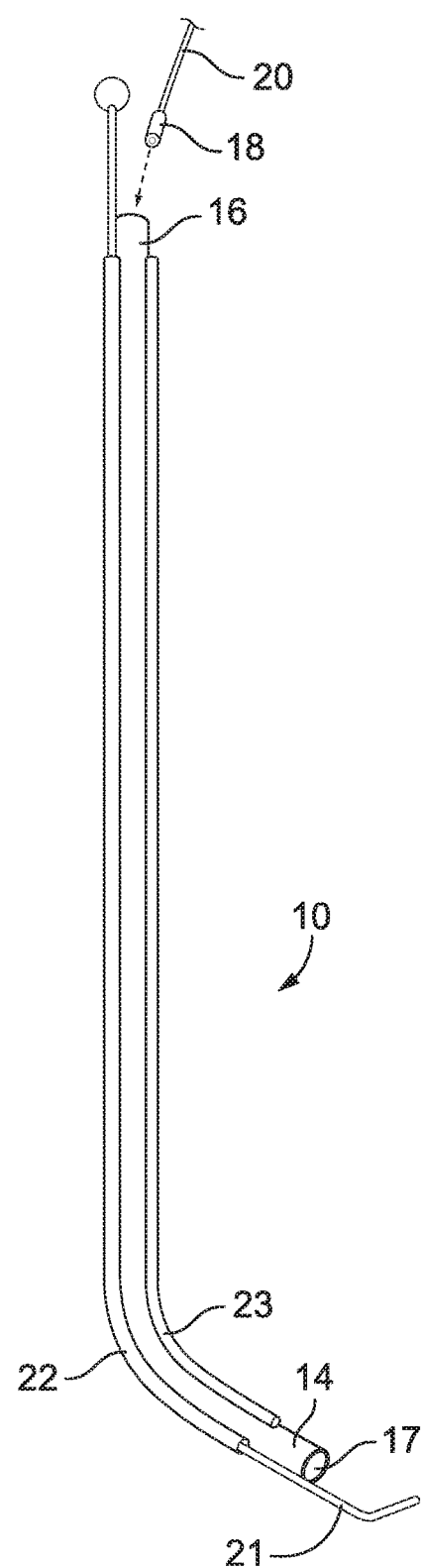

FIGS. 45A and 45B provide further embodiments of a visualization device of FIGS. 1A, 1B and 1C, generally 10. The visualization device 10 comprises a camera tube 12 with a proximal end 16 and a distal end 14. The proximal end 16 is open and the distal end 14 is sealed with transparent material 17. A camera 18 is placed through the open end 16 into the camera tube 12. A tube 22 is attached externally along the camera tube 12. The tube 22 is open on proximal and distal ends and is used for placing a bougie 21 which can extend and retract from the tube 22. A stylet 23 is attached externally along the camera tube 12. In the embodiment of FIG. 45A, the stylet 23 is straight. In the embodiment of FIG. 45B, the stylet 23 is curved. Thus, the stylet 23 provides a backbone and shape to the otherwise flexible camera tube 12.

Figure 46A:
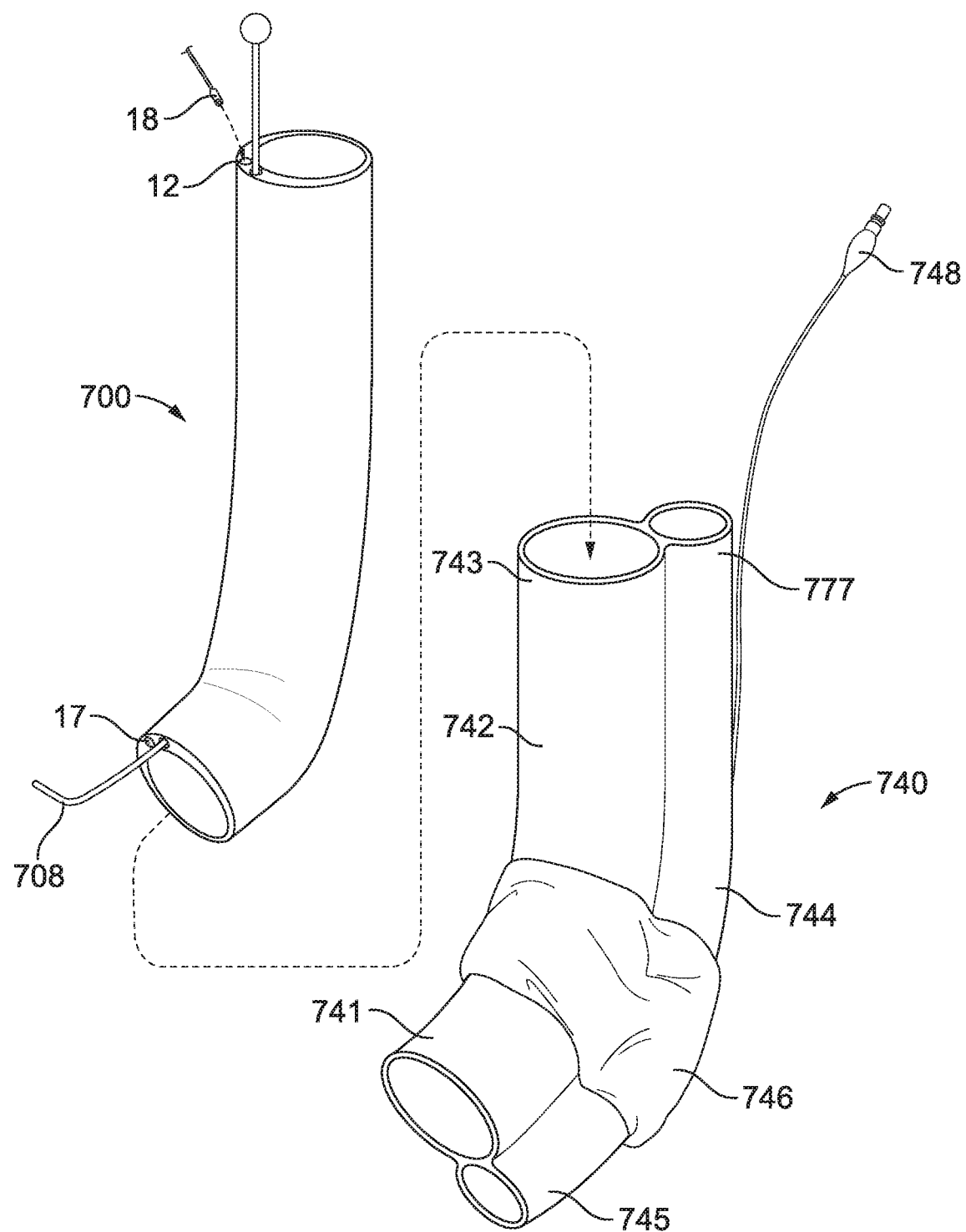
FIG. 46A depicts an intubating/ventilating double-lumen tube with guided sliding bougie into which an oral airway device can be inserted.

FIGS. 46A-46D provide a further embodiment for a double-lumen device comprising a visualization device, generally 740. As can be seen from FIG. 46A, the double-lumen device comprises two tubes, the anterior tube 742 and the posterior tube 744. In some embodiments, the tubes 742 and 744 have the same diameter, but in some other embodiments and as shown in FIG. 46A, the posterior tube 744 may have a diameter smaller than the anterior tube 742. The tubes 742 and 744 are slightly curved at the distal portion and are aligned together along their bodies in the anterior and posterior position, such that the tube 744 curves over the tube 742. The tubes 742 and 744 are made of a flexible material such that while the preformed shape is slightly curved, it is also possible for a practitioner to adjust the curvature of the double-lumen device 740 by bending the tubes 742 and 744, as needed. The distal end 741 of the anterior tube 742 is aligned with the distal end 745 of the posterior tube 744. The proximal end 743 of the anterior tube 742 is aligned with the proximal end 777 of the posterior tube 744. A cuff 746 wraps around the distal portion of the tubes 742 and 744 and keeps them together. The cuff 746 can inflated with means 748. The diameter of the tube 744 is adjusted such that it can fit into an esophagus. The anterior tube 742 can be used for delivery and retrieval of an intubating tube. The anterior tube 742 can be used for supraglottic ventilation or guide an endotracheal tube with the bougie and camera similar to FIG. 43A-43E.

Figures 46B, 46C:
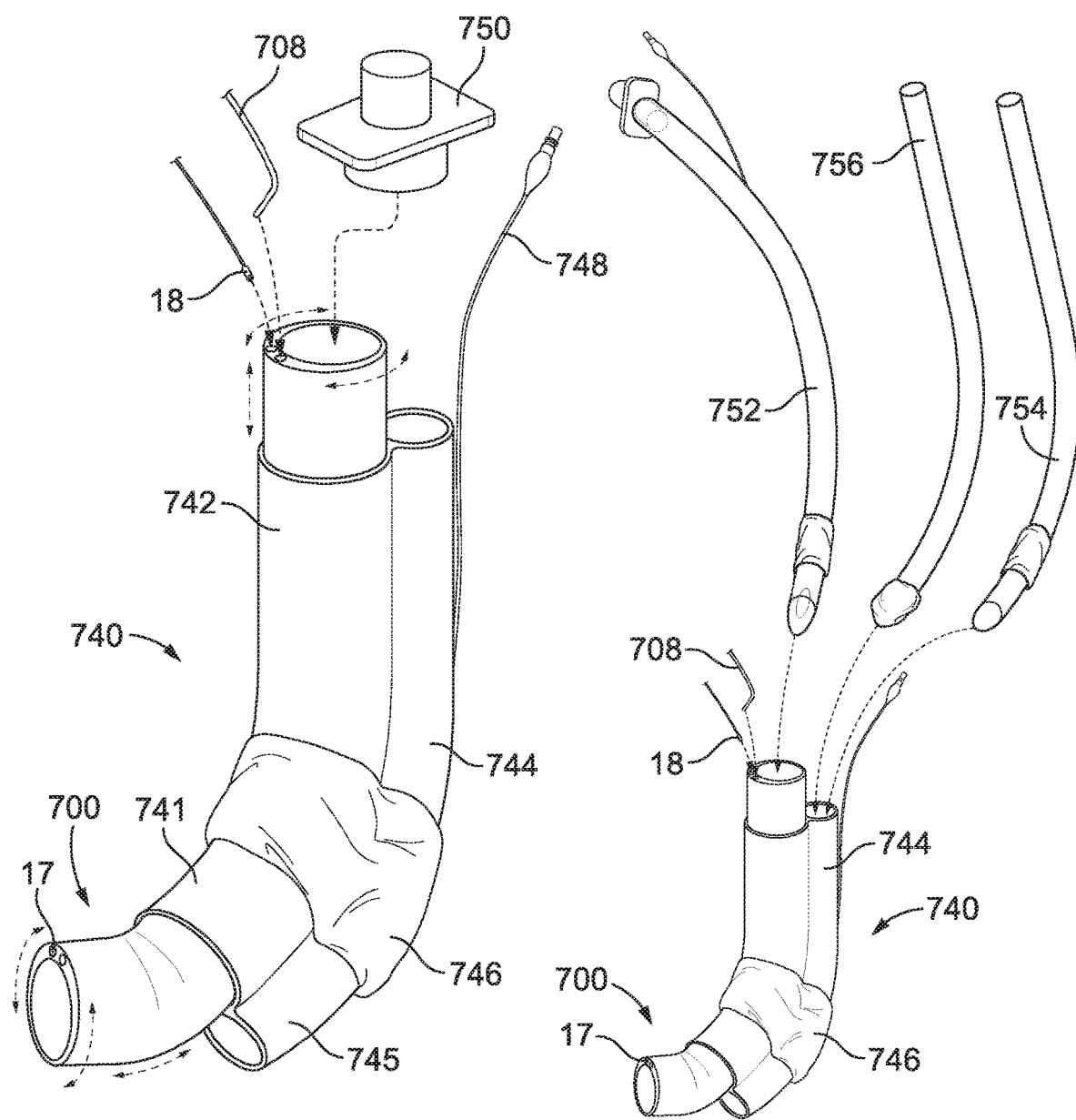
FIG. 46B depicts the double-lumen tube assembled with the oral airway device and a cap.
FIG. 46C depicts a further assembly with an endotracheal tube and either a suction tube or an esophageal blocker.

As shown in FIG. 46A, the device 700 of FIG. 43a can fit into the tube 742 of the device 740. The device 700 is equipped with a bougie 708 and a camera tube 12, both of which are integrated into the wall of the device 700. A camera 18 is then inserted into the camera tube 12 and provides continuous visualization through a transparent window 17 at distal end of the camera tube 12. FIG. 46B depicts the assembly in which the device 700 is inserted into the tube 742 of the device 740.

If the patient needs to be ventilated, the cuff 746 can be inflated and a cap 750 can be used to close the proximal end of the device 700. As shown in the drawing of FIG. 46C, the double-lumen device 740 assembled with the oral airway device 700 can be further assembled with an endotracheal tube 752 which can be inserted into the oral airway device 700.

The posterior tube 744 can be then used to suction from stomach with a suction tube 754. In alternative, an esophageal blocker 756 can be inserted in the posterior tube 744 for blocking the esophagus. Thus, the esophageal blocker 756 can be positioned under direct continuous visualization to occlude the upper esophagus/hypopharynx.

Figure 46D:
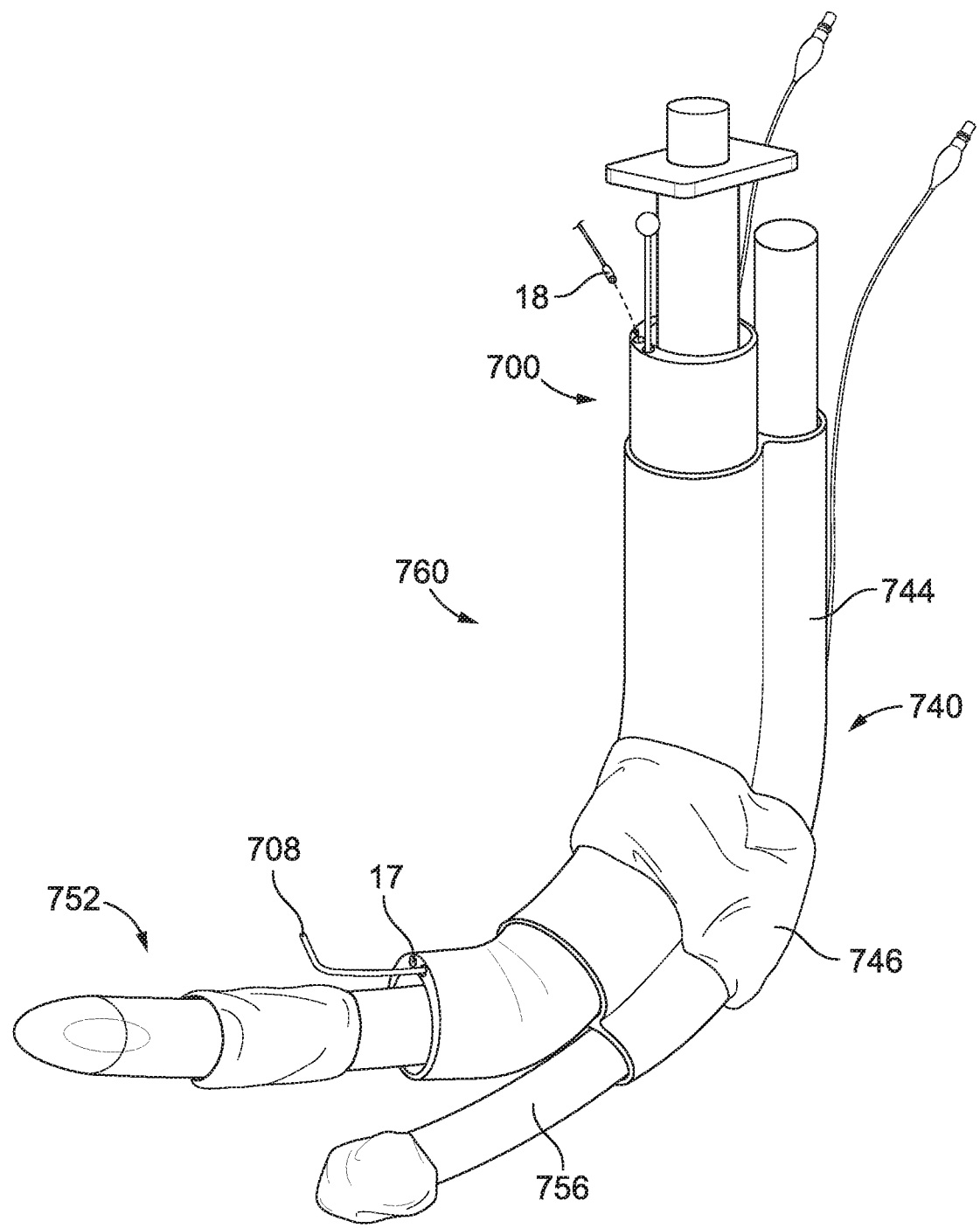
FIG. 46D depicts an assembly with the oral airway device, the endotracheal tube and the esophageal blocker.

The full assembly as shown in FIG. 46D, generally 760, may comprise the double-lumen device 740 into which the oral airway 700 is inserted. The endotracheal tube 752 is positioned in the oral airway 700. The esophageal blocker 756 is inserted into the second tube 744. The camera 18 is inserted into the camera tube 12 which is incorporated into the wall of the oral airway device 700, and provides continuous visualization during intubation and thereafter and while the assembly 760 is positioned in the patient. The patient can be ventilated with the assembly 760 as a closed system can be established by inflating the cuff 756. The assembly can be inserted with the guidance of the bougie 708 under the continuous visualization of the camera 18 through the transparent material window 17 which seals the camera tube 12 at the distal end. It should be noted that the second tube 744 in the double-lumen device 740 can be used for various purposes such as suction, blocking the esophagus or occlusion of a bronchus. A person of skill will appreciate that in other embodiments, a double-lumen device does not include a cuff. In some embodiments, the distal end of the posterior tube may be sealed. Further embodiments include those, in which the double-lumen device 740 is further equipped with tool tube as was discussed in detail in connection with FIG. 42C and FIG. 41C. Various tools, including but not limited to, biopsy forceps or a suction tube can be placed in the tool tube. When the tool tube is not in use or a closed system is to be established for patient's ventilation, the tool tube can be closed with a cap at the proximal end of the tool tube.

While certain medical devices are described above, a person of skill would appreciate that this invention also includes embodiments with various obvious modifications as would be easily apparent to a person of skill.

What is claimed is:

1. An oral airway device comprising a two-part tubal body of adjustable length, with a lumen and open proximal and distal ends, wherein the oral airway device is suitable for ventilating a patient through the lumen,
   wherein the two-part tubal body is made from an inner cylindrical tube insertable into an outer cylindrical tube and wherein the inner cylindrical tube encircles the lumen used for ventilating a patient and for insertion and removal of an endotracheal tube,
   wherein the oral airway device further comprises a bougie and
   wherein the oral airway device further comprises a visualization device comprising a camera tube, and a camera being insertable in the camera tube and removable from the camera tube, wherein the distal end of the camera tube is sealed with a transparent material which creates a sealed distal transparent window;
   wherein the bougie is incorporated into a wall of the inner cylindrical tube and wherein the camera tube is also incorporated into a wall of the inner cylindrical tube, and
   wherein the oral airway device is capable of providing continuous visualization of the patient while the patient is ventilated through the lumen in the two-part tubal body.

2. The oral airway device of claim 1, wherein the inner cylindrical tube can rotate around inside the outer cylindrical tube.

3. The oral airway device of claim 1, wherein the inner cylindrical tube can be extended out from the outer cylindrical tube at least partially and retracted back into the outer cylindrical tube.

4. The oral airway device of claim 1, wherein the inner cylindrical tube can be completely separated and removed from the outer cylindrical tube.

5. The oral airway device of claim 1, wherein the bougie is incorporated in at least one of the inner cylindrical tube wall and the outer cylindrical tube wall.

6. The oral airway device of claim 5, wherein the bougie can slide proximally and distally, and the bougie can rotate inside the wall.

7. The oral airway device of claim 1, wherein the camera tube is incorporated in at least one of the inner cylindrical tube wall and the outer cylindrical tube wall.

8. The oral airway device of claim 1, wherein the camera tube is incorporated in the inner cylindrical tube wall.

9. The oral airway device of claim 1, wherein the camera tube is incorporated in the outer cylindrical tube wall stationary.

10. The oral airway device of claim 1, wherein the camera tube is incorporated in the inner cylindrical tube wall, and the camera tube can slide distally along the wall and is extendable from the distal end of the inner cylindrical tube.

11. The oral airway device of claim 1, wherein the camera tube is incorporated in the outer cylindrical tube wall, and the camera tube can slide distally along the wall and is extendable from the distal end of the outer cylindrical tube.

12. The oral airway device of claim 1, wherein the bougie and the camera tube are both incorporated in the inner cylindrical tube wall, and wherein the bougie and the camera tube can slide distally from the two-part tubal body.

13. The oral airway device of claim 1, wherein the device is assembled together with an endotracheal tube.

14. A method of intubating a patient with the oral airway device of claim 1, the method comprising:
   sliding the bougie of the oral airway device distally from the two-part tubal body of the oral airway device;
   placing the bougie of the oral airway device through the vocal cords of the patient under direct vision from the camera;
   sliding the inner cylindrical tube of the oral airway device over the bougie; and
   placing the inner cylindrical tube of the oral airway device at one of the two locations: through the vocal cords or just proximal to the vocal cords.

15. The method of claim 14, wherein the patient is intubated with an endotracheal tube prior to the first step of claim 14, and wherein the endotracheal tube is removed after the inner cylindrical tube of the oral airway device has been placed at one of the two locations: through the vocal cords or just proximal to the vocal cords.

16. A kit comprising:
   the oral airway device of claim 1,
   a visualization device comprising a camera tube, and a camera insertable in the camera tube, wherein the distal end of the camera tube is sealed with a transparent material which creates a sealed distal transparent window; and
   a bougie.

17. The kit of claim 16, wherein the bougie and the camera tube are incorporated in the outer cylindrical tube wall.

18. The kit of claim 16, wherein the bougie and the camera tube are incorporated in the inner cylindrical tube wall.

19. An assembly comprising the oral airway device of claim 1 and a double-lumen device comprising an anterior tube and a posterior tube aligned in the anterior/posterior position, wherein the oral airway device is inserted in the anterior tube, and wherein a cuff is wrapped around the double lumen device.

20. The assembly of claim 19, wherein at least one of the following devices is inserted in the posterior tube: an esophageal blocker or a suction tube.

21. The assembly of claim 19, wherein an endotracheal tube is inserted into the oral airway device.

* * * * *